(12) United States Patent
Zhang et al.

(10) Patent No.: US 8,377,945 B2
(45) Date of Patent: Feb. 19, 2013

(54) SMALL MOLECULE INHIBITORS OF SPLEEN TYROSINE KINASE (SYK)

(75) Inventors: Jing Zhang, Foster City, CA (US); Rajinder Singh, Belmont, CA (US); Dane Goff, Redwood City, CA (US); Taisei Kinoshita, San Mateo, CA (US)

(73) Assignee: Rigel Pharmaceuticals Inc., South San Francisco, CA (US)

( * ) Notice: Subject to any disclaimer, the term of this patent is extended or adjusted under 35 U.S.C. 154(b) by 276 days.

(21) Appl. No.: 12/815,159

(22) Filed: Jun. 14, 2010

(65) Prior Publication Data

US 2010/0316649 A1  Dec. 16, 2010

Related U.S. Application Data

(60) Provisional application No. 61/187,204, filed on Jun. 15, 2009, provisional application No. 61/187,212, filed on Jun. 15, 2009.

(51) Int. Cl.
| | | |
|---|---|---|
| *A61K 39/395* | (2006.01) | |
| *A61K 31/56* | (2006.01) | |
| *A61K 31/4188* | (2006.01) | |
| *A61K 31/519* | (2006.01) | |
| *C07D 235/02* | (2006.01) | |
| *C12N 5/071* | (2010.01) | |
| *A61P 37/00* | (2006.01) | |

(52) U.S. Cl. ............ 514/262.1; 514/393; 514/171; 548/303.1; 435/325; 424/145.1

(58) Field of Classification Search .......... 548/303.1; 514/171, 393, 262.1; 424/145.1; 435/325
See application file for complete search history.

(56) References Cited

U.S. PATENT DOCUMENTS

| | | | | |
|---|---|---|---|---|
| 4,728,598 A | * | 3/1988 | Bailey et al. ............. | 430/387 |
| 5,206,130 A | * | 4/1993 | Shimada et al. ........... | 430/558 |
| 5,215,982 A | * | 6/1993 | Sakane et al. ............ | 514/202 |
| 5,232,939 A | | 8/1993 | Terada et al. | |
| 5,354,768 A | | 10/1994 | Terada et al. | |
| 5,665,752 A | | 9/1997 | Terada et al. | |
| 5,698,576 A | | 12/1997 | Terada et al. | |
| 5,723,481 A | | 3/1998 | Terada et al. | |

FOREIGN PATENT DOCUMENTS

| | | | |
|---|---|---|---|
| JP | 2001105742 | * | 4/2001 |
| JP | 2004-203748 | | 7/2004 |
| JP | 2006-241089 | | 9/2006 |
| WO | WO0183485 | | 11/2001 |
| WO | WO2007042298 | | 4/2007 |

OTHER PUBLICATIONS

Li et al., Synthetic Communications (2005), 35(4), 493-501.*
Seneci et al., Synthetic Communications (1999), 29(2), 311-341.*
Goddard et al., Anti-Cancer Drug Design (1987), 2(3), 235-45.*
Wood et al., Journal of Organic Chemistry (1984), 49(19), 3534-40.*
Schulze et al., Chemische Berichte (1967), 100(10), 3460-2.*

* cited by examiner

*Primary Examiner* — Niloofar Rahmani
(74) *Attorney, Agent, or Firm* — Rudy J. Ng; Carol L. Francis; Bozicevic, Field & Francis LLP

(57) ABSTRACT

This disclosure concerns compounds which are useful as inhibitors of spleen tyrosine kinase (Syk) and are thus useful for treating a variety of diseases and disorders that are mediated or sustained through the activity of Syk. This disclosure also relates to pharmaceutical compositions containing these compounds, methods of using these compounds in the treatment of various diseases and disorders, processes for preparing these compounds and intermediates useful in these processes.

26 Claims, No Drawings

SMALL MOLECULE INHIBITORS OF SPLEEN TYROSINE KINASE (SYK)

CROSS-REFERENCE TO RELATED APPLICATIONS

This application claims the benefit of Provisional Application Ser. Nos. 61/187,204, filed Jun. 15, 2009 and 61/187,212, filed Jun. 15, 2009, each which application is incorporated by reference in their entireties.

BACKGROUND

Spleen tyrosine kinase (Syk) is an intracellular protein-tyrosine kinase that is widely expressed in hematopoietic cells, cells of the immune system and cells of epithelial lineages. Syk is involved in transducing signals from activated immunoglobulin receptors, such as Fcγ receptors and Fcε receptors. Syk is also implicated in the signaling triggered by receptors for G-CSF, IL-2, IL-3, IL-5, GM-CSF, IL-15, various chemokines, IL-1 and erythropoietin. Thus Syk is a promiscuous messenger in various signal transduction pathways. Syk mediates diverse cellular responses, including proliferation, differentiation, and phagocytosis.

SUMMARY

This disclosure concerns compounds which are useful as inhibitors of Syk and are thus useful for treating a variety of diseases and disorders that are mediated or sustained through the activity of Syk. This disclosure also relates to pharmaceutical compositions containing these compounds, methods of using these compounds in the treatment of various diseases and disorders, processes for preparing these compounds and intermediates useful in these processes.

Exemplary chemical structures are provided throughout the disclosure. By way of example, such compounds are represented by the following formulae.

Formula Iz is shown below:

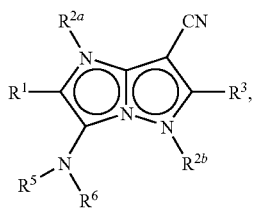

(Iz)

wherein $R^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —$SO_2$-alkyl, —$SO_2$-aryl, —$SO_2$-heteroaryl, aryl, substituted aryl, heteroaryl, heterocyclyl, aralkyl, and heteroaralkyl; and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from hydrogen, alkyl, substituted alkyl, alkenyl, substituted alkenyl, alkynyl, substituted alkynyl, acyl, acylamino, acyloxy, cycloalkyl, substituted cycloalkyl, cycloalkenyl, substituted cycloalkenyl, aralkyl, heteroaralkyl, aryl, substituted aryl, heteroaryl, substituted heteroaryl, heterocyclyl, and substituted heterocyclyl;

or a salt or stereoisomer thereof.

Formula Ib is shown below:

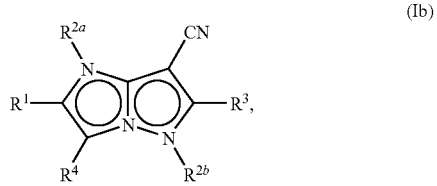

(Ib)

wherein $R^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —$SO_2$-alkyl, —$SO_2$-aryl, —$SO_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^4$ is selected from hydrogen, alkyl, substituted alkyl, amino, or —$NR^5R^6$;

$R^5$ is selected from hydrogen, alkyl, and substituted alkyl; and $R^6$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

or a salt or stereoisomer thereof.

DEFINITIONS

The following terms have the following meanings unless otherwise indicated. Any undefined terms have their art recognized meanings.

The term "alkyl" refers to a monoradical branched or unbranched saturated hydrocarbon chain, e.g., having from 1 to 40 carbon atoms, from 1 to 10 carbon atoms, or from 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, oxo, thioketo, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocylooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

The term "alkylene" refers to a diradical of a branched or unbranched saturated hydrocarbon chain, usually having from 1 to 40 carbon atoms, more usually 1 to 10 carbon atoms and even more usually 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group as defined herein wherein one or more carbon atoms in the alkylene chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, oxo, thioketo, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocylooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

The term "alkane" refers to alkyl group and alkylene group, as defined herein.

The term "aralkyl" refers to the groups -alkylene-aryl and -substituted alkylene-aryl where alkylene, substituted alkylene and aryl are defined herein.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the group alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl, and heterocyclic are as defined herein.

The term "acylamino" refers to the groups —NRC(O)alkyl, —NRC(O) substituted alkyl, —NRC(O)cycloalkyl, —NRC(O) substituted cycloalkyl, —NRC(O)alkenyl, —NRC(O) substituted alkenyl, —NRC(O)alkynyl, —NRC(O) substituted alkynyl, —NRC(O)aryl, —NRC(O) substituted aryl, —NRC(O)heteroaryl, —NRC(O) substituted heteroaryl, —NRC(O)heterocyclic, and —NRC(O) substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

The term "aminoacyl" or "aminocarbonyl" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

The term "acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

The term "oxyacyl" or "carboxyl ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O -cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl, and heterocyclic are as defined herein.

The term "alkenyl" refers to a monoradical of a branched or unbranched unsaturated hydrocarbon group having from 2 to 40 carbon atoms, from 2 to 10 carbon atoms, or from 2 to 6 carbon atoms and having at least 1 site (e.g., from 1-6 sites) of vinyl unsaturation.

The term "substituted alkenyl" refers to an alkenyl group as defined herein having from 1 to 5 substituents, or from 1 to 3 substituents, selected from alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, oxo, thioketo, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

The term "alkynyl" refers to a monoradical of an unsaturated hydrocarbon having from 2 to 40 carbon atoms, from 2 to 20 carbon atoms, or from 2 to 6 carbon atoms and having at least 1 site (e.g., from 1-6 sites) of acetylene (triple bond) unsaturation.

The term "substituted alkynyl" refers to an alkynyl group as defined herein having from 1 to 5 substituents, or from 1 to 3 substituents, selected from alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, oxo, thioketo, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

The term "amino" refers to the group —NH$_2$.

The term "substituted amino" refers to the group —NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —SO$_2$-alkyl, —SO$_2$-substituted alkyl, provided that at least one R is not hydrogen. When one R is hydrogen and the other R is alkyl, the substituted amino group is sometimes referred to herein as alkylamino. When both R and R' are alkyl, the substituted amino group is sometimes referred to herein as dialkylamino. When referring to a monosubstituted amino, it is meant that one of the R's is hydrogen but not both. When referring to a disubstituted amino, it is meant that neither of the R's is hydrogen.

The term "azido" refers to the group —N$_3$.

The term "cyano" refers to the group —CN.

The term "nitro" refers to the group —NO$_2$.

The term "aryl" refers to an unsaturated aromatic carbocyclic group of from 6 to 20 carbon atoms having a single ring (e.g., phenyl) or multiple condensed (fused) rings (e.g., naphthyl or anthryl). Exemplary aryls include phenyl, naphthyl and the like. Unless otherwise constrained by the definition for the aryl substituent, such aryl groups can optionally be substituted with from 1 to 5 substituents, or from 1 to 3 substituents, selected from alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, oxo, thioketo, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl. Substituted aryl includes substituents of an aryl ring together forming a carbocyclic, substituted carbocyclic, heterocyclic or substituted heterocyclic ring. The term "substituted aryl" refers to aryl groups which are substituted with substituents.

The term "aryloxy" refers to the group aryl-O— wherein the aryl group is as defined herein including optionally substituted aryl groups as also defined herein. The term "substituted aryloxy" refers to substituted aryl-O— groups.

The term "carboxyl" or "carboxy" refers to —COOH or salts thereof.

The term "oxo" refers to the group =O.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, oxo, thioketo, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

The term "spirocycloalkyl" refers to cyclic groups from 3 to 20 carbon atoms having a cycloalkyl ring with a spiro union (the union formed by a single atom which is the only common member of the rings).

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl, and the like.

The term "substituted cycloalkenyl" refers to cycloalkenyl groups having from 1 to 5 substituents, or from 1 to 3 substituents, selected from alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, oxo, thioketo, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

The term "halo" or "halogen" refers to fluoro, chloro, bromo and iodo.

The term "hydroxy" of "hydroxyl" refers to the group —OH.

The term "hydroxyamino" refers to the group —NHOH.

The term "alkoxyamino" refers to the group —NH-alkoxy.

The term "heteroaryl" refers to an aromatic group of from 1 to 15 carbon atoms and 1 to 4 heteroatoms selected from oxygen, nitrogen and sulfur within at least one ring (if there is more than one ring). Unless otherwise constrained by the definition for the heteroaryl substituent, such heteroaryl groups can be optionally substituted with 1 to 5 substituents, or from 1 to 3 substituents, selected from alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, oxo, thioketo, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl. Substituted heteroaryl includes substituents of a heteroaryl ring together forming a carbocyclic, substituted carbocyclic, heterocyclic or substituted heterocyclic ring. The term "substituted heteroaryl" refers to heteroaryl groups that are substituted with from 1 to 5 substituents selected from the same group of substituents defined for substituted aryl.

The term "heteroaralkyl" refers to the groups -alkylene-heteroaryl where alkylene and heteroaryl are defined herein. Such heteroaralkyl groups are exemplified by pyridylmethyl, pyridylethyl, indolylmethyl, and the like.

The term "heteroaryloxy" refers to the group —O-heteroaryl and the term "substituted heteroaryloxy" refers to the group —O-substituted heteroaryl wherein heteroaryl and substituted heteroaryl are as defined herein.

The term "heterocycle" or "heterocyclic" or "heterocycloalkyl" or "heterocyclyl" refers to a monoradical saturated or unsaturated group having a single ring or multiple condensed rings, from 1 to 40 carbon atoms and from 1 to 10 hetero atoms, e.g., from 1 to 4 heteroatoms, selected from nitrogen, sulfur, phosphorus, and/or oxygen within the ring. Unless otherwise constrained by the definition for the heterocyclic substituent, such heterocyclic groups can be optionally substituted with 1 to 5, or from 1 to 3 substituents, selected from alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, oxo, thioketo, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl. The term "substituted heterocyclic" or "substituted heterocycloalkyl" or "substituted heterocyclyl" refers to heterocyclyl groups that are substituted with from 1 to 5 of the same substituents as defined for substituted cycloalkyl.

The term "heterocyclene" refers to the diradical group formed from a heterocycle, as defined herein.

The term "heterocyclyloxy" refers to the group —O-heterocyclyl and the term "substituted heterocyclyloxy" refers to the group —O-substituted heterocyclyl wherein heterocyclyl and substituted heterocyclyl are as defined herein.

The term "thiol" refers to the group —SH.

The term "alkylthio" or "thioalkoxy" refers to the group —S-alkyl.

The term "substituted alkylthio" or "substituted thioalkoxy" refers to the group —S-substituted alkyl.

The term "arylthio" refers to the group —S-aryl, where aryl is defined above.

The term "substituted arylthio" refers to the group —S-substituted aryl, where substituted aryl is defined above.

The term "heteroarylthio" refers to the group —S-heteroaryl, where heteroaryl is defined above.

The term "substituted heteroarylthio" refers to the group —S-substituted heteroaryl, where substituted heteroaryl is defined above.

The term "heterocyclylthio" refers to the group —S-heterocyclyl and "substituted heterocyclylthio" refers to the group —S-substituted heterocyclyl, where heterocyclic and substituted heterocyclic are defined above.

The term "heterocyclyloxy" refers to the group heterocyclyl-O— and "substituted heterocyclyloxy refers to the group substituted heterocyclyl-O— where heterocyclyl and substituted heterocyclyl are defined above.

The term "cycloalkylthio" refers to the group —S-cycloalkyl and "substituted cycloalkylthio" refers to the group —S-substituted cycloalkyl, where cycloalkyl and substituted cycloalkyl are defined above.

The term "thioketo" refers to the group =S.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

Similarly, it is understood that the above definitions are not intended to include impermissible substitution patterns (e.g., methyl substituted with 5 fluoro groups or a hydroxy group alpha to ethenylic or acetylenic unsaturation). Such impermissible substitution patterns are well known to the skilled artisan.

Subject compounds may exhibit stereoisomerism by virtue of the presence of one or more asymmetric or chiral centers in the compounds. The present invention contemplates the various stereoisomers and mixtures thereof. Depiction of the compounds can include the stereoisomers thereof. Certain of the compounds contain asymmetrically substituted carbon atoms. Such asymmetrically substituted carbon atoms can result in compositions having mixtures of stereoisomers at a particular asymmetrically substituted carbon atom or a single stereoisomer. As a result, racemic mixtures, mixtures of diastereomers, single enantiomer, as well as single diastereomers of the compounds are included. The terms "S" and "R" configuration, as used herein, are as defined by the IUPAC 1974 "RECOMMENDATIONS FOR SECTION E, FUNDAMENTAL STEREOCHEMISTRY," Pure Appl. Chem. 45:13-30, 1976. Desired enantiomers can be obtained by chiral synthesis from commercially available chiral starting materials by methods well known in the art, or may be obtained from mixtures of the enantiomers by separating the desired enantiomer by using known techniques.

Compounds may also exhibit geometrical isomerism. Geometrical isomers include the cis and trans forms of compounds of the invention having alkenyl or alkenylenyl moieties. The embodiments encompass the individual geometrical isomers and stereoisomers and mixtures thereof.

The term "pharmaceutically acceptable salt" means a salt which is acceptable for administration to a patient, such as a mammal (e.g., salts having acceptable mammalian safety for a given dosage regime). Such salts can be derived from pharmaceutically acceptable inorganic or organic bases and from pharmaceutically acceptable inorganic or organic acids.

The term "salt thereof" means a compound formed when the hydrogen of an acid is replaced by a cation, such as a metal cation or an organic cation and the like. Where applicable, the salt is a pharmaceutically acceptable salt, although this is not required for salts of intermediate compounds that are not intended for administration to a patient.

The term "solvate" as used herein refers to a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

It will be appreciated that the term "or a salt or solvate or stereoisomer thereof" is intended to include all permutations of salts, solvates and stereoisomers, such as a solvate of a pharmaceutically acceptable salt of a stereoisomer of a subject compound.

The term "therapeutically effective amount" means an amount sufficient to effect treatment when administered to a patient in need of treatment.

The term "treating" or "treatment" as used herein means the treating or treatment of a disease or medical condition in a patient, such as a mammal (particularly in a patient suspected of having a condition) that includes: (a) preventing the disease or medical condition from occurring, i.e., prophylactic treatment of a patient; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient.

DETAILED DESCRIPTION

This disclosure concerns compounds which are useful as inhibitors of Syk and are thus useful for treating a variety of diseases and disorders that are mediated or sustained through the activity of Syk. This disclosure also relates to pharmaceutical compositions containing these compounds, methods of using these compounds in the treatment of various diseases and disorders, processes for preparing these compounds and intermediates useful in these processes.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. This nomenclature has generally been derived using the commercially-available AutoNom software (MDL, San Leandro, Calif.).

Representative Embodiments

The following substituents and values are intended to provide representative examples of various aspects and embodiments. These representative values are intended to further define and illustrate such aspects and embodiments and are not intended to exclude other embodiments or to limit the scope of this invention. In this regard, the representation that a particular value or substituent is preferred is not intended in any way to exclude other values or substituents from this invention unless specifically indicated.

These compounds may contain one or more chiral centers and therefore, the embodiments are directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions unless otherwise indicated, provided that the desired utility of the composition as a whole is not eliminated by the presence of such other isomers.

In the following structures, either $R^{2a}$ or $R^{2b}$ is present to satisfy valence requirements. To satisfy valence requirements of the ring, when $R^{2a}$ is present, $R^{2b}$ is absent. Alternatively, when $R^{2b}$ is present, $R^{2a}$ is absent.

The compositions of the present disclosure include compounds of formula Iz, shown below. Pharmaceutical compositions and methods of the present disclosure also contemplate compounds of formulae Iz.

Formula Iz

In one of its composition aspects, the present embodiments provide a compound of formula (Iz):

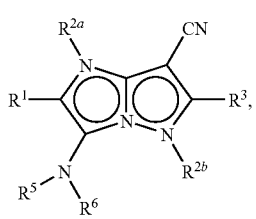

(Iz)

wherein $R^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl; and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from hydrogen, alkyl, substituted alkyl, alkenyl, substituted alkenyl, alkynyl, substituted alkynyl, acyl, acylamino, acyloxy, cycloalkyl, substituted cycloalkyl, cycloalkenyl, substituted cycloalkenyl, aralkyl, heteroaralkyl, aryl, substituted aryl, heteroaryl, substituted heteroaryl, heterocyclyl, and substituted heterocyclyl;

or a salt or stereoisomer thereof.

The compositions of the present disclosure include compounds of formulae Ia-Xa, shown below. Pharmaceutical compositions and methods of the present disclosure also contemplate compounds of formulae Ia-Xa.

Formula Ia

In one of its composition aspects, the present embodiments provide a compound of formula (Ia):

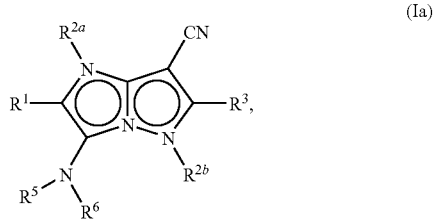

(Ia)

wherein $R^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from hydrogen, alkyl, substituted alkyl, alkenyl, substituted alkenyl, alkynyl, substituted alkynyl, acyl, acylamino, acyloxy, cycloalkyl, substituted cycloalkyl, cycloalkenyl, substituted cycloalkenyl, aralkyl, and heteroaralkyl;

or a salt or stereoisomer thereof.

In formula Ia, $R^1$ can be selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy.

In certain instances, in formula Ia, $R^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, alkyl, and substituted alkyl. In certain instances, $R^1$ is selected from aryl, substituted aryl, heteroaryl, substituted heteroaryl, heterocyclyl, substituted heterocyclyl, aralkyl, heteroaralkyl, alkyl, and substituted alkyl.

In certain cases, in formula Ia, $R^1$ is selected from aryl and substituted aryl. In certain cases, $R^1$ is selected from heteroaryl and substituted heteroaryl. In certain cases, $R^1$ is selected from heterocyclyl and substituted heterocyclyl. In certain cases, $R^1$ is selected from aralkyl, heteroaralkyl, alkyl, and substituted alkyl.

In formula Ia, $R^{2a}$ and $R^{2b}$ can be independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl; wherein either $R^{2a}$ or $R^{2b}$ is present. In certain instances, $R^{2a}$ is present. In certain instances, $R^{2b}$ is present. In certain instances, $R^{2a}$ and $R^{2b}$ are independently selected from hydrogen, alkyl, substituted alkyl, acyl, acylamino, acyloxy, aryl, substituted aryl, heteroaryl, heterocyclyl. In certain cases, $R^{2a}$ and $R^{2b}$ are independently selected from hydrogen, alkyl, substituted alkyl, aryl, and substituted aryl. In certain cases, $R^{2a}$ and $R^{2b}$ are independently selected from hydrogen, alkyl, and substituted alkyl. In certain cases, $R^{2a}$ and $R^{2b}$ are independently selected from hydrogen, aryl, and substituted aryl.

In certain cases, in formula Ia, $R^{2a}$ and $R^{2b}$ are independently selected from —SO-alkyl, —SO-aryl, —SO-heteroaryl, —SO$_2$-alkyl, —SO$_2$-aryl, and —SO$_2$-heteroaryl. In certain cases, $R^{2a}$ and $R^{2b}$ are independently selected from heteroaryl and heterocyclyl. In certain cases, $R^{2a}$ and $R^{2b}$ are independently selected from acyl, acylamino, acyloxy. In certain cases, $R^{2a}$ and $R^{2b}$ are independently selected from aralkyl and heteroaralkyl.

In formula Ia, $R^3$ can be selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl.

In certain instances, in formula Ia, $R^3$ is selected from hydrogen, alkyl, substituted alkyl, halo, nitro, cyano, hydroxy, alkoxy, acyl, amino, substituted amino, aryl, substituted aryl, heteroaryl, and substituted heteroaryl. In certain cases, $R^3$ is selected from hydrogen, alkyl, substituted alkyl, aryl, substituted aryl, heteroaryl, and substituted heteroaryl. In certain cases, $R^3$ is selected from hydrogen, alkyl, substituted alkyl, aryl, and substituted aryl. In certain cases, $R^3$ is hydrogen. In certain cases, $R^3$ is alkyl or substituted alkyl. In certain cases, $R^3$ is aryl or substituted aryl.

In certain cases, in formula Ia, $R^3$ is selected from alkenyl, substituted alkenyl, and carboxyl. In certain cases, $R^3$ is selected from acylamino, aminoacyl, acyloxy, and oxyacyl.

In formula Ia, $R^5$ can be selected from hydrogen, alkyl, and substituted alkyl. In certain instances, $R^5$ is hydrogen. In certain instances, $R^5$ is alkyl. In certain instances, $R^5$ is alkyl or substituted alkyl.

In formula Ia, $R^6$ can be selected from hydrogen, alkyl, substituted alkyl, alkenyl, substituted alkenyl, alkynyl, substituted alkynyl, acyl, acylamino, acyloxy, cycloalkyl, substituted cycloalkyl, cycloalkenyl, substituted cycloalkenyl, aralkyl, and heteroaralkyl.

In certain instances, in formula Ia, $R^6$ is selected from hydrogen, alkyl, substituted alkyl, and acyl. In certain instances, $R^6$ is selected from alkyl and substituted alkyl. In certain instances, $R^6$ is acyl. In certain instances, $R^6$ is hydrogen.

In certain cases, in formula Ia, $R^6$ is selected from alkenyl, substituted alkenyl, alkynyl, and substituted alkynyl. In certain cases, $R^6$ is selected from acylamino and acyloxy. In certain cases, $R^6$ is selected from cycloalkyl, substituted cycloalkyl, cycloalkenyl, substituted cycloalkenyl. In certain cases, $R^6$ is selected from aralkyl and heteroaralkyl.

Formula IIa

In one of its composition aspects, the present embodiments provide a compound of formula (IIa):

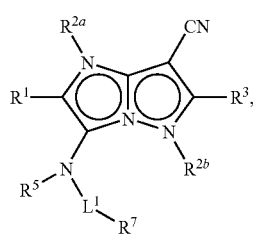

(IIa)

wherein $R^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy; $R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl;

$L^1$ is —(CH$_2$)$_n$—, —C(O)—, or —C(O)—(CH$_2$)$_n$—;

n is an integer from one to five; and $R^7$ is selected from aryl, substituted aryl, heteroaryl, substituted heteroaryl, heterocyclyl, and substituted heterocyclyl;

or a salt or stereoisomer thereof.

In formula IIa, $R^1$ can be selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy.

In certain instances, in formula IIa, $R^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, alkyl, and substituted alkyl. In certain instances, $R^1$ is selected from aryl, substituted aryl, heteroaryl, substituted heteroaryl, heterocyclyl, substituted heterocyclyl, aralkyl, heteroaralkyl, alkyl, and substituted alkyl.

In certain cases, in formula IIa, $R^1$ is selected from aryl and substituted aryl. In certain cases, $R^1$ is selected from heteroaryl and substituted heteroaryl. In certain cases, $R^1$ is selected from heterocyclyl and substituted heterocyclyl. In certain cases, $R^1$ is selected from aralkyl, heteroaralkyl, alkyl, and substituted alkyl.

In formula IIa, $R^{2a}$ and $R^{2b}$ can be independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl; wherein either $R^{2a}$ or $R^{2b}$ is present. In certain instances, $R^{2a}$ is present. In certain instances, $R^{2b}$ is present. In certain instances, $R^{2a}$ and $R^{2b}$ are independently selected from hydrogen, alkyl, substituted alkyl, acyl, acylamino, acyloxy, aryl, substituted aryl, heteroaryl, heterocyclyl. In certain cases, $R^{2a}$ and $R^{2b}$ are independently selected from hydrogen, alkyl, substituted alkyl, aryl, and substituted aryl. In certain cases, $R^{2a}$ and $R^{2b}$ are independently selected from hydrogen, alkyl, and substituted alkyl. In certain cases, $R^{2a}$ and $R^{2b}$ are independently selected from hydrogen, aryl, and substituted aryl.

In certain cases, in formula IIa, $R^{2a}$ and $R^{2b}$ are independently selected from —SO-alkyl, —SO-aryl, —SO-heteroaryl, —SO$_2$-alkyl, —SO$_2$-aryl, and —SO$_2$-heteroaryl. In certain cases, $R^{2a}$ and $R^{2b}$ are independently selected from heteroaryl and heterocyclyl. In certain cases, $R^{2a}$ and $R^{2b}$ are independently selected from acyl, acylamino, acyloxy. In certain cases, $R^{2a}$ and $R^{2b}$ are independently selected from aralkyl and heteroaralkyl.

In formula IIa, $R^3$ can be selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl.

In certain instances, in formula IIa, $R^3$ is selected from hydrogen, alkyl, substituted alkyl, halo, nitro, cyano, hydroxy, alkoxy, acyl, amino, substituted amino, aryl, substituted aryl, heteroaryl, and substituted heteroaryl. In certain cases, $R^3$ is selected from hydrogen, alkyl, substituted alkyl, aryl, substituted aryl, heteroaryl, and substituted heteroaryl. In certain cases, $R^3$ is selected from hydrogen, alkyl, substituted alkyl, aryl, and substituted aryl. In certain cases, $R^3$ is hydrogen. In certain cases, $R^3$ is alkyl or substituted alkyl. In certain cases, $R^3$ is aryl or substituted aryl.

In certain cases, in formula IIa, $R^3$ is selected from alkenyl, substituted alkenyl, and carboxyl. In certain cases, $R^3$ is selected from acylamino, aminoacyl, acyloxy, and oxyacyl.

In formula IIa, $R^5$ can be selected from hydrogen, alkyl, and substituted alkyl. In certain instances, $R^5$ is hydrogen. In certain instances, $R^5$ is alkyl. In certain instances, $R^5$ is alkyl or substituted alkyl.

In formula IIa, $L^1$ is —$(CH_2)_n$—, —C(O)— or —C(O)—$(CH_2)_n$—, where n is an integer from one to five. In certain instances, $L^1$ is —$(CH_2)_n$—. In certain instances, $L^1$ is —C(O)—. In certain instances, $L^1$ is —C(O)—$(CH_2)_n$—. In certain instances, n is one. In certain instances, n is two. In certain instances, n is three. In certain instances, n is four. In certain instances, n is five.

In formula IIa, $R^7$ can be selected from aryl, substituted aryl, heteroaryl, substituted heteroaryl, heterocyclyl, and substituted heterocyclyl. In certain instances, $R^7$ is selected from aryl and substituted aryl. In certain instances, $R^7$ is selected from heteroaryl and substituted heteroaryl. In certain instances, $R^7$ is selected from heterocyclyl and substituted heterocyclyl.

Formula IIIa

In one of its composition aspects, the present embodiments provide a compound of formula (IIIa):

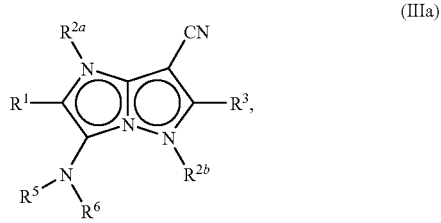

(IIIa)

wherein $R^1$ is selected from aryl, substituted aryl, heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —$SO_2$-alkyl, —$SO_2$-aryl, —$SO_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from heteroaryl, substituted heteroaryl, heterocyclyl, and substituted heterocyclyl;

or a salt or stereoisomer thereof.

In formula IIIa, $R^1$ can be selected from aryl, substituted aryl, heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy.

In certain instances, in formula IIIa, $R^1$ is selected from aryl, substituted aryl, heteroaryl, cycloalkyl, substituted cycloalkyl, cycloalkenyl, substituted cycloalkenyl, heterocyclyl, substituted heterocyclyl, aralkyl, heteroaralkyl, alkyl, and substituted alkyl. In certain instances, $R^1$ is selected from aryl, substituted aryl, heteroaryl, heterocyclyl, substituted heterocyclyl, aralkyl, heteroaralkyl, alkyl, and substituted alkyl.

In certain cases, in formula IIIa, $R^1$ is selected from aryl and substituted aryl. In certain cases, $R^1$ is heteroaryl. In certain cases, $R^1$ is selected from heterocyclyl and substituted heterocyclyl. In certain cases, $R^1$ is selected from aralkyl, heteroaralkyl, alkyl, and substituted alkyl.

In formula IIIa, $R^{2a}$ and $R^{2b}$ can be independently selected from hydrogen, alkyl, substituted alkyl, acyl, acylamino, acyloxy, —SO-alkyl, —SO-aryl, —SO-heteroaryl, —$SO_2$-alkyl, —$SO_2$-aryl, —$SO_2$-heteroaryl, aryl, substituted aryl, heteroaryl, heterocyclyl, aralkyl, and heteroaralkyl; wherein either $R^{2a}$ or $R^{2b}$ is present. In certain instances, $R^{2a}$ is present. In certain instances, $R^{2b}$ is present. In certain instances, $R^{2a}$ and $R^{2b}$ are independently selected from hydrogen, alkyl, substituted alkyl, acyl, acylamino, acyloxy, aryl, substituted aryl, heteroaryl, heterocyclyl. In certain cases, $R^{2a}$ and $R^{2b}$ are independently selected from hydrogen, alkyl, substituted alkyl, aryl, and substituted aryl. In certain cases, $R^{2a}$ and $R^{2b}$ are independently selected from hydrogen, alkyl, and substituted alkyl. In certain cases, $R^{2a}$ and $R^{2b}$ are independently selected from hydrogen, aryl, and substituted aryl.

In certain cases, in formula IIIa, $R^{2a}$ and $R^{2b}$ are independently selected from —SO-alkyl, —SO-aryl, —SO-heteroaryl, —$SO_2$-alkyl, —$SO_2$-aryl, and —$SO_2$-heteroaryl. In certain cases, $R^{2a}$ and $R^{2b}$ are independently selected from heteroaryl and heterocyclyl. In certain cases, $R^{2a}$ and $R^{2b}$ are independently selected from acyl, acylamino, acyloxy. In certain cases, $R^{2a}$ and $R^{2b}$ are independently selected from aralkyl and heteroaralkyl.

In formula IIIa, $R^3$ can be selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl.

In certain instances, in formula IIIa, $R^3$ is selected from hydrogen, alkyl, substituted alkyl, halo, nitro, cyano, hydroxy, alkoxy, acyl, amino, substituted amino, aryl, substituted aryl, heteroaryl, and substituted heteroaryl. In certain cases, $R^3$ is selected from hydrogen, alkyl, substituted alkyl, aryl, substituted aryl, heteroaryl, and substituted heteroaryl. In certain cases, $R^3$ is selected from hydrogen, alkyl, substituted alkyl, aryl, and substituted aryl. In certain cases, $R^3$ is hydrogen. In certain cases, $R^3$ is alkyl or substituted alkyl. In certain cases, $R^3$ is aryl or substituted aryl.

In certain cases, in formula IIIa, $R^3$ is selected from alkenyl, substituted alkenyl, and carboxyl. In certain cases, $R^3$ is selected from acylamino, aminoacyl, acyloxy, and oxyacyl.

In formula IIIa, $R^5$ can be selected from hydrogen, alkyl, and substituted alkyl. In certain instances, $R^5$ is hydrogen. In certain instances, $R^5$ is alkyl. In certain instances, $R^5$ is alkyl or substituted alkyl.

In formula IIIa, $R^6$ can be selected from heteroaryl, substituted heteroaryl, heterocyclyl, and substituted heterocyclyl. In certain instances, $R^6$ is selected from heteroaryl and substituted heteroaryl. In certain instances, $R^6$ is selected from heterocyclyl and substituted heterocyclyl.

Formula IVa

In one of its composition aspects, the present embodiments provide a compound of formula (IVa):

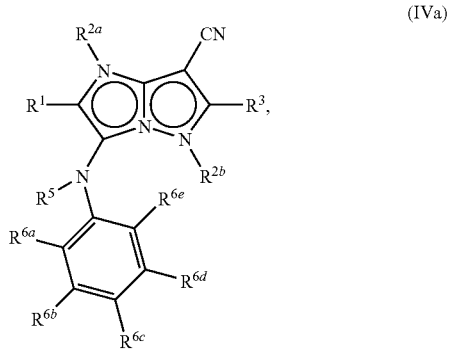

(IVa)

wherein $R^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^{6a}$ and $R^{6e}$ are independently selected from hydrogen, $C_{2-10}$ alkyl, substituted alkyl, $C_{2-10}$ alkoxy, substituted alkoxy, acyl, acylamino, acyloxy, aminoacyl, oxyacyl, amino, substituted amino, aminocarbonyloxy, alkoxycarbonyloxy, azido, cyano, hydroxyl, hydroxylamino, alkoxyamino, nitro, carboxyl, thiol, alkylthio, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl;

$R^{6c}$ is selected from hydrogen, alkyl, substituted alkyl, alkoxy, substituted alkoxy, acyl, acylamino, acyloxy, aminoacyl, amino, substituted amino, aminocarbonyloxy, alkoxycarbonyloxy, azido, cyano, halogen, hydroxyl, hydroxylamino, alkoxyamino, nitro, carboxyl, thiol, alkylthio, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl;

$R^{6b}$ and $R^{6d}$ are independently selected from hydrogen, alkyl, monosubstituted alkyl, disubstituted alkyl, alkoxy, substituted alkoxy, acyl, acylamino, acyloxy, aminoacyl, oxyacyl, amino, substituted amino, aminocarbonyloxy, alkoxycarbonyloxy, azido, halogen, hydroxyl, hydroxylamino, alkoxyamino, nitro, carboxyl, thiol, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl; or wherein any two of $R^{6a}$, $R^{6b}$, $R^{6c}$, $R^{6d}$, and $R^{6e}$ vicinal to one another are taken together with the carbon atoms to which they are attached to form a carbocyclic, substituted carbocyclic, heterocyclic, or substituted heterocyclic ring, wherein the ring is a 6-10 membered ring;

or a salt or stereoisomer thereof.

In formula IVa, $R^1$ can be selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy.

In certain instances, in formula IVa, $R^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, alkyl, and substituted alkyl. In certain instances, $R^1$ is selected from aryl, substituted aryl, heteroaryl, substituted heteroaryl, heterocyclyl, substituted heterocyclyl, aralkyl, heteroaralkyl, alkyl, and substituted alkyl.

In certain cases, in formula IVa, $R^1$ is selected from aryl and substituted aryl. In certain cases, $R^1$ is selected from heteroaryl and substituted heteroaryl. In certain cases, $R^1$ is selected from heterocyclyl and substituted heterocyclyl. In certain cases, $R^1$ is selected from aralkyl, heteroaralkyl, alkyl, and substituted alkyl.

In formula IVa, $R^{2a}$ and $R^{2b}$ can be independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl; wherein either $R^{2a}$ or $R^{2b}$ is present. In certain instances, $R^{2a}$ is present. In certain instances, $R^{2b}$ is present. In certain instances, $R^{2a}$ and $R^{2b}$ are independently selected from hydrogen, alkyl, substituted alkyl, acyl, acylamino, acyloxy, aryl, substituted aryl, heteroaryl, heterocyclyl. In certain cases, $R^{2a}$ and $R^{2b}$ are independently selected from hydrogen, alkyl, substituted alkyl, aryl, and substituted aryl. In certain cases, $R^{2a}$ and $R^{2b}$ are independently selected from hydrogen, alkyl, and substituted alkyl. In certain cases, $R^{2a}$ and $R^{2b}$ are independently selected from hydrogen, aryl, and substituted aryl.

In certain cases, in formula IVa, $R^{2a}$ and $R^{2b}$ are independently selected from —SO-alkyl, —SO-aryl, —SO-heteroaryl, —SO$_2$-alkyl, —SO$_2$-aryl, and —SO$_2$-heteroaryl. In certain cases, $R^{2a}$ and $R^{2b}$ are independently selected from heteroaryl and heterocyclyl. In certain cases, $R^{2a}$ and $R^{2b}$ are independently selected from acyl, acylamino, acyloxy. In certain cases, $R^{2a}$ and $R^{2b}$ are independently selected from aralkyl and heteroaralkyl.

In formula IVa, $R^3$ can be selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl.

In certain instances, in formula IVa, $R^3$ is selected from hydrogen, alkyl, substituted alkyl, halo, nitro, cyano, hydroxy, alkoxy, acyl, amino, substituted amino, aryl, substituted aryl, heteroaryl, and substituted heteroaryl. In certain cases, $R^3$ is selected from hydrogen, alkyl, substituted alkyl, aryl, substituted aryl, heteroaryl, and substituted heteroaryl. In certain cases, $R^3$ is selected from hydrogen, alkyl, substituted alkyl, aryl, and substituted aryl. In certain cases, $R^3$ is hydrogen. In certain cases, $R^3$ is alkyl or substituted alkyl. In certain cases, $R^3$ is aryl or substituted aryl.

In certain cases, in formula IVa, $R^3$ is selected from alkenyl, substituted alkenyl, and carboxyl. In certain cases, $R^3$ is selected from acylamino, aminoacyl, acyloxy, and oxyacyl.

In formula IVa, $R^5$ can be selected from hydrogen, alkyl, and substituted alkyl. In certain instances, $R^5$ is hydrogen. In certain instances, $R^5$ is alkyl. In certain instances, $R^5$ is alkyl or substituted alkyl.

In formula IVa, $R^{6a}$ and $R^{6e}$ can be independently selected from hydrogen, $C_{2-10}$ alkyl, substituted alkyl, $C_{2-10}$ alkoxy, substituted alkoxy, acyl, acylamino, acyloxy, aminoacyl, oxyacyl, amino, substituted amino, aminocarbonyloxy, alkoxycarbonyloxy, azido, cyano, hydroxyl, hydroxylamino, alkoxyamino, nitro, carboxyl, thiol, alkylthio, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In certain instances, in formula IVa, $R^{6a}$ and $R^{6e}$ are independently selected from hydrogen, $C_{2-10}$ alkyl, substituted alkyl, $C_{2-10}$ alkoxy, and substituted alkoxy. In certain instances, $R^{6a}$ and $R^{6e}$ are hydrogen.

In certain instances, in formula IVa, $R^{6a}$ and $R^{6e}$ are independently selected from hydrogen, acyl, acylamino, acyloxy, aminoacyl, oxyacyl, amino, and substituted amino. In certain cases, $R^{6a}$ and $R^{6e}$ are independently selected from hydrogen, azido, cyano, hydroxyl, hydroxylamino, alkoxyamino, nitro, carboxyl, thiol, alkylthio, and substituted alkylthio. In certain cases, $R^{6a}$ and $R^{6e}$ are independently selected from hydrogen, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, and heterocyclyloxy. In certain instances, $R^{6a}$ and $R^{6e}$ are independently selected from hydrogen, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In formula IVa, $R^{6c}$ can be selected from hydrogen, alkyl, substituted alkyl, alkoxy, substituted alkoxy, acyl, acylamino, acyloxy, aminoacyl, amino, substituted amino, aminocarbonyloxy, alkoxycarbonyloxy, azido, cyano, halogen, hydroxyl, hydroxylamino, alkoxyamino, nitro, carboxyl, thiol, alkylthio, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In certain instances, in formula IVa, $R^{6c}$ is selected from hydrogen, alkyl, substituted alkyl, alkoxy, substituted alkoxy, acyl, acylamino, acyloxy, aminoacyl, amino, substituted amino, aminocarbonyloxy, alkoxycarbonyloxy, halogen, hydroxyl, thiol, alkylthio, aryl, substituted aryl, heteroaryl, substituted heteroaryl, heterocyclic, and substituted heterocyclic. In certain instances, $R^{6c}$ is selected from hydrogen, alkyl, substituted alkyl, alkoxy, substituted alkoxy, acyl, acylamino, acyloxy, aminoacyl, amino, substituted amino, aminocarbonyloxy, alkoxycarbonyloxy, halogen, hydroxyl, thiol, alkylthio, heterocyclic, and substituted heterocyclic. In certain instances, $R^{6c}$ is selected from hydrogen, alkyl, substituted alkyl, alkoxy, substituted alkoxy, acyl, acylamino, halogen, thiol, alkylthio, heterocyclic, and substituted heterocyclic. In certain cases, $R^{6c}$ is selected from hydrogen, alkoxy, and halogen.

In certain instances, in formula IVa, $R^{6c}$ is selected from hydrogen, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl. In certain instances, $R^{6c}$ is selected from acyl, acylamino, acyloxy, aminoacyl, amino, substituted amino, aminocarbonyloxy, alkoxycarbonyloxy, halogen, hydroxyl, thiol, alkylthio.

In formula IVa, $R^{6b}$ and $R^{6d}$ can be independently selected from hydrogen, alkyl, monosubstituted alkyl, disubstituted alkyl, alkoxy, substituted alkoxy, acyl, acylamino, acyloxy, aminoacyl, oxyacyl, amino, substituted amino, aminocarbonyloxy, alkoxycarbonyloxy, azido, halogen, hydroxyl, hydroxylamino, alkoxyamino, nitro, carboxyl, thiol, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In certain instances, in formula IVa, $R^{6b}$ and $R^{6d}$ are independently selected from hydrogen, alkyl, monosubstituted alkyl, disubstituted alkyl, alkoxy, substituted alkoxy, acyl, acylamino, acyloxy, aminoacyl, oxyacyl, halogen, hydroxyl, nitro, carboxyl, thiol, and substituted alkylthio. In certain instances, $R^{6b}$ and $R^{6d}$ are independently selected from hydrogen, alkoxy, substituted alkoxy, acyl, acylamino, acyloxy, aminoacyl, oxyacyl, halogen, hydroxyl, nitro, and carboxyl. In certain instances, $R^{6b}$ and $R^{6d}$ are independently selected from hydrogen, alkoxy, substituted alkoxy, acyl, acylamino, acyloxy, aminoacyl, oxyacyl, and halogen.

In certain instances, in formula IVa, $R^{6b}$ and $R^{6d}$ are independently selected from hydrogen, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In formula IVa, any two of $R^{6a}$, $R^{6b}$, $R^{6c}$, $R^{6d}$, and $R^{6e}$ vicinal to one another are taken together with the carbon atoms to which they are attached to can form a carbocyclic, substituted carbocyclic, heterocyclic, or substituted heterocyclic ring, wherein the ring is a 6-10 membered ring.

In certain instances, in formula IVa, any of two $R^{6a}$, $R^{6b}$, $R^{6c}$, $R^{6d}$, and $R^{6e}$ vicinal to one another are taken together with the carbon atoms to which they are attached to form a heterocyclic or substituted heterocyclic ring. In certain instances, any of two $R^{6a}$, $R^{6b}$, $R^{6c}$, $R^{6d}$, and $R^{6e}$ vicinal to one another are taken together with the carbon atoms to which they are attached to form a carbocyclic or substituted carbocyclic. In certain instances, any of two $R^{6a}$, $R^{6b}$, $R^{6c}$, $R^{6d}$, and $R^{6e}$ vicinal to one another are taken together with the carbon atoms to which they are attached to form a 6-8 membered ring. In certain instances, any of two $R^{6a}$, $R^{6b}$, $R^{6c}$, $R^{6d}$, and $R^{6e}$ vicinal to one another are taken together with the carbon atoms to which they are attached to form a 6-membered ring.

Formula Va

In one of its composition aspects, the present embodiments provide a compound of formula (Va):

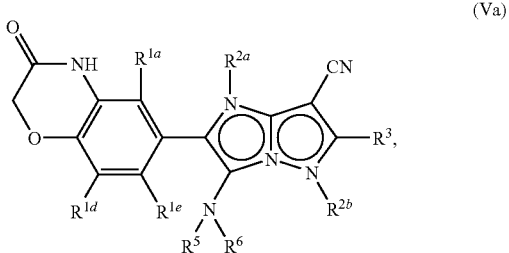

(Va)

wherein $R^{1a}$, $R^{1d}$, and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl, or wherein $R^{1d}$ and $R^{1e}$ are taken together with the carbon atoms to which they are attached to form a carbocyclic, substituted carbocyclic, heterocyclic, or substituted heterocyclic ring, wherein the ring is a 4-10 membered ring;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

or a salt or stereoisomer thereof.

In formula Va, $R^{1a}$, $R^{1d}$, and $R^{1e}$ can be independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In certain instances, in formula Va, $R^{1a}$, $R^{1d}$, and $R^{1e}$ are independently selected from hydrogen, alkyl, substituted alkyl, alkoxy, and substituted alkoxy. In certain instances, $R^{1a}$, $R^{1d}$, and $R^{1e}$ are hydrogen.

In certain instances, in formula Va, $R^{1a}$, $R^{1d}$, and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, and alkoxycarbonylamino. In certain instances, $R^{1a}$, $R^{1d}$, and $R^{1e}$ are independently selected from azido, cyano, halogen, hydroxyl, hydroxyamino, alkoxyamino, nitro, carboxyl, thiol, thioalkoxy, substituted thioalkoxy, arylthio, heteroarylthio, and heterocyclylthio. In certain instances, $R^{1a}$, $R^{1d}$, and $R^{1e}$ are independently selected from cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, and heterocyclooxy. In certain instances, $R^{1a}$, $R^{1d}$, and $R^{1e}$ are independently selected from —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In formula Va, $R^{1d}$ and $R^{1e}$ are taken together with the carbon atoms to which they are attached can to form carbocyclic, substituted carbocyclic, heterocyclic, or substituted heterocyclic ring, wherein the ring is a 4-10 membered ring. In certain instances, in formula Va, $R^{1d}$ and $R^{1e}$ are taken together with the carbon atoms to which they are attached to form a carbocyclic or substituted carbocyclic. In certain instances, $R^{1d}$ and $R^{1e}$ are taken together with the carbon atoms to which they are attached to form a heterocyclic or substituted heterocyclic ring. In certain instances, $R^{1d}$ and $R^{1e}$ are taken together with the carbon atoms to which they are attached to form a 4-8 membered ring. For example, in certain instances, $R^{1d}$ and $R^{1e}$ are taken together with the carbon atoms to which they are attached to form a 6-membered ring.

In formula Va, $R^{2a}$ and $R^{2b}$ can be independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl; wherein either $R^{2a}$ or $R^{2b}$ is present. In certain instances, $R^{2a}$ is present. In certain instances, $R^{2b}$ is present. In certain instances, $R^{2a}$ and $R^{2b}$ are independently selected from hydrogen, alkyl, substituted alkyl, acyl, acylamino, acyloxy, aryl, substituted aryl, heteroaryl, heterocyclyl. In certain cases, $R^{2a}$ and $R^{2b}$ are independently selected from hydrogen, alkyl, substituted alkyl, aryl, and substituted aryl. In certain cases, $R^{2a}$ and $R^{2b}$ are independently selected from hydrogen, alkyl, and substituted alkyl. In certain cases, $R^{2a}$ and $R^{2b}$ are independently selected from hydrogen, aryl, and substituted aryl.

In certain cases, in formula Va, $R^{2a}$ and $R^{2b}$ are independently selected from —SO-alkyl, —SO-aryl, —SO-heteroaryl, —SO$_2$-alkyl, —SO$_2$-aryl, and —SO$_2$-heteroaryl. In certain cases, $R^{2a}$ and $R^{2b}$ are independently selected from heteroaryl and heterocyclyl. In certain cases, $R^{2a}$ and $R^{2b}$ are independently selected from acyl, acylamino, acyloxy. In certain cases, $R^{2a}$ and $R^{2b}$ are independently selected from aralkyl and heteroaralkyl.

In formula Va, $R^3$ can be selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl.

In certain instances, in formula Va, $R^3$ is selected from hydrogen, alkyl, substituted alkyl, halo, nitro, cyano, hydroxy, alkoxy, acyl, amino, substituted amino, aryl, substituted aryl, heteroaryl, and substituted heteroaryl. In certain cases, $R^3$ is selected from hydrogen, alkyl, substituted alkyl, aryl, substituted aryl, heteroaryl, and substituted heteroaryl. In certain cases, $R^3$ is selected from hydrogen, alkyl, substituted alkyl, aryl, and substituted aryl. In certain cases, $R^3$ is hydrogen. In certain cases, $R^3$ is alkyl or substituted alkyl. In certain cases, $R^3$ is aryl or substituted aryl.

In certain cases, in formula Va, $R^3$ is selected from alkenyl, substituted alkenyl, and carboxyl. In certain cases, $R^3$ is selected from acylamino, aminoacyl, acyloxy, and oxyacyl.

In formula Va, $R^5$ can be selected from hydrogen, alkyl, and substituted alkyl. In certain instances, $R^5$ is hydrogen. In certain instances, $R^5$ is alkyl. In certain instances, $R^5$ is alkyl or substituted alkyl.

In formula Va, $R^6$ can be selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy.

In certain cases, in formula Va, $R^6$ is selected from aryl, substituted aryl, heteroaryl, substituted heteroaryl, heterocyclyl, substituted heterocyclyl, alkyl, substituted alkyl, aralkyl, and heteroaralkyl. In certain cases, $R^6$ is selected from aryl and substituted aryl. In certain cases, $R^6$ is selected from alkyl, substituted alkyl, aralkyl, and heteroaralkyl. In certain cases, $R^6$ is selected from heterocyclyl and substituted heterocyclyl. In certain cases, $R^6$ is selected from heteroaryl and substituted heteroaryl.

In certain instances, in formula Va, $R^6$ is selected from cycloalkyl, substituted cycloalkyl, cycloalkenyl, and substituted cycloalkenyl. In certain instances, $R^6$ is selected from heterocyclyl, and substituted heterocyclyl. In certain instances, $R^6$ is selected from aralkyl, heteroaralkyl, hydrogen, alkyl, substituted alkyl, alkenyl, substituted alkenyl, alkynyl, substituted alkynyl, acyl, acylamino, and acyloxy.

Formula VIa

In one of its composition aspects, the present embodiments provide a compound of formula (VIa):

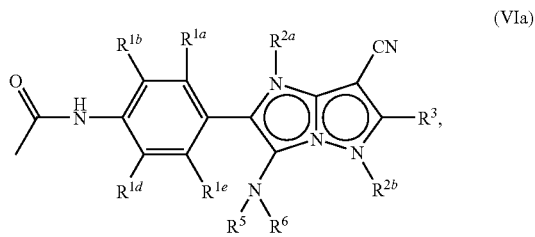

(VIa)

wherein $R^{1a}$, $R^{1b}$, $R^{1d}$, and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl; or wherein $R^{1a}$ and $R^{1b}$ are taken together with the carbon atoms to which they are attached to form a carbocyclic, substituted carbocyclic, heterocyclic, or substituted heterocyclic ring, wherein the ring is a 4-10 membered ring; or wherein $R^{1d}$ and $R^{1e}$ are taken together with the carbon atoms to which they are attached to form a carbocyclic, substituted carbocyclic, heterocyclic, or substituted heterocyclic ring, wherein the ring is a 4-10 membered ring;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

or a salt or stereoisomer thereof.

In formula VIa, $R^{1a}$, $R^{1b}$, $R^{1d}$, and $R^{1e}$ can be independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In certain instances, in formula VIa, $R^{1a}$, $R^{1b}$, $R^{1d}$, and $R^{1e}$ are independently selected from hydrogen, alkyl, substituted alkyl, alkoxy, and substituted alkoxy. In certain instances, $R^{1a}$, $R^{1b}$, $R^{1d}$, and $R^{1e}$ are hydrogen.

In certain instances, in formula VIa, $R^{1a}$, $R^{1b}$, $R^{1d}$, and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, and alkoxycarbonylamino. In certain instances, $R^{1a}$, $R^{1b}$, $R^{1d}$, and $R^{1e}$ are independently selected from azido, cyano, halogen, hydroxyl, hydroxyamino, alkoxyamino, nitro, carboxyl, thiol, thioalkoxy, substituted thioalkoxy, arylthio, heteroarylthio, and heterocyclylthio. In certain instances, $R^{1a}$, $R^{1b}$, $R^{1d}$, and $R^{1e}$ are independently selected from cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, and heterocyclooxy. In certain instances, $R^{1a}$, $R^{1b}$, $R^{1d}$, and $R^{1e}$ are independently selected from —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In formula VIa, $R^{1a}$ and $R^{1b}$ are taken together with the carbon atoms to which they are attached to form a carbocyclic, substituted carbocyclic, heterocyclic, or substituted heterocyclic ring, wherein the ring is a 4-10 membered ring. In certain instances, in formula VIa, $R^{1a}$ and $R^{1b}$ are taken together with the carbon atoms to which they are attached to form a carbocyclic or substituted carbocyclic. In certain instances, $R^{1a}$ and $R^{1b}$ are taken together with the carbon atoms to which they are attached to form a heterocyclic or substituted heterocyclic ring. In certain instances, $R^{1a}$ and $R^{1b}$ are taken together with the carbon atoms to which they are attached to form a 4-8 membered ring. For example, in certain instances, $R^{1a}$ and $R^{1b}$ are taken together with the carbon atoms to which they are attached to form a 6-membered ring.

In formula VIa, $R^{1d}$ and $R^{1e}$ are taken together with the carbon atoms to which they are attached to form a carbocyclic, substituted carbocyclic, heterocyclic, or substituted heterocyclic ring, wherein the ring is a 4-10 membered ring. In certain instances, in formula VIa, $R^{1d}$ and $R^{1e}$ are taken together with the carbon atoms to which they are attached to form a carbocyclic or substituted carbocyclic. In certain instances, $R^{1d}$ and $R^{1e}$ are taken together with the carbon atoms to which they are attached to form a heterocyclic or substituted heterocyclic ring. In certain instances, $R^{1d}$ and $R^{1e}$ are taken together with the carbon atoms to which they are attached to form a 4-8 membered ring. For example, in certain instances, $R^{1d}$ and $R^{1e}$ are taken together with the carbon atoms to which they are attached to form a 6-membered ring.

In formula VIa, $R^{2a}$ and $R^{2b}$ can be independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl; wherein either $R^{2a}$ or $R^{2b}$ is present. In certain instances, $R^{2a}$ is present. In certain instances, $R^{2b}$ is present. In certain instances, $R^{2a}$ and $R^{2b}$ are independently selected from hydrogen, alkyl, substituted alkyl, acyl, acylamino, acyloxy, aryl, substituted aryl, heteroaryl, heterocyclyl. In certain cases, $R^{2a}$ and $R^{2b}$ are independently selected from hydrogen, alkyl, substituted alkyl, aryl, and substituted aryl. In certain cases, $R^{2a}$ and $R^{2b}$ are independently selected from hydrogen, alkyl, and substituted alkyl. In certain cases, $R^{2a}$ and $R^{2b}$ are independently selected from hydrogen, aryl, and substituted aryl.

In certain cases, in formula VIa, $R^{2a}$ and $R^{2b}$ are independently selected from —SO-alkyl, —SO-aryl, —SO-heteroaryl, —SO$_2$-alkyl, —SO$_2$-aryl, and —SO$_2$-heteroaryl. In certain cases, $R^{2a}$ and $R^{2b}$ are independently selected from heteroaryl and heterocyclyl. In certain cases, $R^{2a}$ and $R^{2b}$ are independently selected from acyl, acylamino, acyloxy. In certain cases, $R^{2a}$ and $R^{2b}$ are independently selected from aralkyl and heteroaralkyl.

In formula VIa, $R^3$ can be selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl.

In certain instances, in formula VIa, $R^3$ is selected from hydrogen, alkyl, substituted alkyl, halo, nitro, cyano, hydroxy, alkoxy, acyl, amino, substituted amino, aryl, substituted aryl, heteroaryl, and substituted heteroaryl. In certain cases, $R^3$ is selected from hydrogen, alkyl, substituted alkyl, aryl, substituted aryl, heteroaryl, and substituted heteroaryl. In certain cases, $R^3$ is selected from hydrogen, alkyl, substituted alkyl, aryl, and substituted aryl. In certain cases, $R^3$ is hydrogen. In certain cases, $R^3$ is alkyl or substituted alkyl. In certain cases, $R^3$ is aryl or substituted aryl.

In certain cases, in formula VIa, $R^3$ is selected from alkenyl, substituted alkenyl, and carboxyl. In certain cases, $R^3$ is selected from acylamino, aminoacyl, acyloxy, and oxyacyl.

In formula VIa, $R^5$ can be selected from hydrogen, alkyl, and substituted alkyl. In certain instances, $R^5$ is hydrogen. In certain instances, $R^5$ is alkyl. In certain instances, $R^5$ is alkyl or substituted alkyl.

In formula VIa, $R^6$ can be selected from heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy.

In certain instances, in formula VIa, $R^6$ is selected from heteroaryl, substituted heteroaryl, heterocyclyl, and substituted heterocyclyl. In certain instances, $R^6$ is selected from cycloalkyl, substituted cycloalkyl, cycloalkenyl, and substituted cycloalkenyl. In certain instances, $R^6$ is selected from aralkyl, heteroaralkyl, hydrogen, alkyl, substituted alkyl, alkenyl, substituted alkenyl, alkynyl, substituted alkynyl, acyl, acylamino, and acyloxy.

Formula VIIa

In one of its composition aspects, the present embodiments provide a compound of formula (VIIa):

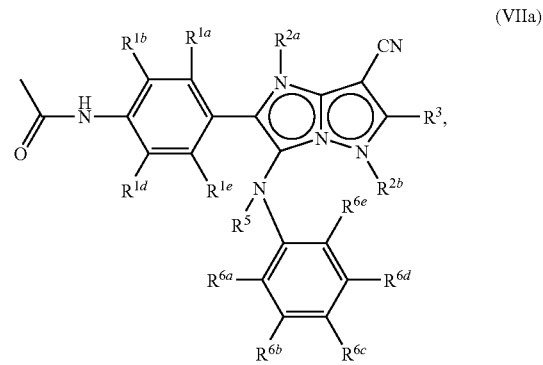

wherein $R^{1a}$, $R^{1b}$, $R^{1d}$, and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl; or wherein $R^{1a}$ and $R^{1b}$ are taken together with the carbon atoms to which they are attached to form a carbocyclic, substituted carbocyclic, heterocyclic, or substituted heterocyclic ring, wherein the ring is a 4-10 membered ring; or wherein $R^{1d}$ and $R^{1e}$ are taken together with the carbon atoms to which they are attached to form a carbocyclic, substituted carbocyclic, heterocyclic, or substituted heterocyclic ring, wherein the ring is a 4-10 membered ring;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^{6a}$ and $R^{6e}$ are independently selected from hydrogen, $C_{2-10}$ alkyl, substituted alkyl, $C_{2-10}$ alkoxy, substituted alkoxy, acyl, acylamino, acyloxy, aminoacyl, oxyacyl, amino, substituted amino, aminocarbonyloxy, alkoxycarbonylamino, azido, cyano, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl;

$R^{6c}$ is selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl;

$R^{6b}$ and $R^{6d}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl; or wherein any two of $R^{6a}$, $R^{6b}$, $R^{6c}$, $R^{6d}$, and $R^{6e}$ vicinal to one another are taken together with the carbon atoms to which they are attached to form a carbocyclic, substituted carbocyclic, heterocyclic, or substituted heterocyclic ring, wherein the ring is a 6-10 membered ring;

or a salt or stereoisomer thereof.

In formula VIIa, $R^{1a}$, $R^{1b}$, $R^{1d}$, and $R^{1e}$ can be independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In certain instances, in formula VIIa, $R^{1a}$, $R^{1b}$, $R^{1d}$, and $R^{1e}$ can be independently selected from hydrogen, alkyl, substituted alkyl, alkoxy, and substituted alkoxy. In certain instances, $R^{1a}$, $R^{1d}$, and $R^{1e}$ are hydrogen.

In certain instances, in formula VIIa, $R^{1a}$, $R^{1b}$, $R^{1d}$, and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, and alkoxycarbonylamino. In certain instances, in formula VIIa, $R^{1a}$, $R^{1b}$, $R^{1d}$, and $R^{1e}$ are independently selected from azido, cyano, halogen, hydroxyl, hydroxyamino, alkoxyamino, nitro, carboxyl, thiol, thioalkoxy, substituted thioalkoxy, arylthio, heteroarylthio, and heterocyclylthio. In certain instances, in formula VIIa, $R^{1a}$, $R^{1b}$, $R^{1d}$ and $R^{1e}$ are independently selected from cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, and heterocyclooxy. In certain instances, in formula VIIa, $R^{1a}$, $R^{1b}$, $R^{1d}$, and $R^{1e}$ are independently selected from —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In formula VIIa, $R^{1a}$ and $R^{1b}$ are taken together with the carbon atoms to which they are attached to form a carbocyclic, substituted carbocyclic, heterocyclic, or substituted heterocyclic ring, wherein the ring is a 4-10 membered ring. In certain instances, in formula VIIa, $R^{1a}$ and $R^{1b}$ are taken together with the carbon atoms to which they are attached to form a carbocyclic or substituted carbocyclic. In certain instances, $R^{1a}$ and $R^{1b}$ are taken together with the carbon atoms to which they are attached to form a heterocyclic or substituted heterocyclic ring. In certain instances, $R^{1a}$ and $R^{1b}$ are taken together with the carbon atoms to which they are attached to form a 4-8 membered ring. For example, in certain instances, $R^{1a}$ and $R^{1b}$ are taken together with the carbon atoms to which they are attached to form a 6-membered ring.

In formula VIIa, $R^{1d}$ and $R^{1e}$ are taken together with the carbon atoms to which they are attached to form a carbocyclic, substituted carbocyclic, heterocyclic, or substituted heterocyclic ring, wherein the ring is a 5-10 membered ring. In certain instances, in formula VIIa, $R^{1d}$ and $R^{1e}$ are taken together with the carbon atoms to which they are attached to form a carbocyclic or substituted carbocyclic. In certain instances, $R^{1d}$ and $R^{1e}$ are taken together with the carbon atoms to which they are attached to form a heterocyclic or substituted heterocyclic ring. In certain instances, $R^{1d}$ and $R^{1e}$ are taken together with the carbon atoms to which they are attached to form a 5-8 membered ring. For example, in certain instances, $R^{1d}$ and $R^{1e}$ are taken together with the carbon atoms to which they are attached to form a 6-membered ring.

In formula VIIa, $R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl; wherein either $R^{2a}$ or $R^{2b}$ is present. In certain instances, $R^{2a}$ is present. In certain instances, $R^{2b}$ is present. In certain instances, $R^{2a}$ and $R^{2b}$ are independently selected from hydrogen, alkyl, substituted alkyl, acyl, acylamino, acyloxy, aryl, substituted aryl, heteroaryl, heterocyclyl. In certain cases, $R^{2a}$ and $R^{2b}$ are independently selected from hydrogen, alkyl, substituted alkyl, aryl, and substituted aryl. In certain cases, $R^{2a}$ and $R^{2b}$ are independently selected from hydrogen, alkyl, and substituted alkyl. In certain cases, $R^{2a}$ and $R^{2b}$ are independently selected from hydrogen, aryl, and substituted aryl.

In certain cases, in formula VIIa, $R^{2a}$ and $R^{2b}$ are independently selected from —SO-alkyl, —SO-aryl, —SO-heteroaryl, —SO$_2$-alkyl, —SO$_2$-aryl, and —SO$_2$-heteroaryl. In certain cases, $R^{2a}$ and $R^{2b}$ are independently selected from heteroaryl and heterocyclyl. In certain cases, $R^{2a}$ and $R^{2b}$ are independently selected from acyl, acylamino, acyloxy. In certain cases, $R^{2a}$ and $R^{2b}$ are independently selected from aralkyl and heteroaralkyl.

In formula VIIa, $R^3$ can be selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl.

In certain instances, in formula VIIa, $R^3$ is selected from hydrogen, alkyl, substituted alkyl, halo, nitro, cyano, hydroxy, alkoxy, acyl, amino, substituted amino, aryl, substituted aryl, heteroaryl, and substituted heteroaryl. In certain cases, $R^3$ is selected from hydrogen, alkyl, substituted alkyl, aryl, substituted aryl, heteroaryl, and substituted heteroaryl. In certain cases, $R^3$ is selected from hydrogen, alkyl, substituted alkyl, aryl, and substituted aryl. In certain cases, $R^3$ is hydrogen. In certain cases, $R^3$ is alkyl or substituted alkyl. In certain cases, $R^3$ is aryl or substituted aryl.

In certain cases, in formula VIIa, $R^3$ is selected from alkenyl, substituted alkenyl, and carboxyl. In certain cases, $R^3$ is selected from acylamino, aminoacyl, acyloxy, and oxyacyl.

In formula VIIa, $R^5$ can be selected from hydrogen, alkyl, and substituted alkyl. In certain instances, $R^5$ is hydrogen. In certain instances, $R^5$ is alkyl. In certain instances, $R^5$ is alkyl or substituted alkyl.

In formula VIIa, $R^{6a}$ and $R^{6e}$ can be independently selected from hydrogen, $C_{2-10}$ alkyl, substituted alkyl, $C_{2-10}$ alkoxy, substituted alkoxy, acyl, acylamino, acyloxy, aminoacyl, oxyacyl, amino, substituted amino, aminocarbonyloxy, alkoxycarbonylamino, azido, cyano, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In certain instances, in formula VIIa, $R^{6a}$ and $R^{6e}$ are independently selected from hydrogen, $C_{2-10}$ alkyl, substituted alkyl, $C_{2-10}$ alkoxy, and substituted alkoxy. In certain instances, $R^{6a}$ and $R^{6e}$ are hydrogen.

In certain instances, in formula VIIa, $R^{6a}$ and $R^{6e}$ are independently selected from hydrogen, acyl, acylamino, acyloxy, aminoacyl, oxyacyl, amino, and substituted amino. In certain cases, $R^{6a}$ and $R^{6e}$ are independently selected from hydrogen, azido, cyano, hydroxyl, hydroxyamino, alkoxyamino, nitro, carboxyl, thiol, alkylthio, and substituted alkylthio. In certain cases, $R^{6a}$ and $R^{6e}$ are independently selected from hydrogen, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, and heterocyclyloxy. In certain instances, $R^{6a}$ and $R^{6e}$ are independently selected from hydrogen, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In formula VIIa, $R^{6c}$ can be selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In certain instances, in formula VIIa, $R^{6c}$ is selected from hydrogen, alkyl, monosubstituted alkyl, disubstituted alkyl, alkoxy, substituted alkoxy, acyl, acylamino, acyloxy, aminoacyl, oxyacyl, halogen, hydroxyl, nitro, carboxyl, thiol, and substituted alkylthio. In certain instances, $R^{6c}$ is selected from hydrogen, alkoxy, substituted alkoxy, acyl, acylamino, acyloxy, aminoacyl, oxyacyl, halogen, hydroxyl, nitro, and carboxyl. In certain instances, $R^{6c}$ is selected from hydrogen, alkoxy, substituted alkoxy, acyl, acylamino, acyloxy, aminoacyl, oxyacyl, and halogen. In certain cases, $R^{6c}$ is selected from hydrogen, alkoxy, and halogen.

In certain instances, in formula VIIa, $R^{6c}$ is selected from hydrogen, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In formula VIIa, $R^{6b}$ and $R^{6d}$ can be independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In certain instances, in formula VIIa, $R^{6b}$ and $R^{6d}$ can be independently selected from hydrogen, alkyl, substituted alkyl, alkoxy, substituted alkoxy, acyl, acylamino, acyloxy, aminoacyl, oxyacyl, halogen, hydroxyl, nitro, carboxyl, thiol, and substituted alkylthio. In certain instances, $R^{6b}$ and $R^{6d}$ can be independently selected from hydrogen, alkyl, substituted alkyl, alkoxy, substituted alkoxy, acyl, acylamino, acyloxy, aminoacyl, oxyacyl, halogen, hydroxyl, nitro, and carboxyl. In certain instances, $R^{6b}$ and $R^{6d}$ can be independently selected from hydrogen, alkyl, substituted alkyl, alkoxy, substituted alkoxy, acyl, acylamino, acyloxy, aminoacyl, oxyacyl, and halogen. In certain cases, $R^{6b}$ and $R^{6d}$ can be independently selected from hydrogen, alkyl, substituted alkyl, alkoxy, acylamino, and halogen.

In certain instances, in formula VIIa, $R^{6b}$ and $R^{6d}$ are independently selected from hydrogen, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In formula VIIa, any two of $R^{6a}$, $R^{6b}$, $R^{6c}$, $R^{6d}$, and $R^{6e}$ vicinal to one another are taken together with the carbon atoms to which they are attached to can form a carbocyclic, substituted carbocyclic, heterocyclic, or substituted heterocyclic ring, wherein the ring is a 6-10 membered ring.

In certain instances, in formula VIIa, any of two $R^{6a}$, $R^{6b}$, $R^{6c}$, $R^{6d}$, and $R^{6e}$ vicinal to one another are taken together with the carbon atoms to which they are attached to form a heterocyclic or substituted heterocyclic ring. In certain instances, any of two $R^{6a}$, $R^{6b}$, $R^{6c}$, $R^{6d}$, and $R^{6e}$ vicinal to one another are taken together with the carbon atoms to which they are attached to form a carbocyclic or substituted carbocyclic. In certain instances, any of two $R^{6a}$, $R^{6b}$, $R^{6c}$, $R^{6d}$, and $R^{6e}$ vicinal to one another are taken together with the carbon atoms to which they are attached to form a 6-8 membered ring. In certain instances, any of two $R^{6a}$, $R^{6b}$, $R^{6c}$, $R^{6d}$, and $R^{6e}$ vicinal to one another are taken together with the carbon atoms to which they are attached to form a 6-membered ring.

Formula VIIIa

In one of its composition aspects, the present embodiments provide a compound of formula (VIIIa):

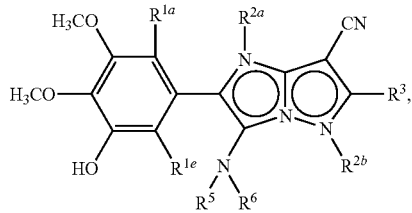

(VIIIa)

wherein $R^{1a}$ and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

or a salt or stereoisomer thereof.

In formula VIIIa, $R^{1a}$ and $R^{1e}$ can be independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In certain instances, in formula VIIIa, $R^{1a}$ and $R^{1e}$ are independently selected from hydrogen, alkyl, substituted alkyl, alkoxy, and substituted alkoxy. In certain instances, $R^{1a}$ and $R^{1e}$ are hydrogen.

In certain instances, in formula VIIIa, $R^{1a}$ and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, and alkoxycarbonylamino. In certain instances, in formula VIIIa, $R^{1a}$ and $R^{1e}$ are independently selected from azido, cyano, halogen, hydroxyl, hydroxyamino, alkoxyamino, nitro, carboxyl, thiol, thioalkoxy, substituted thioalkoxy, arylthio, heteroarylthio, and heterocyclylthio. In certain instances, in formula VIIIa, $R^{1a}$ and $R^{1e}$ are independently selected from cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, and heterocyclooxy. In certain instances, in formula VIIIa, $R^{1a}$ and $R^{1e}$ are independently selected from —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In formula VIIIa, $R^{2a}$ and $R^{2b}$ can be independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl; wherein either $R^{2a}$ or $R^{2b}$ is present. In certain instances, $R^{2a}$ is present. In certain instances, $R^{2b}$ is present. In certain instances, $R^{2a}$ and $R^{2b}$ are independently selected from hydrogen, alkyl, substituted alkyl, acyl, acylamino, acyloxy, aryl, substituted aryl, heteroaryl, heterocyclyl. In certain cases, $R^{2a}$ and $R^{2b}$ are independently selected from hydrogen, alkyl, substituted alkyl, aryl, and substituted aryl. In certain cases, $R^{2a}$ and $R^{2b}$ are independently selected from hydrogen, alkyl, and substituted alkyl. In certain cases, $R^{2a}$ and $R^{2b}$ are independently selected from hydrogen, aryl, and substituted aryl.

In certain cases, in formula VIIIa, $R^{2a}$ and $R^{2b}$ are independently selected from —SO-alkyl, —SO-aryl, —SO-heteroaryl, —SO$_2$-alkyl, —SO$_2$-aryl, and —SO$_2$-heteroaryl. In certain cases, $R^{2a}$ and $R^{2b}$ are independently selected from heteroaryl and heterocyclyl. In certain cases, $R^{2a}$ and $R^{2b}$ are independently selected from acyl, acylamino, acyloxy. In certain cases, $R^{2a}$ and $R^{2b}$ are independently selected from aralkyl and heteroaralkyl.

In formula VIIIa, $R^3$ can be selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl.

In certain instances, in formula, VIIIa, $R^3$ is selected from hydrogen, alkyl, substituted alkyl, halo, nitro, cyano, hydroxy, alkoxy, acyl, amino, substituted amino, aryl, substituted aryl, heteroaryl, and substituted heteroaryl. In certain cases, $R^3$ is selected from hydrogen, alkyl, substituted alkyl, aryl, substituted aryl, heteroaryl, and substituted heteroaryl. In certain cases, $R^3$ is selected from hydrogen, alkyl, substituted alkyl, aryl, and substituted aryl. In certain cases, $R^3$ is hydrogen. In certain cases, $R^3$ is alkyl or substituted alkyl. In certain cases, $R^3$ is aryl or substituted aryl.

In certain cases, in formula VIIIa, $R^3$ is selected from alkenyl, substituted alkenyl, and carboxyl. In certain cases, $R^3$ is selected from acylamino, aminoacyl, acyloxy, and oxyacyl.

In formula VIIIa, $R^5$ can be selected from hydrogen, alkyl, and substituted alkyl. In certain instances, $R^5$ is hydrogen. In certain instances, $R^5$ is alkyl. In certain instances, $R^5$ is alkyl or substituted alkyl.

In formula VIIIa, $R^6$ can be selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy.

In certain instances, in formula VIIIa, $R^6$ is selected from aryl and substituted aryl.

In certain instances, in formula VIIIa, $R^6$ is selected from heteroaryl, substituted heteroaryl, heterocyclyl, and substituted heterocyclyl. In certain instances, $R^6$ is selected from cycloalkyl, substituted cycloalkyl, cycloalkenyl, and substituted cycloalkenyl. In certain instances, $R^6$ is selected from aralkyl, heteroaralkyl, hydrogen, alkyl, substituted alkyl, alkenyl, substituted alkenyl, alkynyl, substituted alkynyl, acyl, acylamino, and acyloxy.

Formula IXa

In one of its composition aspects, the present embodiments provide a compound of formula (IXa):

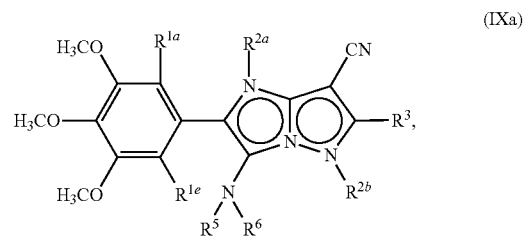

(IXa)

wherein $R^{1a}$ and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

or a salt or stereoisomer thereof.

In formula IXa, $R^{1a}$ and $R^{1e}$ can be independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In certain instances, in formula IXa, $R^{1a}$ and $R^{1e}$ are independently selected from hydrogen, alkyl, substituted alkyl, alkoxy, and substituted alkoxy. In certain instances, $R^{1a}$ and $R^{1e}$ are hydrogen.

In certain instances, in formula IXa, $R^{1a}$ and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, and alkoxycarbonylamino. In certain instances, $R^{1a}$ and $R^{1e}$ are independently selected from azido, cyano, halogen, hydroxyl, hydroxyamino, alkoxyamino, nitro, carboxyl, thiol, thioalkoxy, substituted thioalkoxy, arylthio, heteroarylthio, and heterocyclylthio. In certain instances, $R^{1a}$ and $R^{1e}$ are independently selected from cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, and heterocyclooxy. In certain instances, $R^{1a}$ and $R^{1e}$ are independently selected from —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In formula IXa, $R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl; wherein either $R^{2a}$ or $R^{2b}$ is present. In certain instances, $R^{2a}$ is present. In certain instances, $R^{2b}$ is present. In certain instances, $R^{2a}$ and $R^{2b}$ are independently selected from hydrogen, alkyl, substituted alkyl, acyl, acylamino, acyloxy, aryl, substituted aryl, heteroaryl, heterocyclyl. In certain cases, $R^{2a}$ and $R^{2b}$ are independently selected from hydrogen, alkyl, substituted alkyl, aryl, and substituted aryl. In certain cases, $R^{2a}$ and $R^{2b}$ are independently selected from hydrogen, alkyl, and substituted alkyl. In certain cases, $R^{2a}$ and $R^{2b}$ are independently selected from hydrogen, aryl, and substituted aryl.

In certain cases, in formula IXa, $R^{2a}$ and $R^{2b}$ are independently selected from —SO-alkyl, —SO-aryl, —SO-heteroaryl, —SO$_2$-alkyl, —SO$_2$-aryl, and —SO$_2$-heteroaryl. In certain cases, $R^{2a}$ and $R^{2b}$ are independently selected from heteroaryl and heterocyclyl. In certain cases, $R^{2a}$ and $R^{2b}$ are independently selected from acyl, acylamino, acyloxy. In certain cases, $R^{2a}$ and $R^{2b}$ are independently selected from aralkyl and heteroaralkyl.

In formula IXa, $R^3$ can be selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl.

In certain instances, in formula IXa, $R^3$ is selected from hydrogen, alkyl, substituted alkyl, halo, nitro, cyano, hydroxy, alkoxy, acyl, amino, substituted amino, aryl, substituted aryl, heteroaryl, and substituted heteroaryl. In certain cases, $R^3$ is selected from hydrogen, alkyl, substituted alkyl, aryl, substituted aryl, heteroaryl, and substituted heteroaryl. In certain cases, $R^3$ is selected from hydrogen, alkyl, substituted alkyl, aryl, and substituted aryl. In certain cases, $R^3$ is hydrogen. In certain cases, $R^3$ is alkyl or substituted alkyl. In certain cases, $R^3$ is aryl or substituted aryl.

In certain cases, in formula IXa, $R^3$ is selected from alkenyl, substituted alkenyl, and carboxyl. In certain cases, $R^3$ is selected from acylamino, aminoacyl, acyloxy, and oxyacyl.

In formula IXa, $R^5$ can be selected from hydrogen, alkyl, and substituted alkyl. In certain instances, $R^5$ is hydrogen. In certain instances, $R^5$ is alkyl. In certain instances, $R^5$ is alkyl or substituted alkyl.

In formula IXa, $R^6$ can be selected from heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy.

In certain instances, in formula IXa, $R^6$ is selected from aralkyl, heteroaralkyl, hydrogen, alkyl, substituted alkyl, alkenyl, substituted alkenyl, alkynyl, substituted alkynyl, acyl, acylamino, and acyloxy. In certain instances, $R^6$ is selected from hydrogen, alkyl, substituted alkyl, acyl, acylamino, and acyloxy. In certain instances, $R^6$ is selected from hydrogen, alkyl, substituted alkyl, and acyl. In certain instances, $R^6$ is acyl. In certain instances, $R^6$ is alkyl or substituted alkyl. In certain instances, $R^6$ is hydrogen.

In certain instances, in formula IXa, $R^6$ can be selected from heteroaryl, substituted heteroaryl, heterocyclyl, and substituted heterocyclyl. In certain instances, $R^6$ can be selected from cycloalkyl, substituted cycloalkyl, cycloalkenyl, and substituted cycloalkenyl. In certain instances, $R^6$ can be selected from aralkyl, heteroaralkyl, hydrogen, alkyl, substituted alkyl, alkenyl, substituted alkenyl, alkynyl, substituted alkynyl, acyl, acylamino, and acyloxy.

Formula Xa

In one of its composition aspects, the present embodiments provide a compound of formula (Xa):

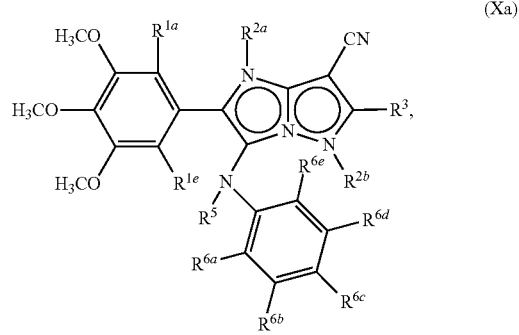

(Xa)

wherein $R^{1a}$ and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either R$^{2a}$ or R$^{2b}$ is present;

R$^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

R$^5$ is selected from hydrogen, alkyl, and substituted alkyl; and

R$^{6a}$ and R$^{6e}$ are independently selected from hydrogen, C$_{2-10}$ alkyl, substituted alkyl, C$_{2-10}$ alkoxy, substituted alkoxy, acyl, acylamino, acyloxy, aminoacyl, oxyacyl, amino, substituted amino, aminocarbonyloxy, alkoxycarbonylamino, azido, cyano, hydroxyl, hydroxyamino, alkoxyamino, nitro, carboxyl, thiol, alkylthio, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl;

R$^{6c}$ is selected from hydrogen, alkyl, substituted alkyl, alkoxy, substituted alkoxy, acyl, acylamino, acyloxy, aminoacyl, amino, substituted amino, aminocarbonyloxy, alkoxycarbonylamino, azido, cyano, halogen, hydroxyl, hydroxyamino, alkoxyamino, nitro, carboxyl, thiol, alkylthio, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl;

R$^{6b}$ and R$^{6d}$ are independently selected from hydrogen, alkyl, substituted C$_{2-10}$ alkyl, alkoxy, substituted alkoxy, acyl, acylamino, acyloxy, aminoacyl, oxyacyl, amino, substituted amino, aminocarbonyloxy, alkoxycarbonylamino, azido, halogen, hydroxyl, hydroxyamino, alkoxyamino, nitro, carboxyl, thiol, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl; or wherein any two of R$^{6a}$, R$^{6b}$, R$^{6c}$, R$^{6d}$, and R$^{6e}$ vicinal to one another are taken together with the carbon atoms to which they are attached to form a carbocyclic, substituted carbocyclic, heterocyclic, or substituted heterocyclic ring, wherein the ring is a 6-10 membered ring;

or a salt or stereoisomer thereof.

In formula Xa, R$^{1a}$ and R$^{1e}$ can be independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In certain instances, in formula Xa, R$^{1a}$ and R$^{1e}$ can be independently selected from hydrogen, alkyl, substituted alkyl, alkoxy, and substituted alkoxy. In certain instances, R$^{1a}$ and R$^{1e}$ are hydrogen.

In certain instances, in formula Xa, R$^{1a}$ and R$^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, and alkoxycarbonylamino. In certain instances, R$^{1a}$ and R$^{1e}$ are independently selected from azido, cyano, halogen, hydroxyl, hydroxyamino, alkoxyamino, nitro, carboxyl, thiol, thioalkoxy, substituted thioalkoxy, arylthio, heteroarylthio, and heterocyclylthio. In certain instances, R$^{1a}$ and R$^{1e}$ are independently selected from cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, and heterocyclooxy. In certain instances, R$^{1a}$ and R$^{1e}$ are independently selected from —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In formula Xa, R$^{2a}$ and R$^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl; wherein either R$^{2a}$ or R$^{2b}$ is present. In certain instances, R$^{2a}$ is present. In certain instances, R$^{2b}$ is present. In certain instances, R$^{2a}$ and R$^{2b}$ are independently selected from hydrogen, alkyl, substituted alkyl, acyl, acylamino, acyloxy, aryl, substituted aryl, heteroaryl, heterocyclyl. In certain cases, R$^{2a}$ and R$^{2b}$ are independently selected from hydrogen, alkyl, substituted alkyl, aryl, and substituted aryl. In certain cases, R$^{2a}$ and R$^{2b}$ are independently selected from hydrogen, alkyl, and substituted alkyl. In certain cases, R$^{2a}$ and R$^{2b}$ are independently selected from hydrogen, aryl, and substituted aryl.

In certain cases, in formula Xa, R$^{2a}$ and R$^{2b}$ are independently selected from —SO-alkyl, —SO-aryl, —SO-heteroaryl, —SO$_2$-alkyl, —SO$_2$-aryl, and —SO$_2$-heteroaryl. In certain cases, R$^{2a}$ and R$^{2b}$ are independently selected from heteroaryl and heterocyclyl. In certain cases, R$^{2a}$ and R$^{2b}$ are independently selected from acyl, acylamino, acyloxy. In certain cases, R$^{2a}$ and R$^{2b}$ are independently selected from aralkyl and heteroaralkyl.

In formula Xa, R$^3$ can be selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl.

In certain instances, in formula Xa, R$^3$ is selected from hydrogen, alkyl, substituted alkyl, halo, nitro, cyano, hydroxy, alkoxy, acyl, amino, substituted amino, aryl, substituted aryl, heteroaryl, and substituted heteroaryl. In certain cases, R$^3$ is selected from hydrogen, alkyl, substituted alkyl, aryl, substituted aryl, heteroaryl, and substituted heteroaryl. In certain cases, R$^3$ is selected from hydrogen, alkyl, substituted alkyl, aryl, and substituted aryl. In certain cases, R$^3$ is hydrogen. In certain cases, R$^3$ is alkyl or substituted alkyl. In certain cases, R$^3$ is aryl or substituted aryl.

In certain cases, in formula Xa, R$^3$ is selected from alkenyl, substituted alkenyl, and carboxyl. In certain cases, R$^3$ is selected from acylamino, aminoacyl, acyloxy, and oxyacyl.

In formula Xa, R$^5$ can be selected from hydrogen, alkyl, and substituted alkyl. In certain instances, R$^5$ is hydrogen. In certain instances, R$^5$ is alkyl. In certain instances, R$^5$ is alkyl or substituted alkyl.

In formula Xa, $R^{6a}$ and $R^{6e}$ can be independently selected from hydrogen, $C_{2-10}$ alkyl, substituted alkyl, $C_{2-10}$ alkoxy, substituted alkoxy, acyl, acylamino, acyloxy, aminoacyl, oxyacyl, amino, substituted amino, aminocarbonyloxy, alkoxycarbonylamino, azido, cyano, hydroxyl, hydroxyamino, alkoxyamino, nitro, carboxyl, thiol, alkylthio, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In certain instances, in formula Xa, $R^{6a}$ and $R^{6e}$ are independently selected from hydrogen, $C_{2-10}$ alkyl, substituted alkyl, $C_{2-10}$ alkoxy, and substituted alkoxy. In certain instances, $R^{6a}$ and $R^{6e}$ are hydrogen.

In certain instances, in formula Xa, $R^{6a}$ and $R^{6e}$ are independently selected from hydrogen, acyl, acylamino, acyloxy, aminoacyl, oxyacyl, amino, and substituted amino. In certain cases, $R^{6a}$ and $R^{6e}$ are independently selected from hydrogen, azido, cyano, hydroxyl, hydroxylamino, alkoxyamino, nitro, carboxyl, thiol, alkylthio, and substituted alkylthio. In certain cases, $R^{6a}$ and $R^{6e}$ are independently selected from hydrogen, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, and heterocyclyloxy. In certain instances, $R^{6a}$ and $R^{6e}$ are independently selected from hydrogen, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In formula Xa, $R^{6c}$ can be selected from hydrogen, alkyl, substituted alkyl, alkoxy, substituted alkoxy, acyl, acylamino, acyloxy, aminoacyl, amino, substituted amino, aminocarbonyloxy, alkoxycarbonylamino, azido, cyano, halogen, hydroxyl, hydroxyamino, alkoxyamino, nitro, carboxyl, thiol, alkylthio, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In certain instances, in formula Xa, $R^{6c}$ is selected from hydrogen, alkyl, substituted alkyl, alkoxy, substituted alkoxy, acyl, acylamino, acyloxy, aminoacyl, amino, substituted amino, halogen, hydroxyl, thiol, alkylthio, substituted alkylthio, aryl, substituted aryl, heteroaryl, substituted heteroaryl, heterocyclic, substituted heterocyclic. In certain instances, in formula Xa, $R^{6c}$ is selected from hydrogen, alkyl, substituted alkyl, alkoxy, substituted alkoxy, acyl, halogen, thiol, alkylthio, heterocyclic, substituted heterocyclic.

In certain instances, in formula Xa, $R^{6c}$ is selected from hydrogen, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In formula Xa, $R^{6b}$ and $R^{6d}$ can be independently selected from hydrogen, alkyl, substituted $C_{2-10}$ alkyl, alkoxy, substituted alkoxy, acyl, acylamino, acyloxy, aminoacyl, oxyacyl, amino, substituted amino, aminocarbonyloxy, alkoxycarbonylamino, azido, halogen, hydroxyl, hydroxyamino, alkoxyamino, nitro, carboxyl, thiol, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In certain instances, in formula Xa, $R^{6b}$ and $R^{6d}$ are independently selected from hydrogen, alkyl, substituted $C_{2-10}$ alkyl, alkoxy, substituted alkoxy, acyl, acylamino, acyloxy, aminoacyl, oxyacyl, halogen, hydroxyl, nitro, carboxyl, thiol, and substituted alkylthio. In certain instances, $R^{6b}$ and $R^{6d}$ are independently selected from hydrogen, alkyl, substituted $C_{2-10}$ alkyl, alkoxy, substituted alkoxy, acyl, acylamino, and halogen.

In certain instances, in formula Xa, $R^{6b}$ and $R^{6d}$ are independently selected from hydrogen, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl.

In formula Xa, any two of $R^{6a}$, $R^{6b}$, $R^{6c}$, $R^{6d}$, and $R^{6e}$ vicinal to one another are taken together with the carbon atoms to which they are attached to form a carbocyclic, substituted carbocyclic, heterocyclic, or substituted heterocyclic ring, wherein the ring is a 6-10 membered ring.

In certain instances, in formula Xa, any of two $R^{6a}$, $R^{6b}$, $R^{6c}$, $R^{6d}$, and $R^{6e}$ vicinal to one another are taken together with the carbon atoms to which they are attached to form a heterocyclic or substituted heterocyclic ring. In certain instances, any of two $R^{6a}$, $R^{6b}$, $R^{6c}$, $R^{6d}$, and $R^{6e}$ vicinal to one another are taken together with the carbon atoms to which they are attached to form a carbocyclic or substituted carbocyclic. In certain instances, any of two $R^{6a}$, $R^{6b}$, $R^{6c}$, $R^{6d}$, and $R^{6e}$ vicinal to one another are taken together with the carbon atoms to which they are attached to form a 6-8 membered ring. In certain instances, any of two $R^{6a}$, $R^{6b}$, $R^{6c}$, $R^{6d}$, and $R^{6e}$ vicinal to one another are taken together with the carbon atoms to which they are attached to form a 6-membered ring.

Pharmaceutical compositions and methods of the present disclosure also contemplate compounds of formulae Ib-VIIb, shown below.

Formula Ib

The present embodiments provide a compound of formula (Ib):

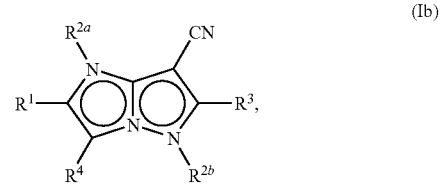

wherein $R^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^4$ is selected from hydrogen, alkyl, substituted alkyl, amino, or —NR$^5$R$^6$;

$R^5$ is selected from hydrogen, alkyl, and substituted alkyl; and $R^6$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy; or a salt or stereoisomer thereof.

Formula IIb

The present embodiments provide a compound of formula (IIb):

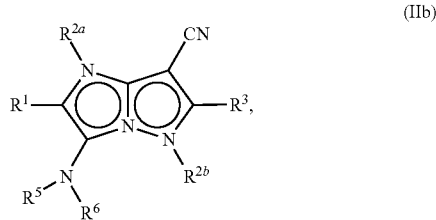

(IIb)

wherein $R^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

or a salt or stereoisomer thereof.

In formulae Ib and IIb, $R^1$ can be selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy.

In certain instances, in formulae Ib and IIb, $R^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, alkyl, and substituted alkyl. In certain instances, $R^1$ is selected from aryl, substituted aryl, heteroaryl, substituted heteroaryl, heterocyclyl, substituted heterocyclyl, aralkyl, heteroaralkyl, alkyl, and substituted alkyl.

In certain cases, in formulae Ib and IIb, $R^1$ is selected from aryl and substituted aryl. In certain cases, $R^1$ is selected from heteroaryl and substituted heteroaryl. In certain cases, $R^1$ is selected from heterocyclyl and substituted heterocyclyl. In certain cases, $R^1$ is selected from aralkyl, heteroaralkyl, alkyl, and substituted alkyl.

In formulae Ib and IIb, $R^{2a}$ and $R^{2b}$ can be independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl; wherein either $R^{2a}$ or $R^{2b}$ is present. In certain instances, $R^{2a}$ is present. In certain instances, $R^{2b}$ is present. In certain instances, $R^{2a}$ and $R^{2b}$ are independently selected from hydrogen, alkyl, substituted alkyl, acyl, acylamino, acyloxy, aryl, substituted aryl, heteroaryl, heterocyclyl. In certain cases, $R^{2a}$ and $R^{2b}$ are independently selected from hydrogen, alkyl, substituted alkyl, aryl, and substituted aryl. In certain cases, $R^{2a}$ and $R^{2b}$ are independently selected from hydrogen, alkyl, and substituted alkyl. In certain cases, $R^{2a}$ and $R^{2b}$ are independently selected from hydrogen, aryl, and substituted aryl.

In certain cases, in formulae Ib and IIb, $R^{2a}$ and $R^{2b}$ are independently selected from —SO-alkyl, —SO-aryl, —SO-heteroaryl, —SO$_2$-alkyl, —SO$_2$-aryl, and —SO$_2$-heteroaryl. In certain cases, $R^{2a}$ and $R^{2b}$ are independently selected from heteroaryl and heterocyclyl. In certain cases, $R^{2a}$ and $R^{2b}$ are independently selected from acyl, acylamino, acyloxy. In certain cases, $R^{2a}$ and $R^{2b}$ are independently selected from aralkyl and heteroaralkyl.

In formulae Ib and IIb, $R^3$ can be selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl.

In certain instances, in formulae Ib and IIb, $R^3$ is selected from hydrogen, alkyl, substituted alkyl, halo, nitro, cyano, hydroxy, alkoxy, acyl, amino, substituted amino, aryl, substituted aryl, heteroaryl, and substituted heteroaryl. In certain cases, $R^3$ is selected from hydrogen, alkyl, substituted alkyl, aryl, substituted aryl, heteroaryl, and substituted heteroaryl. In certain cases, $R^3$ is selected from hydrogen, alkyl, substituted alkyl, aryl, and substituted aryl. In certain cases, $R^3$ is hydrogen. In certain cases, $R^3$ is alkyl or substituted alkyl. In certain cases, $R^3$ is aryl or substituted aryl.

In certain cases, in formulae Ib and IIb, $R^3$ is selected from alkenyl, substituted alkenyl, and carboxyl. In certain cases, $R^3$ is selected from acylamino, aminoacyl, acyloxy, and oxyacyl.

In formulae Ib and IIb, $R^5$ can be selected from hydrogen, alkyl, and substituted alkyl. In certain instances, $R^5$ is hydrogen. In certain instances, $R^5$ is alkyl. In certain instances, $R^5$ is alkyl or substituted alkyl.

In formulae Ib and IIb, $R^6$ can be selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy.

In certain instances, in formulae Ib and IIb, $R^6$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, and acyl. In certain instances, $R^6$ is selected from aryl, substituted aryl, heteroaryl, substituted heteroaryl, aralkyl, heteroaralkyl, hydrogen, alkyl, substituted alkyl, and acyl. In certain cases, $R^6$ is selected from aryl and substituted aryl. In certain cases, $R^6$ is selected from heteroaryl and substituted heteroaryl. In certain case, $R^6$ is selected from aralkyl, heteroaralkyl. In certain cases, $R^6$ is selected from hydrogen, alkyl, substituted alkyl, and acyl.

In formula Ib, $R^4$ can be selected from hydrogen, alkyl, substituted alkyl, amino, or —$NR^5R^6$. In certain instances, $R^4$ is —$NR^5R^6$. In certain instances, $R^4$ is hydrogen. In certain instances, $R^4$ is amino. In certain instances, $R^4$ can be selected from alkyl and substituted alkyl.

A group of compounds of interest are compounds of formulae Ib and IIb, wherein $R^3$ is hydrogen and $R^{2a}$ or $R^{2b}$ is hydrogen.

Another group of compounds of interest are compounds of formulae Ib and IIb, wherein $R^5$ is hydrogen and $R^6$ is selected from aryl, substituted aryl, heteroaryl, substituted heteroaryl, heterocyclyl, substituted heterocyclyl, aralkyl, heteroaralkyl, alkyl, substituted alkyl, and acyl.

Another group of compounds of interest are compounds of formulae Ib and IIb, wherein $R^5$ is hydrogen and $R^6$ is selected from aryl, substituted aryl, and acyl.

Another group of compounds of interest are compounds of formulae Ib and IIb, wherein $R^1$ and $R^6$ are independently selected from aryl, substituted aryl, heteroaryl, substituted heteroaryl, heterocyclyl, substituted heterocyclyl, aralkyl, heteroaralkyl, alkyl, substituted alkyl, and acyl.

Another group of compounds of interest are compounds of formulae Ib and IIb, wherein $R^1$ and $R^6$ are aryl or substituted aryl.

Another group of compounds of interest are compounds of formulae Ib and IIb, wherein $R^1$ is aryl or substituted aryl and $R^6$ is acyl.

Formula IIIb

Certain compounds of interest have formula Ib wherein $R^4$ is —$NR^5R^6$ and $R^1$ is a substituted phenyl group. Particular examples of such compounds have formula IIIb:

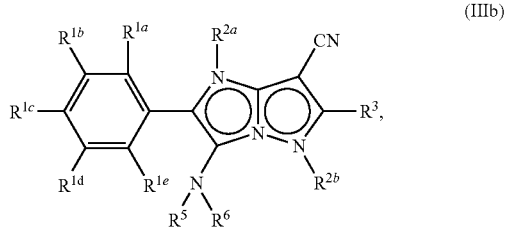

(IIIb)

wherein $R^{1a}, R^{1b}, R^{1c}, R^{1d},$ and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —$SO_2$-alkyl, —$SO_2$-aryl, —$SO_2$-heteroaryl, —NH—SO-alkyl, —NH—SO-aryl, —NH—SO-heteroaryl, —NH—$SO_2$-alkyl, —NH—$SO_2$-aryl, and —NH—$SO_2$-heteroaryl; or wherein any two of $R^{1a}, R^{1b}, R^{1c}, R^{1d},$ and $R^{1e}$ vicinal to one another are taken together with the carbon atoms to which they are attached to form a carbocyclic, substituted carbocyclic, heterocyclic, or substituted heterocyclic ring, wherein the ring is a 4-10 membered ring;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —$SO_2$-alkyl, —$SO_2$-aryl, —$SO_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

or a salt or stereoisomer thereof.

In certain instances of formula IIIb, $R^{1a}, R^{1b}, R^{1c}, R^{1d},$ and $R^{1e}$ are independently selected from hydrogen, alkyl, substituted alkyl, alkoxy, substituted alkoxy, acyl, acylamino, acyloxy, amino, aminoacyl, aminocarbonyloxy, alkoxycarbonylamino, halogen, hydroxyl, carboxyl, arylthio, heteroarylthio, heterocyclylthio, thiol, alkylthio, substituted alkylthio, aryl, aryloxy, heteroaryl, heteroaryloxy, heterocyclic, heterocyclooxy, nitro, —SO-alkyl, —SO-aryl, —SO-heteroaryl, —$SO_2$-alkyl, —$SO_2$-aryl, —$SO_2$-heteroaryl, —NH—SO-alkyl, —NH—SO-aryl, —NH—SO-heteroaryl, —NH—$SO_2$-alkyl, —NH—$SO_2$-aryl, —NH—$SO_2$-heteroaryl, amino, and substituted amino.

In certain instances of formula IIIb, $R^{1a}, R^{1b}, R^{1c}, R^{1d},$ and $R^{1e}$ are independently selected from hydrogen, alkyl, substituted alkyl, alkoxy, substituted alkoxy, acyl, acylamino, acyloxy, amino, aminoacyl, halogen, hydroxyl, carboxyl, alkylthio, substituted alkylthio, aryloxy, heteroaryloxy, heterocyclic, heterocyclooxy, —SO-alkyl, —SO-aryl, —SO-heteroaryl, —$SO_2$-alkyl, —$SO_2$-aryl, —$SO_2$-heteroaryl, —NH—SO-alkyl, —NH—SO-aryl, —NH—SO-heteroaryl, —NH—$SO_2$-alkyl, —NH—$SO_2$-aryl, —NH—$SO_2$-heteroaryl, amino, and substituted amino.

In certain instances of formula IIIb, any two of $R^{1a}, R^{1b}, R^{1c}, R^{1d},$ and $R^{1e}$ vicinal to one another are taken together with the carbon atoms to which they are attached to form a carbocyclic, substituted carbocyclic, heterocyclic or substituted heterocyclic 5-6-membered ring.

Formula IVb

Certain compounds of interest have formula Ib wherein $R^4$ is —$NR^5R^6$ and $R^6$ is a substituted phenyl group. Particular examples of such compounds have formula IVb:

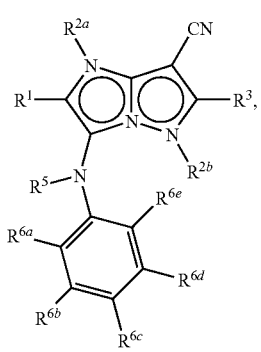

(IVb)

wherein

R$^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

R$^{2a}$ and R$^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either R$^{2a}$ or R$^{2b}$ is present;

R$^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

R$^5$ is selected from hydrogen, alkyl, and substituted alkyl; and

R$^{6a}$, R$^{6b}$, R$^{6c}$, R$^{6d}$, and R$^{6e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl; or wherein any two of R$^{6a}$, R$^{6b}$, R$^{6c}$, R$^{6d}$, and R$^{6e}$ vicinal to one another are taken together with the carbon atoms to which they are attached to form a carbocyclic, substituted carbocyclic, heterocyclic, or substituted heterocyclic ring, wherein the ring is a 6-10 membered ring;

or a salt or stereoisomer thereof.

In certain instances of formula IVb, R$^{6a}$, R$^{6b}$, R$^{6c}$, R$^{6d}$, and R$^{6e}$ are independently selected from hydrogen, alkyl, substituted alkyl, alkoxy, substituted alkoxy, acyl, acylamino, aminoacyl, acyloxy, oxyacyl, amino, aminoacyl, aminocarbonyloxy, alkoxycarbonylamino, alkoxycarbonyl, azido, cyano, halogen, hydroxyl, carboxyl, aryl, aryloxy, heteroaryl, heteroaryloxy, heterocyclic, hydroxyamino, alkoxyamino, nitro, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, —NH—SO$_2$-heteroaryl, amino, and substituted amino.

In certain instances of formula IVb, R$^{6a}$, R$^{6b}$, R$^{6c}$, R$^{6d}$, and R$^{6e}$ are independently selected from hydrogen, alkyl, substituted alkyl, alkoxy, substituted alkoxy, acyl, acylamino, aminoacyl, acyloxy, oxyacyl, amino, aminoacyl, aminocarbonyloxy, alkoxycarbonylamino, alkoxycarbonyl, azido, cyano, halogen, hydroxyl, carboxyl, aryl, aryloxy, heteroaryl, heteroaryloxy, heterocyclic, hydroxyamino, alkoxyamino, amino, and substituted amino.

In certain instances of formula IVb, any two of R$^{6a}$, R$^{6b}$, R$^{6c}$, R$^{6d}$, and R$^{6e}$ vicinal to one another are taken together with the carbon atoms to which they are attached to form a carbocyclic, substituted carbocyclic, heterocyclic or substituted heterocyclic 6-membered ring.

Formula Vb

Certain compounds of interest have formula Ib wherein R$^4$ is —NR$^5$R$^6$ and R$^1$ and R$^6$ are substituted phenyl groups. Particular examples of such compounds have formula Vb:

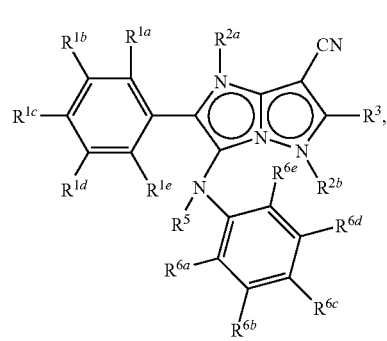

(Vb)

wherein

R$^{1a}$, R$^{1b}$, R$^{1c}$, R$^{1d}$, and R$^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl; or wherein any two of R$^{1a}$, R$^{1b}$, R$^{1c}$, R$^{1d}$, and R$^{1e}$ vicinal to one another are taken together with the carbon atoms to which they are attached to form a carbocyclic, substituted carbocyclic, heterocyclic, or substituted heterocyclic ring, wherein the ring is a 4-10 membered ring;

R$^{2a}$ and R$^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either R$^{2a}$ or R$^{2b}$ is present;

R$^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^{6a}$, $R^{6b}$, $R^{6c}$, $R^{6d}$, and $R^{6e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl; or wherein any two of $R^{6a}$, $R^{6b}$, $R^{6c}$, $R^{6d}$, and $R^{6e}$ vicinal to one another are taken together with the carbon atoms to which they are attached to form a carbocyclic, substituted carbocyclic, heterocyclic, or substituted heterocyclic ring, wherein the ring is a 6-10 membered ring;

or a salt or stereoisomer thereof.

Formula VIb

Certain compounds of interest have formula Ib wherein $R^4$ is —NR$^5$R$^6$ and $R^1$ is selected from heteroaryl and substituted heteroaryl. Particular examples of such compounds have formula VIb:

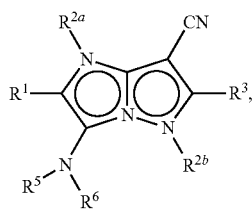

(VIb)

wherein $R^1$ is selected from heteroaryl and substituted heteroaryl;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

or a salt or stereoisomer thereof.

Formula VIIb

Certain compounds of interest have formula (Ib) wherein $R^4$ is —NR$^5$R$^6$ and $R^6$ is aralkyl or heteroaralkyl. Particular examples of such compounds have formula (VIIb):

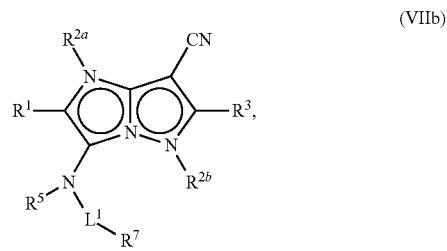

(VIIb)

wherein $R^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl;

$L^1$ is —CH$_2$— or —C(O)—; and $R^7$ is selected from aryl, substituted aryl, heteroaryl, substituted heteroaryl, heterocyclyl, substituted heterocyclyl;

or a salt or stereoisomer thereof.

Particular compounds of interest are shown in the following table. Table 1 provides the details of exemplary substituents for compounds of the following formula:

TABLE 1

| Compound | R¹ | R²ᵃ | R²ᵇ | R³ | R⁵ | R⁶ |
|---|---|---|---|---|---|---|
| 1 | 3-oxo-3,4-dihydro-2H-benzo[b][1,4]oxazin-6-yl | H | — | H | H | 3,4-dimethoxyphenyl |
| 2 | 4-acetamidophenyl | H | — | H | H | 3,4-dimethoxyphenyl |
| 3 | 4-acetamidophenyl | H | — | H | H | 3-(trifluoromethyl)phenyl |
| 4 | 5-methoxy-1H-indol-3-yl | H | — | H | H | 3,4-dimethoxyphenyl |

TABLE 1-continued
| Compound | R¹ | R²ᵃ | R²ᵇ | R³ | R⁵ | R⁶ |
|---|---|---|---|---|---|---|
| 5 | 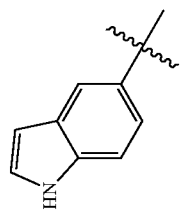 | H | — | H | H | 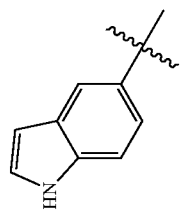 |
| 6 | 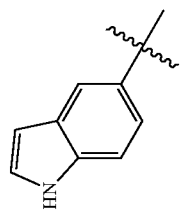 | H | — | H | H | 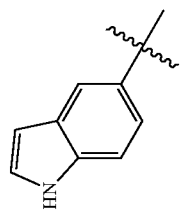 |
| 7 | (6-substituted benzoxazinone) | H | — | H | H | (3,4-dichlorophenyl) |
| 8 | (4-phenoxyphenyl) | H | — | H | H | (3,4-dimethoxyphenyl) |

TABLE 1-continued
| Compound | R¹ | R²ᵃ | R²ᵇ | R³ | R⁵ | R⁶ |
|---|---|---|---|---|---|---|
| 9 |  | H | — | H | H |  |
| 10 | 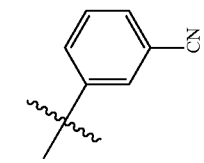 | H | — | H | H | 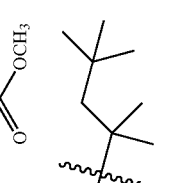 |
| 11 |  | H | — | H | H |  |
| 12 | 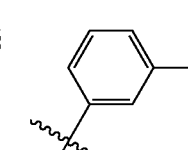 | H | — | H | H | 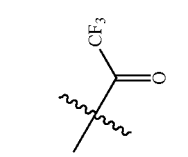 |

TABLE 1-continued

| Compound | R¹ | R²ᵃ | R²ᵇ | R³ | R⁵ | R⁶ |
|---|---|---|---|---|---|---|
| 13 | 3-oxo-3,4-dihydro-2H-benzo[b][1,4]oxazin-6-yl | H | — | H | H | 3-(methoxycarbonyl)phenyl |
| 14 | 3,4,5-trimethoxyphenyl | H | — | H | H | 3-methoxyphenyl |
| 15 | 3-oxo-3,4-dihydro-2H-benzo[b][1,4]oxazin-6-yl | H | — | H | H | 3-methoxyphenyl |
| 16 | 3-oxo-3,4-dihydro-2H-benzo[b][1,4]oxazin-6-yl | H | — | —CH₃ | H | 3,4-dimethoxyphenyl |

TABLE 1-continued
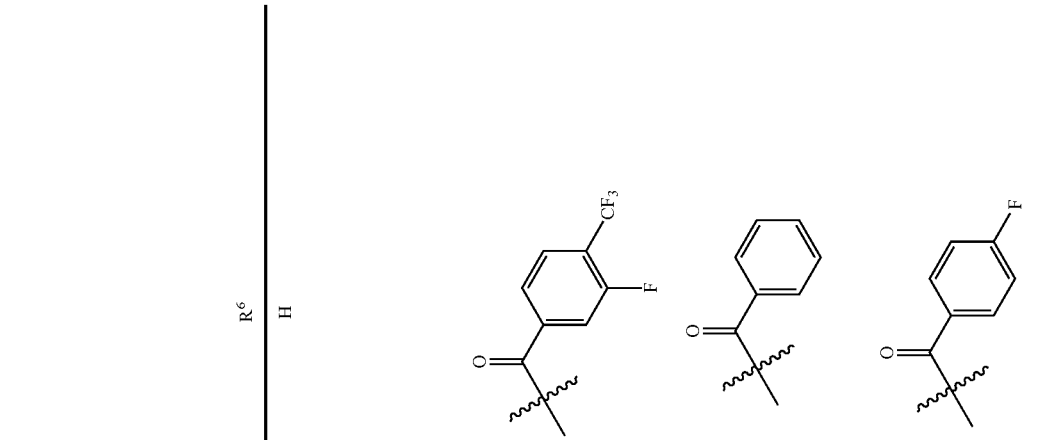
| Compound | R¹ | R²ᵃ | R²ᵇ | R³ | R⁵ | R⁶ |
|---|---|---|---|---|---|---|
| 17 | 3,4,5-tri(H₃CO)phenyl | H | — | H | H | H |
| 18 | 3,4,5-tri(H₃CO)phenyl | H | — | H | H | C(CH₃)₂C(O)-(3-F,4-CF₃-phenyl) |
| 19 | 3,4,5-tri(H₃CO)phenyl | H | — | H | H | C(CH₃)₂C(O)-phenyl |
| 20 | 3,4,5-tri(H₃CO)phenyl | H | — | H | H | C(CH₃)₂C(O)-(4-F-phenyl) |

TABLE 1-continued

| Compound | R¹ | R²ᵃ | R²ᵇ | R³ | R⁵ | R⁶ |
|---|---|---|---|---|---|---|
| 21 | 3,4,5-trimethoxyphenyl | H | — | H | H | 3-methoxybenzoyl-dimethylmethyl |
| 22 | 3,4,5-trimethoxyphenyl | H | — | H | H | 3,4-dichlorophenyl-dimethylmethyl |
| 23 | 3,4,5-trimethoxyphenyl | H | — | H | H | 4-bromophenyl-dimethylmethyl |
| 24 | 6-methoxy-1H-indol-3-yl | H | — | H | H | 3,4-dimethoxyphenyl-dimethylmethyl |

TABLE 1-continued

| Compound | R¹ | R²ᵃ | R²ᵇ | R³ | R⁵ | R⁶ |
|---|---|---|---|---|---|---|
| 25 | 3,4,5-trimethoxyphenyl | H | — | H | H | 4-morpholinophenyl |
| 26 | 1H-indol-6-yl | H | — | H | H | 3,4,5-trimethoxyphenyl |
| 27 | 1H-indol-6-yl | H | — | H | H | 4-morpholinophenyl |

TABLE 1-continued

| Compound | R¹ | R²ᵃ | R²ᵇ | R³ | R⁵ | R⁶ |
|---|---|---|---|---|---|---|
| 28 | 3,4,5-trimethoxyphenyl | H | — | H | H | 3,4-dimethoxyphenyl |
| 29 | 3,4,5-trimethoxyphenyl | H | — | H | H | 3,4,5-trimethoxyphenyl |
| 30 | 3,4,5-trimethoxyphenyl | H | — | H | H | 3-acetamidophenyl |

TABLE 1-continued

| Compound | R¹ | R²ᵃ | R²ᵇ | R³ | R⁵ | R⁶ |
|---|---|---|---|---|---|---|
| 31 | 6-(3-oxo-3,4-dihydro-2H-benzo[b][1,4]oxazinyl) | H | — | H | H | 3-acetamidophenyl |
| 32 | 3,4-dimethoxyphenyl | H | — | H | H | 3-acetamidophenyl |
| 33 | 4-(methylthio)phenyl | H | — | H | H | 3-acetamidophenyl |

TABLE 1-continued

| Compound | R¹ | R²ᵃ | R²ᵇ | R³ | R⁵ | R⁶ |
|---|---|---|---|---|---|---|
| 34 | 4-acetamidophenyl | H | — | H | H | 3-acetamidophenyl |
| 35 | 3,4-dihydro-2H-benzo[b][1,4]oxazin-3-one-6-yl | H | — | H | H | (3-methoxyphenyl)methyl (gem-dimethyl) |
| 36 | 2,4-difluorophenyl | H | — | H | H | 3,4-dimethoxyphenyl (gem-dimethyl) |
| 37 | 3,4-difluorophenyl | H | — | H | H | 3,4-dimethoxyphenyl (gem-dimethyl) |

TABLE 1-continued

| Compound | R¹ | R²ᵃ | R²ᵇ | R³ | R⁵ | R⁶ |
|---|---|---|---|---|---|---|
| 38 | (2,3-dihydro-1,4-benzodioxin-6-yl) | H | — | H | H | (3,4-dimethoxyphenyl) |
| 39 | (3,4,5-trimethoxyphenyl) | H | — | H | H | (5-phenyl-1,3,4-oxadiazol-2-yl)carbonyl |
| 40 | (3-oxo-3,4-dihydro-2H-1,4-benzoxazin-6-yl) | H | — | H | H | 2-(3,4-dimethoxyphenyl)ethyl |
| 41 | (3,4,5-trimethoxyphenyl) | H | — | H | H | 2-(3,4-dimethoxyphenyl)ethyl |

TABLE 1-continued

| Compound | R¹ | R²ᵃ | R²ᵇ | R³ | R⁵ | R⁶ |
|---|---|---|---|---|---|---|
| 42 | 3,4,5-trimethoxyphenyl | H | — | H | H | 3,4-dimethoxyphenyl-CH₂-C(O)-C(CH₃)₂- |
| 43 | 3-oxo-3,4-dihydro-2H-benzo[b][1,4]oxazin-6-yl | H | — | H | H | 4-morpholinophenyl |
| 44 | 1H-indol-6-yl | H | — | H | H | 3-methoxyphenyl |
| 45 | 3-oxo-3,4-dihydro-2H-benzo[b][1,4]oxazin-6-yl | H | — | H | H | 4-bromophenyl |

TABLE 1-continued

| Compound | R¹ | R²ᵃ | R²ᵇ | R³ | R⁵ | R⁶ |
|---|---|---|---|---|---|---|
| 46 | 3,4,5-trimethoxyphenyl | H | — | H | H | 3-methoxybenzyl (α-methyl) |
| 47 | 1H-indol-6-yl | H | — | H | H | 3-acetamidophenyl |
| 48 | 4-(methylsulfonyl)phenyl | H | — | H | H | 3,4-dimethoxyphenyl |
| 49 | 3,4,5-trimethoxyphenyl | H | — | H | H | 2,3-dihydrobenzo[b][1,4]dioxin-6-yl |

TABLE 1-continued

| Compound | R¹ | R²ᵃ | R²ᵇ | R³ | R⁵ | R⁶ |
|---|---|---|---|---|---|---|
| 50 | 3-oxo-3,4-dihydro-2H-benzo[1,4]oxazin-6-yl | H | — | H | H | 2,3-dihydro-benzo[1,4]dioxin-6-yl |
| 51 | benzo[1,3]dioxol-5-yl | H | — | H | H | 3,4-dimethoxyphenyl |
| 52 | 3-fluoro-4-methoxyphenyl | H | — | H | H | 3,4-dimethoxyphenyl |
| 53 | 3,4,5-trimethoxyphenyl | H | — | H | H | 1-bromo-2-methylpropan-2-yl (bromoacetyl-methyl) |

TABLE 1-continued

| Compound | R¹ | R²ᵃ | R²ᵇ | R³ | R⁵ | R⁶ |
|---|---|---|---|---|---|---|
| 54 | 3,4,5-trimethoxyphenyl | H | — | H | H | phenoxyacetone-methyl |
| 55 | benzyl | H | — | H | H | 3,4-dimethoxyphenyl-methyl |
| 56 | 3,4,5-trimethoxyphenyl | H | — | H | H | 3,4-dichlorophenyl-acetone-methyl |
| 57 | 3,4,5-trifluorophenyl | H | — | H | H | 3,4-dimethoxyphenyl-methyl |

TABLE 1-continued

| Compound | R¹ | R²ᵃ | R²ᵇ | R³ | R⁵ | R⁶ |
|---|---|---|---|---|---|---|
| 58 | 3-chloro-4,5-dimethoxyphenyl | H | — | H | H | 3,4-dimethoxyphenyl |
| 59 | 4-fluoro-3-methoxyphenyl | H | — | H | H | 3,4-dimethoxyphenyl |
| 60 | 1H-indol-6-yl | H | — | H | H | 2,3-dihydro-1,4-benzodioxin-6-yl |

TABLE 1-continued

| Compound | R¹ | R²ᵃ | R²ᵇ | R³ | R⁵ | R⁶ |
|---|---|---|---|---|---|---|
| 61 | 3,4,5-trimethoxyphenyl | H | — | H | H | 3-acetamidophenyl |
| 62 | 6-methoxy-1H-indol-3-yl | H | — | H | H | 4-acetamidophenyl |
| 63 | 2,3-dihydrobenzo[1,4]dioxin-6-yl | H | — | H | H | 4-acetamidophenyl |
| 64 | 3,4,5-trimethoxyphenyl | H | — | H | H | 3,4-difluorophenyl |

TABLE 1-continued

| Compound | R¹ | R²ᵃ | R²ᵇ | R³ | R⁵ | R⁶ |
|---|---|---|---|---|---|---|
| 65 | 3,4,5-trimethoxyphenyl | H | — | H | H | 4-(NHBoc-methyl)phenyl |
| 66 | 3,4,5-trimethoxyphenyl | H | — | H | H | 4-(aminomethyl)phenyl |
| 67 | 3,4,5-trimethoxyphenyl | H | — | H | H | 3-(methoxycarbonyl)phenyl |
| 68 | 3-oxo-3,4-dihydro-2H-benzo[b][1,4]oxazin-6-yl | H | — | H | H | 4-acetamidophenyl |

TABLE 1-continued
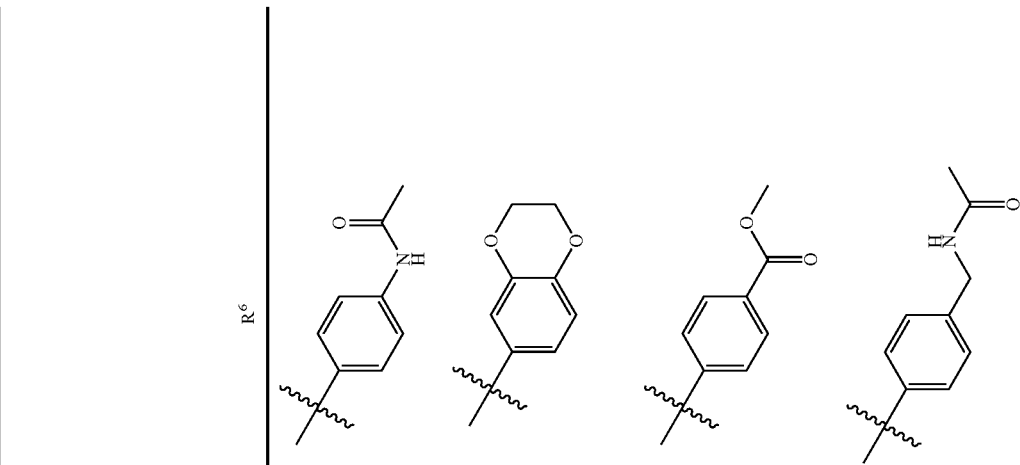
| Compound | R¹ | R²ᵃ | R²ᵇ | R³ | R⁵ | R⁶ |
|---|---|---|---|---|---|---|
| 69 | 3,4-dimethoxyphenyl | H | — | H | H | 4-acetamidophenyl |
| 70 | 7-hydroxy-8-methoxy(chromenyl) | H | — | H | H | 2,3-dihydrobenzo[1,4]dioxin-6-yl |
| 71 | 3-hydroxy-4,5-dimethoxyphenyl | H | — | H | H | 4-(methoxycarbonyl)phenyl |
| 72 | 3,4,5-trimethoxyphenyl | H | — | H | H | 4-(acetamidomethyl)phenyl |

TABLE 1-continued

| Compound | R¹ | R²ᵃ | R²ᵇ | R³ | R⁵ | R⁶ |
|---|---|---|---|---|---|---|
| 73 | 3,4,5-trimethoxyphenyl | H | — | H | H | 4-(N-Boc)piperidinylmethyl |
| 74 | 3,4,5-trimethoxyphenyl | H | — | H | H | 4-piperidinylmethyl |
| 75 | 3,4,5-trimethoxyphenyl | H | — | H | H | 4-(4-pyrrolidinylpiperidin-1-yl)-3-fluorobenzyl |
| 76 | 3,4,5-trimethoxyphenyl | H | — | H | H | methyl 2-benzylpropanoate |

TABLE 1-continued

| Compound | R¹ | R²ᵃ | R²ᵇ | R³ | R⁵ | R⁶ |
|---|---|---|---|---|---|---|
| 77 | 3,4-dimethoxyphenyl | H | — | H | H | 3-(methoxycarbonyl)phenyl |
| 78 | 3-chloro-4,5-dimethoxyphenyl | H | — | H | H | 3-(methoxycarbonyl)phenyl |
| 79 | 4-morpholinophenyl | H | — | H | H | 3,4,5-trimethoxyphenyl |
| 80 | 4-morpholinophenyl | H | — | H | H | 4-bromophenyl |

TABLE 1-continued

| Compound | R¹ | R²ᵃ | R²ᵇ | R³ | R⁵ | R⁶ |
|---|---|---|---|---|---|---|
| 81 | 4-carbamoylphenyl | H | — | H | H | 3,4,5-trimethoxyphenyl |
| 82 | 3,4,5-trimethoxyphenyl | — | 4-methoxyphenyl | H | H | H |
| 83 | 3,4,5-trimethoxyphenyl | H | — | H | H | 4-(pyridine-3-carboxamidomethyl)phenyl |
| 84 | 4-(methoxycarbonylmethoxy)-3-methoxyphenyl | H | — | H | H | 3-(methoxycarbonyl)phenyl |

TABLE 1-continued
| Compound | R$^1$ | R$^{2a}$ | R$^{2b}$ | R$^3$ | R$^5$ | R$^6$ |
|---|---|---|---|---|---|---|
| 85 | 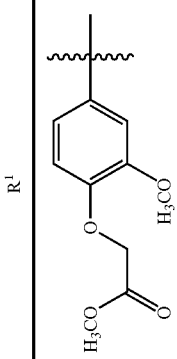 | H | — | H | H | 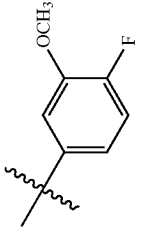 |
| 86 | 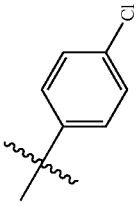 | H | — | H | H | 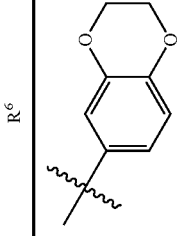 |
| 87 | 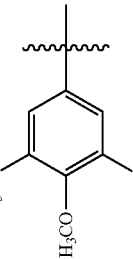 | H | — | H | H | 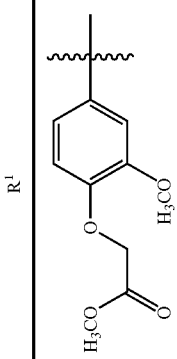 |
| 88 | 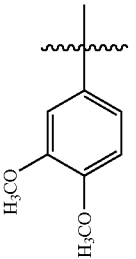 | H | — | 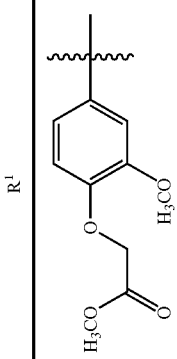 |  |  (no NR$^5$R$^6$) |

TABLE 1-continued

| Compound | R¹ | R²ᵃ | R²ᵇ | R³ | R⁵ | R⁶ |
|---|---|---|---|---|---|---|
| 89 | 3,4,5-trimethoxyphenyl | H | — | H | H | 4-(3,4-dimethoxybenzamidomethyl)phenyl |
| 90 | 3,4,5-trimethoxyphenyl | H | — | H | H | 4-(3-(4-hydroxyphenyl)propanamidomethyl)phenyl |
| 91 | 3,4,5-trimethoxyphenyl | H | — | H | H | 4-(3-(piperidin-1-yl)propanamidomethyl)phenyl |
| 92 | 3,4,5-trimethoxyphenyl | H | — | H | H | 4-(4-cyanobenzamidomethyl)phenyl |

TABLE 1-continued
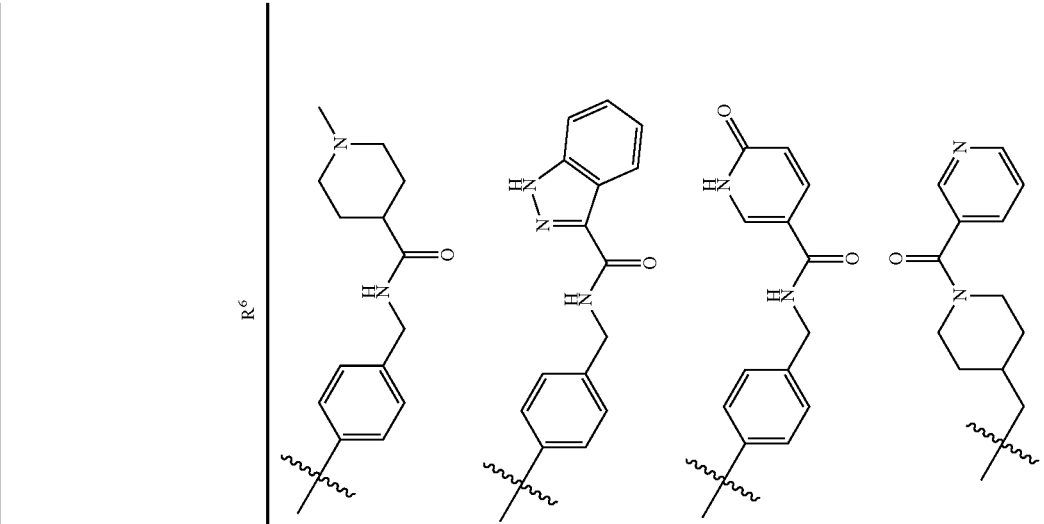

TABLE 1-continued
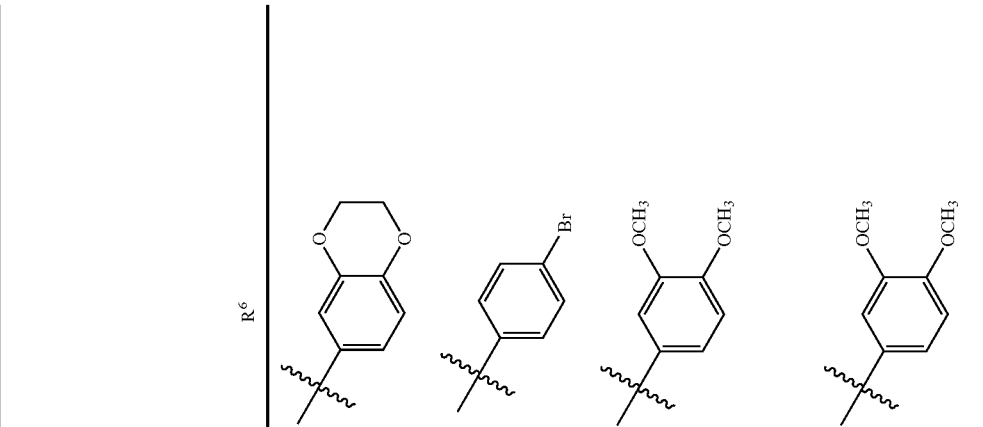
| Compound | R¹ | R²ᵃ | R²ᵇ | R³ | R⁵ | R⁶ |
|---|---|---|---|---|---|---|
| 97 | 4-carbamoylphenyl | H | — | H | H | 2,3-dihydrobenzo[1,4]dioxin-6-yl |
| 98 | 4-carbamoylphenyl | H | — | H | H | 4-bromophenyl |
| 99 | 4-methoxy-3-(methoxycarbonylmethoxy)phenyl | H | — | H | H | 3,4-dimethoxyphenyl |
| 100 | 3-hydroxy-4,5-dimethoxyphenyl | H | — | H | H | 3,4-dimethoxyphenyl |

TABLE 1-continued
| Compound | R¹ | R²ᵃ | R²ᵇ | R³ | R⁵ | R⁶ |
|---|---|---|---|---|---|---|
| 101 |  | H | — | H | H |  |
| 102 |  | H | — | H | H |  |
| 103 |  | H | — | H | H |  |
| 104 |  | H | — | H | H |  |
| 105 |  | H | — | H | H |  |

TABLE 1-continued

| Compound | R¹ | R²ᵃ | R²ᵇ | R³ | R⁵ | R⁶ |
|---|---|---|---|---|---|---|
| 106 | 3-cyclopentyloxy-4-methoxyphenyl | H | — | H | H | 3,4-dimethoxyphenyl |
| 107 | 4-[2-(2-oxopyrrolidin-1-yl)ethoxy]phenyl | H | — | H | H | 3,4-dimethoxyphenyl |
| 108 | 3-methoxy-4-(2-methoxyethoxy)phenyl | H | — | H | H | 3,4-dimethoxyphenyl |
| 109 | 3-oxo-3,4-dihydro-2H-benzo[1,4]oxazin-6-yl | H | — | H | H | 3-methoxy-4-fluorophenyl |

TABLE 1-continued

| Compound | R¹ | R²ᵃ | R²ᵇ | R³ | R⁵ | R⁶ |
|---|---|---|---|---|---|---|
| 110 | 3-OH-4,5-di(OCH₃)-phenyl | H | — | H | H | 3-OCF₃-phenyl |
| 111 | 3-OH-4,5-di(OCH₃)-phenyl | H | — | H | H | 3-Cl-4-OCH₃-phenyl |
| 112 | 3-OH-phenyl | H | — | H | H | 3,4-di(OCH₃)-phenyl |
| 113 | 4-(OCH₂C(O)OCH₃)-phenyl | H | — | H | H | 3,4-di(OCH₃)-phenyl |

TABLE 1-continued

| Compound | R¹ | R²ᵃ | R²ᵇ | R³ | R⁵ | R⁶ |
|---|---|---|---|---|---|---|
| 114 | 3-(methanesulfonamido)phenyl | H | — | H | H | 3,4-dimethoxyphenyl |
| 115 | 3,4,5-trimethoxyphenyl | H | — | H | H | 3-cyclopentyloxy-4-methoxyphenyl |
| 116 | 4-(2-hydroxyethoxy)-3-methoxyphenyl | H | — | H | H | 3-methoxy-4-fluorophenyl |
| 117 | 4-carbamoylphenyl | H | — | H | H | 3-methoxy-4-fluorophenyl |

TABLE 1-continued

| Compound | R¹ | R²ᵃ | R²ᵇ | R³ | R⁵ | R⁶ |
|---|---|---|---|---|---|---|
| 118 | | H | — | H | H | |
| 119 | | H | — | H | H | |
| 120 | | H | — | H | H | |
| 121 | | H | — | H | H | |

TABLE 1-continued
| Compound | R¹ | R²ᵃ | R²ᵇ | R³ | R⁵ | R⁶ |
|---|---|---|---|---|---|---|
| 122 | 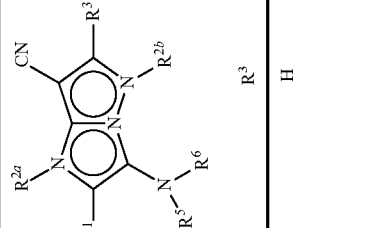 | H | — | H | H | 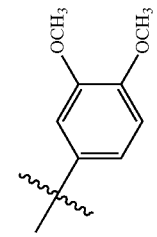 |
| 123 | 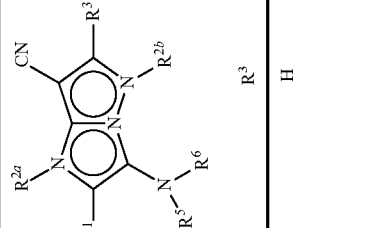 | H | — | H | H | 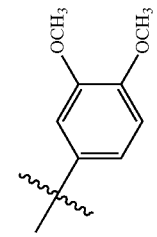 |
| 124 | 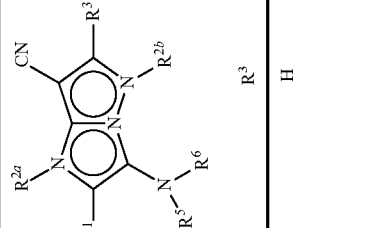 | H | — | H | H | 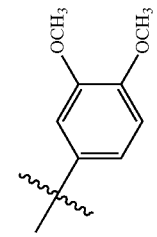 |
| 125 | 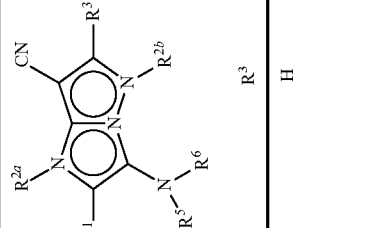 | H | — | H | H | 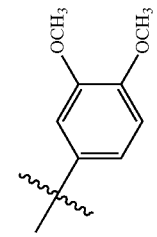 |

TABLE 1-continued
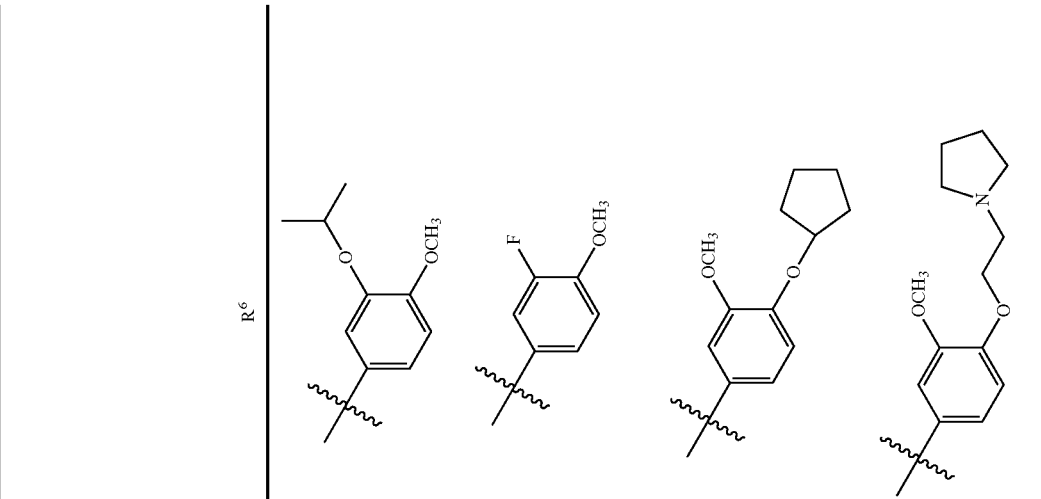
| Compound | R¹ | R²ᵃ | R²ᵇ | R³ | R⁵ | R⁶ |
|---|---|---|---|---|---|---|
| 126 | 3,4,5-tri(H₃CO)-phenyl | H | — | H | H | 4-OCH₃-3-isopropoxy-phenyl |
| 127 | 3,4,5-tri(H₃CO)-phenyl | H | — | H | H | 3-F-4-OCH₃-phenyl |
| 128 | 3,4,5-tri(H₃CO)-phenyl | H | — | H | H | 3-OCH₃-4-cyclopentyloxy-phenyl |
| 129 | 3,4,5-tri(H₃CO)-phenyl | H | — | H | H | 3-OCH₃-4-(2-pyrrolidin-1-yl-ethoxy)-phenyl |

TABLE 1-continued
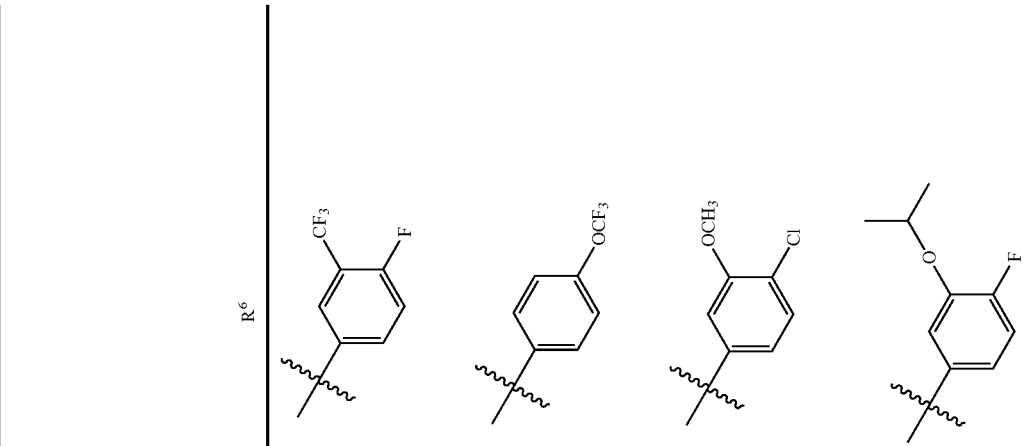
| Compound | R¹ | R²ᵃ | R²ᵇ | R³ | R⁵ | R⁶ |
|---|---|---|---|---|---|---|
| 130 | 3,5-di(H₃CO), 4-(H₃CO) phenyl | H | — | H | H | 3-CF₃, 4-F phenyl |
| 131 | 3,5-di(H₃CO), 4-(H₃CO) phenyl | H | — | H | H | 4-OCF₃ phenyl |
| 132 | 3,5-di(H₃CO), 4-(H₃CO) phenyl | H | — | H | H | 3-OCH₃, 4-Cl phenyl |
| 133 | 3,5-di(H₃CO), 4-(H₃CO) phenyl | H | — | H | H | 3-OiPr, 4-F phenyl |

TABLE 1-continued

| Compound | R¹ | R²ᵃ | R²ᵇ | R³ | R⁵ | R⁶ |
|---|---|---|---|---|---|---|
| 134 | 3,4,5-trimethoxyphenyl | H | — | H | H | 3-fluoro-4-(pyrrolidin-1-yl)phenyl |
| 135 | 3-methoxy-4-(carbamoylmethoxy)phenyl | H | — | H | H | 3,4-dimethoxyphenyl |
| 136 | 3,5-dimethyl-4-methoxyphenyl | H | — | H | H | 3,4-dimethoxyphenyl |
| 137 | 3,4,5-trimethoxyphenyl | H | — | H | H | 3-oxo-3,4-dihydro-2H-benzo[b][1,4]oxazin-6-yl |

TABLE 1-continued
| Compound | R¹ | R²ᵃ | R²ᵇ | R³ | R⁵ | R⁶ |
|---|---|---|---|---|---|---|
| 138 | 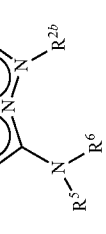 | H | — | H | H | 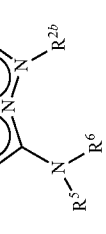 |
| 139 | 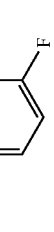 | H | — | H | H | 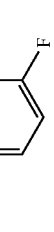 |
| 140 | 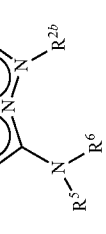 | H | — | H | H | 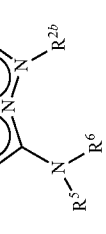 |
| 141 | 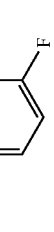 | H | — | H | H | 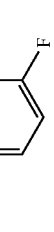 |

TABLE 1-continued
| Compound | R¹ | R²ᵃ | R²ᵇ | R³ | R⁵ | R⁶ |
|---|---|---|---|---|---|---|
| 142 |  | H | — | H | H |  |
| 143 |  | H | — | H | H |  |
| 144 |  | H | — | H | H | 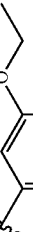 |
| 145 | | H | — | H | H | |

TABLE 1-continued
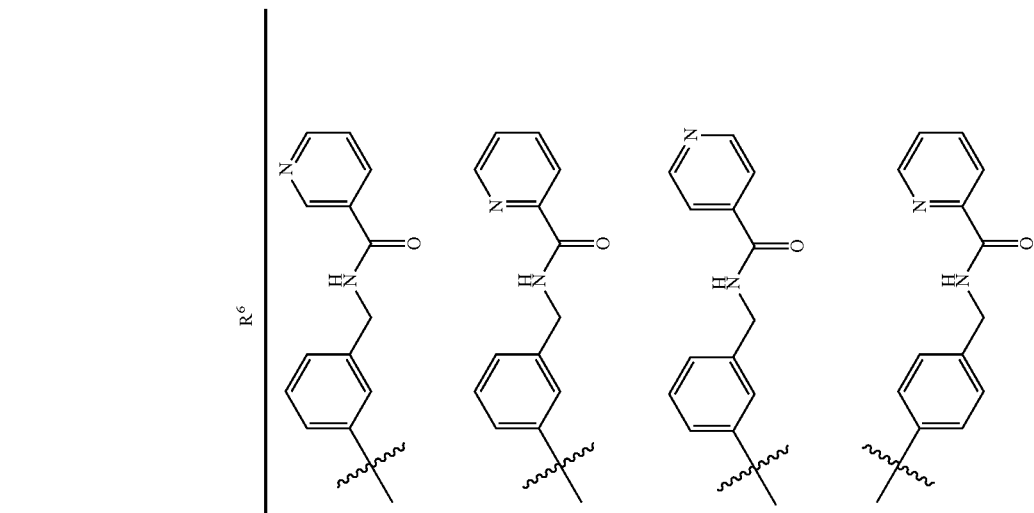
| Compound | R¹ | R²ᵃ | R²ᵇ | R³ | R⁵ | R⁶ |
|---|---|---|---|---|---|---|
| 146 | 3,4,5-tri(H₃CO)-phenyl | H | — | H | H | 3-(pyridin-3-yl-C(O)NH-CH₂)-phenyl |
| 147 | 3,4,5-tri(H₃CO)-phenyl | H | — | H | H | 3-(pyridin-2-yl-C(O)NH-CH₂)-phenyl |
| 148 | 3,4,5-tri(H₃CO)-phenyl | H | — | H | H | 3-(pyridin-4-yl-C(O)NH-CH₂)-phenyl |
| 149 | 3,4,5-tri(H₃CO)-phenyl | H | — | H | H | 4-(pyridin-2-yl-C(O)NH-CH₂)-phenyl |

TABLE 1-continued
| Compound | R¹ | R²ᵃ | R²ᵇ | R³ | R⁵ | R⁶ |
|---|---|---|---|---|---|---|
| 150 |  | H | — | H | H | 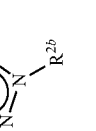 |
| 151 | 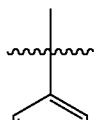 | H | — | H | H |  |
| 152 |  | H | — | H | H |  |
| 153 | 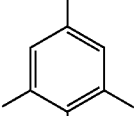 | H | — | H | H |  |

TABLE 1-continued
| Compound | R¹ | R²ᵃ | R²ᵇ | R³ | R⁵ | R⁶ |
|---|---|---|---|---|---|---|
| 154 |  | H | — | H | H |  |
| 155 |  | H | — | H | H |  |
| 156 |  | H | — | H | H |  |
| 157 |  | H | — | H | H |  |

Particular compounds of interest, and salts or solvates or stereoisomers thereof, include:

3-(3,4-Dimethoxyphenylamino)-2-(2,4-dihydro-2-oxo-1H-benzo[d][1,3]oxazin-7-yl)-1H-imidazo[1,2-b]pyrazole-7-carbonitrile;

N-(4-(3-(3,4-Dimethoxyphenylamino)-7-cyano-1H-imidazo[1,2-b]pyrazol-2-yl)phenyl)acetamide;

N-(4-(3-(3-(Trifluoromethyl)phenylamino)-7-cyano-1H-imidazo[1,2-b]pyrazol-2-yl)phenyl)acetamide;

3-(3,4-Dimethoxyphenylamino)-2-(5-methoxy-1H-indol-3-yl)-1H-imidazo[1,2-b]pyrazole-7-carbonitrile;

3-(3,4-Dimethoxyphenylamino)-2-(1H-indol-5-yl)-1H-imidazo[1,2-b]pyrazole-7-carbonitrile;

3-(3,4-Dimethoxyphenylamino)-2-(1H-indol-6-yl)-1H-imidazo[1,2-b]pyrazole-7-carbonitrile;

3-(3,4-Dichlorophenylamino)-2-(2,4-dihydro-2-oxo-1H-benzo[d][1,3]oxazin-7-yl)-1H-imidazo[1,2-b]pyrazole-7-carbonitrile;

3-(3,4-Dimethoxyphenylamino)-2-(4-phenoxyphenyl)-1H-imidazo[1,2-b]pyrazole-7-carbonitrile;

3-(3-Cyanophenylamino)-2-(3,4-dihydro-3-oxo-2H-benzo[b][1,4]oxazin-6-yl)-1H-imidazo[1,2-b]pyrazole-7-carbonitrile;

Methyl 3-(7-cyano-2-(3,4-dihydro-3-oxo-2H-benzo[b][1,4]oxazin-6-yl)-1H-imidazo[1,2-b]pyrazol-3-ylamino)benzoate;

3-(2,4,4-Trimethylpentan-2-ylamino)-2-(3,4,5-trimethoxyphenyl)-1H-imidazo[1,2-b]pyrazole-7-carbonitrile;

N-(7-Cyano-2-(3,4,5-trimethoxyphenyl)-1H-imidazo[1,2-b]pyrazol-3-yl)-2,2,2-trifluoroacetamide;

Methyl 4-(7-cyano-2-(2,4-dihydro-2-oxo-1H-benzo[d][1,3]oxazin-7-yl)-1H-imidazo[1,2-b]pyrazol-3-ylamino)benzoate;

3-(3-Methoxyphenylamino)-2-(3,4,5-trimethoxyphenyl)-1H-imidazo[1,2-b]pyrazole-7-carbonitrile;

3-(3-Methoxyphenylamino)-2-(2,4-dihydro-2-oxo-1H-benzo[d][1,3]oxazin-7-yl)-1H-imidazo[1,2-b]pyrazole-7-carbonitrile;

3-(3,4-Dimethoxyphenylamino)-2-(2,4-dihydro-2-oxo-1H-benzo[d][1,3]oxazin-7-yl)-6-methyl-1H-imidazo[1,2-b]pyrazole-7-carbonitrile;

3-Amino-2-(3,4,5-trimethoxyphenyl)-1H-imidazo[1,2-b]pyrazole-7-carbonitrile;

N-(7-Cyano-2-(3,4,5-trimethoxyphenyl)-1H-imidazo[1,2-b]pyrazol-3-yl)-3-fluoro-4-(trifluoromethyl)benzamide;

N-(7-Cyano-2-(3,4,5-trimethoxyphenyl)-1H-imidazo[1,2-b]pyrazol-3-yl)benzamide;

N-(7-Cyano-2-(3,4,5-trimethoxyphenyl)-1H-imidazo[1,2-b]pyrazol-3-yl)-4-fluorobenzamide;

N-(7-Cyano-2-(3,4,5-trimethoxyphenyl)-1H-imidazo[1,2-b]pyrazol-3-yl)-3-methoxybenzamide;

3-(3,4-Dichlorophenylamino)-2-(3,4,5-trimethoxyphenyl)-1H-imidazo[1,2-b]pyrazole-7-carbonitrile;

3-(4-Bromophenylamino)-2-(3,4,5-trimethoxyphenyl)-1H-imidazo[1,2-b]pyrazole-7-carbonitrile;

3-(3,4-Dimethoxyphenylamino)-2-(6-methoxy-1H-indol-3-yl)-1H-imidazo[1,2-b]pyrazole-7-carbonitrile;

3-(4-Morpholinophenylamino)-2-(3,4,5-trimethoxyphenyl)-1H-imidazo[1,2-b]pyrazole-7-carbonitrile;

3-(3,4,5-Trimethoxyphenylamino)-2-(1H-indol-6-yl)-1H-imidazo[1,2-b]pyrazole-7-carbonitrile;

3-(4-Morpholinophenylamino)-2-(1H-indol-6-yl)-1H-imidazo[1,2-b]pyrazole-7-carbonitrile;

3-(3,4-Dimethoxyphenylamino)-2-(3,4,5-trimethoxyphenyl)-1H-imidazo[1,2-b]pyrazole-7-carbonitrile;

3-(3,4,5-Trimethoxyphenylamino)-2-(3,4,5-trimethoxyphenyl)-1H-imidazo[1,2-b]pyrazole-7-carbonitrile;

N-(3-(7-Cyano-2-(3,4,5-trimethoxyphenyl)-1H-imidazo[1,2-b]pyrazol-3-ylamino)phenyl)acetamide;

N-(3-(7-Cyano-2-(3,4-dihydro-3-oxo-2H-benzo[b][1,4]oxazin-6-yl)-1H-imidazo[1,2-b]pyrazol-3-ylamino)phenyl)acetamide;

N-(3-(7-Cyano-2-(3,4-dimethoxyphenyl)-1H-imidazo[1,2-b]pyrazol-3-ylamino)phenyl)acetamide;

N-(3-(7-Cyano-2-(4-(methylthio)phenyl)-1H-imidazo[1,2-b]pyrazol-3-ylamino)phenyl)acetamide;

N-(4-(7-Cyano-3-(3-acetamidophenylamino)-1H-imidazo[1,2-b]pyrazol-2-yl)phenyl)acetamide;

3-(3-Methoxybenzylamino)-2-(3,4-dihydro-3-oxo-2H-benzo[b][1,4]oxazin-6-yl)-1H-imidazo[1,2-b]pyrazole-7-carbonitrile;

3-(3,4-Dimethoxyphenylamino)-2-(2,4-difluorophenyl)-1H-imidazo[1,2-b]pyrazole-7-carbonitrile;

3-(3,4-Dimethoxyphenylamino)-2-(3,4-difluorophenyl)-1H-imidazo[1,2-b]pyrazole-7-carbonitrile;

3-(3,4-Dimethoxyphenylamino)-2-(2,3-dihydrobenzo[b][1,4]dioxin-7-yl)-1H-imidazo[1,2-b]pyrazole-7-carbonitrile;

N-(7-Cyano-2-(3,4,5-trimethoxyphenyl)-1H-imidazo[1,2-b]pyrazol-3-yl)-5-phenyl-1,3,4-oxadiazole-2-carboxamide;

3-(3,4-Dimethoxyphenethylamino)-2-(3,4-dihydro-3-oxo-2H-benzo[b][1,4]oxazin-6-yl)-1H-imidazo[1,2-b]pyrazole-7-carbonitrile;

3-(3,4-Dimethoxyphenethylamino)-2-(3,4,5-trimethoxyphenyl)-1H-imidazo[1,2-b]pyrazole-7-carbonitrile;

N-(7-Cyano-2-(3,4,5-trimethoxyphenyl)-1H-imidazo[1,2-b]pyrazol-3-yl)-2-(3,4-dimethoxyphenyl)acetamide;

3-(4-Morpholinophenylamino)-2-(3,4-dihydro-3-oxo-2H-benzo[b][1,4]oxazin-6-yl)-1H-imidazo[1,2-b]pyrazole-7-carbonitrile;

3-(3-Methoxyphenylamino)-2-(1H-indol-6-yl)-1H-imidazo[1,2-b]pyrazole-7-carbonitrile;

3-(4-Bromophenylamino)-2-(3,4-dihydro-3-oxo-2H-benzo[b][1,4]oxazin-6-yl)-1H-imidazo[1,2-b]pyrazole-7-carbonitrile;

3-(3-Methoxybenzylamino)-2-(3,4,5-trimethoxyphenyl)-1H-imidazo[1,2-b]pyrazole-7-carbonitrile;

N-(3-(7-Cyano-2-(1H-indol-6-yl)-1H-imidazo[1,2-b]pyrazol-3-ylamino)phenyl)acetamide;

3-(3,4-Dimethoxyphenylamino)-2-(4-(methylsulfonyl)phenyl)-1H-imidazo[1,2-b]pyrazole-7-carbonitrile;

3-(2,3-Dihydrobenzo[b][1,4]dioxin-6-ylamino)-2-(3,4,5-trimethoxyphenyl)-1H-imidazo[1,2-b]pyrazole-7-carbonitrile;

3-(2,3-Dihydrobenzo[b][1,4]dioxin-6-ylamino)-2-(3,4-dihydro-3-oxo-2H-benzo[b][1,4]oxazin-6-yl)-1H-imidazo[1,2-b]pyrazole-7-carbonitrile;

3-(3,4-Dimethoxyphenylamino)-2-(benzo[d][1,3]dioxol-6-yl)-1H-imidazo[1,2-b]pyrazole-7-carbonitrile;

3-(3,4-Dimethoxyphenylamino)-2-(3-fluoro-4-methoxyphenyl)-1H-imidazo[1,2-b]pyrazole-7-carbonitrile;

2-Bromo-N-(7-cyano-2-(3,4,5-trimethoxyphenyl)-1H-imidazo[1,2-b]pyrazol-3-yl)acetamide;

N-(7-Cyano-2-(3,4,5-trimethoxyphenyl)-1H-imidazo[1,2-b]pyrazol-3-yl)-2-phenoxyacetamide;

3-(3,4-Dimethoxyphenylamino)-2-benzyl-1H-imidazo[1,2-b]pyrazole-7-carbonitrile;

2-(3,4-Dichlorophenyl)-N-(7-cyano-2-(3,4,5-trimethoxyphenyl)-1H-imidazo[1,2-b]pyrazol-3-yl)acetamide;

3-(3,4-Dimethoxyphenylamino)-2-(3,4,5-trifluorophenyl)-1H-imidazo[1,2-b]pyrazole-7-carbonitrile;

3-(3,4-Dimethoxyphenylamino)-2-(3-chloro-4,5-dimethoxyphenyl)-1H-imidazo[1,2-b]pyrazole-7-carbonitrile;

3-(3,4-Dimethoxyphenylamino)-2-(4-fluoro-3-methoxyphenyl)-1H-imidazo[1,2-b]pyrazole-7-carbonitrile;
3-(2,3-Dihydrobenzo[b][1,4]dioxin-6-ylamino)-2-(1H-indol-6-yl)-1H-imidazo[1,2-b]pyrazole-7-carbonitrile;
N-(4-(7-Cyano-2-(3,4,5-trimethoxyphenyl)-1H-imidazo[1,2-b]pyrazol-3-ylamino)phenyl)acetamide;
N-(4-(7-Cyano-2-(6-methoxy-1H-indol-3-yl)-1H-imidazo[1,2-b]pyrazol-3-ylamino)phenyl)acetamide;
N-(4-(7-Cyano-2-(2,3-dihydrobenzo[b][1,4]dioxin-7-yl)-1H-imidazo[1,2-b]pyrazol-3-ylamino)phenyl)acetamide;
3-(3,4-Difluorophenylamino)-2-(3,4,5-trimethoxyphenyl)-1H-imidazo[1,2-b]pyrazole-7-carbonitrile;
tert-Butyl 4-(7-cyano-2-(3,4,5-trimethoxyphenyl)-1H-imidazo[1,2-b]pyrazol-3-ylamino)benzylcarbamate;
3-(4-(Aminomethyl)phenylamino)-2-(3,4,5-trimethoxyphenyl)-1H-imidazo[1,2-b]pyrazole-7-carbonitrile;
Methyl 3-(7-cyano-2-(3,4,5-trimethoxyphenyl)-1H-imidazo[1,2-b]pyrazol-3-ylamino)benzoate;
N-(4-(7-Cyano-2-(3,4-dihydro-3-oxo-2H-benzo[b][1,4]oxazin-6-yl)-1H-imidazo[1,2-b]pyrazol-3-ylamino)phenyl)acetamide;
N-(4-(7-Cyano-2-(3,4-dimethoxyphenyl)-1H-imidazo[1,2-b]pyrazol-3-ylamino)phenyl)acetamide;
3-(2,3-Dihydrobenzo[b][1,4]dioxin-6-ylamino)-2-(3-hydroxy-4,5-dimethoxyphenyl)-1H-imidazo[1,2-b]pyrazole-7-carbonitrile;
Methyl 4-(7-cyano-2-(3-hydroxy-4,5-dimethoxyphenyl)-1H-imidazo[1,2-b]pyrazol-3-ylamino)benzoate;
N-(4-(7-Cyano-2-(3,4,5-trimethoxyphenyl)-1H-imidazo[1,2-b]pyrazol-3-ylamino)benzyl)acetamide;
tert-Butyl-4-((7-cyano-2-(3,4,5-trimethoxyphenyl)-1H-imidazo[1,2-b]pyrazol-3-ylamino)methyl)piperidine-1-carboxylate;
3-((Piperidin-4-yl)methylamino)-2-(3,4,5-trimethoxyphenyl)-1H-imidazo[1,2-b]pyrazole-7-carbonitrile;
3-(3-Fluoro-4-(pyrrolidin-1-yl)piperidin-1-yl)phenylamino)-2-(3,4,5-trimethoxyphenyl)-1H-imidazo[1,2-b]pyrazole-7-carbonitrile;
(S)-Methyl 2-(7-cyano-2-(3,4,5-trimethoxyphenyl)-1H-imidazo[1,2-b]pyrazol-3-ylamino)-3-phenylpropanoate;
Methyl 3-(7-cyano-2-(3,4-dimethoxyphenyl)-1H-imidazo[1,2-b]pyrazol-3-ylamino)benzoate;
Methyl 3-(2-(3-chloro-4,5-dimethoxyphenyl)-7-cyano-1H-imidazo[1,2-b]pyrazol-3-ylamino)benzoate;
3-(4,5-Trimethoxyphenylamino)-2-(4-morpholinophenyl)-1H-imidazo[1,2-b]pyrazole-7-carbonitrile;
3-(4-Bromophenylamino)-2-(4-morpholinophenyl)-1H-imidazo[1,2-b]pyrazole-7-carbonitrile;
4-(3-(3,4,5-Trimethoxyphenylamino)-7-cyano-1H-imidazo[1,2-b]pyrazol-2-yl)benzamide;
3-Amino-2-(3,4,5-trimethoxyphenyl)-5-(4-methoxyphenyl)-5H-imidazo[1,2-b]pyrazole-7-carbonitrile;
N-(4-(7-Cyano-2-(3,4,5-trimethoxyphenyl)-5H-imidazo[1,2-b]pyrazol-3-ylamino)benzyl)nicotinamide;
Methyl 3-(2-(4-((methoxycarbonyl)methoxy)-3-methoxyphenyl)-7-cyano-1H-imidazo[1,2-b]pyrazol-3-ylamino)benzoate;
3-(2,3-Dihydrobenzo[b][1,4]dioxin-6-ylamino)-2-(4-((methoxycarbonyl)methoxy)-3-methoxyphenyl)-1H-imidazo[1,2-b]pyrazole-7-carbonitrile;
2-(5-(7-Cyano-3-(3-(methoxycarbonyl)phenylamino)-1H-imidazo[1,2-b]pyrazol-2-yl)-2-methoxyphenoxy)acetic acid;
3-(4-Fluoro-3-methoxyphenylamino)-2-(3,4,5-trimethoxyphenyl)-1H-imidazo[1,2-b]pyrazole-7-carbonitrile;
6-(4-Chlorophenyl)-2-(3,4-dimethoxyphenyl)-5H-imidazo[1,2-b]pyrazole-7-carbonitrile;
N-(4-(7-Cyano-2-(3,4,5-trimethoxyphenyl)-5H-imidazo[1,2-b]pyrazol-3-ylamino)benzyl)-3,4-dimethoxybenzamide;
N-(4-(7-Cyano-2-(3,4,5-trimethoxyphenyl)-5H-imidazo[1,2-b]pyrazol-3-ylamino)benzyl)-3-(4-hydroxyphenyl)propanamide;
N-(4-(7-Cyano-2-(3,4,5-trimethoxyphenyl)-5H-imidazo[1,2-b]pyrazol-3-ylamino)benzyl)-3-(piperidin-1-yl)propanamide;
N-(4-(7-Cyano-2-(3,4,5-trimethoxyphenyl)-5H-imidazo[1,2-b]pyrazol-3-ylamino)benzyl)-4-cyanobenzamide;
N-(4-(7-Cyano-2-(3,4,5-trimethoxyphenyl)-5H-imidazo[1,2-b]pyrazol-3-ylamino)benzyl)-1-methylpiperidine-4-carboxamide;
N-(4-(7-Cyano-2-(3,4,5-trimethoxyphenyl)-5H-imidazo[1,2-b]pyrazol-3-ylamino)benzyl)-1H-indazole-3-carboxamide;
N-(4-(7-Cyano-2-(3,4,5-trimethoxyphenyl)-5H-imidazo[1,2-b]pyrazol-3-ylamino)benzyl)-1,6-dihydro-6-oxopyridine-3-carboxamide;
3-((1-Nicotinoylpiperidin-4-yl)methylamino)-2-(3,4,5-trimethoxyphenyl)-5H-imidazo[1,2-b]pyrazole-7-carbonitrile;
4-(3-(2,3-Dihydrobenzo[b][1,4]dioxin-6-ylamino)-7-cyano-1H-imidazo[1,2-b]pyrazol-2-yl)benzamide;
4-(3-(4-Bromophenylamino)-7-cyano-1H-imidazo[1,2-b]pyrazol-2-yl)benzamide;
Methyl 2-(4-(7-cyano-3-(3,4-dimethoxyphenylamino)-1H-imidazo[1,2-b]pyrazol-2-yl)-2-methoxyphenoxy)acetate;
3-(3,4-Dimethoxyphenylamino)-2-(3-hydroxy-4,5-dimethoxyphenyl)-1H-imidazo[1,2-b]pyrazole-7-carbonitrile;
2-(4-(2-Hydroxyethoxy)-3-methoxyphenyl)-3-(3,4-dimethoxyphenylamino)-1H-imidazo[1,2-b]pyrazole-7-carbonitrile;
3-(4-Fluoro-3-methoxyphenylamino)-2-(3,4-dimethoxyphenyl)-5H-imidazo[1,2-b]pyrazole-7-carbonitrile;
4-(3-(3,4-Dimethoxyphenylamino)-7-cyano-1H-imidazo[1,2-b]pyrazol-2-yl)benzamide;
3-(3,4-Dimethoxyphenylamino)-2-(4-morpholinophenyl)-1H-imidazo[1,2-b]pyrazole-7-carbonitrile;
3-(3,4-Dimethoxyphenylamino)-2-(3-morpholinophenyl)-1H-imidazo[1,2-b]pyrazole-7-carbonitrile;
3-(3,4-Dimethoxyphenylamino)-2-(3-(cyclopentyloxy)-4-methoxyphenyl)-1H-imidazo[1,2-b]pyrazole-7-carbonitrile;
3-(3,4-Dimethoxyphenylamino)-2-(4-(2-pyrrolidin-1-yl)ethoxy)-1H-imidazo[1,2-b]pyrazole-7-carbonitrile;
2-(4-(2-Methoxyethoxy)-3-methoxyphenyl)-3-(3,4-dimethoxyphenylamino)-1H-imidazo[1,2-b]pyrazole-7-carbonitrile;
3-(4-Fluoro-3-methoxyphenylamino)-2-(3,4-dihydro-3-oxo-2H-benzo[b][1,4]oxazin-6-yl)-1H-imidazo[1,2-b]pyrazole-7-carbonitrile;
3-(3-(Trifluoromethoxy)phenylamino)-2-(3,4,5-trimethoxyphenyl)-1H-imidazo[1,2-b]pyrazole-7-carbonitrile;
3-(3-Chloro-4-methoxyphenylamino)-2-(3,4,5-trimethoxyphenyl)-1H-imidazo[1,2-b]pyrazole-7-carbonitrile;
3-(3,4-Dimethoxyphenylamino)-2-(3-hydroxyphenyl)-1H-imidazo[1,2-b]pyrazole-7-carbonitrile;
Methyl 2-(4-(7-cyano-3-(3,4-dimethoxyphenylamino)-1H-imidazo[1,2-b]pyrazol-2-yl)phenoxy)acetate;
N-(3-(7-Cyano-3-(3,4-dimethoxyphenylamino)-1H-imidazo[1,2-b]pyrazol-2-yl)phenyl)methane sulfonamide;
3-(3-(Cyclopentyloxy)-4-methoxyphenylamino)-2-(3,4,5-trimethoxyphenyl)-1H-imidazo[1,2-b]pyrazole-7-carbonitrile;

2-(4-(2-Hydroxyethoxy)-3-methoxyphenyl)-3-(4-fluoro-3-methoxyphenylamino)-1H-imidazo[1,2-b]pyrazole-7-carbonitrile;

4-(3-(4-Fluoro-3-methoxyphenylamino)-7-cyano-1H-imidazo[1,2-b]pyrazol-2-yl)benzamide;

3-(4-Fluoro-3-methoxyphenylamino)-2-(3-hydroxy-4,5-dimethoxyphenyl)-1H-imidazo[1,2-b]pyrazole-7-carbonitrile;

3-(4-Fluoro-3-methoxyphenylamino)-2-(3-(cyclopentyloxy)-4-methoxyphenyl)-1H-imidazo[1,2-b]pyrazole-7-carbonitrile;

3-(4-Fluoro-3-methylphenylamino)-2-(3,4,5-trimethoxyphenyl)-1H-imidazo[1,2-b]pyrazole-7-carbonitrile;

3-(3-Fluoro-4-methylphenylamino)-2-(3,4,5-trimethoxyphenyl)-1H-imidazo[1,2-b]pyrazole-7-carbonitrile;

2-(4-(2-Methoxyethoxy)-3-methoxyphenyl)-3-(4-fluoro-3-methoxyphenylamino)-1H-imidazo[1,2-b]pyrazole-7-carbonitrile;

Methyl 2-(4-(7-cyano-3-(4-fluoro-3-methoxyphenylamino)-1H-imidazo[1,2-b]pyrazol-2-yl)-2-methoxyphenoxy)acetate;

2-(4-(2-Morpholinoethoxy)phenyl)-3-(3,4-dimethoxyphenylamino)-1H-imidazo[1,2-b]pyrazole-7-carbonitrile;

2-(5-(7-Cyano-3-(3,4-dimethoxyphenylamino)-1H-imidazo[1,2-b]pyrazol-2-yl)-2-methoxyphenoxy)acetamide;

3-(3-Isopropoxy-4-methoxyphenylamino)-2-(3,4,5-trimethoxyphenyl)-1H-imidazo[1,2-b]pyrazole-7-carbonitrile;

3-(3-Fluoro-4-methoxyphenylamino)-2-(3,4,5-trimethoxyphenyl)-1H-imidazo[1,2-b]pyrazole-7-carbonitrile;

3-(4-(Cyclopentyloxy)-3-methoxyphenylamino)-2-(3,4,5-trimethoxyphenyl)-1H-imidazo[1,2-b]pyrazole-7-carbonitrile;

3-(4-(2-(Pyrrolidin-1-yl)ethoxy)-3-methoxyphenylamino)-2-(3,4,5-trimethoxyphenyl)-1H-imidazo[1,2-b]pyrazole-7-carbonitrile;

3-(4-Fluoro-3-(trifluoromethyl)phenylamino)-2-(3,4,5-trimethoxyphenyl)-1H-imidazo[1,2-b]pyrazole-7-carbonitrile;

3-(4-(Trifluoromethoxy)phenylamino)-2-(3,4,5-trimethoxyphenyl)-1H-imidazo[1,2-b]pyrazole-7-carbonitrile;

3-(4-Chloro-3-methoxyphenylamino)-2-(3,4,5-trimethoxyphenyl)-1H-imidazo[1,2-b]pyrazole-7-carbonitrile;

3-(4-Fluoro-3-isopropoxyphenylamino)-2-(3,4,5-trimethoxyphenyl)-1H-imidazo[1,2-b]pyrazole-7-carbonitrile;

3-(3-Fluoro-4-(pyrrolidin-1-yl)phenylamino)-2-(3,4,5-trimethoxyphenyl)-1H-imidazo[1,2-b]pyrazole-7-carbonitrile;

2-(4-(7-Cyano-3-(3,4-dimethoxyphenylamino)-1H-imidazo[1,2-b]pyrazol-2-yl)-2-methoxyphenoxy)acetamide;

3-(3,4-Dimethoxyphenylamino)-2-(4-methoxy-3,5-dimethylphenyl)-1H-imidazo[1,2-b]pyrazole-7-carbonitrile;

3-(3,4-Dihydro-3-oxo-2H-benzo[b][1,4]oxazin-6-ylamino)-2-(3,4,5-trimethoxyphenyl)-1H-imidazo[1,2-b]pyrazole-7-carbonitrile;

2-(5-(7-Cyano-3-(4-fluoro-3-methoxyphenylamino)-1H-imidazo[1,2-b]pyrazol-2-yl)-2-methoxyphenoxy)acetamide;

2-(4-(7-Cyano-3-(4-fluoro-3-methoxyphenylamino)-1H-imidazo[1,2-b]pyrazol-2-yl)-2-methoxyphenoxy)acetamide;

2-(4-(7-Cyano-3-(3,4-dimethoxyphenylamino)-1H-imidazo[1,2-b]pyrazol-2-yl)-2-methoxyphenoxy)-N-cyclopropylacetamide;

3-(3-Chloro-4-isopropoxyphenylamino)-2-(3,4,5-trimethoxyphenyl)-1H-imidazo[1,2-b]pyrazole-7-carbonitrile;

3-(3,5-Dimethoxyphenylamino)-2-(3,4,5-trimethoxyphenyl)-1H-imidazo[1,2-b]pyrazole-7-carbonitrile;

3-(3,5-Difluoro-4-methoxyphenylamino)-2-(3,4,5-trimethoxyphenyl)-1H-imidazo[1,2-b]pyrazole-7-carbonitrile;

3-(3-Ethoxy-4-fluorophenylamino)-2-(3,4,5-trimethoxyphenyl)-1H-imidazo[1,2-b]pyrazole-7-carbonitrile;

3-(3-(Cyclopentyloxy)-4-fluorophenylamino)-2-(3,4,5-trimethoxyphenyl)-1H-imidazo[1,2-b]pyrazole-7-carbonitrile;

N-(3-(7-Cyano-2-(3,4,5-trimethoxyphenyl)-1H-imidazo[1,2-b]pyrazol-3-ylamino)benzyl)nicotinamide;

N-(3-(7-Cyano-2-(3,4,5-trimethoxyphenyl)-1H-imidazo[1,2-b]pyrazol-3-ylamino)benzyl)picolinamide;

N-(3-(7-Cyano-2-(3,4,5-trimethoxyphenyl)-1H-imidazo[1,2-b]pyrazol-3-ylamino)benzyl)isonicotinamide;

N-(4-(7-Cyano-2-(3,4,5-trimethoxyphenyl)-1H-imidazo[1,2-b]pyrazol-3-ylamino)benzyl)picolinamide;

N-(4-(7-Cyano-2-(3,4,5-trimethoxyphenyl)-1H-imidazo[1,2-b]pyrazol-3-ylamino)benzyl)isonicotinamide;

N-(4-(7-Cyano-2-(3,4,5-trimethoxyphenyl)-1H-imidazo[1,2-b]pyrazol-3-ylamino)benzyl)-6-cyanopyridine-3-carboxamide;

N-(4-(7-Cyano-2-(3,4,5-trimethoxyphenyl)-1H-imidazo[1,2-b]pyrazol-3-ylamino)benzyl)-2-methylpyridine-3-carboxamide;

N-(4-(7-Cyano-2-(3,4,5-trimethoxyphenyl)-1H-imidazo[1,2-b]pyrazol-3-ylamino)benzyl)-2-methoxypyridine-3-carboxamide;

N-(4-(7-Cyano-2-(3,4,5-trimethoxyphenyl)-1H-imidazo[1,2-b]pyrazol-3-ylamino)benzyl)-6-methylpyridine-3-carboxamide;

N-(4-(7-Cyano-2-(3,4,5-trimethoxyphenyl)-1H-imidazo[1,2-b]pyrazol-3-ylamino)benzyl)-4-(trifluoromethyl)pyridine-3-carboxamide;

N-(4-(7-Cyano-2-(3,4,5-trimethoxyphenyl)-1H-imidazo[1,2-b]pyrazol-3-ylamino)benzyl)-6-(trifluoromethyl)pyridine-3-carboxamide; and 3-(3-Fluoro-4-(methylthio)phenylamino)-2-(3,4,5-trimethoxyphenyl)-1H-imidazo[1,2-b]pyrazole-7-carbonitrile.

Where desired, one or more compounds may be excluded from the formulae Ib-VIIb, as set out below:

N-(4-(7-cyano-3-(3-(methylthio)phenylamino)-5H-imidazo[1,2-b]pyrazol-2-yl)phenyl)acetamide;

2-(4-(dimethylamino)phenyl)-3-(3-(methylthio)phenylamino)-5H-imidazo[1,2-b]pyrazole-7-carbonitrile;

3-(3-(methylthio)phenylamino)-2-(3,4,5-trimethoxyphenyl)-5H-imidazo[1,2-b]pyrazole-7-carbonitrile;

3-(3-(methylthio)phenylamino)-2-(thiophen-2-yl)-5H-imidazo[1,2-b]pyrazole-7-carbonitrile;

3-(3-(methylthio)phenylamino)-2-phenyl-5H-imidazo[1,2-b]pyrazole-7-carbonitrile;

N-(4-(3-(2-bromophenylamino)-7-cyano-5H-imidazo[1,2-b]pyrazol-2-yl)phenyl)acetamide;

3-(2-bromophenylamino)-2-(4-(dimethylamino)phenyl)-5H-imidazo[1,2-b]pyrazole-7-carbonitrile;

3-(2-bromophenylamino)-2-(3,4,5-trimethoxyphenyl)-5H-imidazo[1,2-b]pyrazole-7-carbonitrile;

3-(2-bromophenylamino)-2-(2-fluorophenyl)-5H-imidazo[1,2-b]pyrazole-7-carbonitrile;

3-(2-bromophenylamino)-2-(3,4-difluorophenyl)-5H-imidazo[1,2-b]pyrazole-7-carbonitrile;

3-(2-bromophenylamino)-2-(furan-2-yl)-5H-imidazo[1,2-b]pyrazole-7-carbonitrile;

3-(2-bromophenylamino)-2-(3,4-dichlorophenyl)-5H-imidazo[1,2-b]pyrazole-7-carbonitrile;

3-(2-bromophenylamino)-2-(thiophen-2-yl)-5H-imidazo[1,2-b]pyrazole-7-carbonitrile;
3-(2-bromophenylamino)-2-(3-(trifluoromethyl)phenyl)-5H-imidazo[1,2-b]pyrazole-7-carbonitrile;
3-(2-bromophenylamino)-2-phenyl-5H-imidazo[1,2-b]pyrazole-7-carbonitrile;
4-(3-(2-bromophenylamino)-7-cyano-5H-imidazo[1,2-b]pyrazol-2-yl)benzoic acid;
3-(3-cyanophenylamino)-2-(4-(dimethylamino)phenyl)-5H-imidazo[1,2-b]pyrazole-7-carbonitrile;
3-(3-cyanophenylamino)-2-(3,4,5-trimethoxyphenyl)-5H-imidazo[1,2-b]pyrazole-7-carbonitrile;
2-(4-(dimethylamino)phenyl)-3-(3-(trifluoromethyl)phenylamino)-5H-imidazo[1,2-b]pyrazole-7-carbonitrile;
3-(3-(trifluoromethyl)phenylamino)-2-(3,4,5-trimethoxyphenyl)-5H-imidazo[1,2-b]pyrazole-7-carbonitrile;
2-(thiophen-2-yl)-3-(3-(trifluoromethyl)phenylamino)-5H-imidazo[1,2-b]pyrazole-7-carbonitrile;
2-phenyl-3-(3-(trifluoromethyl)phenylamino)-5H-imidazo[1,2-b]pyrazole-7-carbonitrile;
N-(4-(7-cyano-3-(2,4-dimethylphenylamino)-5H-imidazo[1,2-b]pyrazol-2-yl)phenyl)acetamide;
2-(4-(dimethylamino)phenyl)-3-(2,4-dimethylphenylamino)-5H-imidazo[1,2-b]pyrazole-7-carbonitrile;
3-(2,4-dimethylphenylamino)-2-(3,4,5-trimethoxyphenyl)-5H-imidazo[1,2-b]pyrazole-7-carbonitrile;
3-(2,4-dimethylphenylamino)-2-(2-fluorophenyl)-5H-imidazo[1,2-b]pyrazole-7-carbonitrile;
2-(3,4-difluorophenyl)-3-(2,4-dimethylphenylamino)-5H-imidazo[1,2-b]pyrazole-7-carbonitrile;
3-(2,4-dimethylphenylamino)-2-(furan-2-yl)-5H-imidazo[1,2-b]pyrazole-7-carbonitrile;
2-(3,4-dichlorophenyl)-3-(2,4-dimethylphenylamino)-5H-imidazo[1,2-b]pyrazole-7-carbonitrile;
3-(2,4-dimethylphenylamino)-2-(thiophen-2-yl)-5H-imidazo[1,2-b]pyrazole-7-carbonitrile;
3-(2,4-dimethylphenylamino)-2-(3-(trifluoromethyl)phenyl)-5H-imidazo[1,2-b]pyrazole-7-carbonitrile;
3-(2,4-dimethylphenylamino)-2-phenyl-5H-imidazo[1,2-b]pyrazole-7-carbonitrile;
4-(7-cyano-3-(2,4-dimethylphenylamino)-5H-imidazo[1,2-b]pyrazol-2-yl)benzoic acid;
methyl 4-(7-cyano-2-(4-(dimethylamino)phenyl)-5H-imidazo[1,2-b]pyrazol-3-ylamino)benzoate;
methyl 4-(7-cyano-2-(3,4,5-trimethoxyphenyl)-5H-imidazo[1,2-b]pyrazol-3-ylamino)benzoate;
methyl 4-(7-cyano-2-phenyl-5H-imidazo[1,2-b]pyrazol-3-ylamino)benzoate;
N-(4-(3-(5-chloro-2-methoxyphenylamino)-7-cyano-5H-imidazo[1,2-b]pyrazol-2-yl)phenyl)acetamide;
3-(5-chloro-2-methoxyphenylamino)-2-(4-(dimethylamino)phenyl)-5H-imidazo[1,2-b]pyrazole-7-carbonitrile;
3-(5-chloro-2-methoxyphenylamino)-2-(3,4,5-trimethoxyphenyl)-5H-imidazo[1,2-b]pyrazole-7-carbonitrile;
3-(5-chloro-2-methoxyphenylamino)-2-(furan-2-yl)-5H-imidazo[1,2-b]pyrazole-7-carbonitrile;
3-(5-chloro-2-methoxyphenylamino)-2-(3,4-dichlorophenyl)-5H-imidazo[1,2-b]pyrazole-7-carbonitrile;
3-(5-chloro-2-methoxyphenylamino)-2-(thiophen-2-yl)-5H-imidazo[1,2-b]pyrazole-7-carbonitrile;
3-(5-chloro-2-methoxyphenylamino)-2-phenyl-5H-imidazo[1,2-b]pyrazole-7-carbonitrile;
4-(3-(5-chloro-2-methoxyphenylamino)-7-cyano-5H-imidazo[1,2-b]pyrazol-2-yl)benzoic acid;
2-(biphenyl-4-yl)-3-(3-(methylthio)phenylamino)-5H-imidazo[1,2-b]pyrazole-7-carbonitrile;
2-(4-chlorophenyl)-3-(3-(methylthio)phenylamino)-5H-imidazo[1,2-b]pyrazole-7-carbonitrile;
3-(3-(methylthio)phenylamino)-2-(pyridin-2-yl)-5H-imidazo[1,2-b]pyrazole-7-carbonitrile;
2-(4-(methylthio)phenyl)-3-(3-(methylthio)phenylamino)-5H-imidazo[1,2-b]pyrazole-7-carbonitrile;
2-(6-methylpyridin-2-yl)-3-(3-(methylthio)phenylamino)-5H-imidazo[1,2-b]pyrazole-7-carbonitrile;
3-(3-(methylthio)phenylamino)-2-(quinolin-4-yl)-5H-imidazo[1,2-b]pyrazole-7-carbonitrile;
2-(6-methylpyridin-2-yl)-3-(pyridin-2-ylamino)-5H-imidazo[1,2-b]pyrazole-7-carbonitrile;
2-(biphenyl-4-yl)-3-(2-bromophenylamino)-5H-imidazo[1,2-b]pyrazole-7-carbonitrile;
3-(2-bromophenylamino)-2-(pyridin-3-yl)-5H-imidazo[1,2-b]pyrazole-7-carbonitrile;
3-(2-bromophenylamino)-2-(4-chlorophenyl)-5H-imidazo[1,2-b]pyrazole-7-carbonitrile;
3-(2-bromophenylamino)-2-(pyridin-2-yl)-5H-imidazo[1,2-b]pyrazole-7-carbonitrile;
3-(2-bromophenylamino)-2-(4-(methylthio)phenyl)-5H-imidazo[1,2-b]pyrazole-7-carbonitrile;
3-(2-bromophenylamino)-2-(6-methylpyridin-2-yl)-5H-imidazo[1,2-b]pyrazole-7-carbonitrile;
3-(2-bromophenylamino)-2-(pyridin-4-yl)-5H-imidazo[1,2-b]pyrazole-7-carbonitrile;
2-(biphenyl-4-yl)-3-(3-cyanophenylamino)-5H-imidazo[1,2-b]pyrazole-7-carbonitrile;
3-(3-cyanophenylamino)-2-(pyridin-3-yl)-5H-imidazo[1,2-b]pyrazole-7-carbonitrile;
2-(4-chlorophenyl)-3-(3-cyanophenylamino)-5H-imidazo[1,2-b]pyrazole-7-carbonitrile;
3-(3-cyanophenylamino)-2-(pyridin-2-yl)-5H-imidazo[1,2-b]pyrazole-7-carbonitrile;
3-(3-cyanophenylamino)-2-(4-(methylthio)phenyl)-5H-imidazo[1,2-b]pyrazole-7-carbonitrile;
3-(3-cyanophenylamino)-2-(6-methylpyridin-2-yl)-5H-imidazo[1,2-b]pyrazole-7-carbonitrile;
2-(biphenyl-4-yl)-3-(3-(trifluoromethyl)phenylamino)-5H-imidazo[1,2-b]pyrazole-7-carbonitrile;
2-(4-chlorophenyl)-3-(3-(trifluoromethyl)phenylamino)-5H-imidazo[1,2-b]pyrazole-7-carbonitrile;
2-(pyridin-2-yl)-3-(3-(trifluoromethyl)phenylamino)-5H-imidazo[1,2-b]pyrazole-7-carbonitrile;
2-(4-(methylthio)phenyl)-3-(3-(trifluoromethyl)phenylamino)-5H-imidazo[1,2-b]pyrazole-7-carbonitrile;
2-(6-methylpyridin-2-yl)-3-(3-(trifluoromethyl)phenylamino)-5H-imidazo[1,2-b]pyrazole-7-carbonitrile;
2-(6-methylpyridin-2-yl)-3-(3-(trifluoromethyl)phenylamino)-5H-imidazo[1,2-b]pyrazole-7-carbonitrile;
3-(2,4-dimethylphenylamino)-2-(pyridin-3-yl)-5H-imidazo[1,2-b]pyrazole-7-carbonitrile;
2-(4-chlorophenyl)-3-(2,4-dimethylphenylamino)-5H-imidazo[1,2-b]pyrazole-7-carbonitrile;
3-(2,4-dimethylphenylamino)-2-(pyridin-2-yl)-5H-imidazo[1,2-b]pyrazole-7-carbonitrile;
3-(2,4-dimethylphenylamino)-2-(4-(methylthio)phenyl)-5H-imidazo[1,2-b]pyrazole-7-carbonitrile;
3-(2,4-dimethylphenylamino)-2-(6-methylpyridin-2-yl)-5H-imidazo[1,2-b]pyrazole-7-carbonitrile;
3-(2,4-dimethylphenylamino)-2-(quinolin-4-yl)-5H-imidazo[1,2-b]pyrazole-7-carbonitrile;
3-(2,4-dimethylphenylamino)-2-(pyridin-4-yl)-5H-imidazo[1,2-b]pyrazole-7-carbonitrile;
methyl 4-(2-(biphenyl-4-yl)-7-cyano-5H-imidazo[1,2-b]pyrazol-3-ylamino)benzoate;

methyl 4-(2-(4-chlorophenyl)-7-cyano-5H-imidazo[1,2-b]pyrazol-3-ylamino)benzoate;
methyl 4-(7-cyano-2-(pyridin-2-yl)-5H-imidazo[1,2-b]pyrazol-3-ylamino)benzoate;
methyl 4-(7-cyano-2-(4-(methylthio)phenyl)-5H-imidazo[1,2-b]pyrazol-3-ylamino)benzoate;
methyl 4-(7-cyano-2-(6-methylpyridin-2-yl)-5H-imidazo[1,2-b]pyrazol-3-ylamino)benzoate;
2-(biphenyl-4-yl)-3-(5-chloro-2-methoxyphenylamino)-5H-imidazo[1,2-b]pyrazole-7-carbonitrile;
3-(5-chloro-2-methoxyphenylamino)-2-(pyridin-3-yl)-5H-imidazo[1,2-b]pyrazole-7-carbonitrile;
3-(5-chloro-2-methoxyphenylamino)-2-(pyridin-2-yl)-5H-imidazo[1,2-b]pyrazole-7-carbonitrile;
3-(5-chloro-2-methoxyphenylamino)-2-(4-(methylthio)phenyl)-5H-imidazo[1,2-b]pyrazole-7-carbonitrile;
3-(5-chloro-2-methoxyphenylamino)-2-(6-methylpyridin-2-yl)-5H-imidazo[1,2-b]pyrazole-7-carbonitrile;
3-(5-chloro-2-methoxyphenylamino)-2-(quinolin-4-yl)-5H-imidazo[1,2-b]pyrazole-7-carbonitrile;
3-(benzo[d][1,3]dioxol-5-ylamino)-2-(pyridin-2-yl)-5H-imidazo[1,2-b]pyrazole-7-carbonitrile;
3-(benzo[d][1,3]dioxol-5-ylamino)-2-(6-methylpyridin-2-yl)-5H-imidazo[1,2-b]pyrazole-7-carbonitrile;
3-(benzo[d][1,3]dioxol-5-ylamino)-2-tert-butyl-5H-imidazo[1,2-b]pyrazole-7-carbonitrile;
N-(4-(3-(benzo[d][1,3]dioxol-5-ylamino)-7-cyano-5H-imidazo[1,2-b]pyrazol-2-yl)phenyl)acetamide;
3-(benzo[d][1,3]dioxol-5-ylamino)-2-(4-(dimethylamino)phenyl)-5H-imidazo[1,2-b]pyrazole-7-carbonitrile;
4-(3-(benzo[d][1,3]dioxol-5-ylamino)-7-cyano-5H-imidazo[1,2-b]pyrazol-2-yl)benzoic acid;
3-(benzo[d][1,3]dioxol-5-ylamino)-2-p-tolyl-5H-imidazo[1,2-b]pyrazole-7-carbonitrile;
3-(benzo[d][1,3]dioxol-5-ylamino)-2-(4-(benzyloxy)phenyl)-5H-imidazo[1,2-b]pyrazole-7-carbonitrile;
3-(2-chlorophenylamino)-2-(pyridin-4-yl)-5H-imidazo[1,2-b]pyrazole-7-carbonitrile;
3-(2-chlorophenylamino)-2-(pyridin-3-yl)-5H-imidazo[1,2-b]pyrazole-7-carbonitrile;
3-(2-chlorophenylamino)-2-(pyridin-2-yl)-5H-imidazo[1,2-b]pyrazole-7-carbonitrile;
3-(2-chlorophenylamino)-2-(6-methylpyridin-2-yl)-5H-imidazo[1,2-b]pyrazole-7-carbonitrile;
3-(2-chlorophenylamino)-2-(quinolin-4-yl)-5H-imidazo[1,2-b]pyrazole-7-carbonitrile;
3-(2-chlorophenylamino)-2-cyclopropyl-5H-imidazo[1,2-b]pyrazole-7-carbonitrile;
2-tert-butyl-3-(2-chlorophenylamino)-5H-imidazo[1,2-b]pyrazole-7-carbonitrile;
3-(2-chlorophenylamino)-2-phenethyl-5H-imidazo[1,2-b]pyrazole-7-carbonitrile;
3-(2-chlorophenylamino)-2-(4-(methylthio)phenyl)-5H-imidazo[1,2-b]pyrazole-7-carbonitrile;
N-(4-(3-(2-chlorophenylamino)-7-cyano-5H-imidazo[1,2-b]pyrazol-2-yl)phenyl)acetamide;
3-(2-chlorophenylamino)-2-(4-(dimethylamino)phenyl)-5H-imidazo[1,2-b]pyrazole-7-carbonitrile;
3-(2-chlorophenylamino)-2-(3,4,5-trimethoxyphenyl)-5H-imidazo[1,2-b]pyrazole-7-carbonitrile;
2-(biphenyl-4-yl)-3-(2-chlorophenylamino)-5H-imidazo[1,2-b]pyrazole-7-carbonitrile;
3-(2-chlorophenylamino)-2-(2-fluorophenyl)-5H-imidazo[1,2-b]pyrazole-7-carbonitrile;
3-(2-chlorophenylamino)-2-(3,4-difluorophenyl)-5H-imidazo[1,2-b]pyrazole-7-carbonitrile;
3-(2-chlorophenylamino)-2-(5-methylthiophen-2-yl)-5H-imidazo[1,2-b]pyrazole-7-carbonitrile;
3-(2-chlorophenylamino)-2-(furan-2-yl)-5H-imidazo[1,2-b]pyrazole-7-carbonitrile;
3-(2-chlorophenylamino)-2-(3,4-dichlorophenyl)-5H-imidazo[1,2-b]pyrazole-7-carbonitrile;
3-(2-chlorophenylamino)-2-phenyl-5H-imidazo[1,2-b]pyrazole-7-carbonitrile;
4-(3-(2-chlorophenylamino)-7-cyano-5H-imidazo[1,2-b]pyrazol-2-yl)benzoic acid;
2-(4-tert-butylphenyl)-3-(2-chlorophenylamino)-5H-imidazo[1,2-b]pyrazole-7-carbonitrile;
3-(2-chlorophenylamino)-2-(2,4-difluorophenyl)-5H-imidazo[1,2-b]pyrazole-7-carbonitrile;
3-(2-chlorophenylamino)-2-p-tolyl-5H-imidazo[1,2-b]pyrazole-7-carbonitrile;
3-(2-chlorophenylamino)-2-(3,4-dimethoxyphenyl)-5H-imidazo[1,2-b]pyrazole-7-carbonitrile;
3-(2-chlorophenylamino)-2-(naphthalen-1-yl)-5H-imidazo[1,2-b]pyrazole-7-carbonitrile;
(5-(3-(2-chlorophenylamino)-7-cyano-5H-imidazo[1,2-b]pyrazol-2-yl)furan-2-yl)methyl acetate;
2-(4-(benzyloxy)phenyl)-3-(2-chlorophenylamino)-5H-imidazo[1,2-b]pyrazole-7-carbonitrile;
3-(2-chlorophenylamino)-2-(3-(3-(trifluoromethyl)phenoxy)phenyl)-5H-imidazo[1,2-b]pyrazole-7-carbonitrile;
3-(2,4-dimethoxyphenylamino)-2-(pyridin-3-yl)-5H-imidazo[1,2-b]pyrazole-7-carbonitrile;
3-(2,4-dimethoxyphenylamino)-2-(6-methylpyridin-2-yl)-5H-imidazo[1,2-b]pyrazole-7-carbonitrile;
2-cyclopropyl-3-(2,4-dimethoxyphenylamino)-5H-imidazo[1,2-b]pyrazole-7-carbonitrile;
2-tert-butyl-3-(2,4-dimethoxyphenylamino)-5H-imidazo[1,2-b]pyrazole-7-carbonitrile;
3-(2,4-dimethoxyphenylamino)-2-(4-(methylthio)phenyl)-5H-imidazo[1,2-b]pyrazole-7-carbonitrile;
N-(4-(7-cyano-3-(2,4-dimethoxyphenylamino)-5H-imidazo[1,2-b]pyrazol-2-yl)phenyl)acetamide;
3-(2,4-dimethoxyphenylamino)-2-(4-(dimethylamino)phenyl)-5H-imidazo[1,2-b]pyrazole-7-carbonitrile;
2-(3,4-difluorophenyl)-3-(2,4-dimethoxyphenylamino)-5H-imidazo[1,2-b]pyrazole-7-carbonitrile;
2-(3,4-dichlorophenyl)-3-(2,4-dimethoxyphenylamino)-5H-imidazo[1,2-b]pyrazole-7-carbonitrile;
3-(2,4-dimethoxyphenylamino)-2-phenyl-5H-imidazo[1,2-b]pyrazole-7-carbonitrile;
4-(7-cyano-3-(2,4-dimethoxyphenylamino)-5H-imidazo[1,2-b]pyrazol-2-yl)benzoic acid;
3-(2,4-dimethoxyphenylamino)-2-(2-(trifluoromethyl)phenyl)-5H-imidazo[1,2-b]pyrazole-7-carbonitrile;
2-(2,4-difluorophenyl)-3-(2,4-dimethoxyphenylamino)-5H-imidazo[1,2-b]pyrazole-7-carbonitrile;
3-(2,4-dimethoxyphenylamino)-2-p-tolyl-5H-imidazo[1,2-b]pyrazole-7-carbonitrile;
2-(3,4-dimethoxyphenyl)-3-(2,4-dimethoxyphenylamino)-5H-imidazo[1,2-b]pyrazole-7-carbonitrile;
2-(4-(benzyloxy)phenyl)-3-(2,4-dimethoxyphenylamino)-5H-imidazo[1,2-b]pyrazole-7-carbonitrile;
3-(2,4-dimethoxyphenylamino)-2-(3-(3-(trifluoromethyl)phenoxy)phenyl)-5H-imidazo[1,2-b]pyrazole-7-carbonitrile.

Pharmaceutical Compositions and Methods of Use

The present disclosure also provides pharmaceutical compositions containing a pharmaceutically acceptable carrier and a therapeutically effective amount of a compound of formulae Ia-Xa and Ib-VIIb or a pharmaceutically acceptable salt or solvate or stereoisomer thereof.

A disclosed compound can be administered alone, as the sole active pharmaceutical agent, or in combination with one or more additional subject compounds or in conjunction with other agents. When administered as a combination, the therapeutic agents can be formulated as separate compositions that are administered simultaneously or at different times, or the therapeutic agents can be administered together as a single composition combining two or more therapeutic agents. Thus, the pharmaceutical compositions disclosed herein containing a subject compound optionally contain other therapeutic agents. Accordingly, certain embodiments are directed to such pharmaceutical composition, wherein the composition further contains a therapeutically effective amount of an agent selected as is known to those of skill in the art.

The subject compounds can inhibit a Syk activity. Accordingly, the compounds are useful for treating a disease or disorder that is mediated through the activity of a Syk activity in a subject. The present disclosure provides methods of treating conditions such as inflammatory conditions or diseases, autoimmune diseases, cell proliferative disorders, and degenerative bone disorders in a subject by administering an effective amount of a subject compound, including a salt or solvate or stereoisomer thereof.

The present disclosure provides a method of treating inflammatory conditions or diseases in a subject, the method involving administering to the subject with a compound of formulae Ia-Xa and Ib-VIIb or a salt or solvate or stereoisomer thereof.

Inflammatory conditions or diseases include, but are not limited to, anaphylactic reactions, anaphylactoid reactions, hay fever, allergic conjunctivitis, allergic rhinitis, allergic asthma, COPD, atopic dermatitis, eczema, urticaria, mucosal disorders, tissue disorders, and certain gastrointestinal disorders.

Other inflammatory conditions or diseases include, but are not limited to, osteoarthritis, inflammatory bowel disease, ulcerative colitis, Crohn's disease, idiopathic inflammatory bowel disease, irritable bowel syndrome, spastic colon, low grade scarring, scleroderma, increased fibrosis, keloids, post-surgical scars, pulmonary fibrosis, vascular spasms, migraine, reperfusion injury, post myocardial infarction, and sicca complex or syndrome.

Other inflammatory conditions or diseases include, but are not limited to, asthma, COPD, lung inflammation, chronic granulomatous diseases such as tuberculosis, leprosy, sarcoidosis, and silicosis, nephritis, amyloidosis, rheumatoid arthritis, ankylosing spondylitis, chronic bronchitis, scleroderma, lupus, polymyositis, appendicitis, inflammatory bowel disease, Crohn's disease, ulcerative colitis, psoriasis, pelvic inflammatory disease, irritable bowel syndrome, orbital inflammatory disease, thrombotic disease, and inappropriate allergic responses to environmental stimuli such as poison ivy, pollen, insect stings and certain foods, including atopic dermatitis and contact dermatitis.

The present disclosure provides a method of treating autoimmune diseases in a subject, the method involving administering to the subject with a compound of formulae Ia-Xa and Ib-VIIb or a salt or solvate or stereoisomer thereof.

Autoimmune diseases include, but are not limited to, Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy. Non-limiting examples of diseases often designated as involving systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid. A particular autoimmune disease of interest is rheumatoid arthritis.

The present disclosure provides a method of treating cell proliferative disorders in a subject, the method involving administering to the subject with a compound of formulae Ia-Xa and Ib-VIIb or a salt or solvate or stereoisomer thereof.

Cell proliferative disorders include, but are not limited to, breast cancer, ovarian cancer, renal cancer, gastrointestinal cancer, kidney cancer, bladder cancer, pancreatic cancer, lung squamous carcinoma, and adenocarcinoma.

A particular proliferative disorder is hematopoietic neoplasm. Hematopoietic neoplasm includes lymphoid neoplasm and myeloid neoplasm.

Other cell proliferative disorders include, but are not limited to, acute myeloid leukemias, virally mediated tumors, and tumor metastasis.

The present disclosure provides a method of treating degenerative bone disorders in a subject, the method involving administering to the subject with a compound of formulae Ia-Xa and Ib-VIIb or a salt or solvate or stereoisomer thereof.

Degenerative bone disorders include, but are not limited to, primary osteoporosis, idiopathic osteoporosis, juvenile osteoporosis, osteodystrophy, Paget's Disease, periodontal disease, degenerative bone disorders arising from a secondary condition, and bone degeneration associated with heritable genetic disorders.

The embodiments are also directed to a compound of formulae Ia-Xa and Ib-VIIb or a salt or solvate or stereoisomer thereof, for use in therapy or as a medicament.

Additionally, the embodiments are directed to the use of a compound of formulae Ia-Xa and Ib-VIIb or a salt or solvate or stereoisomer thereof, for the manufacture of a medicament; especially for the manufacture of a medicament for the inhibition of Syk activity.

The embodiments are also directed to the use of a compound of formulae Ia-Xa and Ib-VIIb or a salt or solvate or stereoisomer thereof for the manufacture of a medicament for the treatment of a disease or disorder mediated or sustained through the activity of Syk activity. Diseases or conditions of interest include, but are not limited to, inflammatory conditions or diseases, autoimmune diseases, cell proliferative disorders, and degenerative bone disorders.

Since subject compounds possess Syk inhibitory properties, such compounds are also useful as research tools. Accordingly, the disclosure also provides for a method for using a compound of formulae Ia-Xa and Ib-VIIb or a salt or solvate or stereoisomer thereof as a research tool for studying a biological system or sample, or for discovering new chemical compounds having Syk inhibitory properties.

Processes and Intermediates

The embodiments are also directed to processes and intermediates useful for preparing subject compounds or a salt or solvate or stereoisomer thereof. Accordingly, the present disclosure provides a process of preparing a subject compound, the process involves: contacting a compound of formula 1:

a compound of formula 3:

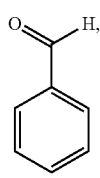

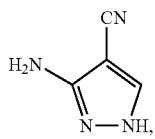

and a compound of formula 6:

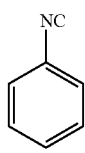

together, wherein compounds of formulae 1 and 6 are appropriately substituted.

In one instance, the above process further involving the step of forming a salt of a subject compound. Embodiments are directed to the other processes described herein; and to the product prepared by any of the processes described herein.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001.)

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis", Fourth edition, Wiley, New York 2006. The protecting groups may be removed at a convenient subsequent stage using methods known from the art.

A representative synthesis for subject compounds is shown in Scheme 1.

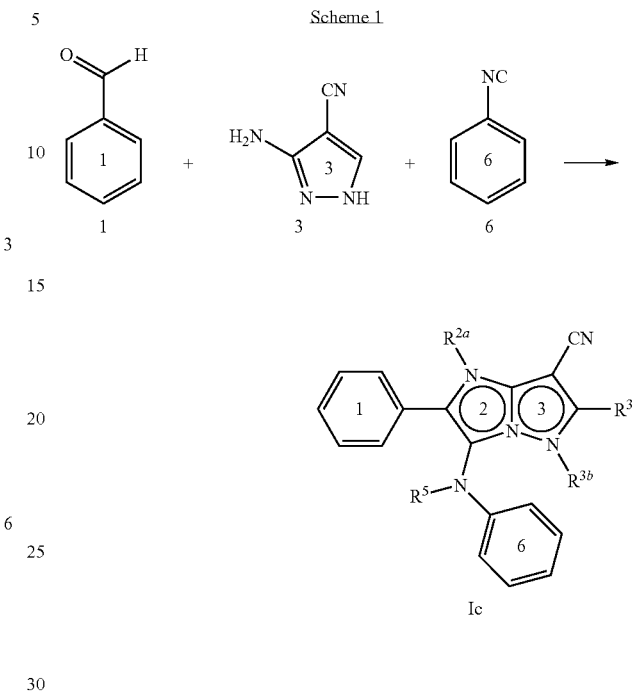

In Scheme 1, Compounds 1, 3, and 6 react to form Compound Ic. Compound Ic is an embodiment wherein $R^1$ is shown as Ring 1 and $R^6$ is shown as Ring 6. Rings 1 and 6 can be appropriately substituted, for example, as set forth in Formulas Ia-Xa and Ib-VIIb.

Compounds 1, 3, and 6 are commercially available starting materials. Alternatively, Compounds 1, 3, and 6 can be synthesized via a variety of different synthetic routes using commercially available starting materials and/or starting materials prepared by conventional synthetic methods.

With continued reference to Scheme 1, Compounds 1, 3, and 6 are combined with an acid to react in a condensation reaction such that the aldehyde of Compound 1 and the isonitrile of Compound 6 react with the amino groups of Compound 3 to form the imidazole (Ring 2) in Compound Ib.

The reaction can be run in a solvent. In certain cases, the solvent is a polar solvent, such as, but not limited to, methanol, ethanol, isopropanol, dimethylformanide, dimethylacetamide, N-methylpyrrolidinone, dimethylsulfoxide, and acetonitrile. The reaction can be run at various temperatures, including with cooling, at room temperature, or with heating. One skilled in the art would be able to determine suitable reaction conditions according to the specific reactants.

An acid is added to the reaction. In certain instances, the acid is a strong acid. Examples of suitable strong acids include perchloric acid, hydroiodic acid, hydrobromic acid, hydrochloric acid, sulfuric acid, nitric acid, chloric acid, bromic acid, perbromic acid, iodic acid, and periodic acid.

Compound 6 can be synthesized via a variety of different synthetic routes using commercially available starting materials and/or starting materials prepared by conventional synthetic methods. A representative synthesis for Compound 6 is shown in Scheme 2. As stated herein, Compound 6 can be appropriately substituted.

Scheme 2

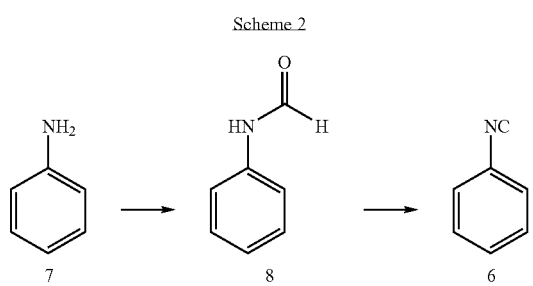

Compound 7 is a commercially available starting material. Alternatively, Compound 7 can be synthesized via a variety of different synthetic routes using commercially available starting materials and/or starting materials prepared by conventional synthetic methods.

In Scheme 2, the amine of Compound 7 is converted to a formamide of Compound 8. In a formylation reaction, Compound 7 can react with a formylating reagent. Examples of suitable formylating reagents include, but are not limited to, acetic formic anhydride, formic acid, dimethylformamide, and 2,2,2-trifluoroethyl formate. Certain formylating reagents are listed in Greene and Wuts in Protective Groups in Organic Synthesis, 3rd edition, Wiley-Interscience.

With continued reference to Scheme 2, the formamide of Compound 8 is converted to an isonitrile of Compound 6. A formamide can be converted to an isonitrile under dehydrating conditions. Suitable dehydrating reagents include, but are not limited to, phosphorus chloride oxide, trichlorotriazine, thionyl chloride, and phosphorus oxychloride. The reaction conditions can include a base with the dehydrating reagent. Suitable bases include amines such as diisopropylethylamine, pyridine, and triethylamine.

Pharmaceutical Compositions

The disclosed compounds are useful, at least, for the inhibition of Syk activity and the treatment of a disease or disorder that is mediated through the activity of a Syk activity. Accordingly, pharmaceutical compositions containing at least one disclosed compound are also described herein.

A pharmaceutical composition containing a subject compound may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A subject compound may be administered to the host using any convenient means capable of resulting in the desired reduction in disease condition or symptom. Thus, a subject compound can be incorporated into a variety of formulations for therapeutic administration. More particularly, a subject compound can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Formulations for pharmaceutical compositions are well known in the art. For example, Remington's Pharmaceutical Sciences, by E. W. Martin, Mack Publishing Co., Easton, Pa., 19th Edition, 1995, describes exemplary formulations (and components thereof) suitable for pharmaceutical delivery of disclosed compounds. Pharmaceutical compositions containing at least one of the subject compounds can be formulated for use in human or veterinary medicine. Particular formulations of a disclosed pharmaceutical composition may depend, for example, on the mode of administration and/or on the location of the infection to be treated. In some instances, formulations include a pharmaceutically acceptable carrier in addition to at least one active ingredient, such as a subject compound. In other instances, other medicinal or pharmaceutical agents, for example, with similar, related or complementary effects on the affliction being treated can also be included as active ingredients in a pharmaceutical composition.

Pharmaceutically acceptable carriers useful for the disclosed methods and compositions are conventional in the art. The nature of a pharmaceutical carrier will depend on the particular mode of administration being employed. For example, parenteral formulations usually contain injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The disclosed pharmaceutical compositions may be formulated as a pharmaceutically acceptable salt of a disclosed compound. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydroiodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Lists of other suitable pharmaceutically acceptable salts are found in Remington's Pharmaceutical Sciences, 17th Edition, Mack Publishing Company, Easton, Pa., 1985. A pharmaceutically acceptable salt may also serve to adjust the osmotic pressure of the composition.

A subject compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The preparation may also be emulsified or the active ingredient encapsulated in liposome vehicles. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

In certain instances, a subject compound can be delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

A subject compound can be utilized in aerosol formulation to be administered via inhalation. A subject compound can be formulated into pressurized acceptable propellants such as dichlorodifluoromethane, propane, nitrogen and the like.

Furthermore, a subject compound can be made into suppositories by mixing with a variety of bases such as emulsifying bases or water-soluble bases. A subject compound can be administered rectally via a suppository. The suppository can include vehicles such as cocoa butter, carbowaxes and polyethylene glycols, which melt at body temperature, yet are solidified at room temperature.

The term "unit dosage form," as used herein, refers to physically discrete units suitable as unitary dosages for human and animal subjects, each unit containing a predetermined quantity of a subject compound calculated in an amount sufficient to produce the desired effect in association with a pharmaceutically acceptable diluent, carrier or vehicle. The specifications for a subject compound depend on the particular compound employed and the effect to be achieved, and the pharmacodynamics associated with each compound in the host.

The dosage form of a disclosed pharmaceutical composition will be determined by the mode of administration chosen. For example, in addition to injectable fluids, topical or oral dosage forms may be employed. Topical preparations may include eye drops, ointments, sprays and the like. Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions contain a subject compound may be formulated in unit dosage form suitable for individual administration of precise dosages. The amount of active ingredient administered will depend on the subject being treated, the severity of the affliction, and the manner of administration, and is known to those skilled in the art. Within these bounds, the formulation to be administered will contain a quantity of the extracts or compounds disclosed herein in an amount effective to achieve the desired effect in the subject being treated.

Each therapeutic compound can independently be in any dosage form, such as those described herein, and can also be administered in various ways, as described herein. For example, the compounds may be formulated together, in a single dosage unit (that is, combined together in one form such as capsule, tablet, powder, or liquid, etc.) as a combination product. Alternatively, when not formulated together in a single dosage unit, an individual subject compound may be administered at the same time as another therapeutic compound or sequentially, in any order thereof.

Methods of Administration

The subject compounds can inhibit a Syk activity. Accordingly, the subject compounds are useful for treating a disease or disorder that is mediated through the activity of a Syk activity in a subject.

The route of administration will be selected according to a variety of factors including, but not necessarily limited to, the condition to be treated, the formulation and/or device used, the patient to be treated, and the like. Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described herein.

An effective amount of a subject compound will depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (host) being treated. For example, this may be the amount of a subject compound necessary to prevent, inhibit, reduce or relieve a disease or disorder that is mediated through the activity of a Syk activity in a subject. Ideally, a therapeutically effective amount of a compound is an amount sufficient to prevent, inhibit, reduce or relieve a disease or disorder that is mediated through the activity of a Syk activity in a subject without causing a substantial cytotoxic effect on host cells.

Therapeutically effective doses (or growth inhibitory amounts) of a subject compound or pharmaceutical composition can be determined by one of skill in the art, with a goal of achieving local (e.g., tissue) concentrations that are at least as high as the $IC_{50}$ of an applicable compound disclosed herein.

An example of a dosage range is from about 0.1 to about 200 mg/kg body weight orally in single or divided doses. In particular examples, a dosage range is from about 1.0 to about 100 mg/kg body weight orally in single or divided doses, including from about 1.0 to about 50 mg/kg body weight, from about 1.0 to about 25 mg/kg body weight, from about 1.0 to about 10 mg/kg body weight (assuming an average body weight of approximately 70 kg; values adjusted accordingly for persons weighing more or less than average). For oral administration, the compositions are, for example, provided in the form of a tablet containing from about 50 to about 1000 mg of the active ingredient, particularly about 75 mg, about 100 mg, about 200 mg, about 400 mg, about 500 mg, about 600 mg, about 750 mg, or about 1000 mg of the active ingredient for the symptomatic adjustment of the dosage to the subject being treated. In one exemplary oral dosage regimen, a tablet containing from about 500 mg to about 1000 mg active ingredient is administered once (e.g., a loading dose) followed by administration of ½ dosage tablets (e.g., from about 250 to about 500 mg) each 6 to 24 hours for at least 3 days.

The specific dose level and frequency of dosage for any particular subject may be varied and will depend upon a variety of factors, including the activity of the subject compound, the metabolic stability and length of action of that compound, the age, body weight, general health, sex and diet of the subject, mode and time of administration, rate of excretion, drug combination, and severity of the condition of the host undergoing therapy.

The present disclosure also contemplates combinations of one or more disclosed compounds with one or more other agents or therapies useful in the treatment of a disease or disorder. In certain instances, the disease or disorder is mediated through the activity of a Syk activity in a subject. In certain instances, the disease or disorder is cell proliferative disorder. For example, one or more disclosed compounds may be administered in combination with effective doses of other medicinal and pharmaceutical agents, or in combination other non-medicinal therapies, such as hormone or radiation therapy. The term "administration in combination with" refers to both concurrent and sequential administration of the active agents.

Syk Kinase

"Syk" or "Syk kinase" refers to the 72 kDa non-receptor (cytoplasmic) spleen protein tyrosine kinase expressed in B-cells and other hematopoetic cells. Syk kinase is characterized by two consensus Src-homology 2 (SH2) domains in tandem that bind to phosphorylated immunoreceptor tyrosine-based activation motifs ("ITAMs"), a "linker" domain and a catalytic domain. Syk kinase is also used for tyrosine phosphorylation of multiple proteins which regulate pathways leading from immunoreceptors, such as $Ca^{2+}$ mobilization and mitogen-activated protein kinase (MAPK) cascades and degranulation. Syk kinase also plays a role in integrin signaling in neutrophils. Syk kinase includes kinases from any species of animal, including but not limited to, human, simian, bovine, porcine, rodent, etc., recognized as belonging to the Syk family. Specifically included are isoforms, splice variants, allelic variants, mutants, both naturally occurring and man-made. The amino acid sequences of such Syk kinases are available from GENBANK. Specific examples of mRNAs encoding different isoforms of human Syk kinase are available at GENBANK accession no. gi|21361552|ref|NM_003177.2, gi|496899|emb|Z29630.1|HSSYKPTK[496899] and gi|15030258|gb|BC011399.1|BC011399[15030258], which are incorporated herein by reference.

Therapeutic Applications

The subject compounds are useful for treating a disease or disorder that is mediated through, or exacerbated by, the activity of a Syk in a subject in need of treatment. The present disclosure provides methods of treating conditions such as inflammatory conditions or diseases, autoimmune diseases, cell proliferative disorders, and degenerative bone disorders in a subject by administering an effective amount of a subject compound, including a salt or solvate or stereoisomer thereof.

Inflammatory Conditions

Accordingly, the present disclosure provides methods of treating an inflammatory condition or disease in a subject by administering an effective amount of a subject compound, including a salt or solvate or stereoisomer thereof. Inflammatory conditions contemplated for therapy include acute and chronic inflammation mediated or exacerbated by Syk activity.

The subject compounds can be used to treat a variety of inflammatory conditions or diseases in which an inflammatory response is associated with the condition or disease. Diagnosis and clinical indications of such diseases and conditions will be well known to the skilled artisan, and guidance is provided in various reference works, such as The Merck Manual of Diagnosis and Therapy, 1999, 17$^{th}$ Ed., John Wiley & Sons; and International Classification of Disease and Related Health Problems (ICD 10), 2003, World Health Organization.

The disclosure provides methods of regulating or inhibiting signal transduction cascades in which Syk plays a role. The method generally involves contacting a Syk-dependent receptor or a cell expressing a Syk-dependent receptor with an amount of a subject compound effective to regulate or inhibit the signal transduction cascade. The methods may also be used to regulate or inhibit downstream processes or cellular responses elicited by activation of the particular Syk-dependent signal transduction cascade. The methods may be practiced in in vitro contexts or in in vivo contexts as a therapeutic approach towards the treatment or prevention of diseases characterized by, caused by or associated with activation of the Syk-dependent signal transduction cascade.

Syk is involved in release of preformed mediators of atopic and/or Type I hypersensitivity reactions (e.g., histamine, proteases such as tryptase, etc.) via the degranulation process in mast cells and basophil cells. Such atopic or Type I hypersensitivity reactions include, but are not limited to, anaphylactic reactions to environmental and other allergens (e.g., pollens, insect and/or animal venoms, foods, drugs, contrast dyes, etc.), anaphylactoid reactions, hay fever, allergic conjunctivitis, allergic rhinitis, allergic asthma, atopic dermatitis, eczema, urticaria, mucosal disorders, tissue disorders, and certain gastrointestinal disorders.

The immediate release of the preformed mediators via degranulation is followed by the release and/or synthesis of a variety of other chemical mediators, including, but not limited to, platelet activating factor (PAF), prostaglandins and leukotrienes (e.g., LTC4) and the de novo synthesis and release of cytokines such as TNFα, IL-4, IL-5, IL-6, IL-13, etc. These "late stage" mediators can be responsible for the chronic symptoms of the above-listed atopic and Type I hypersensitivity reactions, and in addition are chemical mediators of inflammation and inflammatory conditions, including, but not limited to, osteoarthritis, inflammatory bowel disease, ulcerative colitis, Crohn's disease, idiopathic inflammatory bowel disease, irritable bowel syndrome, spastic colon, low grade scarring, scleroderma, increased fibrosis, keloids, post-surgical scars, pulmonary fibrosis, vascular spasms, migraine, reperfusion injury, post myocardial infarction, and sicca complex or syndrome.

Additional diseases which can be treated or prevented according to the subject methods include diseases associated with basophil cell and/or mast cell pathology. Examples of such diseases include, but are not limited to, diseases of the skin such as scleroderma, cardiac diseases such as post myocardial infarction, pulmonary diseases such as pulmonary muscle changes or remodeling and chronic obstructive pulmonary disease (COPD, and diseases of the gut such as inflammatory bowel syndrome (spastic colon).

Certain inflammatory diseases or disorders that can be treated using the subject compound include, but not limited to, asthma, COPD, lung inflammation, chronic granulomatous diseases such as tuberculosis, leprosy, sarcoidosis, and silicosis, nephritis, amyloidosis, rheumatoid arthritis, ankylosing spondylitis, chronic bronchitis, scleroderma, lupus, polymyositis, appendicitis, inflammatory bowel disease, Crohn's disease, ulcerative colitis, psoriasis, pelvic inflammatory disease, irritable bowel syndrome, orbital inflammatory disease, thrombotic disease, and inappropriate allergic responses to environmental stimuli such as poison ivy, pollen, insect stings and certain foods, including atopic dermatitis and contact dermatitis.

Because the exemplary compounds inhibit the FcεRI and/or FcγR signal cascades that lead to degranulation of immune cells such as mast cells, such compounds can be used to inhibit the development and progression of atherosclerosis and associated symptoms. For example, activation of the IgE receptor signal transduction pathway leads to degranulation of the cells and consequent release and/or synthesis of a host of chemical mediators, including histamine, proteases (e.g., tryptase and chymase), lipid mediators such as leukotrienes (e.g., LTC4), platelet-activating factor (PAP) and prostaglandins (e.g., PGD2) and a series of cytokines, including TNF-a, IL-4, IL-13, IL-5, IL-6, IL-8, GMCSF, VEGF and TGF-β. The release and/or synthesis of these mediators from mast cells can lead to degradation of the extracellular matrix, deposition of fatty streaks in the vasculature and rupture of existing atherosclerotic plaques. Accordingly, inhibition of mast cell degranulation using the presently disclosed compounds can be used to treat atherosclerosis.

The subject compounds can be used, either independently or in combination with other anti-inflammatory compositions, as discussed below.

Autoimmune Diseases

The present disclosure provides methods of treating an autoimmune disease in a subject by administering an effective amount of a subject compound, including a salt or solvate or stereoisomer thereof.

The subject compounds can also be used to treat or prevent autoimmune diseases and/or symptoms of such diseases. Autoimmune diseases that can be treated or prevented with the subject compounds include those diseases that are commonly associated with nonanaphylactic hypersensitivity reactions (Type II, Type III and/or Type IV hypersensitivity reactions) and/or those diseases that are mediated, at least in part, by activation of the FcγR signaling cascade in monocyte cells. Such autoimmune disease include autoimmune diseases that are frequently designated as single organ or single cell-type autoimmune disorders and autoimmune disease that are frequently designated as involving systemic autoimmune disorder. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy. Non-limiting examples of diseases often designated as involving systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid.

As a certain example of a treatment, rheumatoid arthritis is thought to be an autoimmune disease that commonly affects the joints in a polyarticular manner (polyarthritis). The disease is characterized by chronically inflamed synovium that is densely crowded with lymphocytes. Chronic inflammatory condition arising from an autoimmune reaction can lead to led to erosion and destruction of the joint surface, which impairs the range of joint movement and leads to deformity. The subject compounds can be used to treat or ameliorate any one, several or all of these symptoms of rheumatoid arthritis.

The subject compounds can be used, either independently or in combination with other anti-inflammatory compositions, as discussed below.

Cellular Proliferation Disorders

Although the art suggests that Syk may act as a tumor suppressor, the present disclosure is based on indications that Syk functions contrary to that posited role. For instance, forced expression of Syk kinase in tumor cells does not appear to reverse the transformed phenotype of tumor cells. To the contrary, it is suggested herein that Syk acts in an oncogenic capacity to promote and/or maintain cell proliferation. With this perspective on the role of Syk, the present disclosure provides methods of treating a cell proliferative disorder in a subject by administering an effective amount of a subject compound, including a salt or solvate or stereoisomer thereof.

Generally, cell proliferative disorders treatable with the subject compound disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, but not limited to, breast cancer, ovarian cancer, renal cancer, gastrointestinal cancer, kidney cancer, bladder cancer, pancreatic cancer, lung squamous carcinoma, and adenocarcinoma.

In certain instances, the cell proliferative disorder treated is a hematopoietic neoplasm, which is aberrant growth of cells of the hematopoietic system.

In certain instances, the hematopoietic neoplasm is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Certain B-cell neoplasms are precursor B-lymphoblastic leukemia/lymphoma (precursor B-cell acute lymphoblastic leukemia) while certain mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms can be further subdivided into precursor T-cell neoplasm and mature (peripheral) T-cell neoplasms. A certain precursor T-cell neoplasm is precursor T-lymphoblastic lymphoma/leukemia (precursor T-cell acute lymphoblastic leukemia) while certain mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, mycosis fungoides/Sezary syndrome, anaplastic large-cell lymphoma, T/null cell, primary cutaneous type, peripheral T-cell lymphoma, not otherwise characterized, angioimmunoblastic T-cell lymphoma, anaplastic large-cell lymphoma, T/null cell, primary systemic type. Another member of lymphoid neoplasms is Hodgkin's lymphoma, also referred to as Hodgkin's disease. Certain diagnoses of this class that include, among others, nodular lymphocyte-predominant Hodgkin's lymphoma, and various classical forms of Hodgkin's disease, certain members of which are nodular sclerosis Hodgkin's lymphoma (grades 1 and 2), lymphocyte-rich classical Hodgkin's lymphoma, mixed cellularity Hodgkin's lymphoma, and lymphocyte depletion Hodgkin's lymphoma.

In certain instances, the hematopoietic neoplasm is a myeloid neoplasm. This group includes a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Certain myeloproliferative diseases include chronic myelogenous leukemia (e.g., Philadelphia chromosome positive (t(9;22) (qq34;q11)), chronic neutrophilic leukemia, chronic eosinophilic leukemialhypereosinophilic syndrome, chronic idiopathic myelofibrosis, polycythemia vera, and essential thrombocythemia. Certain myelodysplastic/myeloproliferative diseases include chronic myelomonocytic leukemia, atypical chronic myelogenous leukemia, and juvenile myelomonocytic leukemia. Certain myelodysplastic syndromes include refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome with t(9;12) (q22;p12) (TEL-Syk fusion).

In certain instances, the composition can be used to treat acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Certain AMLs with recurrent cytogenetic translocations include, among others, AML with t(8;21)(q22;q22), AML1 (CBF-alpha)/ETO, acute promyelocytic leukemia (AML with t(15;17)(q22;q11-12) and variants, PML/RAR-alpha), AML with abnormal bone marrow eosinophils (inv(16) (p13q22) or t(16;16)(p13;q11), CBFb/MYH11X), and AML with 11q23 (MLL) abnormalities. Certain AML with multilineage dysplasia are those that are associated with or without prior myelodysplastic syndrome. Other acute myeloid leukemias not classified within any definable group include, AML minimally differentiated, AML without maturation, AML with maturation, acute myelomonocytic leukemia, acute monocytic leukemia, acute erythroid leukemia, acute megakaryocytic leukemia, acute basophilic leukemia, and acute panmyelosis with myelofibrosis.

In certain instances, cell proliferative disorders include virally mediated tumors. These can arise from infection of cells by an oncogenic virus that has a capability of transforming a normal cell into a tumor cell.

In certain instances, the virally mediated tumor can be associated with any virus that encodes an immunoreceptor tyrosine-based activation motif (ITAM) capable of modulating Syk activity. This motif can refer to a conserved amino acid sequence motif that functions by interacting with and activating nonreceptor tyrosine kinases. ITAM motifs are found in, among others, the p and y chains of FcεRI, the ε subunit of the T cell receptor, and immunoglobulin β (Igβ) and Igα of the B cell receptor. The canonical sequence motif is typically $Yxx(L/I)x_{6-8}Yxx(L/I)$, where x represents any amino acid.

Accordingly, in certain instances, the virally mediated tumor can be associated with Kaposi's sarcoma (KS) associated herpes virus, a lymphotropic virus implicated in Kaposi's sarcoma. The KS associated herpes virus encodes a transmembrane protein termed KI having an immunoreceptor tyrosine-based activation motif (ITAM)-like sequence.

In certain instances, the virally mediated tumor can be associated with Epstein Barr Virus (EBV). Epstein Barr Virus is a member of the Herpesviridae family that, following primary infection, replicates in the epithelial cells of the oropharynx and infect recirculating B lymphocytes. EBV infection can be associated with Burkitt's lymphoma, Hodgkin's lymphoma, and adult T cell leukemia.

In certain instances, the virally mediated tumor can be associated with Human T-cell Lymphotropic Virus (HTLV-1 virus), a retrovirus in the same class of virus as HIV-1.

In certain instances, the virally mediated tumor can be associated with mammary tumor virus (MTV). ITAM sequences can be found within the Env gene of murine mammary tumor virus (MMTV), a B type retrovirus identified as an etiological agent for breast cancer in mice. Murine mammary tumor virus-like sequences can be present in human cancers, such as breast cancer and T cell lymphomas.

It is to be understood that use of subject composition for treating virally mediated tumors is not limited to tumors associated with the viruses specified above. As noted, any tumors associated with an oncogenic virus in which Syk is activated as part of its oncogenic mechanism, whether or not it involves ITAM sequences, can be targeted using the subject compounds.

In certain instances, the subject compounds can be used for the treatment of tumor metastasis. Metastasis is a characteristic of malignant tumor cells whereby tumor cells detach from its site of origin and then spread to colonize at other sites. These secondary tumors can form in tissues unrelated to the cells from which the tumor cells originate.

Various tumor types capable of metastasis can be treated with the subject compounds. Such tumors include, but not limited to, breast cancer, ovarian cancer, renal cancer, gastrointestinal cancer, kidney cancer, bladder cancer, pancreatic cancer, lung squamous carcinoma, and adenocarcinoma. Therapeutic treatment to attenuate the metastasis of established tumors can follow a diagnosis of metastasis. If no diagnosis of metastasis has been made, the subject compounds can be administered prophylactically to reduce the probability of metastasis.

The subject compounds can be used, either independently or in combination with other chemotherapeutic compositions, as recognized in the art.

Degenerative Bone Disorders

The present disclosure provides methods of treating a degenerative bone disorder in a subject by administering an effective amount of a subject compound, including a salt or solvate or stereoisomer thereof.

The subject compounds can be used for treating degenerative bone disorders as well as prophylactic approaches for preventing bone loss that can lead to increased fracture risk. These treatments are based on the use of Syk inhibitors to attenuate or inhibit osteoclastogenesis and osteoclast activity, thereby decreasing or inhibiting the excessive bone loss associated with abnormal activity of osteoclasts. In addition, in those degenerative bone disorders where inappropriate remodeling results in compromised bone integrity but without significant bone loss, an increase in bone mass resulting from inhibition of bone resorption can increase bone strength sufficiently to decrease the fracture risk. The subject compounds can be used independently or in combination with other modulators of bone remodeling (i.e., antiresorptive agents and osteo-anabolic agents), for treatment as well as prophylaxis.

The diagnosis of a particular disorder can be based on clinical presentations typically used by those skilled in the art to diagnose the disorder. As further discussed herein, other diagnostic criteria such as the presence of biochemical and molecular markers of the disease, can be used independently or as a supplement to the examination of the clinical presentations. Standard diagnostic criteria can be found in various references, including, by way of example and not limitation, the World Health Organization's International Classification of Diseases, Tenth Revision (lCD-i 0); Resnick, D., Diagnosis of Bone and Joint Disorders, 4th Ed., W.B. Saunders Company (2002); and AACE Medical Guidelines for Clinical Practice for the Prevention and Treatment of Postmenopausal Osteoporosis: 2001 Edition, with Selected Updates for 2003.

In certain instances, the subject compounds can be used to treat primary osteoporosis, which is a loss of bone mass unrelated to any other underlying disease or illness. There are general types of primary osteoporosis. Type I, also referred to as high turnover or postmenopausal osteoporosis, is correlated with a decrease in hormone levels secreted by the ovaries in the postmenopausal period. Type II, also referred to as low turnover or senile osteoporosis, can arise when the processes of bone resorption and bone formation are not coordinated such that there is a net excess of bone resorption over bone formation.

Other forms of primary osteoporosis are idiopathic osteoporosis, an osteoporotic condition where there is no identifiable cause for the bone loss. Idiopathic osteoporosis can affect children and adults. Juvenile osteoporosis is osteoporosis occurring in children between the ages of about 8 and about 14 years of age.

In certain instances, the subject compounds can be used to treat osteodystrophy, a degeneration of bone resulting from compromised kidney function. Clinical presentations of osteodystrophy can be in the form of osteoporosis, osteomalacia, osteitis fibrosa, osteoscierosis, osteomalacia, and secondary hyperparathyroidism.

In certain instances, the subject compounds can be used to treat Paget's Disease, also known as osteitis deformans.

In certain instances, the subject compounds can be used to treat periodontal disease.

In certain instances, the subject compounds can be used to treat degenerative bone disorders arising from a secondary condition, where the bone degeneration is a consequence of the underlying medical condition or disease. Thus, subject compounds can be administered to subjects with the secondary condition to treat or prevent degenerative bone disorder associated with the secondary condition.

A certain secondary condition is encrinopathy, which is a condition characterized by abnormal hormone secretion. Abnormal hormone secretion can be either an increase or reduction in hormone levels. Various hormones can affect bone metabolism, including but not limited to, estrogen, testosterone, growth hormone, calcitonin, parathyroid hormone, parathyroid hormone related protein, glucocorticoids, and calcitriol. Various forms of endocrinopathies are associated with loss of bone mass and corresponding bone degeneration. In certain instances, the subject compounds can be used to treat bone degeneration arising from hypercorticolism or an abnormal increase in the production of glucocorticoids by the adrenal glands (e.g., Cushing's syndrome). In certain instances, the subject compounds can be used to treat bone degeneration arising from hypogonadism. In certain instances, the bone degeneration treatable with the subject compounds can be bone loss associated with destruction of one or both of the gonads, such as by surgery (i.e., ovariectomy or oophorectomy). In certain instances, the subject compounds can be used to treat bone degeneration arising from hyperparathyroidism.

In certain instances, the methods can be directed to use of the subject compounds to treat bone degeneration associated with heritable genetic disorders. Thus, subject compounds can be administered to subjects with a heritable genetic disorder to treat or prevent degenerative bone disorder associated with the heritable genetic disorder. Inherited genetic disorders can arise from, among others, single gene inheritance, multifactorial or polygenic inheritance, chromosome abnormalities, and parental imprinting abnormalities. Various inherited genetic abnormalities affecting bone metabolism have been identified, including, osteogenesis imperfecta, homocystinurea, gonadal dysgenesis, and hypophosphatasia.

It is to be understood that the use of Syk inhibitors are not limited to the degenerative bone disorders described herein, but may be applied to degenerative bone disorder characterized by a net excess of bone resorption over bone formation. This condition may arise from increased osteoclastogenesis, increased osteoclast activation, decreased osteoblastogeneis, decreased osteoblast activity, or a combination of increased osteclastogenesis and decreased osteoblastogenesis. Thus, the methods herein encompass treatments for degenerative bone disorders generally in which there is an imbalance of bone resorption over bone formation.

The subject compounds can be used, either independently or in combination with other bone modulating agents, as recognized in the art. In addition to the treatment of degenerative bone disorders, the subject compounds can be used, either independently or in combination with bone modulating agents, as prophylaxis to prevent bone loss in subjects at risk of bone loss and increased fracture risk.

Combination Therapy

The subject compounds may be administered individually or as compatible combinations along with an anti-inflammatory agent. Different combinations of the subject compounds may be used to adjust bioavailability, duration of effect, and efficacy for the particular inflammatory condition. Identifying appropriate combinations for the purposes herein are within the skill of those in the art.

Steroidal Anti-inflammatory Agents

For treating inflammatory disorders, the subject compounds can be administered in combination with an additional chemotherapeutic agent, such as an anti-inflammatory agent. In certain instances, the anti-inflammatory agent for use in combination with the presently disclosed compounds is a steroidal anti-inflammatory agent. As used herein, "steroidal anti-inflammatory agent" or "anti-inflammatory steroid" is a compound or composition based on a structure with a steroid nucleus and having anti-inflammatory activity, either alone or in combination with other agents. With the exception of vitamin D compounds, steroid compounds are derived from a steroid nucleus based on a saturated tetracyclic hydrocarbon, 1,2-cyclopentanoperhydrophenanthrene, also referred to as sterane or gonane. Steroidal compounds include both naturally occurring and synthetically produced steroidal compounds. Different groups of steroid compounds include, among others, adrenocorticosteroids, estrogens/progestins, and androgens.

In certain instances, the steroidal anti-inflammatory agents are adrenocorticosteroids, which refer to steroidal compounds that are released from the adrenal cortex. These steroid compounds include the groups of glucocorticosteroids and mineralocorticosteoids. As used herein, adrenocorticosteroids also include various synthetic analogs that display the biological properties displayed by the naturally occurring steroids. Certain structural features may enhance anti-inflammatory activities of steroids, such as all trans steroid skeleton, presence of $\Delta^4$-3-keto, 11β-OH, 17 β-OH, and substitutions at 9α-, 6α-, 16α-positions, with F>Cl>Br>I.

In certain instances, the anti-inflammatory steroidal agent is a glucocorticosteroid (synonymously "glucocorticoid"). Various anti-inflammatory glucocorticoids can be used. These include, by way of example and not limitation, natural and synthetic steroidal compounds such as 21-acetoxypregnenolone, alclometasone, algestone, amcinonide, beclomethasone, budesonide, chloroprednisone, ciclesonide, clobetasol, clobetasone, clocortolone, cloprednol, corticosterone, cortisone, contrivazol, deflazacort, desonide, desoximetasone, dexamethansone, diflorasone, diflucortolone, difluprednate, enoxolone, fluazacort, flurandrenolone acetonide, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinode, halobetasol propionate, halometasone, halopredone acetate, hydrocortamate, hydrocortisone, hydrocortisone 17-butyrate, hydrocortisone 17-valerate, loteprednol etabonate, maziprednone, medrysone, meprednisone, methylprednisolone, mometasone furoate, paramethasone, prednicarbate, prednisolone, prednisolone 21-dimethylaminoacetate, prenisolone sodium phosphate, prednisone, prednival, prednylidene, rimexolone, tixocortol, triamcinolone, triamcinolone acetonide, triamcinolone benetonide, and triamcinolone hexacetonide. Other glucocorticosteroids will be apparent to the skilled artisan.

In certain instances, the anti-inflammatory steroid is a mineralocorticosteroid (synonymously "mineralocorticoid"). Various mineralocorticoids include, among others, aldosterone, deoxycorticosterone, deoxycorticosterone acetate, and fludrocortisone. It is to be understood, however, that the characterization of a steroid as a glucocorticosteroid or mineralocorticosteroid are used for descriptive purposes and is not meant to be exclusionary. Glucocorticoids display some mineralocorticosteroid activity while some mineralocorticoids display some glucocorticoid activity. For the purposes herein, a mineralocorticoid with anti-inflammatory properties may be used. Generally, mineralocorticosteroids with some glucocorticosteroid activity appears to have anti-inflammatory effects. A certain anti-inflammatory mineralocorticoid is fludrocortisone.

In certain instances, the anti-inflammatory steroidal agents have varying biologic effect half-life, and can be divided into short acting, intermediate acting, or long acting steroidal compounds. Certain short-acting steroidal compounds include, by way of example and not limitation, cortisol and cortisone. Certain intermediate-acting steroidal compounds include, by way of example and not limitation, prednisone, prednisolone, triamcinolone, and methylprednisolone. Certain long-acting steroidal compounds include, by way of example and not limitation, dexamethasone, betamethasone, and budesonide.

In certain instances, the anti-inflammatory steroid is a nitro-steroidal compound. As used herein a "nitro-steroidal" compound is steroid having NO-releasing activity (the nitrosterols), and include NO-releasing forms of prednisolone, flunisolide and hydrocortisone.

In certain instances, the steroidal anti-inflammatory agent can be an inhaled steroidal agent, which is useful for nasal administration and/or absorption through the lungs. These forms are effective agents for treating asthma and reaction to inhaled allergens. Various forms of steroidal anti-inflammatory compounds formulated as inhalants include, among others, beclomethasone, bedesonide, dexamethasone, flunisolide, triamcinolone acetonide, and antedrugs noted above.

In certain instances, the steroidal anti-inflammatory agent is an estrogen or a synthetic estrogen analog. Various estrogen and estrogen analogs that may be used include, by way of example and not limitation, estrogen, 17β-estradiol, estrogen conjugates, medroxyprogesterone, 2-methoxyestradiol (estrogen metabolite), diethystilbesterol, reveratrol, phytoestrogens (e.g., genestein), and tamoxifen.

In certain instances, the steroidal anti-inflammatory compound is vitamin D or an analog thereof. Various anti-inflammatory agents of this group include, by way of example and not limitation, 7-dehydrocholesterol, cholecaciferol, ergosterol, 1,25-dihydroxyvitamin D3, and 22-ene-25-oxa-vitamin D. Other vitamin D analogs are described in U.S. Pat. Nos. 6,924,400; 6,858,595; 6,689,922; and 6,573,256.

Non-Steroidal Anti-inflammatory Agents

In certain instances, the anti-inflammatory agent is a non-steroidal anti-inflammatory agent (NSAID). This class of agents includes a heterogeneous group of compounds with varying structures but which act through common therapeutic targets. NSAIDs are classified based on their chemical structures and biological activities. In certain instances, the NSAIDs useful with the subject compounds are non-selective COX-2 inhibitors, which inhibit the activity of both COX-1 and COX-2 isoforms. A certain non-selective COX inhibitor is salicylic acid and derivatives thereof. Certain compounds of this class include, by way of example and not limitation, acetylsalicylic acid, sodium salicylate, choline magnesium trisalicylate, salsalate, diflunisal, sulfasalazine, olsalazine, and mesalamine.

In certain instances, a class of non-selective COX inhibitors is indole and indene acetic acids. Certain compounds of this class include, among others, indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac.

In certain instances, a class of non-selective COX inhibitors is heteroaryl acetic acids. Certain compounds of this class include, among others, tolmetin, diclofenac, and ketorolac.

In certain instances, a class of non-selective COX inhibitors is arylpropionic acids or propionic acid derivatives (profens). Certain compounds of this class include among others, alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen.

In certain instances, a class of non-selective COX inhibitors is anthranilic acids (fenamates). Certain compounds of this class include, among others, flufenamic acid, meclofenamic acid, mefenamic acid, niflumic acid and tolfenamic acid.

In certain instances, a class of non-selective COX inhibitors is enolic acids (e.g., oxicams). Certain compounds of this class include, among others, piroxicam and meloxicam, isoxicam, and sudoxicam and tenoxican.

In certain instances, a class of non-selective COX inhibitors is phenylpyrazolones. Certain compounds of this class include, among others, phenylbutazone, apazone, bezpiperylon, feprazone, mofebutazone, oxyphenbutazone.

In certain instances, a class of non-selective COX inhibitors is biphenylcarboxylic acid derivatives. Certain compounds of this class include, among others, diflunisal and flufenisal.

In certain instances, the NSAIDs are selective COX-2 inhibitors. As used herein, a selective COX-2 inhibitor preferably inhibits the activity of COX-2 isozyme as compared to the inhibition of the COX-1 isozyme. A selective COX-2 inhibitor can have a selectivity (i.e., inhibition of COX-2/COX-1) of about 10, of about 20 of about 50, of about 100, of about 200, of about 500, and of about 1000 or more. Selectivity is based on assay typically used to measure COX activity.

In certain instances, a class of selective COX-2 inhibitors is diaryl-substituted furanones. A certain compound of this class includes, among others, refocoxib, available under the tradeanme Vioxx™.

In certain instances, a class of selective COX-2 inhibitors is diaryl-substituted pyrazoles. A certain compound of this class includes, among others, celecoxib, available under the tradename Celebrex™.

In certain instances, a class of selective COX-2 inhibitors is indole acetic acids. A certain compound of this class includes, among others, etodolac, available under the tradename Lodine™.

In certain instances, a class of selective COX-2 inhibitors is sulfonanilides. A certain compound of this class includes, among others, nimesulide.

Lipoxygenase and 5-Lipoxygenase Activating Protein (FLAP) Antagonists

In certain instances, the non-steroidal anti-inflammatory agent that can be used with the subject compounds is a lipoxygenase or a 5-lipoxygenase activating protein (FLAP) antagonist.

In certain instances, various antagonists of lipoxygenase may be used to ameliorate the inflammatory response mediated by the leukotrienes. Classes of lipoxygenase inhibitors include, among others, N-hydroxyurea derivatives, redox inhibitors, and non-redox inhibitors. Certain N-hydroxyurea derived inhibitors include, by way of example and not limitation, 1-(1-benzothiophen-2-ylethyl)-1-hydroxy-urea (leutrol), 1-[4-[5-(4-fluorophenoxy)-2-furyl]but-3-yn-2-yl]-1-hydroxy-urea; 1-[(2R)-4-[5-[(4-fluorophenyl)methyl]thiophen-2-yl]but-3-yn-2-yl]-1-hydro-xy-urea (atreleuton); 3-(1-benzothiophen-2-ylethyl)-1-hydroxy-urea. A certain redox inhibitor includes, by way of example and not limitation, 2-(12-hydroxydodeca-5,10-diynyl)-3,5,6-trimethyl-cyclohexa-2,5-diene-1,4-dione (docebenone). A certain non-redox inhibitor includes, by way of example and not limitation, 6-[[3-fluoro-5-(4-methoxyoxan-4-yl)phenoxy]methyl]-1-methyl-quinolin-2-one (i.e., ZD2138).

In certain instances, a FLAP antagonist may be used as the anti-inflammatory agent. FLAP antagonists include, among others, indole derivatives and quinoline derivatives. Certain indole derivatives with FLAP inhibitory activity include, by way of example and not limitation, 3-[3-butylsulfanyl-1-[(4-chlorophenyl)methyl]-5-propan-2-yl-indol-2-yl]-2-, 2-dimethyl-propanoic acid (i.e., MK-866) and 3-[1-[(4-chlorophenyl)methyl]-5-(quinolin-2-ylmethoxy)-3-tert-butylsulfanyl-indol-2-yl]-2,2-dimethyl-propanoic acid (i.e., MK0591 or quiflapon). Certain quinoline derivatives include, by way of example and not limitation, (2R)-2-cyclopentyl-2-[4-(quinolin-2-ylmethoxy)phenyl]acetic acid (i.e., BAY-X1005 and veliflapon).

Anti-histamines

In certain instances, the subject compounds are used in combination with anti-histamines, which are generally H1-receptor antagonists. Certain H1 receptor antagonists include, among others, doxepin, cabinoxamine, clemastine, diphenylhydramine, dimenhydrinate, pyrilamine, tripelennamine, chlorpheniramine, bromopheniramine, hydroxyzine, cyclizine, meclizine, promethazine, cyproheptadine, phenindamine, acrivastine, citirizine, azelastine, levocabastine, loratadine, fexofenadine, and various salts, hydrates, N-oxides, and prodrugs thereof.

Beta-agonists

In certain instances, the subject compounds are used in combination with β-adrenergic receptor agonists (synonymously "β-agonists" or "β-adrenergic agonists"), which includes non-selective β-adrenergic agonists as well as $β_2$-selective adrenergic agonists. There are generally two types of β-agonists, short-acting β-agonists and long-acting β-adrenergic agonists.

Certain short acting β-adrenergic agonists include, by way of example and not limitation, albuterol (salbutamol), isotharine, fenoterol, levalbuterol, metaproterenol (orciprenaline), procaterol, terbutaline, and pirbuterol. Certain long-acting β-adrenergic agonists include, by way of example and not limitation, salmeterol xinafoate, formoterol, and bitolterol. Certain non-selective β-agonists include, by way of example and not limitation, isoproterenol and dobutamine.

Anti-metabolite Anti-inflammatory Agents

In certain instances, the anti-inflammatory agent is an anti-metabolite that attenuates or inhibits the activation and/or proliferation of cells involved in inflammation. Anti-metabolites may have cytostatic or cytotoxic effects and thus generally display immunosuppressive characteristics.

Various anti-inflammatory anti-metabolites may be used in combination with the subject compounds. In certain instances, the anti-proliferative agent is methotrexate.

In certain instances, the anti-proliferative anti-metabolite includes an inhibitor of inosine monophosphate dehydrogenase (IMPDH), the enzyme acting in the salvage pathway for the synthesis of guanosine monophosphate (GMP) from inosine. IMPDH inhibitors useful as anti-inflammatory agents include, among others, mycophenolic acid, mycophenolate mofetil, ribavirin, taizofurin, selenazofurin, benazamide adenine dinucleotide, and benzamide riboside.

Other anti-metabolites include azathioprine, 6-mercaptopurine (6-MP), leflunomide, and malononitriloamides.

Another anti-metabolite is methotrexate (amethopterin or (2S)-2-[(4-{[(2,4-diamino-7,8-dihydropteridin-6-yl)methyl](methyl)amino}phenyl)formamido]pentanedioic acid).

Anti-TNF-alpha Agents

It is to be understood that anti-inflammatory agents other than those described above may be used in combination with the subject compounds. These include various agents directed against the cellular factors thought to be involved in promoting the inflammatory response. In certain instances, the anti-inflammatory agent is an agent that blocks the action of TNFα, the major cytokine implicated in inflammatory disorders. In certain instances, the anti-TNF is an antibody that blocks the action of TNFα. A certain anti-TNF antibody is infliximab, available under the tradename Remicade™.

In certain instances, the anti-TNFα agent is a receptor construct that binds TNFα and prevents its interaction with TNF receptors on present on cells. A certain anti-inflammatory agent based on TNFα receptor is entanercept, available under the tradename Enbrel™.

Statins

In certain instances, the subject compounds are used in combination with statins. Statins are a class of drugs that can lower cholesterol and act as HMG-CoA reductase inhibitor. Examples of statins include atorvastatin, cerivastatin, fluvastatin, lovastatin, mevastatin, pitastatin, pravastatin, rosuvastatin, and simvastatin. A certain statin is atorvastatin, available under the tradename Lipitor™. Another statin is simvastatin, available under the tradename Zocor™.

Characterization of Functional Properties

The following are exemplary assays useful in characterizing activities of a compound of interest.

As used herein, a "Syk inhibitor" or "Syk kinase inhibitory compound" refers to any compound that directly inhibits the activity of Syk kinase itself or inhibits Syk interaction with other cellular targets needed for proper Syk function in the $IC_{50}$ range described herein.

Inhibitors as used herein include the classical description of enzyme inhibitors, such as competitive, noncompetitive and uncompetitive inhibitors, and thus encompasses compounds that inhibit Syk kinase activity by, for example, binding to Syk kinase so as to inhibit access of a substrate to an active site, binding to Syk kinase so as to distort the active site to reduce binding to substrate, and/or bind a Syk kinase-substrate complex. Compounds that are Syk inhibitors are generally those that display an $IC_{50}$ with respect to a Syk kinase activity, such as the ability of Syk kinase to phosphorylate a synthetic or endogenous substrate, in an in vitro or cellular assay, in the range of about 5 µM or lower, about 1 µM or lower, about 500 nm or lower, about 100 nM or lower, about 50 nM or lower, about 10 mM or lower, or about 1 nM or lower Skilled artisans will appreciate that compounds exhibiting lower $IC_{50}$, such as in the range of about 100 nM, 10 nM, 1 nM, or even lower, are useful for the methods herein.

Biochemical and Cellular Assays

Compounds can be tested in various biochemical and cellular assays for their inhibitory effect on Syk. Syk phosphorylates LAT and PLC-γ1, which leads to, among other things, degranulation in mast and/or basophil cells. Syk activity is also observed in response to T-cell receptor stimulation. It is to be understood that any of these activities can be used to confirm the activity of the Syk inhibitor compounds. In certain instances, the Syk kinase assay is a degranulation assay based on measurement of granule content release following stimulation with anti-IgE. These assays include, for example, measurement of tryptase, histamine, leukotriene LTC4, or hexosaminidase release.

In certain instances, the activity is determined by contacting an isolated Syk, or an active fragment thereof with an inhibitor compound in the presence of a Syk substrate (e.g., a synthetic peptide or a protein that is known to be phosphorylated by Syk in a signaling cascade) and assessing whether the Syk phosphorylates the substrate. Alternatively, the assay can be carried out with cells that express a Syk. The cells can express the Syk endogenously or they can be engineered to express a recombinant Syk.

The cells can optionally also express the Syk substrate. Cells suitable for performing such confirmation assays, as well as methods of engineering suitable cells will be apparent to those of skill in the art. Suitable Syk substrate include, by way of example and not limitation, human band 3 protein, protein kinase C, tubulin, cortactin, and p50/HS1. Other examples of biochemical and cellular assays suitable for confirming the activity of the Syk inhibitor compounds are described in Fox et al., 1998, Protein Science, 7:2249, U.S. application Ser. No. 10/631,029, WO 2004/014382, and references cited therein, all of which are incorporated herein by reference.

Determining the effect of the inhibitor compounds on cell proliferation can use any number of in vitro and in vivo assays. For example, proliferating cells can be suitably cultured in vitro and treated with the subject compounds. Proliferative capacity in the cell populations can be determined use dye staining (e.g., trypan blue dye-exclusion; 3-4,5-dimethylthiazol-2,5-diphenyltetrazolium (MTT); and annexin V), or cell sorting techniques (e.g., fluorescence activated cell sorting with propidium iodide). In vivo assays for cell proliferation can be based on transplantation of tumor cells into experimental animals followed by administration of the inhibitor compounds. These and other methods of assessing cell proliferation will be apparent to the skilled artisan.

Research Applications

Since subject compounds can inhibit a Syk activity, such compounds are also useful as research tools. The present disclosure also provides a method for using a subject compound or a salt or solvate or stereoisomer thereof as a research tool for studying a biological system or sample, or for discovering new chemical compounds that can inhibit a Syk activity.

The disclosure provides for a method of studying a biological system or sample known to contain Syk, the method involving: (a) contacting the biological sample with a subject compound or a salt or solvate or stereoisomer thereof; and (b) determining the inhibiting effects caused by the subject compound on the biological sample.

Any suitable biological sample having Syk can be employed in such studies which can be conducted either in vitro or in vivo. Representative biological samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest.

When used as a research tool, a biological sample containing Syk is typically contacted with a Syk activity-inhibiting amount of a subject compound. After the biological sample is exposed to the compound, the effects of inhibition of a Syk activity are determined using conventional procedures and equipment, such as the assays disclosed herein. Exposure encompasses contacting the biological sample with the compound or administering the compound to a subject. The determining step can involve measuring a response (a quantitative analysis) or can involve making an observation (a qualitative analysis). Measuring a response involves, for example, determining the effects of the compound on the biological sample using conventional procedures and equipment, such as radioligand binding assays and measuring ligand-mediated changes in functional assays. The assay results can be used to determine the activity level as well as the amount of compound necessary to achieve the desired result, that is, a Syk activity-inhibiting amount.

Additionally, subject compounds can be used as research tools for evaluating other chemical compounds, and thus are also useful in screening assays to discover, for example, new compounds having a Syk inhibiting activity. In this manner, a subject compound can be used as a standard in an assay to allow comparison of the results obtained with a test compound and with the subject compounds to identify those test compounds that have about equal or superior activity, if any. For example, $IC_{50}$ data for a test compound or a group of test compounds is compared to the $IC_{50}$ data for a subject compound to identify those test compounds that have the desired properties, for example, test compounds having an $IC_{50}$ about equal or superior to a subject compound, if any.

This aspect includes both the generation of comparison data (using the appropriate assays) and the analysis of test data to identify test compounds of interest. Thus, a test compound can be evaluated in a biological assay, by a method involving the steps of: (a) conducting a biological assay with a test compound to provide a first assay value; (b) conducting the biological assay with a subject compound to provide a second assay value; wherein step (a) is conducted either before, after or concurrently with step (b); and (c) comparing the first assay value from step (a) with the second assay value from step (b). The assays that can be used for generation of comparison data are disclosed herein, such as the Syk assays.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used.

Synthesis of Compounds

The compounds of the present disclosure, including compounds from Examples 1-157, were prepared in accordance with the general synthetic methods described below and are illustrated in the scheme that follows. In Scheme 3, Rings 1 and 6 can be appropriately substituted, as shown in the following examples.

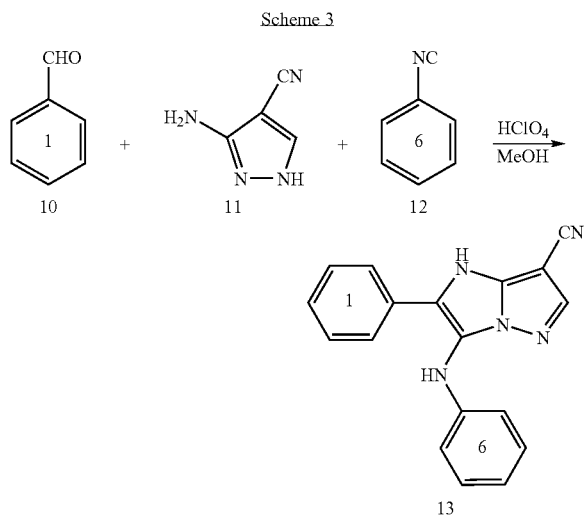

3-Aminopyrazole-4-carbonitrile 11 (1.0 mmol) was dissolved in 2 mL of methanol. The aldehyde 10 (1.0 mmol) and isonitrile 12 (1.0 mmol) were added at room temperature. A 1M solution of perchloric acid ($HClO_4$) in methanol (0.1 mL) was then added. The reaction mixture was stirred at room temperature overnight. The precipitate (if formed) were filtered, washed with MeOH, saturated $NaHCO_3$ and $H_2O$ and dried to yield Compound 13. If the reaction mixture was a clear solution, the solvent was then removed in vacuo and the residue was triturated with methanol to give the solid Compound 13. Otherwise purification of the residue by semi-preparative HPLC gave the pure product.

Compound 12 can be prepared in accordance with the general synthetic methods described below and is illustrated in the scheme that follows. In Scheme 4, Ring 6 can be appropriately substituted, as shown in the following examples.

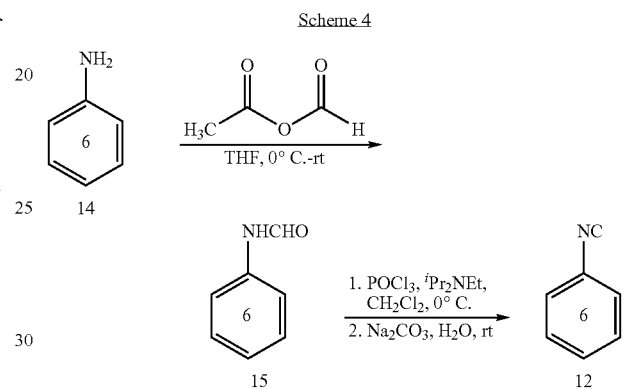

To a stirred mixture of sodium formate (7.0 g, 103 mmol, 1.2 equiv) in 6 mL of ethyl ether was added acetyl chloride (6.3 mL, 88.7 mmol, 1.0 equiv) quickly (temperature maintained at about 23-27° C.). The reaction mixture was stirred at room temperature for 5 hours. The upper ethyl ether layer was directly used for the formylation reaction. The aniline 14 (33.3 mmol) was dissolved in 100 mL of tetrahydrofuran, then the solution of acetic formic anhydride in ethyl ether was added at 0° C. The reaction mixture was warmed to room temperature and stirred overnight. The solvent was evaporated and the residue was triturated with ethyl ether to give the crude product 15 which was directly used for the next step. The formamide 15 and diisopropylethylamine (4.0 mL, 22.8 mmol, 2.7 equiv) were dissolved in 8 mL of methylene chloride and cooled to 0° C. $POCl_3$ (0.87 mL, 9.3 mmol, 1.1 equiv) was slowly added and stirring was continued at 0° C. for 90 min. A solution of sodium carbonate (1.7 g, 16.0 mmol, 1.9 equiv) in 8 mL of water was added at room temperature in a rate so that the temperature was maintained at about 25-35° C. The reaction mixture was stirred at room temperature for another 90 minutes. Water and methylene chloride were added and the organic layer was separated, washed with water. The solvent was removed and the residue was triturated with ethyl ether and hexane (~1:3) to give the isonitrile 12 which is pure enough for use.

Example 1

3-(3,4-Dimethoxyphenylamino)-2-(2,4-dihydro-2-oxo-1H-benzo[d][1,3]oxazin-7-yl)-1H-imidazo[1,2-b]pyrazole-7-carbonitrile $^1$H-NMR (DMSO-d6, 300 MHz) 10.93 (br. s, 1H), 7.98 (s, 1H), 7.81 (br. s, 1H), 7.28 (s, 1H), 7.27 (d, J=9.3 Hz, 1H), 7.01

(d, J=8.1 Hz, 1H), 6.67 (d, J=9.0 Hz, 1H), 6.36 (d, J=2.1 Hz, 1H), 5.92 (dd, J=8.4, 2.1 Hz, 1H), 4.57 (s, 2H), 3.62 (s, 3H), 3.61 (s, 3H) ppm; MS (ES) 430.91 (M+H), 428.96 (M−H).

Example 2

N-(4-(3-(3,4-Dimethoxyphenylamino)-7-cyano-1H-imidazo[1,2-b]pyrazol-2-yl)phenyl)acetamide $^1$H-NMR (DMSO-d6, 300 MHz) 10.03 (br. s, 1H), 7.99 (s, 1H), 7.87 (br. s, 1H), 7.62 (dd, J=9.0, 7.5 Hz, 2H), 6.67 (d, J=8.7 Hz, 1H), 6.35 (d, J=2.1 Hz, 1H), 5.94 (dd, J=8.1, 1.8 Hz, 1H), 3.61 (s, 6H), 2.03 (s, 3H) ppm; MS (ES) 417.35 (M+H).

Example 3

N-(4-(3-(3-(Trifluoromethyl)phenylamino)-7-cyano-1H-imidazo[1,2-b]pyrazol-2-yl)phenyl)acetamide $^1$H-NMR (DMSO-d6, 300 MHz) 10.05 (br. s, 1H), 8.64 (br. s, 1H), 8.02 (s, 1H), 7.63 (s, 4H), 7.31 (t, J=7.5 Hz, 1H), 7.04 (d, J=8.1 Hz, 1H), 6.91 (br. s, 1H), 6.78 (d, J=8.1 Hz, 1H), 2.04 (s, 3H) ppm; MS (ES) 425.36 (M+H).

Example 4

3-(3,4-Dimethoxyphenylamino)-2-(5-methoxy-1H-indol-3-yl)-1H-imidazo[1,2-b]pyrazole-7-carbonitrile $^1$H NMR (DMSO-d$_6$, 300 MHz) 12.26 (s, 1H), 11.38 (s, 1H), 7.96 (s, 1H), 7.81 (s, 1H), 7.57 (d, 1H), 7.27 (d, 1H), 7.15 (s, 1H), 6.70 (d, 2H), 6.35 (d, 1H), 6.05 (d, 1H), 3.59 (d, 6H), 3.40 (s, 3H) ppm; MS (ES) 429.26 (M+H).

Example 5

3-(3,4-Dimethoxyphenylamino)-2-(1H-indol-5-yl)-1H-imidazo[1,2-b]pyrazole-7-carbonitrile $^1$H-NMR (DMSO-d6, 300 MHz) 11.21 (br. s, 1H), 7.97 (s, 1H), 7.96 (br. s, 1H), 7.83 (s, 1H), 7.50-7.36 (m, 3H), 6.67 (d, J=8.4 Hz, 1H), 6.43 (s, 1H), 6.37 (d, J=2.1 Hz, 1H), 5.95 (dd, J=8.7, 2.4 Hz, 1H), 3.61 (s, 3H), 3.60 (s, 3H) ppm; MS (ES) 399.34 (M+H).

Example 6

3-(3,4-Dimethoxyphenylamino)-2-(1H-indol-6-yl)-1H-imidazo[1,2-b]pyrazole-7-carbonitrile $^1$H-NMR (DMSO-d6, 300 MHz) 11.30 (br. s, 1H), 7.97 (s, 1H), 7.98 (s, 1H), 7.87 (s, 1H), 7.78 (br. s, 1H), 7.56 (d, J=8.1 Hz, 1H), 7.42-7.36 (m, 2H), 6.67 (d, J=8.4 Hz, 1H), 6.40-6.38 (m, 2H), 5.97 (dd, J=8.7, 2.7 Hz, 1H), 3.62 (s, 3H), 3.60 (s, 3H) ppm; MS (ES) 399.32 (M+H).

Example 7

3-(3,4-Dichlorophenylamino)-2-(2,4-dihydro-2-oxo-1H-benzo[d][1,3]oxazin-7-yl)-1H-imidazo[1,2-b]pyrazole-7-carbonitrile $^1$H-NMR (DMSO-d6, 300 MHz) 10.94 (br. s, 1H), 8.56 (br. s, 1H), 8.02 (s, 1H), 7.32 (d, J=8.7 Hz, 1H), 7.25-7.23 (m, 1H), 7.04 (d, J=9.0 Hz, 1H), 6.78 (d, J=2.1 Hz, 1H), 6.55 (dd, J=8.7, 2.4 Hz, 1H), 4.58 (s, 2H) ppm; MS (ES) 439.20 (M).

Example 8

3-(3,4-Dimethoxyphenylamino)-2-(4-phenoxyphenyl)-1H-imidazo[1,2-b]pyrazole-7-carbonitrile $^1$H-NMR (DMSO-d6, 300 MHz) 8.00 (s, 1H), 7.91 (br. s, 1H), 7.73 (d, J=7.5 Hz, 2H), 7.38 (t, J=7.8 Hz, 2H), 7.14 (t, J=8.4 Hz, 1H), 7.06 (d, J=7.2 Hz, 1H), 7.01 (d, J=7.8 Hz, 2H), 6.68 (d, J=8.4 Hz, 1H), 6.35 (s, 1H), 5.94 (d, J=8.4 Hz, 1H), 3.61 (s, 6H) ppm; MS (ES) 452.35 (M+H).

Example 9

3-(3-Cyanophenylamino)-2-(3,4-dihydro-3-oxo-2H-benzo[b][1,4]oxazin-6-yl)-1H-imidazo[1,2-b]pyrazole-7-carbonitrile $^1$H NMR (DMSO-d$_6$, 300 MHz) 10.92 (s, 1H), 8.61 (s, 1H), 8.00 (s, 1H), 7.31-7.24 (m, 3H), 7.14 (d, 1H), 7.03 (d, 1H), 6.94 (m, 2H), 4.57 (s, 2H) ppm; MS (ES) 396.30 (M+H).

Example 10

Methyl 3-(7-cyano-2-(3,4-dihydro-3-oxo-2H-benzo[b][1,4]oxazin-6-yl)-1H-imidazo[1,2-b]pyrazol-3-ylamino)benzoate $^1$H NMR (DMSO-d$_6$, 300 MHz) 10.92 (s, 1H), 8.43 (s, 1H), 8.00 (s, 1H), 7.33-7.20 (m, 5H), 7.03 (d, 1H), 6.78 (d, 1H), 4.57 (s, 2H), 3.77 (s, 3H) ppm; MS (ES) 429.30 (M+H).

Example 11

3-(2,4,4-Trimethylpentan-2-ylamino)-2-(3,4,5-trimethoxyphenyl)-1H-imidazo[1,2-b]pyrazole-7-carbonitrile $^1$H-NMR (DMSO-d6, 300 MHz) 12.22 (br. s, 1H), 8.01 (s, 1H), 7.26 (s, 2H), 4.33 (br. s, 1H), 3.84 (s, 3H), 3.83 (s, 3H), 3.67 (s, 3H), 1.63 (s, 2H), 1.08 (s, 6H), 0.99 (s, 9H) ppm; MS (ES) 425.53 (M).

Example 12

N-(7-Cyano-2-(3,4,5-trimethoxyphenyl)-1H-imidazo[1,2-b]pyrazol-3-yl)-2,2,2-trifluoroacetamide $^1$H-NMR (DMSO-d6, 300 MHz) 12.03 (br. s, 1H), 8.14 (s, 1H), 6.96 (s, 2H), 3.81 (s, 6H), 3.69 (s, 3H) ppm; MS (ES) 410.31 (M).

Example 13

Methyl 4-(7-cyano-2-(2,4-dihydro-2-oxo-1H-benzo[d][1,3]oxazin-7-yl)-1H-imidazo[1,2-b]pyrazol-3-ylamino)benzoate $^1$H-NMR (DMSO-d6, 300 MHz) 10.95 (br. s, 1H), 8.80 (br. s, 1H), 8.02 (s, 1H), 7.44 (d, J=8.7 Hz, 2H), 7.25-7.23 (m, 2H), 7.03 (d, J=9.0 Hz, 1H), 6.64 (d, J=8.7 Hz, 2H), 4.57 (s, 2H), 3.75 (s, 3H) ppm; MS (ES) 429.31 (M+H).

Example 14

3-(3-Methoxyphenylamino)-2-(3,4,5-trimethoxyphenyl)-1H-imidazo[1,2-b]pyrazole-7-carbonitrile $^1$H-NMR (DMSO-d6, 300 MHz) 8.27 (br. s, 1H), 8.05 (s, 1H), 7.05 (s, 2H), 7.02-6.99 (m, 1H), 6.30 (dd, J=8.4, 2.1 Hz, 1H), 6.17 (d, J=7.2 Hz, 1H), 6.12 (t, J=2.1 Hz 1H), 3.66 (s, 6H), 3.64 (s, 3H), 3.61 (s, 3H) ppm; MS (ES) 420.39 (M+H).

Example 15

3-(3-Methoxyphenylamino)-2-(2,4-dihydro-2-oxo-1H-benzo[d][1,3]oxazin-7-yl)-1H-imidazo[1,2-b]pyrazole-7-carbonitrile $^1$H-NMR (DMSO-d6, 300 MHz) 10.96 (br. s, 1H), 8.12 (br. s, 1H), 8.00 (s, 1H), 7.28 (s, 1H), 7.24 (d, J=2.1 Hz, 1H), 7.03-6.97 (m, 2H), 6.29 (dd, J=9.3, 2.4 Hz, 1H), 6.13 (d, J=9.0 Hz, 1H), 6.12 (s, 1H), 4.57 (s, 2H), 3.62 (s, 3H) ppm; MS (ES) 401.12 (M+H).

Example 16

3-(3,4-Dimethoxyphenylamino)-2-(2,4-dihydro-2-oxo-1H-benzo[d][1,3]oxazin-7-yl)-6-methyl-1H-imidazo[1,2-b]pyrazole-7-carbonitrile $^1$H-NMR (DMSO-d6, 300 MHz) 10.93 (br. s, 1H), 7.78 (br. s, 1H), 7.26 (s, 1H), 7.22 (d, J=1.8 Hz, 1H), 7.00 (d, J=8.1 Hz, 1H), 6.67 (d, J=8.7 Hz, 1H), 6.36 (d, J=2.4 Hz, 1H), 5.90 (dd, J=8.7, 2.4 Hz, 2H), 4.56 (s, 2H), 3.63 (s, 3H), 3.61 (s, 3H) ppm; MS (ES) 445.37 (M+H).

Example 17

3-Amino-2-(3,4,5-trimethoxyphenyl)-1H-imidazo[1,2-b]pyrazole-7-carbonitrile $^1$H NMR (DMSO-d$_6$, 300 MHz) 11.90 (s, 1H), 8.03 (s, 1H), 6.93 (s, 2H), 5.80 (s, 2H), 3.84 (s, 6H), 3.65 (s, 3H) ppm; MS (ES) 314.17 (M+H).

Example 18

N-(7-Cyano-2-(3,4,5-trimethoxyphenyl)-1H-imidazo[1,2-b]pyrazol-3-yl)-3-fluoro-4-(trifluoromethyl)benzamide $^1$H NMR (DMSO-d$_6$, 300 MHz) 11.01 (s, 1H), 8.04 (m, 4H), 7.02 (s, 2H), 3.74 (s, 6H), 3.67 (s, 3H) ppm; MS (ES) 504.24 (M+H).

Example 19

N-(7-Cyano-2-(3,4,5-trimethoxyphenyl)-1H-imidazo[1,2-b]pyrazol-3-yl)benzamide $^1$H NMR (DMSO-d$_6$, 300 MHz) 10.64 (s, 1H), 8.08 (s, 1H), 8.02 (d, 2H), 7.64-7.55 (m, 4H), 7.04 (s, 2H), 3.71 (s, 6H), 3.65 (s, 3H) ppm; MS (ES) 418.30 (M+H).

Example 20

N-(7-Cyano-2-(3,4,5-trimethoxyphenyl)-1H-imidazo[1,2-b]pyrazol-3-yl)-4-fluorobenzamide $^1$H NMR (DMSO-d$_6$, 300 MHz) 10.67 (s, 1H), 8.08 (m, 3H), 7.39 (s, 2H), 7.03 (s, 2H), 3.72 (s, 6H), 3.63 (s, 3H) ppm; MS (ES) 436.21 (M+H).

Example 21

N-(7-Cyano-2-(3,4,5-trimethoxyphenyl)-1H-imidazo[1,2-b]pyrazol-3-yl)-3-methoxybenzamide $^1$H NMR (DMSO-d$_6$, 300 MHz) 10.63 (s, 1H), 8.09 (s, 1H), 7.60 (d, 1H), 7.55 (s, 1H), 7.47 (t, 1H), 7.21 (d, 1H), 7.04 (s, 2H), 3.81 (s, 3H), 3.72 (s, 6H), 3.66 (s, 3H) ppm; MS (ES) 448.62 (M+H).

Example 22

3-(3,4-Dichlorophenylamino)-2-(3,4,5-trimethoxyphenyl)-1H-imidazo[1,2-b]pyrazole-7-carbonitrile $^1$H-NMR (DMSO-d6, 300 MHz) 8.71 (br. s, 1H), 8.07 (s, 1H), 7.34 (d, J=8.7 Hz, 1H), 7.03 (s, 2H), 6.78 (d, J=2.7 Hz, 1H), 6.60 (dd, J=8.7, 2.4 Hz, 1H), 3.70 (s, 6H), 3.65 (s, 3H) ppm; MS (ES) 458.24 (M).

Example 23

3-(4-Bromophenylamino)-2-(3,4,5-trimethoxyphenyl)-1H-imidazo[1,2-b]pyrazole-7-carbonitrile $^1$H-NMR (DMSO-d6, 300 MHz) 8.48 (br. s, 1H), 8.05 (s, 1H), 7.27 (d, J=8.7 Hz, 2H), 7.04 (s, 2H), 6.55 (d, J=8.7 Hz, 2H), 6.60 (dd, J=8.7, 2.4 Hz, 1H), 3.67 (s, 6H), 3.64 (s, 3H) ppm; MS (ES) 468.25 (M).

Example 24

3-(3,4-Dimethoxyphenylamino)-2-(6-methoxy-1H-indol-3-yl)-1H-imidazo[1,2-b]pyrazole-7-carbonitrile $^1$H-NMR (DMSO-d6, 300 MHz) 12.30 (br. s, 1H), 11.22 (br. s, 1H), 7.97 (s, 1H), 7.74 (br. s, 1H), 7.67 (d, J=8.7 Hz, 1H), 7.44 (d, J=2.1 Hz, 1H), 6.89 (s, 1H), 6.60 (d, J=8.7 Hz, 2H), 6.31 (d, J=2.1 Hz, 1H), 5.98 (dd, J=8.7, 2.1 Hz, 1H), 3.75 (s, 3H), 3.59 (s, 3H), 3.58 (s, 3H) ppm; MS (ES) 429.29 (M+H).

Example 25

3-(4-Morpholinophenylamino)-2-(3,4,5-trimethoxyphenyl)-1H-imidazo[1,2-b]pyrazole-7-carbonitrile $^1$H-NMR (DMSO-d6, 300 MHz) 8.04 (s, 1H), 7.96 (s, 1H), 7.06 (s, 2H), 6.77 (d, J=7.5 Hz, 2H), 6.52 (d, J=8.7 Hz, 2H), 3.68 (br. s, 4H), 3.65 (s, 6H), 3.63 (s, 3H), 3.33 (br. s, 4H) ppm; MS (ES) 475.35 (M+H).

Example 26

3-(3,4,5-Trimethoxyphenylamino)-2-(1H-indol-6-yl)-1H-imidazo[1,2-b]pyrazole-7-carbonitrile $^1$H-NMR (DMSO-d6, 300 MHz) 11.30 (br. s, 1H), 8.01 (d, J=12.0 Hz, 1H), 7.78 (s, 1H), 7.57 (d, J=8.4 Hz, 1H), 7.41-

7.37 (m, 1H), 6.42 (s, 1H), 5.89 (s, 2H), 3.55 (s, 6H), 3.52 (s, 3H) ppm; MS (ES) 429.37 (M+H).

Example 27

3-(4-Morpholinophenylamino)-2-(1H-indol-6-yl)-1H-imidazo[1,2-b]pyrazole-7-carbonitrile $^1$H-NMR (DMSO-d6, 300 MHz) 11.30 (br. s, 1H), 7.96 (s, 1H), 7.82 (s, 2H), 7.55 (d, J=8.7 Hz, 1H), 7.42 (d, J=8.7 Hz, 1H), 7.37 (t, J=2.7 Hz, 1H), 6.75 (d, J=9.0 Hz, 2H), 6.53 (d, J=8.7 Hz, 2H), 6.41 (s, 1H), 3.68 (t, J=4.5 Hz, 2H), 3.33 (t, J=4.5 Hz, 4H) ppm; MS (ES) 424.37 (M+H).

Example 28

3-(3,4-Dimethoxyphenylamino)-2-(3,4,5-trimethoxyphenyl)-1H-imidazo[1,2-b]pyrazole-7-carbonitrile $^1$H-NMR (DMSO-d6, 300 MHz) 8.04 (s, 1H), 7.99 (br. s 1H), 7.05 (s, 2H), 6.70 (d, J=8.7 Hz, 1H), 6.37 (d, J=2.4 Hz, 1H), 5.97 (dd, J=8.4, 2.7 Hz, 1H), 3.67 (s, 6H), 3.64 (s, 3H), 3.60 (s, 3H), 3.59 (s, 3H) ppm; MS (ES) 450.38 (M+H).

Example 29

3-(3,4,5-Trimethoxyphenylamino)-2-(3,4,5-trimethoxyphenyl)-1H-imidazo[1,2-b]pyrazole-7-carbonitrile $^1$H-NMR (DMSO-d6, 300 MHz) 8.15 (br. s, 1H), 8.05 (s 1H), 7.01 (s, 2H), 5.89 (s, 2H), 3.67 (s, 6H), 3.64 (s, 3H), 3.55 (s, 6H), 3.51 (s, 3H) ppm; MS (ES) 480.41 (M+H).

Example 30

N-(3-(7-Cyano-2-(3,4,5-trimethoxyphenyl)-1H-imidazo[1,2-b]pyrazol-3-ylamino)phenyl)acetamide $^1$H-NMR (DMSO-d6, 300 MHz) 9.68 (br. s, 1H), 8.26 (br. s 1H), 8.05 (s, 2H), 7.06 (s, 2H), 6.99 (d, J=9.6 Hz, 1H), 6.98 (s, 1H), 6.88 (s, 1H), 6.28 (d, J=6.6 Hz, 1H), 3.66 (s, 6H), 3.64 (s, 3H), 1.94 (s, 3H) ppm; MS (ES) 447.25 (M+H).

Example 31

N-(3-(7-Cyano-2-(3,4-dihydro-3-oxo-2H-benzo[b][1,4]oxazin-6-yl)-1H-imidazo[1,2-b]pyrazol-3-ylamino)phenyl)acetamide $^1$H-NMR (DMSO-d6, 300 MHz) 10.97 (br. s, 1H), 9.66 (br. s, 1H), 8.10 (br. s, 1H), 7.99 (s, 1H), 7.28 (s, 1H), 7.27 (d, J=8.4 Hz, 1H), 7.03-6.98 (m, 3H), 6.83 (s, 1H), 6.26 (m, 1H), 4.57 (s, 2H), 1.94 (s, 3H) ppm; MS (ES) 428.22 (M+H).

Example 32

N-(3-(7-Cyano-2-(3,4-dimethoxyphenyl)-1H-imidazo[1,2-b]pyrazol-3-ylamino)phenyl)acetamide $^1$H-NMR (DMSO-d6, 300 MHz) 9.67 (br. s, 1H), 8.17 (br. s, 1H), 8.01 (d, J=1.2 Hz, 1H), 7.31 (s, 1H), 7.29 (d, J=9.3 Hz, 1H), 7.01 (d, J=7.8 Hz, 1H), 6.98 (d, J=6.9 Hz, 1H), 6.86 (s, 1H), 6.26 (d, J=6.9 Hz, 1H), 3.74 (s, 3H), 3.65 (s, 3H), 1.93 (s, 3H) ppm; MS (ES) 417.20 (M+H).

Example 33

N-(3-(7-Cyano-2-(4-(methylthio)phenyl)-1H-imidazo[1,2-b]pyrazol-3-ylamino)phenyl)acetamide $^1$H-NMR (DMSO-d6, 300 MHz) 9.67 (br. s, 1H), 8.19 (br. s, 1H), 8.01 (d, J=1.2 Hz, 1H), 7.66 (d, J=7.2 Hz, 2H), 7.31 (d, J=7.2 Hz, 2H), 6.98 (d, J=6.6 Hz, 1H), 6.97 (s, 1H), 6.86 (s, 1H), 6.24 (d, J=6.9 Hz, 1H), 1.94 (s, 3H) ppm; MS (ES) 403.22 (M+H).

Example 34

N-(4-(7-Cyano-3-(3-acetamidophenylamino)-1H-imidazo[1,2-b]pyrazol-2-yl)phenyl)acetamide $^1$H-NMR (DMSO-d6, 300 MHz) 10.05 (br. s, 1H), 9.67 (br. s, 1H), 8.15 (br. s, 1H), 8.00 (d, J=1.5 Hz, 1H), 7.62 (quart, J=9.0, 8.7, 5.1 Hz, 4H), 6.98 (s, 2H), 6.85 (s, 1H), 6.26 (d, J=6.9 Hz, 1H), 2.03 (s, 3H), 1.94 (s, 3H) ppm; MS (ES) 414.31 (M+H).

Example 35

3-(3-Methoxybenzylamino)-2-(3,4-dihydro-3-oxo-2H-benzo[b][1,4]oxazin-6-yl)-1H-imidazo[1,2-b]pyrazole-7-carbonitrile $^1$H-NMR (DMSO-d6, 300 MHz) 12.14 (br. s, 1H), 10.88 (br. s, 1H), 8.05 (s, 1H), 7.26 (s, 1H), 7.18 (d, J=8.7 Hz, 1H), 7.10 (t, J=9.0 Hz, 1H), 7.00 (d, J=8.7 Hz, 1H), 6.80 (s, 1H), 6.75 (d, J=7.2 Hz, 1H), 6.70 (d, J=6.9 Hz, 1H), 5.55 (br. s, 1H), 4.59 (s, 2H), 4.35 (d, J=2.7 Hz, 2H), 3.56 (s, 3H) ppm; MS (ES) 415.24 (M+H).

Example 36

3-(3,4-Dimethoxyphenylamino)-2-(2,4-difluorophenyl)-1H-imidazo[1,2-b]pyrazole-7-carbonitrile $^1$H NMR (DMSO-d$_6$, 300 MHz) 8.04 (s, 1H), 7.84 (s, 1H), 7.60 (m, 1H), 7.42 (t, 1H), 7.20 (7, 1H), 6.67 (d, 1H), 5.96 (d, 1H), 3.58 (d, 6H) ppm; MS (ES) 396.20 (M+H).

Example 37

3-(3,4-Dimethoxyphenylamino)-2-(3,4-difluorophenyl)-1H-imidazo[1,2-b]pyrazole-7-carbonitrile $^1$H NMR (DMSO-d$_6$, 300 MHz) 8.04 (s, 1H), 8.01 (s, 1H), 7.75 (m, 1H), 7.57 (m, 2H), 6.68 (d, 1H), 6.36 (s, 1H), 5.95 (d, 1H), 3.60 (d, 6H) ppm; MS (ES) 396.37 (M+H).

Example 38

3-(3,4-Dimethoxyphenylamino)-2-(2,3-dihydrobenzo[b][1,4]dioxin-7-yl)-1H-imidazo[1,2-b]pyrazole-7-carbonitrile $^1$H NMR (DMSO-d$_6$, 300 MHz) 7.98 (s, 1H), 7.84 (s, 1H), 7.26 (s, 1H), 7.20 (d, 1H), 6.92 (d, 1H), 6.67 (d, 1H), 6.35 (s, 1H), 5.90 (d, 1H), 4.23 (s, 4H), 3.61 (d, 6H) ppm; MS (ES) 418.23 (M+H).

Example 39

N-(7-Cyano-2-(3,4,5-trimethoxyphenyl)-1H-imidazo[1,2-b]pyrazol-3-yl)-5-phenyl-1,3,4-oxadiazole-2-carboxamide $^1$H NMR (DMSO-d$_6$, 300 MHz) 11.75 (s, 1H), 8.12 (s, 1H), 8.07 (d, 2H), 7.63 (m, 3H), 7.09 (s, 2H), 3.78 (s, 6H), 3.67 (s, 3H) ppm; MS (ES) 486.43 (M+H).

Example 40

3-(3,4-Dimethoxyphenethylamino)-2-(3,4-dihydro-3-oxo-2H-benzo[b][1,4]oxazin-6-yl)-1H-imidazo[1,2-b]pyrazole-7-carbonitrile $^1$H NMR (DMSO-d$_6$, 300 MHz) 12.11 (s, 1H), 10.85 (s, 1H), 8.02 (s, 1H), 7.29 (s, 1H), 7.15 (m, 1H), 6.95 (m, 1H), 6.73 (m, 2H), 6.60 (m, 1H), 4.92 (s, 1H), 4.58 (m, 2H), 3.65 (m, 7H), 2.70 (s, 2H) ppm; MS (ES) 459.45 (M+H).

Example 41

3-(3,4-Dimethoxyphenethylamino)-2-(3,4,5-trimethoxyphenyl)-1H-imidazo[1,2-b]pyrazole-7-carbonitrile $^1$H NMR (DMSO-d$_6$, 300 MHz) 12.12 (s, 1H), 8.05 (s, 1H), 7.05 (s, 3H), 6.71 (m, 3H), 6.58 (d, 1H), 5.14 (t, 1H), 3.78 (d, 6H), 3.65 (d, 6H), 3.61 (s, 3H), 2.46 (m, 2H), 2.70 (t, 1H) ppm; MS (ES) 478.47 (M+H).

Example 42

N-(7-Cyano-2-(3,4,5-trimethoxyphenyl)-1H-imidazo[1,2-b]pyrazol-3-yl)-2-(3,4-dimethoxyphenyl)acetamide $^1$H NMR (DMSO-d$_6$, 300 MHz) 10.15 (s, 1H), 8.06 (s, 1H), 6.91 (s, 3H), 6.85 (m, 2H), 5.77 (s, 2H), 3.68 (m, 15H) ppm; MS (ES) 492.33 (M+H).

Example 43

3-(4-Morpholinophenylamino)-2-(3,4-dihydro-3-oxo-2H-benzo[b][1,4]oxazin-6-yl)-1H-imidazo[1,2-b]pyrazole-7-carbonitrile $^1$H-NMR (DMSO-d6, 300 MHz) 10.94 (br. s, 1H), 8.16 (d, J=8.7 Hz, 1H), 7.76 (br. s, 1H), 7.31 (s, 1H), 7.28 (d, J=8.1 Hz, 1H), 7.00 (d, J=8.1 Hz, 1H), 6.74 (d, J=9.0 Hz, 2H), 6.48 (d, J=8.7 Hz, 2H), 4.56 (s, 2H), 3.67 (br. s, 4H), 2.90 (br. s, 4H) ppm; MS (ES) 456.28 (M+H).

Example 44

3-(3-Methoxyphenylamino)-2-(1H-indol-6-yl)-1H-imidazo[1,2-b]pyrazole-7-carbonitrile $^1$H-NMR (DMSO-d6, 300 MHz) 11.32 (br. s, 1H), 8.16 (br. s, 1H), 7.99 (s, 1H), 7.78 (br. s, 1H), 7.56 (d, J=7.5 Hz, 1H), 7.39 (d, J=8.7 Hz, 1H), 7.38 (s, 1H), 7.00 (t, J=7.8 Hz, 1H), 6.52 (s, 1H), 6.41 (s, 1H), 6.28 (d, J=7.5 Hz, 1H), 6.18 (d, J=7.8 Hz, 1H), 6.14 (s, 1H), 3.61 (s, 3H) ppm; MS (ES) 369.27 (M+H).

Example 45

3-(4-Bromophenylamino)-2-(3,4-dihydro-3-oxo-2H-benzo[b][1,4]oxazin-6-yl)-1H-imidazo[1,2-b]pyrazole-7-carbonitrile $^1$H-NMR (DMSO-d6, 300 MHz) 10.95 (br. s, 1H), 8.33 (br. s, 1H), 8.00 (s, 1H), 7.27-7.23 (m, 4H), 7.03 (d, J=9.0 Hz, 1H), 6.53 (d, J=9.0 Hz, 2H), 4.57 (s, 2H) ppm; MS (ES) 449.19 (M).

Example 46

3-(3-Methoxybenzylamino)-2-(3,4,5-trimethoxyphenyl)-1H-imidazo[1,2-b]pyrazole-7-carbonitrile $^1$H-NMR (DMSO-d6, 300 MHz) 12.11 (br. s, 1H), 8.08 (s, 1H), 7.12 (t, J=8.1 Hz, 1H), 6.93 (s, 2H), 6.80-6.70 (m, 2H), 5.69 (t, J=6.3 Hz, 1H), 4.42 (d, J=6.0 Hz, 2H), 3.76 (s, 6H), 3.65 (s, 3H), 3.57 (s, 3H) ppm; MS (ES) 434.33 (M+H).

Example 47

N-(3-(7-Cyano-2-(1H-indol-6-yl)-1H-imidazo[1,2-b]pyrazol-3-ylamino)phenyl)acetamide $^1$H-NMR (DMSO-d6, 300 MHz) 11.32 (br. s, 1H), 9.67 (br. s, 1H), 8.15 (br. s, 1H), 7.98 (s, 1H), 7.79 (s, 1H), 7.56 (d, J=8.1 Hz, 1H), 7.41-7.37 (m, 2H), 6.98 (s, 2H), 6.87 (s, 1H), 6.41 (s, 1H), 6.29-6.27 (m, 1H), 1.93 (s, 3H) ppm; MS (ES) 396.31 (M+H).

Example 48

3-(3,4-Dimethoxyphenylamino)-2-(4-(methylsulfonyl)phenyl)-1H-imidazo[1,2-b]pyrazole-7-carbonitrile $^1$H-NMR (DMSO-d6, 300 MHz) 8.14 (br. s, 1H), 8.07 (s, 1H), 7.97 (s, 4H), 6.68 (d, J=8.4 Hz, 1H), 6.40 (s, 1H), 5.97 (d, J=8.1 Hz, 1H), 3.62 (s, 3H), 3.61 (s, 3H), 3.21 (s, 3H) ppm; MS (ES) 438.23 (M+H).

Example 49

3-(2,3-Dihydrobenzo[b][1,4]dioxin-6-ylamino)-2-(3,4,5-trimethoxyphenyl)-1H-imidazo[1,2-b]pyrazole-7-carbonitrile $^1$H-NMR (DMSO-d6, 300 MHz) 8.04 (br. s, 1H), 7.96 (s, 1H), 7.06 (s, 2H), 6.63 (d, J=8.7 Hz, 1H), 6.12 (dt, J=9.0, 2.4 Hz, 1H), 5.97 (d, J=2.7 Hz, 1H), 4.12-4.08 (m, 4H), 3.69 (s, 6H), 3.64 (s, 3H) ppm; MS (ES) 448.26 (M+H).

Example 50

3-(2,3-Dihydrobenzo[b][1,4]dioxin-6-ylamino)-2-(3,4-dihydro-3-oxo-2H-benzo[b][1,4]oxazin-6-yl)-1H-imidazo[1,2-b]pyrazole-7-carbonitrile $^1$H-NMR (DMSO-d6, 300 MHz) 10.96 (br. s, 1H), 7.99 (s, 1H), 7.80 (s, 1H), 7.30-7.25 (m, 2H), 7.02 (d, J=8.1, 2.4 Hz, 1H), 6.61 (dd, J=9.0, 2.1 Hz, 1H), 6.06 (dt, J=8.4, 2.4 Hz, 1H), 6.02 (d, J=2.4 Hz, 1H), 4.57 (s, 2H), 4.12-4.10 (m, 4H) ppm; MS (ES) 429.29 (M+H).

Example 51

3-(3,4-Dimethoxyphenylamino)-2-(benzo[d][1,3]dioxol-6-yl)-1H-imidazo[1,2-b]pyrazole-7-carbonitrile ¹H-NMR (DMSO-d6, 300 MHz) 7.98 (br. s, 1H), 7.85 (s, 1H), 7.28-7.26 (m, 1H), 7.25-7.22 (m, 1H), 7.00 (d, J=7.8 Hz, 1H), 6.68 (d, J=8.7 Hz, 1H), 6.34 (d, J=2.1 Hz, 1H), 6.02 (s, 2H), 5.91 (dd, J=8.4, 2.4 Hz, 1H), 3.62 (s, 3H), 3.61 (s, 3H) ppm; MS (ES) 404.25 (M+H).

Example 52

3-(3,4-Dimethoxyphenylamino)-2-(3-fluoro-4-methoxyphenyl)-1H-imidazo[1,2-b]pyrazole-7-carbonitrile ¹H-NMR (DMSO-d6, 300 MHz) 8.00 (s, 1H), 7.91 (br. s, 1H), 7.60-7.51 (m, 2H), 7.26 (t, J=9.0 Hz, 1H), 6.68 (d, J=8.7 Hz, 1H), 6.36 (d, J=2.7 Hz, 1H), 5.94 (d, J=8.7 Hz, 1H), 3.84 (s, 3H), 3.62 (s, 3H), 3.61 (s, 3H) ppm; MS (ES) 408.28 (M+H).

Example 53

2-Bromo-N-(7-cyano-2-(3,4,5-trimethoxyphenyl)-1H-imidazo[1,2-b]pyrazol-3-yl)acetamide ¹H NMR (DMSO-d₆, 300 MHz) 11.56 (d, 1H), 8.07 (s, 1H), 6.97 (s, 2H), 4.41 (s, 1H), 4.17 (s, 1H), 3.83 (d, 6H), 3.69 (s, 3H) ppm; MS (ES) 435.83 (M+H).

Example 54

N-(7-Cyano-2-(3,4,5-trimethoxyphenyl)-1H-imidazo[1,2-b]pyrazol-3-yl)-2-phenoxyacetamide ¹H NMR (DMSO-d₆, 300 MHz) 10.44 (s, 1H), 8.08 (s, 1H), 7.66 (m, 1H), 7.28 (m, 2H), 6.99 (m, 5H), 4.80 (s, 2H), 3.77 (s, 6H), 3.67 (s, 3H) ppm; MS (ES) 447.94 (M+H).

Example 55

3-(3,4-Dimethoxyphenylamino)-2-benzyl-1H-imidazo[1,2-b]pyrazole-7-carbonitrile

¹H NMR (DMSO-d₆, 300 MHz) 12.12 (s, 1H), 7.91 (s, 1H), 7.85 (s, 1H), 7.25 (m, 5H), 6.68 (d, 1H), 6.28 (s, 1H), 5.98 (d, 1H), 3.88 (s, 2H), 3.62 (s, 3H), 3.59 (s, 3H) ppm; MS (ES) 373.99 (M+H).

Example 56

2-(3,4-Dichlorophenyl)-N-(7-cyano-2-(3,4,5-trimethoxyphenyl)-1H-imidazo[1,2-b]pyrazol-3-yl)acetamide ¹H NMR (DMSO-d₆, 300 MHz) 10.39 (s, 1H), 8.07 (s, 1H), 8.57 (m, 2H), 7.30 (d, 1H), 6.91 (s, 2H), 3.80 (s, 2H), 3.72 (s, 6H), 3.66 (s, 3H) ppm; MS (ES) 499.87 (M+).

Example 57

3-(3,4-Dimethoxyphenylamino)-2-(3,4,5-trifluorophenyl)-1H-imidazo[1,2-b]pyrazole-7-carbonitrile ¹H-NMR (DMSO-d6, 300 MHz) 8.09 (br. s, 1H), 8.06 (t, J=2.1 Hz, 1H), 7.63 (t, J=9.0 Hz, 1H), 6.69 (d, J=8.7 Hz, 1H), 6.37 (d, J=1.2 Hz, 1H), 5.95 (d, J=8.4 Hz, 1H), 3.62 (s, 3H), 3.61 (s, 3H) ppm; MS (ES) 414.23 (M+H).

Example 58

3-(3,4-Dimethoxyphenylamino)-2-(3-chloro-4,5-dimethoxyphenyl)-1H-imidazo[1,2-b]pyrazole-7-carbonitrile ¹H-NMR (DMSO-d6, 300 MHz) 8.04 (t, J=2.1 Hz, 1H), 8.02 (br. s, 1H), 7.45 (s, 1H), 7.35 (s, 1H), 6.70 (d, J=9.0 Hz, 1H), 6.37 (s, 1H), 5.97 (d, J=8.4 Hz, 1H), 3.74 (s, 3H), 3.73 (s, 3H), 3.61 (s, 3H), 3.60 (s, 3H) ppm; MS (ES) 454.24 (M+H).

Example 59

3-(3,4-Dimethoxyphenylamino)-2-(4-fluoro-3-methoxyphenyl)-1H-imidazo[1,2-b]pyrazole-7-carbonitrile ¹H-NMR (DMSO-d6, 300 MHz) 8.03 (d, J=2.1 Hz, 1H), 7.98 (br. s, 1H), 7.47 (d, J=8.1 Hz, 1H), 7.31-7.28 (m, 2H), 6.69 (d, J=8.4 Hz, 1H), 6.36 (s, 1H), 5.95 (dt, J=8.4, 2.1 Hz, 1H), 3.76 (s, 3H), 3.61 (s, 3H), 3.60 (s, 3H) ppm; MS (ES) 408.23 (M+H).

Example 60

3-(2,3-Dihydrobenzo[b][1,4]dioxin-6-ylamino)-2-(1H-indol-6-yl)-1H-imidazo[1,2-b]pyrazole-7-carbonitrile ¹H-NMR (DMSO-d6, 300 MHz) 11.31 (br. s, 1H), 7.98 (d, J=2.4 Hz, 1H), 7.84 (s, 1H), 7.80 (s, 1H), 7.56 (d, J=8.1 Hz, 1H), 7.42-7.38 (m, 2H), 6.61 (d, J=9.0 Hz, 1H), 6.41 (s, 1H), 6.13 (d, J=8.1 Hz, 1H), 6.04 (s, 1H), 4.09 (m, 4H) ppm; MS (ES) 397.33 (M+H).

Example 61

N-(4-(7-Cyano-2-(3,4,5-trimethoxyphenyl)-1H-imidazo[1,2-b]pyrazol-3-ylamino)phenyl)acetamide ¹H-NMR (DMSO-d6, 300 MHz) 9.62 (br. s, 1H), 8.14 (br. s, 1H), 8.04 (s, 1H), 7.29 (d, J=6.9 Hz, 2H), 7.05 (s, 2H), 6.52 (d, J=6.9 Hz, 2H), 3.66 (s, 6H), 3.63 (s, 3H), 1.95 (s, 3H) ppm; MS (ES) 447.36 (M+H).

Example 62

N-(4-(7-Cyano-2-(6-methoxy-1H-indol-3-yl)-1H-imidazo[1,2-b]pyrazol-3-ylamino)phenyl)acetamide ¹H-NMR (DMSO-d6, 300 MHz) 12.31 (br. s, 1H), 11.25 (br. s, 1H), 9.59 (s, 1H), 7.96 (s, 1H), 7.90 (br. s, 1H), 7.56 (d, J=8.1 Hz, 1H), 7.44 (s, 1H), 7.24 (d, J=6.9 Hz, 2H), 6.89 (s, 1H), 6.66 (d, J=8.1 Hz, 1H), 6.47 (d, J=6.9 Hz, 2H), 3.74 (s, 3H), 1.94 (s, 3H) ppm; MS (ES) 426.29 (M+H).

Example 63

N-(4-(7-Cyano-2-(2,3-dihydrobenzo[b][1,4]dioxin-7-yl)-1H-imidazo[1,2-b]pyrazol-3-ylamino)phenyl)acetamide ¹H-NMR (DMSO-d6, 300 MHz) 9.62 (br. s, 1H), 8.00 (br. s, 1H), 7.98 (s, 1H), 7.29-7.20 (m, 2H), 6.91 (d, J=8.4 Hz, 1H), 6.48 (d, J=8.7 Hz, 2H), 4.22 (s, 4H), 1.95 (s, 3H) ppm; MS (ES) 415.22 (M–H), 413.12 (M+H).

Example 64

3-(3,4-Difluorophenylamino)-2-(3,4,5-trimethoxyphenyl)-1H-imidazo[1,2-b]pyrazole-7-carbonitrile ¹H-NMR (DMSO-d6, 300 MHz) 8.48 (s, 1H), 8.05 (s, 1H), 7.19 (m, 1H), 7.03 (s, 2H), 6.56 (m, 1H), 6.40 (m, 1H), 3.69 (s, 6H), 3.65 (s, 3H), 2.82 (m, 2H), 2.70 (m, 2H); MS (ES) 426.3 (M+H).

Example 65 tert-Butyl 4-(7-cyano-2-(3,4,5-trimethoxyphenyl)-1H-imidazo[1,2-b]pyrazol-3-ylamino)benzylcarbamate ¹H-NMR (DMSO-d6, 300 MHz) 8.16 (s, 1H), 8.02 (s, 1H), 7.18 (m, 1H), 7.05 (s, 2H), 6.97 (d, 2H), 6.52 (d, 2H), 3.94 (m, 2H), 3.64 (s, 9H), 1.35 (s, 9H); MS (ES) 519.5 (M+H).

Example 66

3-(4-(Aminomethyl)phenylamino)-2-(3,4,5-trimethoxyphenyl)-1H-imidazo[1,2-b]pyrazole-7-carbonitrile ¹H-NMR (DMSO-d6, 300 MHz) 8.33 (s, 1H), 7.96 (s, 1H), 7.18 (d, 2H), 7.09 (s, 2H), 6.58 (d, 2H), 3.83 (m, 2H), 3.66 (s, 3H), 3.64 (s, 3H), 3.63 (s, 3H), 3.32 (m, 4H); MS (ES) 419.5 (M+H).

Example 67

Methyl 3-(7-cyano-2-(3,4,5-trimethoxyphenyl)-1H-imidazo[1,2-b]pyrazol-3-ylamino)benzoate ¹H NMR (DMSO-d₆, 300 MHz) 8.60 (s, 1H), 8.07 (s, 1H), 7.32 (m, 2H), 7.19 (s, 1H), 7.04 (s, 2H), 6.84 (d, 1H), 3.76 (s, 3H), 3.64 (d, 9H) ppm; MS (ES) 447.87 (M+H).

Example 68

N-(4-(7-Cyano-2-(3,4-dihydro-3-oxo-2H-benzo[b][1,4]oxazin-6-yl)-1H-imidazo[1,2-b]pyrazol-3-ylamino)phenyl)acetamide ¹H-NMR (DMSO-d6, 300 MHz) 10.95 (br. s, 1H), 9.62 (br. s, 1H), 7.98 (s, 2H), 7.28 (s, 1H), 7.26 (d, J=8.4 Hz, 2H), 7.01 (d, J=8.4 Hz, 1H), 6.49 (d, J=7.8 Hz, 2H), 4.57 (s, 2H), 1.95 (s, 3H) ppm; MS (ES) 428.38 (M+H).

Example 69

N-(4-(7-Cyano-2-(3,4-dimethoxyphenyl)-1H-imidazo[1,2-b]pyrazol-3-ylamino)phenyl)acetamide ¹H-NMR (DMSO-d6, 300 MHz) 10.95 (br. s, 1H), 9.61 (br. s, 1H), 8.05 (br. s, 1H), 8.00 (d, J=1.5 Hz, 1H), 7.58 (d, J=8.4 Hz, 1H), 7.31 (s, 1H), 7.27 (d, J=7.5 Hz, 2H), 7.01 (d, J=8.7 Hz, 1H), 6.50 (d, J=7.5 Hz, 2H), 3.73 (s, 3H), 3.65 (s, 3H), 1.94 (s, 3H) ppm; MS (ES) 417.27 (M+H).

Example 70

3-(2,3-Dihydrobenzo[b][1,4]dioxin-6-ylamino)-2-(3-hydroxy-4,5-dimethoxyphenyl)-1H-imidazo[1,2-b]pyrazole-7-carbonitrile ¹H-NMR (DMSO-d6, 300 MHz) 9.31 (br. s, 1H), 8.00 (s, 1H), 7.85 (br. s, 1H), 6.93 (s, 1H), 6.87 (s, 1H), 6.62 (d, J=9.0 Hz, 1H), 6.09 (d, J=9.3 Hz, 1H), 6.01 (s, 1H), 4.12 (m, 4H), 3.71 (s, 3H), 3.65 (s, 3H) ppm; MS (ES) 434.25 (M+H).

Example 71

Methyl 4-(7-cyano-2-(3-hydroxy-4,5-dimethoxyphenyl)-1H-imidazo[1,2-b]pyrazol-3-ylamino)benzoate ¹H-NMR (DMSO-d6, 300 MHz) 9.35 (br. s, 1H), 8.85 (br. s, 1H), 8.03 (s, 1H), 7.74 (d, J=8.1 Hz, 2H), 6.86 (d, J=9.0 Hz, 1H), 6.65 (d, J=8.1 Hz, 2H), 3.75 (s, 3H), 3.68 (s, 3H), 3.64 (s, 3H) ppm; MS (ES) 434.31 (M+H).

Example 72

N-(4-(7-Cyano-2-(3,4,5-trimethoxyphenyl)-1H-imidazo[1,2-b]pyrazol-3-ylamino)benzyl)acetamide ¹H-NMR (DMSO-d6, 300 MHz) none obtained. No sample remains. MS (ES) 461.0 (M+H).

Example 73 tert-Butyl-4-((7-cyano-2-(3,4,5-trimethoxyphenyl)-1H-imidazo[1,2-b]pyrazol-3-ylamino)methyl)piperidine-1-carboxylate ¹H-NMR (DMSO-d6, 300 MHz) 12.13 (s, 1H), 8.03 (s, 1H), 7.12 (s, 2H), 5.08 (m, 1H), 3.83 (s, 6H), 3.68 (s, 3H), 3.12 (m, 2H), 2.60 (m, 2H), 1.68 (m, 4H), 1.36 (s, 9H), 1.00 (m, 3H); MS (ES) 511.0 (M+H).

Example 74

3-((Piperidin-4-yl)methylamino)-2-(3,4,5-trimethoxyphenyl)-1H-imidazo[1,2-b]pyrazole-7-carbonitrile ¹H-NMR (DMSO-d6, 300 MHz) 7.99 (s, 1H), 7.11 (s, 2H), 5.02 (m, 1H), 3.85 (s, 6H), 3.74 (s, 3H), 3.17 (m, 3H), 2.76 (m, 2H), 1.90 (m, 2H), 1.75 (m, 1H), 1.36 (m, 2H); MS (ES) 411.3 (M+H).

Example 75

3-(3-Fluoro-4-(4-(pyrrolidin-1-yl)piperidin-1-yl)phenylamino)-2-(3,4,5-trimethoxyphenyl)-1H-imidazo[1,2-b]pyrazole-7-carbonitrile ¹H-NMR (DMSO-d6, 300 MHz) 9.40 (broad s, 1H), 8.28 (s, 1H), 8.04 (s, 1H), 7.05 (s, 2H), 6.83 (m, 1H), 6.36 (m, 2H), 5.73 (s, 1H), 3.68 (s, 3H), 3.64 (s, 3H), 3.62 (s, 3H), 3.50 (m, 2H), 3.00-3.22 (m, 4H), 2.57 (m, 2H), 1.65-2.10 (m, 8H); MS (ES) 560.1 (M+H).

Example 76

(S)-Methyl 2-(7-cyano-2-(3,4,5-trimethoxyphenyl)-1H-imidazo[1,2-b]pyrazol-3-ylamino)-3-phenylpropanoate $^1$H-NMR (DMSO-d6, 300 MHz) 12.15 (s, 1H), 8.04 (s, 1H), 7.19 (m, 5H), 7.12 (s, 2H), 5.69 (d, 1H), 4.70 (m, 1H), 3.81 (s, 6H), 3.68 (s, 3H), 3.46 (s, 3H), 3.09 (m, 2H); MS (ES) 476.4 (M+H).

Example 77

Methyl 3-(7-cyano-2-(3,4-dimethoxyphenyl)-1H-imidazo[1,2-b]pyrazol-3-ylamino)benzoate $^1$H-NMR (DMSO-d6, 300 MHz) 8.51 (br. s, 1H), 8.03 (s, 1H), 7.30 (s, 2H), 7.32-7.23 (m, 2H), 7.19 (s, 1H), 7.01 (d, J=7.8 Hz, 1H), 6.81 (d, J=7.5 Hz, 1H), 3.77 (s, 3H), 3.74 (s, 3H), 3.66 (s, 3H) ppm; MS (ES) 418.30 (M+H).

Example 78

Methyl 3-(2-(3-chloro-4,5-dimethoxyphenyl)-7-cyano-1H-imidazo[1,2-b]pyrazol-3-ylamino)benzoate $^1$H-NMR (DMSO-d6, 300 MHz) 8.63 (br. s, 1H), 8.07 (s, 1H), 7.44 (d, J=1.8 Hz, 1H), 7.36 (s, 1H), 7.32 (s, 1H), 7.26 (t, J=7.8 Hz, 1H), 7.20 (s, 1H), 6.83 (d, J=7.5 Hz, 1H), 3.77 (s, 3H), 3.73 (s, 6H) ppm; MS (ES) 452.25 (M+H).

Example 79

3-(3,4,5-Trimethoxyphenylamino)-2-(4-morpholinophenyl)-1H-imidazo[1,2-b]pyrazole-7-carbonitrile $^1$H-NMR (DMSO-d6, 300 MHz) 7.99 (br. s, 1H), 7.98 (s, 1H), 7.58 (d, J=8.7 Hz, 2H), 7.00 (d, J=8.4 Hz, 2H), 5.84 (s, 2H), 3.71 (t, J=4.5 Hz, 4H), 3.55 (s, 6H), 3.52 (s, 3H), 3.14 (t, J=4.8 Hz, 4H) ppm; MS (ES) 475.33 (M+H), 473.17 (M−H).

Example 80

3-(4-Bromophenylamino)-2-(4-morpholinophenyl)-1H-imidazo[1,2-b]pyrazole-7-carbonitrile $^1$H-NMR (DMSO-d6, 300 MHz) 8.32 (br. s, 1H), 7.98 (s, 1H), 7.57 (d, J=8.4 Hz, 2H), 7.25 (d, J=8.7 Hz, 2H), 6.99 (d, J=8.7 Hz, 2H), 6.52 (d, J=8.4 Hz, 2H), 3.70 (t, J=4.8 Hz, 4H), 3.13 (t, J=4.8 Hz, 4H) ppm; MS (ES) 464.97 (M+H).

Example 81

4-(3-(3,4,5-Trimethoxyphenylamino)-7-cyano-1H-imidazo[1,2-b]pyrazol-2-yl)benzamide $^1$H-NMR (DMSO-d6, 300 MHz) 8.23 (br. s, 1H), 8.06 (s, 1H), 7.96 (br. s, 1H), 7.91 (d, J=8.1 Hz, 2H), 7.78 (d, J=8.4 Hz, 2H), 7.41 (br. s, 1H), 5.88 (s, 2H), 3.55 (s, 6H), 3.52 (s, 3H) ppm; MS (ES) 433.22 (M+H), 431.15 (M−H).

Example 82

3-Amino-2-(3,4,5-trimethoxyphenyl)-5-(4-methoxyphenyl)-5H-imidazo[1,2-b]pyrazol-7-carbonitrile $^1$H NMR (DMSO-d6, 300 MHz) 8.94 (s, 1H), 7.55 (d, 1H), 7.37 (d, 2H), 7.28 (s, 1H), 7.06 (m, 3H), 6.81 (s, 2H), 3.81 (s, 3H), 3.78 (s, 3H), 3.74 (s, 3H), 3.64 (s, 3H) ppm; MS (ES) 419.95 (M+H).

Example 83

N-(4-(7-Cyano-2-(3,4,5-trimethoxyphenyl)-5H-imidazo[1,2-b]pyrazol-3-ylamino)benzyl)nicotinamide $^1$H-NMR (DMSO-d6, 300 MHz) 12.65 (s, 1H), 9.07 (m, 1H), 8.98 (s, 1H), 8.68 (m, 1H), 8.23 (s, 1H), 8.18 (m, 1H), 8.02 (s, 1H), 7.11 (m, 4H), 6.55 (d, 2H), 4.33 (m, 2H), 3.64 (s, 6H), 3.63 (s, 3H); MS (ES) 524.2 (M+H).

Example 84

Methyl 3-(2-(4-((methoxycarbonyl)methoxy)-3-methoxyphenyl)-7-cyano-1H-imidazo[1,2-b]pyrazol-3-ylamino)benzoate $^1$H-NMR (DMSO-d6, 300 MHz) 8.52 (br. s, 1H), 8.03 (d, J=0.9 Hz, 1H), 7.33 (s, 1H), 7.29 (d, J=6.9 Hz, 1H), 7.25 (s, 1H), 7.23 (s, 1H), 7.19 (s, 1H), 6.94 (d, J=8.4 Hz, 1H), 6.82 (d, J=9.0 Hz, 1H), 4.78 (s, 2H), 3.76 (s, 3H), 3.69 (s, 3H), 3.66 (s, 3H) ppm; MS (ES) 476.23 (M+H), 474.13 (M−H).

Example 85

3-(2,3-Dihydrobenzo[b][1,4]dioxin-6-ylamino)-2-(4-((methoxycarbonyl)methoxy)-3-methoxyphenyl)-1H-imidazo[1,2-b]pyrazole-7-carbonitrile $^1$H-NMR (DMSO-d6, 300 MHz) 8.00 (d, J=0.9 Hz, 1H), 7.88 (br. s, 1H), 7.35 (s, 1H), 7.25 (d, J=8.4 Hz, 1H), 6.94 (d, J=8.7 Hz, 1H), 6.62 (d, J=8.4 Hz, 1H), 6.09 (dd, J=8.1, 2.4 Hz, 1H), 6.01 (d, J=2.1 Hz, 1H), 4.79 (s, 2H), 4.10 (quart, J=5.1 Hz, 4H), 3.72 (s, 3H), 3.67 (s, 3H) ppm; MS (ES) 476.22 (M+H), 474.13 (M−H).

Example 86

2-(5-(7-Cyano-3-(3-(methoxycarbonyl)phenylamino)-1H-imidazo[1,2-b]pyrazol-2-yl)-2-methoxyphenoxy)acetic acid $^1$H-NMR (DMSO-d6, 300 MHz) 8.36 (br. s, 1H), 7.90 (s, 1H), 7.28-7.24 (m, 2H), 7.22-7.19 (m, 2H), 7.15 (s, 1H), 6.91 (d, J=8.7 Hz, 1H), 6.77 (d, J=8.4 Hz, 1H), 4.22 (s, 2H), 3.76 (s, 3H), 3.72 (s, 3H) ppm; MS (ES) 462.32 (M+H).

Example 87

3-(4-Fluoro-3-methoxyphenylamino)-2-(3,4,5-trimethoxyphenyl)-1H-imidazo[1,2-b]pyrazole-7-carbonitrile $^1$H-NMR (DMSO-d6, 300 MHz) 12.66 (s, 1H), 8.22 (s, 1H), 8.04 (s, 1H), 7.03 (s, 2H), 6.90 (m, 1H), 6.44 (m, 1H), 6.01 (m, 1H), 3.67 (s, 6H), 3.64 (s, 3H); MS (ES) 438.3 (M+H).

Example 88

6-(4-Chlorophenyl)-2-(3,4-dimethoxyphenyl)-5H-imidazo[1,2-b]pyrazole-7-carbonitrile $^1$H NMR (DMSO-d$_6$, 300 MHz) 8.32 (s, 1H), 7.92 (d, 2H), 7.58 (d, 2H), 7.36 (m, 2H), 7.05 (d, 1H), 3.83 (s, 3H), 3.79 (s, 3H) ppm; MS (ES) 378.92 (M+).

Example 89

N-(4-(7-Cyano-2-(3,4,5-trimethoxyphenyl)-5H-imidazo[1,2-b]pyrazol-3-ylamino)benzyl)-3,4-dimethoxybenzamide $^1$H-NMR (DMSO-d6, 300 MHz) 8.71 (m, 1H), 8.20 (s, 1H), 8.02 (s, 1H), 7.42 (m, 2H), 7.04 (m, 4H), 6.97 (d, 1H), 6.54 (d, 2H), 4.30 (m, 2H), 3.76 (s, 6H), 3.63 (s, 9H); MS (ES) 583.5 (M+H).

Example 90

N-(4-(7-Cyano-2-(3,4,5-trimethoxyphenyl)-5H-imidazo[1,2-b]pyrazol-3-ylamino)benzyl)-3-(4-hydroxyphenyl)propanamide $^1$H-NMR (DMSO-d6, 300 MHz) 12.65 (s, 1H), 8.12 (s, 1H), 8.09 (m, 1H), 8.02 (s, 1H), 7.06 (s, 2H), 6.93 (d, 4H), 6.60 (d, 2H), 6.52 (d, 2H), 4.07 (m, 2H), 3.66 (s, 6H), 3.63 (s, 3H), 2.67 (m, 2H), 2.30 (m, 2H); MS (ES) 567.4 (M+H).

Example 91

N-(4-(7-Cyano-2-(3,4,5-trimethoxyphenyl)-5H-imidazo[1,2-b]pyrazol-3-ylamino)benzyl)-3-(piperidin-1-yl)propanamide $^1$H-NMR (DMSO-d6, 300 MHz) 9.39 (m, 1H), 8.23 (s, 1H), 8.03 (s, 1H), 7.05 (s, 2H), 7.02 (d, 2H), 6.54 (d, 2H), 4.12 (m, 2H), 3.66 (s, 6H), 3.64 (s, 3H), 2.60-2.00 (m, 8H), 1.61 (m, 4H), 1.46 (m, 2H); MS (ES) 558.4 (M+H).

Example 92

N-(4-(7-Cyano-2-(3,4,5-trimethoxyphenyl)-5H-imidazo[1,2-b]pyrazol-3-ylamino)benzyl)-4-cyanobenzamide $^1$H-NMR (DMSO-d6, 300 MHz) 12.65 (s, 1H), 9.11 (m, 1H), 8.23 (s, 1H), 7.96 (s, 1H), 7.92 (m, 4H), 7.04 (m, 4H), 6.55 (d, 2H), 4.32 (m, 2H), 3.64 (s, 9H); MS (ES) 548.3 (M+H).

Example 93

N-(4-(7-Cyano-2-(3,4,5-trimethoxyphenyl)-5H-imidazo[1,2-b]pyrazol-3-ylamino)benzyl)-1-methylpiperidine-4-carboxamide $^1$H-NMR (DMSO-d6, 300 MHz) 8.24 (m, 2H), 8.02 (s, 1H), 7.05 (s, 2H), 6.98 (d, 2H), 6.53 (d, 2H), 4.09 (m, 2H), 3.65 (s, 6H), 3.63 (m, 3H), 3.20 (m, 2H), 2.66 (m, 2H), 2.63 (s, 3H), 2.25 (m, 1H), 1.67-1.81 (m, 4H); MS (ES) 544.5 (M+H).

Example 94

N-(4-(7-Cyano-2-(3,4,5-trimethoxyphenyl)-5H-imidazo[1,2-b]pyrazol-3-ylamino)benzyl)-1H-indazole-3-carboxamide $^1$H-NMR (DMSO-d6, 300 MHz) 13.49 (s, 1H), 12.63 (s, 1H), 8.72 (t, 1H), 8.20 (s, 1H), 8.13 (d, 1H), 8.01 (s, 1H), 7.56 (d, 1H), 7.37 (t, 1H), 7.20 (t, 1H), 7.18 (d, 2H), 7.03 (s, 2H), 6.54 (d, 2H), 4.33 (m, 2H), 3.62 (s, 6H), 3.61 (s, 3H); MS (ES) 563.4 (M+H).

Example 95

N-(4-(7-Cyano-2-(3,4,5-trimethoxyphenyl)-5H-imidazo[1,2-b]pyrazol-3-ylamino)benzyl)-1,6-dihydro-6-oxopyridine-3-carboxamide $^1$H-NMR (DMSO-d6, 300 MHz) 12.40 (s, 1H), 8.42 (broad s, 1H), 8.02 (s, 1H), 7.98 (s, 1H), 7.76 (m, 1H), 7.22 (m, 1H), 7.04 (m, 4H), 6.63 (m, 1H), 6.54 (d, 2H), 4.28 (m, 2H), 3.65 (s, 9H); MS (ES) 540.5 (M+H).

Example 96

3-((1-Nicotinoylpiperidin-4-yl)methylamino)-2-(3,4,5-trimethoxyphenyl)-5H-imidazo[1,2-b]pyrazole-7-carbonitrile $^1$H-NMR (CDCl$_3$/MeOH-d4, 300 MHz) 8.53 (m, 1H), 8.50 (s, 1H), 7.94 (s, 1H), 7.66 (m, 1H), 7.57 (s, 1H), 7.30 (m, 1H), 6.64 (s, 2H), 3.78 (s, 6H), 3.74 (s, 3H), 3.13 (m, 2H), 2.71 (m, 4H), 1.74 (m, 1H), 1.59 (m, 2H), 1.14 (m, 2H); MS (ES) 516.3 (M+H).

Example 97

4-(3-(2,3-Dihydrobenzo[b][1,4]dioxin-6-ylamino)-7-cyano-1H-imidazo[1,2-b]pyrazol-2-yl)benzamide $^1$H-NMR (DMSO-d6, 300 MHz) 8.04 (s, 1H), 8.00 (br. s, 1H), 7.95 (br. s, 1H), 7.90 (d, J=8.4 Hz, 2H), 7.79 (d, J=8.1 Hz, 2H), 7.39 (br. s, 1H), 6.32 (d, J=9.0 Hz, 1H), 6.11 (dd, J=8.7, 1.8 Hz, 1H), 6.04 (d, J=1.8 Hz, 1H), 4.10 (d, J=3.9 Hz, 4H) ppm; MS (ES) 400.95 (M).

Example 98

4-(3-(4-Bromophenylamino)-7-cyano-1H-imidazo[1,2-b]pyrazol-2-yl)benzamide $^1$H-NMR (DMSO-d6, 300 MHz) 8.52 (br. s, 1H), 8.05 (s, 1H), 7.95 (br. s, 1H), 7.90 (d, J=8.1 Hz, 2H), 7.78 (d, J=8.7 Hz, 2H), 7.40 (br. s, 1H), 7.26 (d, J=8.4 Hz, 2H), 6.56 (d, J=8.7 Hz, 2H) ppm; MS (ES) 421.10 (M).

Example 99

Methyl 2-(4-(7-cyano-3-(3,4-dimethoxyphenylamino)-1H-imidazo[1,2-b]pyrazol-2-yl)-2-methoxyphenoxy)acetate $^1$H-NMR (DMSO-d6, 300 MHz) 8.01 (s, 1H), 7.90 (br. s, 1H), 7.34 (d, J=1.8 Hz, 1H), 7.25 (dd, J=8.4, 1.5 Hz, 1H), 6.93

(d, J=8.7 Hz, 1H), 6.68 (d, J=8.7 Hz, 1H), 6.36 (d, J=2.4 Hz, 1H), 5.94 (dd, J=9.0, 2.4 Hz, 1H), 4.78 (s, 2H), 3.69 (s, 3H), 3.66 (s, 3H), 3.60 (s, 3H) ppm; MS (ES) 478.25 (M+H).

Example 100

3-(3,4-Dimethoxyphenylamino)-2-(3-hydroxy-4,5-dimethoxyphenyl)-1H-imidazo[1,2-b]pyrazole-7-carbonitrile $^1$H-NMR (DMSO-d6, 300 MHz) 9.28 (br. s, 1H), 7.99 (s, 1H), 7.87 (br. s, 1H), 6.92 (d, J=1.8 Hz, 1H), 6.86 (s, 1H), 6.69 (d, J=8.4 Hz, 1H), 6.36 (d, J=2.4 Hz, 1H), 5.94 (dd, J=8.4, 2.1 Hz, 1H), 3.69 (s, 3H), 3.65 (s, 3H), 3.62 (s, 3H), 3.61 (s, 3H) ppm; MS (ES) 436.31 (M+H).

Example 101

2-(4-(2-Hydroxyethoxy)-3-methoxyphenyl)-3-(3,4-dimethoxyphenylamino)-1H-imidazo[1,2-b]pyrazole-7-carbonitrile $^1$H-NMR (DMSO-d6, 300 MHz) 8.00 (s, 1H), 7.89 (br. s, 1H), 7.31 (s, 1H), 7.28 (d, J=8.4 Hz, 1H), 7.01 (d, J=8.1 Hz, 1H), 6.68 (d, J=8.7 Hz, 1H), 6.36 (d, J=2.1 Hz, 1H), 5.95 (d, J=8.4 Hz, 1H), 4.82 (br. s, 1H), 3.96 (t, J=5.1 Hz, 2H), 3.68 (m, 2H), 3.67 (s, 3H), 3.61 (s, 6H) ppm; MS (ES) 450.24 (M+H), 448.14 (M−H).

Example 102

3-(4-Fluoro-3-methoxyphenylamino)-2-(3,4-dimethoxyphenyl)-5H-imidazo[1,2-b]pyrazole-7-carbonitrile $^1$H NMR (DMSO-d$_6$, 300 MHz) 8.15 (s, 1H), 8.01 (s, 1H), 7.29 (m, 2H), 7.03 (d, 1H), 6.91 (t, 1H), 6.42 (d, 1H), 5.97 (d, 1H), 3.74 (s, 3H), 3.67 (s, 6H) ppm; MS (ES) 408.23 (M+H).

Example 103

4-(3-(3,4-Dimethoxyphenylamino)-7-cyano-1H-imidazo[1,2-b]pyrazol-2-yl)benzamide $^1$H-NMR (DMSO-d6, 300 MHz) 8.05 (s, 1H), 7.96 (br. s, 1H), 7.89 (d, J=8.1 Hz, 2H), 7.79 (d, J=8.4 Hz, 2H), 7.41 (br. s, 1H), 6.68 (d, J=8.7 Hz, 1H), 6.38 (d, J=2.4 Hz, 1H), 5.96 (dd, J=8.4, 2.4 Hz, 1H), 3.61 (s, 3H), 3.60 (s, 3H) ppm; MS (ES) 403.42 (M+H).

Example 104

3-(3,4-Dimethoxyphenylamino)-2-(4-morpholinophenyl)-1H-imidazo[1,2-b]pyrazole-7-carbonitrile $^1$H-NMR (DMSO-d6, 300 MHz) 7.97 (s, 1H), 7.82 (br. s, 1H), 7.59 (d, J=9.0 Hz, 2H), 6.98 (d, J=8.7 Hz, 2H), 6.67 (d, J=8.4 Hz, 1H), 6.35 (s, 1H), 5.91 (d, J=8.1 Hz, 1H), 3.71 (m, 4H), 3.61 (s, 3H), 3.60 (s, 3H), 3.13 (m, 4H) ppm; MS (ES) 445.34 (M+H).

Example 105

3-(3,4-Dimethoxyphenylamino)-2-(3-morpholinophenyl)-1H-imidazo[1,2-b]pyrazole-7-carbonitrile $^1$H-NMR (DMSO-d6, 300 MHz) 8.02 (s, 1H), 7.94 (br. s, 1H), 7.27-7.18 (m, 2H), 6.88 (d, J=7.5 Hz, 1H), 6.68 (d, J=8.7 Hz, 1H), 6.35 (s, 1H), 5.94 (d, J=8.4 Hz, 1H), 3.68 (m, 4H), 3.60 (s, 6H), 3.02 (m, 4H) ppm; MS (ES) 445.43 (M+H).

Example 106

3-(3,4-Dimethoxyphenylamino)-2-(3-(cyclopentyloxy)-4-methoxyphenyl)-1H-imidazo[1,2-b]pyrazole-7-carbonitrile $^1$H-NMR (DMSO-d6, 300 MHz) 8.00 (s, 1H), 7.89 (br. s, 1H), 7.26 (d, J=8.1 Hz, 1H), 7.24 (s, 1H), 7.01 (d, J=7.8 Hz, 1H), 6.69 (d, J=8.4 Hz, 1H), 6.37 (d, J=2.1 Hz, 1H), 5.94 (d, J=6.0 Hz, 1H), 4.50 (m, 1H), 3.73 (s, 3H), 3.61 (s, 3H), 3.60 (s, 3H), 1.70-1.46 (m, 8H) ppm; MS (ES) 474.36 (M+H).

Example 107

3-(3,4-Dimethoxyphenylamino)-2-(4-(2-pyrrolidin-1-yl)ethoxy)-1H-imidazo[1,2-b]pyrazole-7-carbonitrile $^1$H-NMR (DMSO-d6, 300 MHz) 7.98 (s, 1H), 7.86 (br. s, 1H), 7.65 (d, J=8.4 Hz, 2H), 7.01 (d, J=8.7 Hz, 2H), 6.67 (d, J=8.7 Hz, 1H), 6.35 (s, 1H), 5.92 (dd, J=9.0, 2.4 Hz, 1H), 4.08 (t, J=5.7 Hz, 2H), 3.61 (s, 3H), 3.60 (s, 3H), 3.51 (t, J=5.4 Hz, 2H), 3.42 (t, J=7.2 Hz, 2H), 2.19 (t, J=7.8 Hz, 2H), 1.88 (quint, J=7.8 Hz, 2H) ppm; MS (ES) 487.32 (M+H).

Example 108

2-(4-(2-Methoxyethoxy)-3-methoxyphenyl)-3-(3,4-dimethoxyphenylamino)-1H-imidazo[1,2-b]pyrazole-7-carbonitrile $^1$H-NMR (DMSO-d6, 300 MHz) 8.00 (d, J=1.5 Hz, 1H), 7.90 (br. s, 1H), 7.31 (s, 1H), 7.27 (d, J=8.4 Hz, 1H), 7.01 (d, J=7.8 Hz, 1H), 6.68 (d, J=6.9 Hz, 1H), 6.36 (s, 1H), 5.94 (d, J=9.0 Hz, 1H), 4.06 (t, J=5.7 Hz, 2H), 3.66 (s, 3H), 3.61 (t, J=5.4 Hz, 2H), 3.60 (s, 6H), 3.27 (d,), 3.51 (t, J=1.5 Hz, 3H) ppm; MS (ES) 464.29 (M+H).

Example 109

3-(4-Fluoro-3-methoxyphenylamino)-2-(3,4-dihydro-3-oxo-2H-benzo[b][1,4]oxazin-6-yl)-1H-imidazo[1,2-b]pyrazole-7-carbonitrile $^1$H NMR (DMSO-d6, 300 MHz) 10.93 (s, 1H), 8.09 (s, 1H), 7.99 (s, 1H), 7.25 (m, 2H), 7.02 (d, 1H), 6.90 (t, 1H), 6.42 (d, 1H), 5.95 (d, 1H), 4.57 (s, 2H), 3.69 (s, 3H) ppm; MS (ES) 419.26 (M+H).

Example 110

3-(3-(Trifluoromethoxy)phenylamino)-2-(3,4,5-trimethoxyphenyl)-1H-imidazo[1,2-b]pyrazole-7-carbonitrile $^1$H-NMR (DMSO-d6, 300 MHz) 12.74 (broad s, 1H), 8.66 (s, 1H), 8.05 (s, 1H), 7.24 (m, 2H), 7.01 (s, 2H), 6.66 (m, 1H), 6.57 (m, 1H), 3.65 (s, 9H); MS (ES) 474.2 (M+H).

Example 111

3-(3-Chloro-4-methoxyphenylamino)-2-(3,4,5-trimethoxyphenyl)-1H-imidazo[1,2-b]pyrazole-7-carbonitrile ¹H-NMR (DMSO-d6, 300 MHz) 12.63 (s, 1H), 8.11 (s, 1H), 8.01 (s, 1H), 7.03 (s, 2H), 6.96 (d, 2H), 6.62 (m, 1H), 6.52 (m, 1H), 3.65 (m, 6H), 3.63 (m, 3H); MS (ES) 454.3 (M+H).

Example 112

3-(3,4-Dimethoxyphenylamino)-2-(3-hydroxyphenyl)-1H-imidazo[1,2-b]pyrazole-7-carbonitrile ¹H-NMR (DMSO-d6, 300 MHz) 9.59 (s, 1H), 7.99 (s, 1H), 7.88 (br. s, 1H), 7.19 (quart, J=8.7 Hz, 1H), 7.16 (s, 2H), 6.72 (d, J=7.2 Hz, 1H), 6.68 (d, J=8.4 Hz, 1H), 6.35 (d, J=1.5 Hz, 1H), 5.93 (dd, J=8.7, 2.1 Hz, 1H), 3.62 (s, 3H), 3.61 (s, 3H) ppm; MS (ES) 376.30 (M+H).

Example 113

Methyl 2-(4-(7-cyano-3-(3,4-dimethoxyphenylamino)-1H-imidazo[1,2-b]pyrazol-2-yl)phenoxy)acetate ¹H-NMR (DMSO-d6, 300 MHz) 7.98 (d, J=1.2 Hz, 1H), 7.86 (br. s, 1H), 7.65 (d, J=8.1 Hz, 2H), 7.01 (d, J=8.4 Hz, 2H), 6.68 (d, J=7.8 Hz, 1H), 6.35 (d, J=1.5 Hz, 1H), 5.92 (dd, J=7.5, 1.8 Hz, 1H), 4.81 (s, 2H), 3.68 (s, 3H), 3.61 (s, 3H), 3.60 (s, 3H) ppm; MS (ES) 448.33 (M+H).

Example 114

N-(3-(7-Cyano-3-(3,4-dimethoxyphenylamino)-1H-imidazo[1,2-b]pyrazol-2-yl)phenyl)methanesulfonamide ¹H-NMR (DMSO-d6, 300 MHz) 9.85 (br. s, 1H), 8.02 (s, 1H), 7.94 (br. s, 1H), 7.58 (s, 1H), 7.43 (t, J=7.5 Hz, 1H), 7.37 (t, J=7.8 Hz, 1H), 7.10 (d, J=8.1 Hz, 1H), 6.67 (d, J=8.4 Hz, 1H), 6.34 (d, J=2.4 Hz, 1H), 5.95 (dd, J=8.1, 2.4 Hz, 1H), 3.60 (s, 6H), 2.90 (s, 3H) ppm; MS (ES) 453.27 (M+H).

Example 115

3-(3-(Cyclopentyloxy)-4-methoxyphenylamino)-2-(3,4,5-trimethoxyphenyl)-1H-imidazo[1,2-b]pyrazole-7-carbonitrile ¹H-NMR (DMSO-d6, 300 MHz) 12.60 (s, 1H), 8.04 (s, 1H), 7.98 (s, 1H), 7.04 (s, 2H), 6.70 (m, 1H), 6.28 (m, 1H), 6.03 (m, 1H), 4.51 (m, 1H), 3.72 (s, 3H), 3.66 (s, 3H), 3.61 (s, 3H), 1.49-1.71 (m, 8H); MS (ES) 504.4 (M+H).

Example 116

2-(4-(2-Hydroxyethoxy)-3-methoxyphenyl)-3-(4-fluoro-3-methoxyphenylamino)-1H-imidazo[1,2-b]pyrazole-7-carbonitrile ¹H NMR (DMSO-d₆, 300 MHz) 8.14 (s, 1H), 8.00 (s, 1H), 7.27 (m, 2H), 7.02 (d, 1H), 6.90 (t, 1H), 6.42 (d, 1H), 5.97 (d, 1H), 4.82 (t, 1H), 3.96 (t, 2H), 3.70 (m, 8H) ppm; MS (ES) 437.96 (M+H).

Example 117

4-(3-(4-Fluoro-3-methoxyphenylamino)-7-cyano-1H-imidazo[1,2-b]pyrazol-2-yl)benzamide ¹H NMR (DMSO-d₆, 300 MHz) 8.29 (s, 1H), 8.05 (s, 1H), 7.91 (m, 3H), 7.78 (d, 2H), 7.39 (s, 1H), 6.91 (t, 1H), 6.45 (d, 1H), 6.00 (d, 1H), 3.68 (s, 3H) ppm; MS (ES) 391.25 (M+H).

Example 118

3-(4-Fluoro-3-methoxyphenylamino)-2-(3-hydroxy-4,5-dimethoxyphenyl)-1H-imidazo[1,2-b]pyrazole-7-carbonitrile ¹H NMR (DMSO-d₆, 300 MHz) 9.30 (s, 1H), 8.12 (s, 1H), 8.00 (s, 1H), 6.90 (m, 3H), 6.44 (d, 2H), 3.69 (d, 6H), 3.64 (s, 3H) ppm; MS (ES) 424.22 (M+H).

Example 119

3-(4-Fluoro-3-methoxyphenylamino)-2-(3-(cyclopentyloxy)-4-methoxyphenyl)-1H-imidazo[1,2-b]pyrazole-7-carbonitrile ¹H NMR (DMSO-d₆, 300 MHz) 8.14 (s, 1H), 8.01 (s, 1H), 7.23 (m, 2H), 7.02 (d, 1H), 6.91 (t, 1H), 6.44 (d, 1H), 5.97 (d, 1H), 4.53 (m, 1H), 3.74 (s, 3H), 3.67 (s, 3H), 1.71-1.45 (m, 8H) ppm; MS (ES) 462.29 (M+H).

Example 120

3-(4-Fluoro-3-methylphenylamino)-2-(3,4,5-trimethoxyphenyl)-1H-imidazo[1,2-b]pyrazole-7-carbonitrile ¹H-NMR (DMSO-d6, 300 MHz) 12.65 (s, 1H), 8.13 (s, 1H), 8.04 (s, 1H), 7.05 (s, 1H), 6.88 (m, 1H), 6.46 (m, 1H), 6.40 (m, 1H), 3.67 (s, 6H), 3.64 (s, 3H), 2.08 (s, 3H); MS (ES) 422.3 (M+H).

Example 121

3-(3-Fluoro-4-methylphenylamino)-2-(3,4,5-trimethoxyphenyl)-1H-imidazo[1,2-b]pyrazole-7-carbonitrile ¹H-NMR (DMSO-d6, 300 MHz) 12.68 (s, 1H), 8.35 (s, 1H), 8.04 (s, 1H), 7.04 (s, 2H), 6.99 (m, 1H), 6.34 (m, 2H), 3.66 (s, 6H), 3.65 (s, 3H), 2.07 (s, 3H); MS (ES) 422 (M+H).

Example 122

2-(4-(2-Methoxyethoxy)-3-methoxyphenyl)-3-(4-fluoro-3-methoxyphenylamino)-1H-imidazo[1,2-b]pyrazole-7-carbonitrile ¹H NMR (DMSO-d₆, 300 MHz) 8.15 (s, 1H), 8.01 (s, 1H), 7.29 (s, 1H), 7.25 (d, 1H), 7.02 (d, 1H), 6.90 (d, 1H), 6.43 (d, 1H), 5.98 (d, 1H), 4.06 (t, 2H), 3.67 (d, 6H), 3.62 (t, 2H), 3.27 (s, 3H) ppm; MS (ES) 452.28 (M+H).

Example 123

Methyl 2-(4-(7-cyano-3-(4-fluoro-3-methoxyphenylamino)-1H-imidazo[1,2-b]pyrazol-2-yl)-2-methoxyphenoxy)acetate ¹H NMR (DMSO-d₆, 300 MHz) 8.16 (s, 1H), 8.01 (s, 1H), 7.32 (s, 1H), 7.23 (d, 1H), 6.95-6.87 (m, 2H), 6.42 (d, 1H), 5.97 (d, 1H), 4.78 (s, 2H), 3.70 (s, 3H), 3.67 (s, 6H), 2.60 (m, 4H), 2.42 (t, 1H), 1.98 (m, 2H), 1.68 (m, 4H) ppm; MS (ES) 466.30 (M+H).

Example 124

2-(4-(2-Morpholinoethoxy)phenyl)-3-(3,4-dimethoxyphenylamino)-1H-imidazo[1,2-b]pyrazole-7-carbonitrile ¹H-NMR (DMSO-d6, 300 MHz) 7.98 (d, J=3.9 Hz, 1H), 7.83 (br. s, 1H), 7.64 (d, J=9.0 Hz, 2H), 7.00 (d, J=8.4 Hz, 2H), 6.67 (d, J=8.7 Hz, 1H), 6.35 (d, J=2.4 Hz, 1H), 5.91 (dd, J=8.4, 2.4 Hz, 1H), 4.08 (m, 2H), 3.61 (s, 6H), 3.54 (m, 4H), 3.31 (m, 4H), 2.66 (m, 2H) ppm; MS (ES) 489.38 (M+H).

Example 125

2-(5-(7-Cyano-3-(3,4-dimethoxyphenylamino)-1H-imidazo[1,2-b]pyrazol-2-yl)-2-methoxyphenoxy)acetamide ¹H-NMR (DMSO-d6, 300 MHz) 8.00 (d, J=0.9 Hz, 1H), 7.88 (br. s, 1H), 7.43 (br. s, 1H), 7.34 (d, J=8.1 Hz, 1H), 7.33 (s, 1H), 7.18 (d, J=8.4 Hz, 1H), 6.67 (d, J=8.4 Hz, 1H), 6.35 (s, 1H), 5.92 (d, J=8.1 Hz, 1H), 4.36 (s, 2H), 3.78 (s, 3H), 3.61 (s, 3H), 3.60 (s, 3H) ppm; MS (ES) 463.30 (M+H).

Example 126

3-(3-Isopropoxy-4-methoxyphenylamino)-2-(3,4,5-trimethoxyphenyl)-1H-imidazo[1,2-b]pyrazole-7-carbonitrile ¹H-NMR (DMSO-d6, 300 MHz) 12.60 (s, 1H), 8.04 (s, 1H), 7.96 (s, 1H), 7.04 (s, 2H), 6.72 (m, 1H), 6.29 (m, 1H), 6.05 (m, 1H), 4.27 (m, 1H), 3.66 (s, 3H), 3.63 (s, 3H), 3.61 (s, 3H), 1.13 (d, 6H); MS (ES) 477 (M+H).

Example 127

3-(3-Fluoro-4-methoxyphenylamino)-2-(3,4,5-trimethoxyphenyl)-1H-imidazo[1,2-b]pyrazole-7-carbonitrile ¹H-NMR (DMSO-d6, 300 MHz) 12.66 (s, 1H), 8.19 (s, 1H), 8.03 (s, 1H), 7.05 (s, 2H), 6.94 (m, 1H), 6.46 (m, 1H), 6.33 (m, 1H), 3.69 (s, 6H), 3.65 (s, 3H); MS (ES) 438.0 (M+H).

Example 128

3-(4-(Cyclopentyloxy)-3-methoxyphenylamino)-2-(3,4,5-trimethoxyphenyl)-1H-imidazo[1,2-b]pyrazole-7-carbonitrile ¹H-NMR (DMSO-d6, 300 MHz) 12.61 (s, 1H), 8.04 (s, 1H), 7.99 (s, 1H), 7.03 (s, 2H), 6.67 (m, 1H), 6.35 (m, 1H), 5.97 (m, 1H), 4.55 (m, 1H), 3.66 (s, 6H), 3.64 (s, 3H), 3.59 (s, 3H), 1.50-1.80 (m, 8H); MS (ES) 504.3 (M+H).

Example 129

3-(4-(2-(Pyrrolidin-1-yl)ethoxy)-3-methoxyphenylamino)-2-(3,4,5-trimethoxyphenyl)-1H-imidazo[1,2-b]pyrazole-7-carbonitrile ¹H-NMR (DMSO-d6, 300 MHz) 12.66 (s, 1H), 8.14 (s, 1H), 8.05 (s, 1H), 7.04 (s, 2H), 6.83 (m, 1H), 6.40 (m, 1H), 5.99 (m, 1H), 4.07 (m, 2H), 3.67 (s, 3H), 3.64 (s, 3H), 3.63 (s, 3H), 3.48 (m, 2H), 3.10 (m, 2H), 1.87-2.00 (m, 6H); MS (ES) 533 (M+H).

Example 130

3-(4-Fluoro-3-(trifluoromethyl)phenylamino)-2-(3,4,5-trimethoxyphenyl)-1H-imidazo[1,2-b]pyrazole-7-carbonitrile ¹H-NMR (DMSO-d6, 300 MHz) 12.75 (s, 1H), 8.67 (s, 1H), 8.06 (s, 1H), 7.25 (m, 1H), 7.01 (s, 2H), 6.92 (m, 1H), 6.83 (m, 1H), 3.68 (s, 6H), 3.65 (s, 3H)); MS (ES) 476.3 (M+H).

Example 131

3-(4-(Trifluoromethoxy)phenylamino)-2-(3,4,5-trimethoxyphenyl)-1H-imidazo[1,2-b]pyrazole-7-carbonitrile ¹H-NMR (DMSO-d6, 300 MHz) 12.72 (s, 1H), 8.53 (s, 1H), 8.05 (s, 1H), 7.14 (d, 2H), 7.02 (s, 2H), 6.66 (d, 2H), 3.66 (s, 6H), 3.64 (s, 3H); MS (ES) 474.3 (M+H)

Example 132

3-(4-Chloro-3-methoxyphenylamino)-2-(3,4,5-trimethoxyphenyl)-1H-imidazo[1,2-b]pyrazole-7-carbonitrile ¹H-NMR (DMSO-d6, 300 MHz) 12.69 (s, 1H), 8.44 (s, 1H), 8.05 (s, 1H), 7.10 (m, 1H), 7.03 (s, 2H), 6.42 (m, 1H), 6.08 (m, 1H), 3.68 (s, 3H), 3.66 (s, 3H), 3.65 (s, 3H); MS (ES) 454.2 (M+H).

Example 133

3-(4-Fluoro-3-isopropoxyphenylamino)-2-(3,4,5-trimethoxyphenyl)-1H-imidazo[1,2-b]pyrazole-7-carbonitrile ¹H-NMR (DMSO-d6, 300 MHz) 12.65 (s, 1H), 8.21 (s, 1H), 8.05 (s, 1H), 7.03 (s, 2H), 6.92 (m, 1H), 6.37 (m, 1H), 6.09 (m, 1H), 4.33 (m, 1H), 3.66 (s, 6H), 3.64 (s, 3H), 1.15 (d, 6H); MS (ES) 466.3 (M+H).

Example 134

3-(3-Fluoro-4-(pyrrolidin-1-yl)phenylamino)-2-(3,4,5-trimethoxyphenyl)-1H-imidazo[1,2-b]pyrazole-7-carbonitrile ¹H-NMR (DMSO-d6, 300 MHz) 12.67 (s, 1H), 8.22 (s, 1H), 8.04 (s, 1H), 7.05 (s, 2H), 6.79 (m, 1H), 6.36 (m, 2H), 3.69 (s, 6H), 3.64 (s, 3H), 3.20 (m, 4H), 1.87 (m, 4H); MS (ES) 477.3 (M+H).

Example 135

2-(4-(7-Cyano-3-(3,4-dimethoxyphenylamino)-1H-imidazo[1,2-b]pyrazol-2-yl)-2-methoxyphenoxy)acetamide ¹H-NMR (DMSO-d6, 300 MHz) 8.01 (s, 1H), 7.91 (br. s, 1H), 7.37 (br. s, 1H), 7.34 (s, 1H), 7.28 (s, 1H), 7.25 (br. s, 1H), 6.94 (d, J=8.7 Hz, 1H), 6.68 (d, J=8.4 Hz, 1H), 6.36 (d, J=2.4 Hz, 1H), 5.94 (d, J=8.1, 2.1 Hz, 1H), 4.42 (s, 2H), 3.69 (s, 3H), 3.60 (s, 6H) ppm; MS (ES) 463.13 (M+H), 461.12 (M−H).

Example 136

3-(3,4-Dimethoxyphenylamino)-2-(4-methoxy-3,5-dimethylphenyl)-1H-imidazo[1,2-b]pyrazole-7-carbonitrile $^1$H-NMR (DMSO-d6, 300 MHz) 7.99 (s, 1H), 7.85 (br. s, 1H), 7.42 (s, 2H), 6.68 (d, J=8.4 Hz, 1H), 6.34 (d, J=2.4 Hz, 1H), 5.92 (d, J=8.7, 2.4 Hz, 1H), 3.64 (s, 3H), 3.61 (s, 3H), 3.60 (s, 3H), 2.19 (s, 6H) ppm; MS (ES) 418.31 (M+H).

Example 137

3-(3,4-Dihydro-3-oxo-2H-benzo[b][1,4]oxazin-6-ylamino)-2-(3,4,5-trimethoxyphenyl)-1H-imidazo[1,2-b]pyrazole-7-carbonitrile $^1$H-NMR (DMSO-d6, 300 MHz) 10.36 (br. s, 1H), 8.13 (br. s, 1H), 8.05 (s, 1H), 7.06 (s, 2H), 6.72 (d, J=8.1 Hz, 1H), 6.19 (s, 1H), 6.16 (d, J=8.7 Hz, 1H), 4.39 (s, 2H), 3.69 (s, 6H), 3.64 (s, 3H) ppm; MS (ES) 461.30 (M+H).

Example 138

2-(5-(7-Cyano-3-(4-fluoro-3-methoxyphenylamino)-1H-imidazo[1,2-b]pyrazol-2-yl)-2-methoxyphenoxy)acetamide $^1$H NMR (DMSO-d$_6$, 300 MHz) 8.13 (s, 1H), 8.00 (s, 1H), 7.42 (s, 1H), 7.31 (s, 2H), 7.18 (s, 1H), 7.06 (d, 1H), 6.89 (t, 1H), 6.42 (d, 1H), 5.95 (d, 1H), 4.37 (s, 2H), 3.78 (s, 3H), 3.67 (s, 3H) ppm; MS (ES) 451.27 (M+H).

Example 139

2-(4-(7-Cyano-3-(4-fluoro-3-methoxyphenylamino)-1H-imidazo[1,2-b]pyrazol-2-yl)-2-methoxyphenoxy)acetamide $^1$H NMR (DMSO-d$_6$, 300 MHz) 8.16 (s, 1H), 8.01 (s, 1H), 7.36-7.23 (m, 4H), 6.95 (d, 1H), 6.88 (d, 1H), 6.42 (d, 1H), 5.96 (d, 1H), 4.42 (s, 2H), 3.70 (s, 3H), 3.67 (s, 3H) ppm; MS (ES) 451.21 (M+H).

Example 140

2-(4-(7-Cyano-3-(3,4-dimethoxyphenylamino)-1H-imidazo[1,2-b]pyrazol-2-yl)-2-methoxyphenoxy)-N-cyclopropylacetamide $^1$H-NMR (DMSO-d6, 300 MHz) 8.01 (s, 1H), 7.91 (br. s, 1H), 7.33 (s, 1H), 7.25 (d, J=8.4 Hz, 1H), 6.93 (t, J=8.4 Hz, 1H), 6.68 (d, J=8.4 Hz, 1H), 6.36 (d, J=2.4 Hz, 1H), 5.95 (dd, J=8.4, 2.4 Hz, 1H), 4.41 (s, 2H), 3.69 (s, 3H), 3.60 (s, 6H), 2.68-2.60 (m, 1H), 0.61 (quart, J=5.1 Hz, 2H), 0.46-0.42 (m, 2H) ppm; MS (ES) 503.14 (M+H), 501.19 (M−H).

Example 141

3-(3-Chloro-4-isopropoxyphenylamino)-2-(3,4,5-trimethoxyphenyl)-1H-imidazo[1,2-b]pyrazole-7-carbonitrile $^1$H-NMR (DMSO-d6, 300 MHz) 12.68 (s, 1H), 8.22 (s, 1H), 8.05 (s, 1H), 7.03 (s, 2H), 6.95 (m, 1H), 6.63 (m, 1H), 6.51 (m, 1H), 4.35 (m, 1H), 3.68 (s, 6H), 3.64 (s, 3H), 1.19 (d, 6H); MS (ES) 482.2 (M+H).

Example 142

3-(3,5-Dimethoxyphenylamino)-2-(3,4,5-trimethoxyphenyl)-1H-imidazo[1,2-b]pyrazole-7-carbonitrile $^1$H-NMR (DMSO-d6, 300 MHz) 12.66 (s, 1H), 8.23 (s, 1H), 8.05 (s, 1H), 7.05 (s, 2H), 5.90 (s, 1H), 5.75 (s, 2H), 3.68 (s, 6H), 3.64 (s, 3H), 3.59 (s, 6H); MS (ES) 450.2 (M+H).

Example 143

3-(3,5-Difluoro-4-methoxyphenylamino)-2-(3,4,5-trimethoxyphenyl)-1H-imidazo[1,2-b]pyrazole-7-carbonitrile $^1$H-NMR (DMSO-d6, 300 MHz) 12.72 (s, 1H), 8.57 (s, 1H), 8.05 (s, 1H), 7.03 (s, 2H), 6.32 (d, 2H), 3.73 (s, 3H), 3.70 (s, 3H), 3.65 (s, 3H); MS (ES) 456.2 (M+H).

Example 144

3-(3-Ethoxy-4-fluorophenylamino)-2-(3,4,5-trimethoxyphenyl)-1H-imidazo[1,2-b]pyrazole-7-carbonitrile $^1$H-NMR (DMSO-d6, 300 MHz) 12.62 (s, 1H), 8.19 (s, 1H), 8.04 (s, 1H), 7.03 (s, 1H), 6.90 (m, 1H), 6.38 (m, 1H), 6.03 (m, 1H), 3.89 (q, 2H), 3.67 (s, 6H), 3.64 (s, 3H), 1.22 (t, 3H); MS (ES) 452.3 (M+H).

Example 145

3-(3-(Cyclopentyloxy)-4-fluorophenylamino)-2-(3,4,5-trimethoxyphenyl)-1H-imidazo[1,2-b]pyrazole-7-carbonitrile $^1$H-NMR (DMSO-d6, 300 MHz) 12.65 (s, 1H), 8.22 (s, 1H), 8.05 (s, 1H), 7.02 (s, 2H), 6.91 (m, 1H), 6.32 (m, 1H), 6.06 (m, 1H), 4.58 (m, 1H), 3.66 (s, 6H), 3.64 (s, 3H), 1.50-1.73 (m, 8H); MS (ES) 492.3 (M+H).

Example 146

N-(3-(7-Cyano-2-(3,4,5-trimethoxyphenyl)-1H-imidazo[1,2-b]pyrazol-3-ylamino)benzyl)nicotinamide $^1$H-NMR (DMSO-d6, 300 MHz) 12.64 (s, 1H), 9.16 (m, 1H), 8.96 (s, 1H), 8.71 (m, 1H), 8.26 (s, 1H), 8.16 (m, 1H), 7.99 (s, 1H), 7.58 (m, 1H), 7.04 (m, 2H), 7.01 (s, 2H), 6.70 (m, 1H), 6.62 (s, 1H), 6.43 (m, 1H), 4.34 (m, 2H), 3.61 (s, 9H); MS (ES) 524.2 (M+H).

Example 147

N-(3-(7-Cyano-2-(3,4,5-trimethoxyphenyl)-1H-imidazo[1,2-b]pyrazol-3-ylamino)benzyl)picolinamide $^1$H-NMR (DMSO-d6, 300 MHz) 12.63 (s, 1H), 9.16 (m, 1H), 8.59 (m, 1H), 8.22 (s, 1H), 7.96 (m, 3H), 7.57 (m, 1H), 7.00 (m, 3H), 6.66 (m, 2H), 6.38 (m, 1H), 4.34 (m, 2H), 3.61 (s, 9H); MS (ES) 524.2 (M+H).

Example 148

N-(3-(7-Cyano-2-(3,4,5-trimethoxyphenyl)-1H-imidazo[1,2-b]pyrazol-3-ylamino)benzyl)isonicotinamide $^1$H-NMR (DMSO-d6, 300 MHz) 12.65 (s, 1H), 9.28 (m, 1H), 8.74 (m, 2H), 8.27 (m, 1H), 8.00 (s, 1H), 7.75 (m, 2H), 7.07 (m, 1H), 7.01 (s, 2H), 6.67 (m, 1H), 6.59 (s, 1H), 6.45 (m, 1H), 4.34 (m, 2H), 3.61 (s, 9H); MS (ES) 524.2 (M+H).

Example 149

N-(4-(7-Cyano-2-(3,4,5-trimethoxyphenyl)-1H-imidazo[1,2-b]pyrazol-3-ylamino)benzyl)picolinamide $^1$H-NMR (DMSO-d6, 300 MHz) 12.64 (s, 1H), 9.08 (m, 1H), 8.59 (m, 1H), 8.21 (s, 1H), 7.97 (m, 3H), 7.55 (m, 1H), 7.10 (d, 2H), 7.03 (s, 2H), 6.53 (d, 2H), 4.34 (m, 2H), 3.62 (s, 9H); MS (ES) 524.2 (M+H).

Example 150

N-(4-(7-Cyano-2-(3,4,5-trimethoxyphenyl)-1H-imidazo[1,2-b]pyrazol-3-ylamino)benzyl)isonicotinamide $^1$H-NMR (DMSO-d6, 300 MHz) 12.65 (s, 1H), 9.20 (m, 1H), 8.73 (d, 2H), 8.21 (s, 1H), 8.02 (s, 1H), 7.82 (d, 2H), 7.09 (d, 2H), 7.05 (s, 2H), 6.55 (d, 2H), 4.33 (m, 2H), 3.63 (s, 9H); MS (ES) 524.3 (M+H).

Example 151

N-(4-(7-Cyano-2-(3,4,5-trimethoxyphenyl)-1H-imidazo[1,2-b]pyrazol-3-ylamino)benzyl)-6-cyanopyridine-3-carboxamide $^1$H-NMR (DMSO-d6, 300 MHz) 12.65 (s, 1H), 9.27 (m, 1H), 9.08 (s, 1H), 8.37 (d, 1H), 8.25 (s, 1H), 8.12 (d, 1H), 8.02 (s, 1H), 7.10 (d, 2H), 7.05 (s, 2H), 6.55 (d, 2H), 4.34 (m, 2H), 3.64 (s, 9H); MS (ES) 549.2 (M+H).

Example 152

N-(4-(7-Cyano-2-(3,4,5-trimethoxyphenyl)-1H-imidazo[1,2-b]pyrazol-3-ylamino)benzyl)-2-methylpyridine-3-carboxamide $^1$H-NMR (DMSO-d6, 300 MHz) 12.67 (s, 1H), 8.91 (m, 1H), 8.56 (m, 1H), 8.25 (s, 1H), 8.03 (s, 1H), 7.92 (m, 1H), 7.46 (m, 1H), 7.11 (d, 2H), 7.06 (s, 2H), 6.56 (d, 2H), 4.30 (m, 2H), 3.65 (s, 6H), 3.63 (s, 3H), 2.54 (s, 3H); MS (ES) 538.2 (M+H).

Example 153

N-(4-(7-Cyano-2-(3,4,5-trimethoxyphenyl)-1H-imidazo[1,2-b]pyrazol-3-ylamino)benzyl)-2-methoxypyridine-3-carboxamide $^1$H-NMR (DMSO-d6, 300 MHz) 12.65 (s, 1H), 8.58 (m, 1H), 8.25 (m, 2H), 8.08 (m, 1H), 8.03 (s, 1H), 7.10 (m, 2H), 7.05 (s, 2H), 6.55 (d, 2H), 4.33 (m, 2H) 3.92 (s, 3H), 3.65 (s, 9H); MS (ES) 554.3 (M+H).

Example 154

N-(4-(7-Cyano-2-(3,4,5-trimethoxyphenyl)-1H-imidazo[1,2-b]pyrazol-3-ylamino)benzyl)-6-methylpyridine-3-carboxamide $^1$H-NMR (DMSO-d6, 300 MHz) 12.65 (s, 1H), 9.03 (m, 1H), 8.90 (m, 1H), 8.23 (s, 1H), 8.18 (m, 1H), 8.02 (s, 1H), 7.43 (d, 1H), 7.09 (d, 2H), 7.05 (s, 2H), 6.55 (d, 2H), 4.33 (m, 2H), 3.64 (s, 9H), 2.54 (s, 3H); MS (ES) 538.3 (M+H).

Example 155

N-(4-(7-Cyano-2-(3,4,5-trimethoxyphenyl)-1H-imidazo[1,2-b]pyrazol-3-ylamino)benzyl)-4-(trifluoromethyl)pyridine-3-carboxamide $^1$H-NMR (DMSO-d6, 300 MHz) 12.66 (s, 1H), 9.07 (m, 1H), 8.66 (m, 1H), 8.75 (s, 1H), 8.25 (s, 1H), 8.03 (s, 1H), 7.78 (m, 1H), 7.10 (d, 2H), 7.06 (s, 2H), 6.57 (d, 2H), 4.31 (m, 2H), 3.65 (s, 6H), 3.63 (s, 3H); MS (ES) 592.3 (M+H).

Example 156

N-(4-(7-Cyano-2-(3,4,5-trimethoxyphenyl)-1H-imidazo[1,2-b]pyrazol-3-ylamino)benzyl)-6-(trifluoromethyl)pyridine-3-carboxamide $^1$H-NMR (DMSO-d6, 300 MHz) 12.65 (s, 1H), 9.26 (m, 1H), 9.11 (s, 1H), 8.42 (m, 1H), 8.25 (s, 1H), 8.01 (m, 2H), 7.11 (d, 2H), 7.06 (s, 2H), 6.55 (d, 2H), 4.35 (m, 2H), 3.65 (s, 6H), 3.63 (s, 3H); MS (ES) 592.3 (M+H).

Example 157

3-(3-Fluoro-4-(methylthio)phenylamino)-2-(3,4,5-trimethoxyphenyl)-1H-imidazo[1,2-b]pyrazole-7-carbonitrile $^1$H-NMR (DMSO-d6, 300 MHz) 12.73 (s, 1H), 8.62 (s, 1H), 8.05 (s, 1H), 7.22 (m, 1H), 7.04 (s, 2H), 6.44 (m, 2H), 3.68 (s, 6H), 3.65 (s, 3H), 2.31 (s, 3H); MS (ES) 454.2 (M+H).

Example 158

Tryptase Release Assay of Exemplary Compounds

Compounds were assayed for inhibition of mast cell activation induced by FcγR cross-linking by measuring the activity of tryptase released upon degranulation as follows:

Human mast cells were cultured and differentiated from CD38-negative progenitor cell as described in U.S. Patent Publication No. 2005-234049, incorporated herein by reference. For example, 65 µl of various concentrations of the compound to be assayed were prepared in MT (137 mM NaCl, 2.7 mM KCl, 1.8 mM CaCl$_2$, 1.0 mM MgCl$_2$, 5.6 mM Glucose, 20 mM Hepes (pH 7.4), 0.1% Bovine Serum Albumin, (Sigma A4503)) containing 2% MeOH and 1% DMSO, or control buffer were added to duplicate 96-well V-bottom plates. Pelleted and resuspended (in warm MT) CHMC cells (65 µl) were added to each 96-well plate, mixed and incubated for 1 hour at 37° C. 25 µl of 6× anti-IgG Rabbit anti-human IgG, Affinity purified (Bethyl Laboratories Cat No. A80-105A3) final concentration 1 µg/ml, was added to the test wells. MT (25 µl) was added to control wells. After a 60-minute incubation at 37° C., cells and cell debris were pelleted by centrifugation at 1000 rpm for 10 min and tryptase and leukotriene $C_4$ levels were measured.

To measure tryptase levels, 25 µl of supernatant from each well was transferred to a fresh 96-well black bottom plate, to which 100 µl of fresh tryptase substrate solution [(Z-Ala-Lys-Arg-AMC2TFA; Enzyme Systems Products, #AMC-246)] 1:2000 in tryptase assay buffer [0.1 M Hepes (pH 7.5), 10% w/v Glycerol, 10 µM Heparin (Sigma H-4898) 0.01% $NaN_3$] was added. After 30 minute incubation at room temperature, the optical density of the plates is measured at 355 nm/460 nm on a spectrophotometric plate reader. Table 2 provides the $IC_{50}$ values.

Leukotriene C4 (LTC4) levels were quantified using an ELISA kit on appropriately diluted supernatant samples following the supplier's instructions (Cayman Chemical Co., Cat No. 520211).

Inhibition of release and/or synthesis of lipid mediators was assessed by measuring the release of LTC4 and inhibition of release and/or synthesis of cytokines was monitored by quantifying TNF α, IL-8, GM-CSF, IL-10 and IL-13. Cytokine (TNF α, IL-8, GM-CSF, IL-10, IL-13) production was measured 6-8 hours post-IgG crosslinking. Leukotriene and cytokine levels were quantified using the following commercial ELISA kits: LTC4 (Cayman Chemical #520211), TNFα (Biosource #KHC3011), GM-CSF (Biosource #KHC0901), IL-10 (Biosource #KHC0122), and IL-13 (Biosource #KHC0132).

Assay data are provided for certain compounds in Table 2. For LD Tryptase data in Table 2, "A" indicates an $IC_{50}$ in the indicated assay of less than 10 µM; "B" is 11-100 µM; "C" is 101-5000 µM; and "D" is from greater than 5000 µM. Blank entries indicate that the $IC_{50}$ was not determined.

Example 159

ELISA-based Syk kinase Assay of Exemplary Compounds

Compounds were tested for the ability to inhibit Syk kinase catalyzed phosphorylation of a peptide substrate in an assay with isolated Syk kinase.

An assay was carried out in a Costar white 96 well plate (Fisher Scientific, Cat No. 07-200-591) coated overnight with 0.01 mg/ml Neutravidin (Pierce, 100 µl/well) at 4° C. Neutravidin pre-coated 96 well plates were blocked with 2% BSA in PBST buffer for at least 1 hour before starting the assay at room temperature. Serially diluted compound stock solution containing a subject compound was prepared separately in DMSO solution starting from 300 µM and 2 µl of this diluted compound (3% DMSO final concentration) was added directly to neutravidin coated assay plate containing 55.5 µl/well of kinase reaction buffer composed of 20 mM HEPES, pH 7.4, 5 mM $MgCl_2$, 2 mM $MnCl_2$, 1 mM DTT, 0.01% Tween 20 pre-mixed with ATP and kinase substrate (HS1 peptide). Reaction was initiated by adding of 2.5 µl/well Syk kinase (Millipore, Cat No. 14-314) resulting in a final reaction volume of 60 µl and then the reaction was allowed to continue for 30 minutes at room temperature. Final enzyme reaction conditions were 20 mM HEPES, pH 7.4, 5 mM $MgCl_2$, 2 mM $MnCl_2$, 1 mM DTT, 0.01% Tween 20, 0.25 ng Syk, 2 µM ATP, 2 µM peptide substrate (Biotin-EQEDE-PEGDYEEVLE-CONH2, SynPep Corporation). After completing the reaction, assay plate was washed three times with PBST and incubated for 1 hour at room temperature with 100 µl/well of phosphopeptide detection antibody solution prepared by mixing 1-1000 diluted mouse anti-pTyr monoclonal antibody (Cell Signal Technology, Cat No. 9411) and 1-1000 diluted goat HRP-conjugated anti-mouse IgG (Jackson Immunoresearch, Cat. No. 115-035-003). Before developing the plate with supersignal ELISA pico chemiluminescent substrate (Pierce), plate was washed three times again with PBST and were read on a SpectraMax M5 microplate reader (Moleculear Devices).

For ELISA data for Syk kinase inhibition in Table 2, "E" indicates an $IC_{50}$ in the indicated assay of less than 0.5 µM; "F" is 0.51-2.99 µM; "G" is 3-25 µM; and "H" is from greater than 25 µM. Blank entries indicate that the $IC_{50}$ was not determined.

TABLE 2

| Compound | LD Tryptase | ELISA-Syk |
|---|---|---|
| 1 | D | F |
| 2 | A | F |
| 3 | B | F |
| 4 | A | F |
| 5 | A | F |
| 6 | A | F |
| 7 | B | F |
| 8 | A | G |
| 9 | — | G |
| 10 | B | F |
| 11 | — | H |
| 12 | — | H |
| 13 | B | G |
| 14 | A | F |
| 15 | B | F |
| 16 | — | H |
| 17 | — | G |
| 18 | — | G |
| 19 | — | G |
| 20 | — | G |
| 21 | — | H |
| 22 | — | F |
| 23 | A | F |
| 24 | A | F |
| 25 | A | F |
| 26 | — | G |
| 27 | — | F |
| 28 | A | E |
| 29 | — | G |
| 30 | A | F |
| 31 | — | F |
| 32 | A | F |
| 33 | A | F |
| 34 | — | G |
| 35 | — | G |
| 36 | — | G |
| 37 | — | F |
| 38 | D | F |
| 39 | — | G |
| 40 | — | G |
| 41 | — | H |
| 42 | — | H |
| 43 | B | G |
| 44 | A | G |
| 45 | C | F |
| 46 | — | G |
| 47 | A | F |
| 48 | A | F |
| 49 | A | F |
| 50 | D | F |
| 51 | A | F |
| 52 | D | G |
| 53 | — | H |
| 54 | — | H |
| 55 | — | G |
| 56 | — | G |
| 57 | — | G |
| 58 | — | F |
| 59 | — | F |
| 60 | — | G |
| 61 | — | F |
| 62 | — | G |
| 63 | — | G |

TABLE 2-continued

| Compound | LD Tryptase | ELISA-Syk |
|---|---|---|
| 64 | A | F |
| 65 | — | F |
| 66 | — | G |
| 67 | — | F |
| 68 | — | G |
| 69 | — | F |
| 70 | — | F |
| 71 | — | F |
| 72 | A | F |
| 73 | — | G |
| 74 | — | G |
| 75 | — | F |
| 76 | — | G |
| 77 | — | F |
| 78 | — | G |
| 79 | — | G |
| 80 | — | F |
| 81 | — | G |
| 82 | — | G |
| 83 | B | E |
| 84 | — | F |
| 85 | A | E |
| 86 | — | F |
| 87 | A | E |
| 88 | — | F |
| 89 | A | F |
| 90 | — | F |
| 91 | — | F |
| 92 | B | F |
| 93 | D | F |
| 94 | — | F |
| 95 | D | F |
| 96 | — | G |
| 97 | B | F |
| 98 | C | F |
| 99 | A | F |
| 100 | A | E |
| 101 | A | F |
| 102 | A | F |
| 103 | B | E |
| 104 | A | F |
| 105 | B | F |
| 106 | A | E |
| 107 | A | F |
| 108 | A | E |
| 109 | B | F |
| 110 | — | F |
| 111 | A | E |
| 112 | A | F |
| 113 | A | F |
| 114 | A | F |
| 115 | — | F |
| 116 | A | E |
| 117 | D | F |
| 118 | A | E |
| 119 | A | F |
| 120 | A | F |
| 121 | — | F |
| 122 | A | F |
| 123 | — | F |
| 124 | A | F |
| 125 | A | F |
| 126 | B | E |
| 127 | A | E |
| 128 | — | F |
| 129 | — | F |
| 130 | — | F |
| 131 | — | F |
| 132 | A | F |
| 133 | A | F |
| 134 | — | F |
| 135 | A | E |
| 136 | A | F |
| 137 | A | E |
| 138 | A | F |
| 139 | A | E |
| 140 | A | E |
| 141 | A | F |
| 142 | A | E |
| 143 | A | E |
| 144 | A | F |
| 145 | A | F |
| 146 | B | F |
| 147 | A | E |
| 148 | C | E |
| 149 | A | F |
| 150 | B | F |
| 151 | D | F |
| 152 | D | E |
| 153 | A | E |
| 154 | B | F |
| 155 | A | F |
| 156 | A | F |
| 157 | B | E |

Example 160

Fluorescence Polarization Syk kinase assay

Compounds are tested for the ability to inhibit Syk kinase catalyzed phosphorylation of a peptide substrate in a biochemical fluorescenced polarization assay with isolated Syk kinase.

Compound stock solution (10 mM) containing subject compound are serially diluted in DMSO starting from 2.5 mM and then further diluted to desired concentration of 50 μM (5×) to yield 2% DMSO concentration in kinase buffer (20 mM HEPES, pH 7.4, 5 mM $MgCl_2$, 2 mM $MnCl_2$, 1 mM DTT, 0.1 mg/mL acetylated Bovine Gamma Globulin). Assay is carried out in a black 96 well low volume plate (Molecular Devices, Cat No. 42-000-0117) by transferring compound in 2% DMSO (0.4% DMSO final) pre-mixed with ATP/substrate (TK2 peptide) in kinase buffer at room temperature. Syk kinase (Millipore, Cat No. 14-314) is added to a final reaction volume of 20 μL, and the reaction is incubated for 30 minutes at room temperature. Final enzyme reaction conditions are 20 mM HEPES, pH 7.4, 5 mM $MgCl_2$, 2 mM $MnCl_2$, 1 mM DTT, 0.1 mg/mL acetylated Bovine Gamma Globulin (Invitrogen, Cat No. P2255), 25 ng Syk, 2.5 μM ATP, 5 μM peptide substrate (Biotin-EGPWLEEEEEAYGWMDF-$CONH_2$, Anaspec, Cat No. 60329-1). The reaction is stopped by addition of 20 μl of PTK quench mix containing EDTA (10 mM final)/anti-phosphotyrosine antibody (1X final)/fluorescent phosphopeptide tracer (0.5× final) diluted in FP dilution buffer to stop the reaction for a total volume of 40 μL according to manufacturer's instructions (Invitrogen Corporation) The plate is incubated in the dark for additional 30 minutes at room temperature and then read on a Polarion fluorescence polarization plate reader (Tecan). Data are converted to amount of phosphopeptide present using a calibration curve generated by competition with the phosphopeptide competitor provided in the Tyrosine Kinase Assay Kit, Green (Invitrogen, Cat No. P2837).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound having the formula Iz:

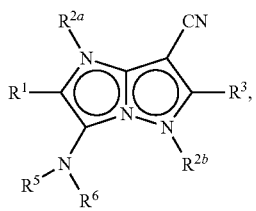

(Iz)

wherein

R¹ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl; and wherein either $R^{2a}$ or $R^{2b}$ is present;

R³ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

R⁵ is selected from hydrogen, alkyl, and substituted alkyl; and

R⁶ is selected from hydrogen, alkyl, substituted alkyl, alkenyl, substituted alkenyl, alkynyl, substituted alkynyl, acyl, acylamino, acyloxy, cycloalkyl, substituted cycloalkyl, cycloalkenyl, substituted cycloalkenyl, aralkyl, heteroaralkyl, aryl, substituted aryl, heteroaryl, substituted heteroaryl, heterocyclyl, and substituted heterocyclyl;

or a salt or stereoisomer thereof.

2. The compound of claim 1 having the formula Ia:

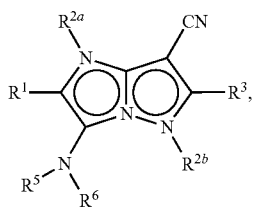

(Ia)

wherein

R¹ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl; and wherein either $R^{2a}$ or $R^{2b}$ is present;

R³ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

R⁵ is selected from hydrogen, alkyl, and substituted alkyl; and

R⁶ is selected from hydrogen, alkyl, substituted alkyl, alkenyl, substituted alkenyl, alkynyl, substituted alkynyl, acyl, acylamino, acyloxy, cycloalkyl, substituted cycloalkyl, cycloalkenyl, substituted cycloalkenyl, aralkyl, and heteroaralkyl;

or a salt or stereoisomer thereof.

3. A compound having the formula IIa:

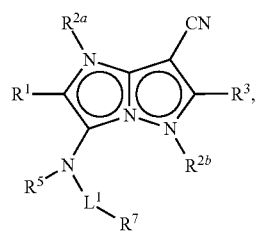

(IIa)

wherein

R¹ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

R³ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

R⁵ is selected from hydrogen, alkyl, and substituted alkyl;

L¹ is —(CH$_2$)$_n$—, —C(O)—, or —C(O)—(CH$_2$)$_n$—;

n is an integer from one to five; and

R⁷ is selected from aryl, substituted aryl, heteroaryl, substituted heteroaryl, heterocyclyl, and substituted heterocyclyl;

or a salt or stereoisomer thereof.

4. The compound of claim 1 having the formula IIIa:

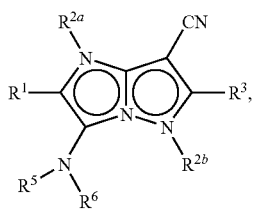

(IIIa)

wherein
R¹ is selected from aryl, substituted aryl, heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —$SO_2$-alkyl, —$SO_2$-aryl, —$SO_2$-heteroaryl, aryl, substituted aryl, heteroaryl, heterocyclyl, aralkyl, and heteroaralkyl, and wherein either $R^{2a}$ or $R^{2b}$ is present;

R³ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

R⁵ is selected from hydrogen, alkyl, and substituted alkyl; and

R⁶ is selected from heteroaryl, substituted heteroaryl, heterocyclyl, and substituted heterocyclyl;

or a salt or stereoisomer thereof.

5. The compound of claim 1 having the formula IVa:

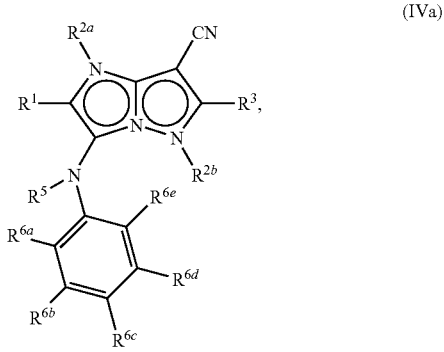

(IVa)

wherein
R¹ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —$SO_2$-alkyl, —$SO_2$-aryl, —$SO_2$-heteroaryl, aryl, substituted aryl, heteroaryl, heterocyclyl, aralkyl, and heteroaralkyl, and wherein either $R^{2a}$ or $R^{2b}$ is present;

R³ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

R⁵ is selected from hydrogen, alkyl, and substituted alkyl; and $R^{6a}$ and $R^{6e}$ are independently selected from hydrogen, $C_{2-10}$ alkyl, substituted alkyl, $C_{2-10}$ alkoxy, substituted alkoxy, acyl, acylamino, acyloxy, aminoacyl, oxyacyl, amino, substituted amino, aminocarbonyloxy, alkoxycarbonyloxy, azido, cyano, hydroxyl, hydroxylamino, alkoxyamino, nitro, carboxyl, thiol, alkylthio, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —$SO_2$-alkyl, —$SO_2$-aryl, —$SO_2$-heteroaryl, —NH—SO-alkyl, —NH—SO-aryl, —NH—SO-heteroaryl, —NH—$SO_2$-alkyl, —NH—$SO_2$-aryl, and —NH—$SO_2$-heteroaryl;

$R^{6c}$ is selected from hydrogen, alkyl, substituted alkyl, alkoxy, substituted alkoxy, acyl, acylamino, acyloxy, aminoacyl, amino, substituted amino, aminocarbonyloxy, alkoxycarbonyloxy, azido, cyano, halogen, hydroxyl, hydroxylamino, alkoxyamino, nitro, carboxyl, thiol, alkylthio, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —$SO_2$-alkyl, —$SO_2$-aryl, —$SO_2$-heteroaryl, —NH—SO-alkyl, —NH—SO-aryl, —NH—SO-heteroaryl, —NH—$SO_2$-alkyl, —NH—$SO_2$-aryl, and —NH—$SO_2$-heteroaryl;

$R^{6b}$ and $R^{6d}$ are independently selected from hydrogen, alkyl, monosubstituted alkyl, disubstituted alkyl, alkoxy, substituted alkoxy, acyl, acylamino, acyloxy, aminoacyl, oxyacyl, amino, substituted amino, aminocarbonyloxy, alkoxycarbonyloxy, azido, halogen, hydroxyl, hydroxylamino, alkoxyamino, nitro, carboxyl, thiol, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —$SO_2$-alkyl, —$SO_2$-aryl, —$SO_2$-heteroaryl, —NH—SO-alkyl, —NH—SO-aryl, —NH—SO-heteroaryl, —NH—$SO_2$-alkyl, —NH—$SO_2$-aryl, and —NH—$SO_2$-heteroaryl; or wherein any two of $R^{6a}$, $R^{6b}$, $R^{6c}$, $R^{6d}$, and $R^{6e}$ vicinal to one another are taken together with the carbon atoms to which they are attached to form a carbocyclic, substituted carbocyclic, heterocyclic, or substituted heterocyclic ring, wherein the ring is a 6-10 membered ring;

or a salt or stereoisomer thereof.

6. The compound of claim 1 having the formula Va:

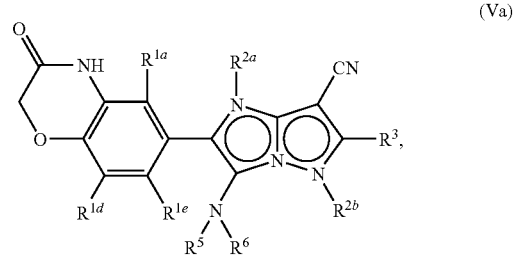

(Va)

wherein
$R^{1a}$, $R^{1d}$ and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl; or wherein $R^{1d}$ and $R^{1e}$ are taken together with the carbon atoms to which they are attached to form a carbocyclic, substituted carbocyclic, heterocyclic, or substituted heterocyclic ring, wherein the ring is a 4-10 membered ring;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

or a salt or stereoisomer thereof.

7. The compound of claim 1 having the formula VIa:

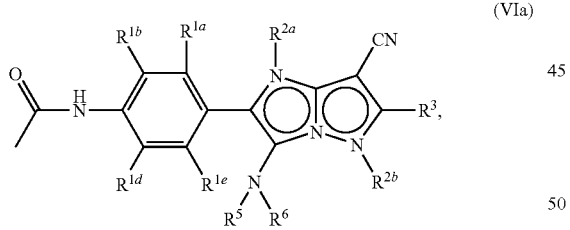

(VIa)

wherein $R^{1a}$, $R^{1b}$, $R^{1d}$ and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl; or wherein $R^{1a}$ and $R^{1b}$ are taken together with the carbon atoms to which they are attached to form a carbocyclic, substituted carbocyclic, heterocyclic, or substituted heterocyclic ring, wherein the ring is a 4-10 membered ring; or wherein $R^{1d}$ and $R^{1e}$ are taken together with the carbon atoms to which they are attached to form a carbocyclic, substituted carbocyclic, heterocyclic, or substituted heterocyclic ring, wherein the ring is a 4-10 membered ring;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

or a salt or stereoisomer thereof.

8. The compound of claim 1 having the formula VIIa:

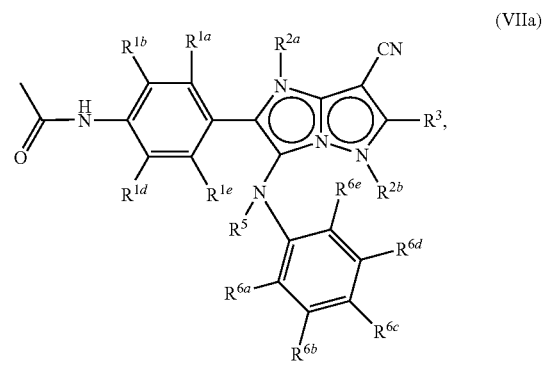

(VIIa)

wherein $R^{1a}$, $R^{1b}$, $R^{1d}$, and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl; or wherein $R^{1a}$ and $R^{1b}$ are taken together with the carbon atoms to which they are attached to form a carbocyclic, substituted carbocyclic, heterocyclic, or substituted heterocyclic ring, wherein the ring is a 4-10 membered ring; or wherein $R^{1d}$ and $R^{1e}$ are taken together with the carbon atoms to which they are attached to form a carbocyclic, substituted carbocyclic, heterocyclic, or substituted heterocyclic ring, wherein the ring is a 4-10 membered ring;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^{6a}$ and $R^{6e}$ are independently selected from hydrogen, $C_{2-10}$ alkyl, substituted alkyl, $C_{2-10}$ alkoxy, substituted alkoxy, acyl, acylamino, acyloxy, aminoacyl, oxyacyl, amino, substituted amino, aminocarbonyloxy, alkoxycarbonylamino, azido, cyano, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl;

$R^{6c}$ is selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl;

$R^{6b}$ and $R^{6d}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl; or wherein any two of $R^{6a}$, $R^{6b}$, $R^{6c}$, $R^{6d}$, and $R^{6e}$ vicinal to one another are taken together with the carbon atoms to which they are attached to form a carbocyclic, substituted carbocyclic, heterocyclic, or substituted heterocyclic ring, wherein the ring is a 6-10 membered ring;

or a salt or stereoisomer thereof.

9. The compound of claim 1 having the formula VIIIa:

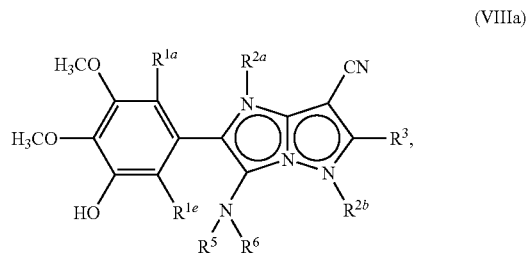

(VIIIa)

wherein $R^{1a}$ and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

or a salt or stereoisomer thereof.

10. The compound of claim 1 having the formula IXa:

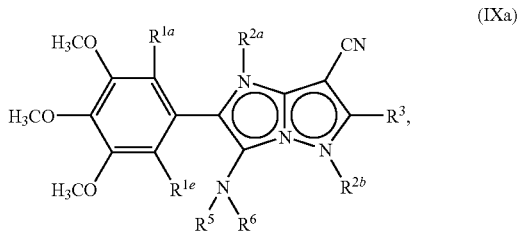

(IXa)

wherein
$R^{1a}$ and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

or a salt or stereoisomer thereof.

11. The compound of claim 1 having the formula Xa:

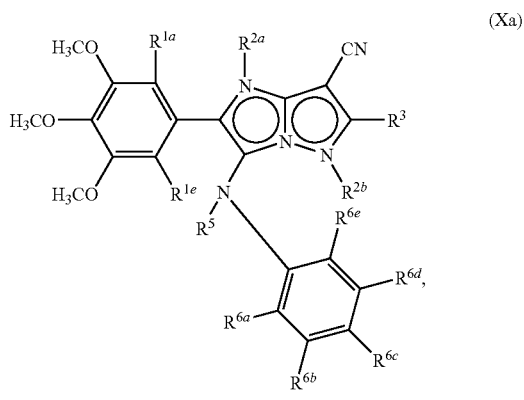

(Xa)

wherein
$R^{1a}$ and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^{6a}$ and $R^{6e}$ are independently selected from hydrogen, $C_{2-10}$ alkyl, substituted alkyl, $C_{2-10}$ alkoxy, substituted alkoxy, acyl, acylamino, acyloxy, aminoacyl, oxyacyl, amino, substituted amino, aminocarbonyloxy, alkoxycarbonylamino, azido, cyano, hydroxyl, hydroxyamino, alkoxyamino, nitro, carboxyl, thiol, alkylthio, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl;

$R^{6c}$ is selected from hydrogen, alkyl, substituted alkyl, alkoxy, substituted alkoxy, acyl, acylamino, acyloxy, aminoacyl, amino, substituted amino, aminocarbonyloxy, alkoxycarbonylamino, azido, cyano, halogen, hydroxyl, hydroxyamino, alkoxyamino, nitro, carboxyl, thiol, alkylthio, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl;

R$^{6b}$ and R$^{6d}$ are independently selected from hydrogen, alkyl, substituted C$_{2-10}$ alkyl, alkoxy, substituted alkoxy, acyl, acylamino, acyloxy, aminoacyl, oxyacyl, amino, substituted amino, aminocarbonyloxy, alkoxycarbonylamino, azido, halogen, hydroxyl, hydroxyamino, alkoxyamino, nitro, carboxyl, thiol, substituted alkylthio, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclyloxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl; or wherein any two of R$^{6a}$, R$^{6b}$, R$^{6c}$, R$^{6d}$, and R$^{6e}$ vicinal to one another are taken together with the carbon atoms to which they are attached to form a carbocyclic, substituted carbocyclic, heterocyclic, or substituted heterocyclic ring, wherein the ring is a 6-10 membered ring;

or a salt or stereoisomer thereof.

12. The compound of claim 1 selected from 3-(3,4-Dimethoxyphenylamino)-2-(2,4-dihydro-2-oxo-1H-benzo[d][1,3]oxazin-7-yl)-1H-imidazo[1,2-b]pyrazole-7-carbonitrile;

N-(4-(3-(3,4-Dimethoxyphenylamino)-7-cyano-1H-imidazo[1,2-b]pyrazol-2-yl)phenyl)acetamide;

N-(4-(3-(3-(Trifluoromethyl)phenylamino)-7-cyano-1H-imidazo[1,2-b]pyrazol-2-yl)phenyl)acetamide;

3-(3,4-Dimethoxyphenylamino)-2-(5-methoxy-1H-indol-3-yl)-1H-imidazo[1,2-b]pyrazole-7-carbonitrile;

3-(3,4-Dimethoxyphenylamino)-2-(1H-indol-5-yl)-1H-imidazo[1,2-b]pyrazole-7-carbonitrile;

3-(3,4-Dimethoxyphenylamino)-2-(1H-indol-6-yl)-1H-imidazo[1,2-b]pyrazole-7-carbonitrile;

3-(3,4-Dichlorophenylamino)-2-(2,4-dihydro-2-oxo-1H-benzo[d][1,3]oxazin-7-yl)-1H-imidazo[1,2-b]pyrazole-7-carbonitrile;

3-(3,4-Dimethoxyphenylamino)-2-(4-phenoxyphenyl)-1H-imidazo[1,2-b]pyrazole-7-carbonitrile;

3-(3-Cyanophenylamino)-2-(3,4-dihydro-3-oxo-2H-benzo[b][1,4]oxazin-6-yl)-1H-imidazo[1,2-b]pyrazole-7-carbonitrile;

Methyl 3-(7-cyano-2-(3,4-dihydro-3-oxo-2H-benzo[b][1,4]oxazin-6-yl)-1H-imidazo[1,2-b]pyrazol-3-ylamino)benzoate;

3-(2,4,4-Trimethylpentan-2-ylamino)-2-(3,4,5-trimethoxyphenyl)-1H-imidazo[1,2-b]pyrazole-7-carbonitrile;

N-(7-Cyano-2-(3,4,5-trimethoxyphenyl)-1H-imidazo[1,2-b]pyrazol-3-yl)-2,2,2-trifluoroacetamide;

Methyl 4-(7-cyano-2-(2,4-dihydro-2-oxo-1H-benzo[d][1,3]oxazin-7-yl)-1H-imidazo[1,2-b]pyrazol-3-ylamino)benzoate;

3-(3-Methoxyphenylamino)-2-(3,4,5-trimethoxyphenyl)-1H-imidazo[1,2-b]pyrazole-7-carbonitrile;

3-(3-Methoxyphenylamino)-2-(2,4-dihydro-2-oxo-1H-benzo[d][1,3]oxazin-7-yl)- 1H-imidazo[1,2-b]pyrazole-7-carbonitrile;

3-(3,4-Dimethoxyphenylamino)-2-(2,4-dihydro-2-oxo-1H-benzo[d][1,3]oxazin-7-yl)-6-methyl- 1H-imidazo[1,2-b]pyrazole-7-carbonitrile;

3-Amino-2-(3,4,5-trimethoxyphenyl)- 1H-imidazo [1,2-b]pyrazole-7-carbonitrile;

N-(7-Cyano-2-(3,4,5-trimethoxyphenyl)-1H-imidazo[1,2-b]pyrazol-3-yl)-3-fluoro-4-(trifluoromethyl)benzamide;

N-(7-Cyano-2-(3,4,5-trimethoxyphenyl)-1H-imidazo[1,2-b]pyrazol-3-yl)benzamide;

N-(7-Cyano-2-(3,4,5-trimethoxyphenyl)-1H-imidazo[1,2-b]pyrazol-3-yl)-4-fluorobenzamide;

N-(7-Cyano-2-(3,4,5-trimethoxyphenyl)-1H-imidazo[1,2-b]pyrazol-3-yl)-3-methoxybenzamide;

3-(3,4-Dichlorophenylamino)-2-(3,4,5-trimethoxyphenyl)-1H-imidazo[1,2-b]pyrazole-7-carbonitrile;

3-(4-Bromophenylamino)-2-(3,4,5-trimethoxyphenyl)-1H-imidazo[1,2-b]pyrazole-7-carbonitrile;

3-(3,4-Dimethoxyphenylamino)-2-(6-methoxy- 1H-indol-3-yl)- 1H-imidazo[1,2-b]pyrazole-7-carbonitrile;

3-(4-Morpholinophenylamino)-2-(3,4,5-trimethoxyphenyl)-1H-imidazo[1,2-b]pyrazole-7-carbonitrile;

3-(3,4,5-Trimethoxyphenylamino)-2-(1H-indol-6-yl)-1H-imidazo[1,2-b]pyrazole-7-carbonitrile;

3-(4-Morpholinophenylamino)-2-(1H-indol-6-yl)-1H-imidazo[1,2-b]pyrazole-7-carbonitrile;

3-(3,4-Dimethoxyphenylamino)-2-(3,4,5-trimethoxyphenyl)- 1H-imidazo[1,2-b]pyrazole-7-carbonitrile;

3-(3,4,5-Trimethoxyphenylamino)-2-(3,4,5-trimethoxyphenyl)- 1H-imidazo [1,2-b]pyrazole-7-carbonitrile;

N-(3-(7-Cyano-2-(3,4,5-trimethoxyphenyl)-1H-imidazo[1,2-b]pyrazol-3-ylamino)phenyl)acetamide;

N-(3-(7-Cyano-2-(3,4-dihydro-3-oxo-2H-benzo[b][1,4]oxazin-6-yl)-1H-imidazo[1,2-b]pyrazol-3-ylamino)phenyl)acetamide;

N-(3-(7-Cyano-2-(3,4-dimethoxyphenyl)-1H-imidazo[1,2-b]pyrazol-3-ylamino)phenyl)acetamide;

N-(3-(7-Cyano-2-(4-(methylthio)phenyl)-1H-imidazo[1,2-b]pyrazol-3-ylamino)phenyl)acetamide;

N-(4-(7-Cyano-3-(3-acetamidophenylamino)-1H-imidazo[1,2-b]pyrazol-2-yl)phenyl)acetamide;

3-(3-Methoxybenzylamino)-2-(3,4-dihydro-3-oxo-2H-benzo[b][1,4]oxazin-6-yl)-1H-imidazo[1,2-b]pyrazole-7-carbonitrile;

3-(3,4-Dimethoxyphenylamino)-2-(2,4-difluorophenyl)-1H-imidazo[1,2-b]pyrazole-7-carbonitrile;

3-(3,4-Dimethoxyphenylamino)-2-(3,4-difluorophenyl)-1H-imidazo[1,2-b]pyrazole-7-carbonitrile;

3-(3,4-Dimethoxyphenylamino)-2-(2,3-dihydrobenzo[b][1,4]dioxin-7-yl)-1H-imidazo[1,2-b]pyrazole-7-carbonitrile;

N-(7-Cyano-2-(3,4,5-trimethoxyphenyl)-1H-imidazo[1,2-b]pyrazol-3-yl)-5-phenyl-1,3,4-oxadiazole-2-carboxamide;

3-(3,4-Dimethoxyphenethylamino)-2-(3,4-dihydro-3-oxo-2H-benzo[b][1,4]oxazin-6-yl)-1H-imidazo[1,2-b]pyrazole-7-carbonitrile;

3-(3,4-Dimethoxyphenethylamino)-2-(3,4,5-trimethoxyphenyl)-1H-imidazo[1,2-b]pyrazole-7-carbonitrile;

N-(7-Cyano-2-(3,4,5-trimethoxyphenyl)-1H-imidazo[1,2-b]pyrazol-3-yl)-2-(3,4-dimethoxyphenyl)acetamide;

3-(4-Morpholinophenylamino)-2-(3,4-dihydro-3-oxo-2H-benzo[b][1,4]oxazin-6-yl)-1H-imidazo[1,2-b]pyrazole-7-carbonitrile;

3-(3-Methoxyphenylamino)-2-(1H-indol-6-yl)-1H-imidazo[1,2-b]pyrazole-7-carbonitrile;

3-(4-Bromophenylamino)-2-(3,4-dihydro-3-oxo-2H-benzo[b][1,4]oxazin-6-yl)-1H-imidazo[1,2-b]pyrazole-7-carbonitrile;

3-(3-Methoxybenzylamino)-2-(3,4,5-trimethoxyphenyl)-1H-imidazo[1,2-b]pyrazole-7-carbonitrile;

N-(3-(7-Cyano-2-(1H-indol-6-yl)-1H-imidazo[1,2-b]pyrazol-3-ylamino)phenyl)acetamide;

3-(3,4-Dimethoxyphenylamino)-2-(4-(methylsulfonyl)phenyl)-1H-imidazo[1,2-b]pyrazole-7-carbonitrile;

3-(2,3-Dihydrobenzo[b][1,4]dioxin-6-ylamino)-2-(3,4,5-trimethoxyphenyl)-1H-imidazo[1,2-b]pyrazole-7-carbonitrile;

3-(2,3-Dihydrobenzo[b][1,4]dioxin-6-ylamino)-2-(3,4-dihydro-3-oxo-2H-benzo[b][1,4]oxazin-6-yl)-1H-imidazo[1,2-b]pyrazole-7-carbonitrile;

3-(3,4-Dimethoxyphenylamino)-2-(benzo[d][1,3]dioxol-6-yl)-1H-imidazo[1,2-b]pyrazole-7-carbonitrile;

3-(3,4-Dimethoxyphenylamino)-2-(3-fluoro-4-methoxyphenyl)-1H-imidazo[1,2-b]pyrazole-7-carbonitrile;

2-Bromo-N-(7-cyano-2-(3,4,5-trimethoxyphenyl)-1H-imidazo[1,2-b]pyrazol-3-yl)acetamide;

N-(7-Cyano-2-(3,4,5-trimethoxyphenyl)-1H-imidazo[1,2-b]pyrazol-3-yl)-2-phenoxyacetamide;

3-(3,4-Dimethoxyphenylamino)-2-benzyl-1H-imidazo[1,2-b]pyrazole-7-carbonitrile;

2-(3,4-Dichlorophenyl)-N-(7-cyano-2-(3,4,5-trimethoxyphenyl)-1H-imidazo[1,2-b]pyrazol-3-yl)acetamide;

3-(3,4-Dimethoxyphenylamino)-2-(3,4,5-trifluorophenyl)-1H-imidazo[1,2-b]pyrazole-7-carbonitrile;

3-(3,4-Dimethoxyphenylamino)-2-(3-chloro-4,5-dimethoxyphenyl)-1H-imidazo[1,2-b]pyrazole-7-carbonitrile;

3-(3,4-Dimethoxyphenylamino)-2-(4-fluoro-3-methoxyphenyl)-1H-imidazo[1,2-b]pyrazole-7-carbonitrile;

3-(2,3-Dihydrobenzo[b][1,4]dioxin-6-ylamino)-2-(1H-indol-6-yl)-1H-imidazo[1,2-b]pyrazole-7-carbonitrile;

N-(4-(7-Cyano-2-(3,4,5-trimethoxyphenyl)-1H-imidazo[1,2-b]pyrazol-3-ylamino)phenyl)acetamide;

N-(4-(7-Cyano-2-(6-methoxy-1H-indol-3-yl)-1H-imidazo[1,2-b]pyrazol-3-ylamino)phenyl)acetamide;

N-(4-(7-Cyano-2-(2,3-dihydrobenzo[b][1,4]dioxin-7-yl)-1H-imidazo[1,2-b]pyrazol-3-ylamino)phenyl)acetamide;

3-(3,4-Difluorophenylamino)-2-(3,4,5-trimethoxyphenyl)-1H-imidazo[1,2-b]pyrazole-7-carbonitrile;

tert-Butyl 4-(7-cyano-2-(3,4,5-trimethoxyphenyl)-1H-imidazo[1,2-b]pyrazol-3-ylamino)benzylcarbamate;

3-(4-(Aminomethyl)phenylamino)-2-(3,4,5-trimethoxyphenyl)-1H-imidazo[1,2-b]pyrazole-7-carbonitrile;

Methyl 3-(7-cyano-2-(3,4,5-trimethoxyphenyl)-1H-imidazo[1,2-b]pyrazol-3-ylamino)benzoate;

N-(4-(7-Cyano-2-(3,4-dihydro-3-oxo-2H-benzo[b][1,4]oxazin-6-yl)-1H-imidazo[1,2-b]pyrazol-3-ylamino)phenyl)acetamide;

N-(4-(7-Cyano-2-(3,4-dimethoxyphenyl)-1H-imidazo[1,2-b]pyrazol-3-ylamino)phenyl)acetamide;

3-(2,3-Dihydrobenzo[b][1,4]dioxin-6-ylamino)-2-(3-hydroxy-4,5-dimethoxyphenyl)-1H-imidazo[1,2-b]pyrazole-7-carbonitrile;

Methyl 4-(7-cyano-2-(3-hydroxy-4,5-dimethoxyphenyl)-1H-imidazo[1,2-b]pyrazol-3-ylamino)benzoate;

N-(4-(7-Cyano-2-(3,4,5-trimethoxyphenyl)-1H-imidazo[1,2-b]pyrazol-3-ylamino)benzyl)acetamide;

tert-Butyl-4-((7-cyano-2-(3,4,5-trimethoxyphenyl)-1H-imidazo[1,2-b]pyrazol-3-ylamino)methyl)piperidine-1-carboxylate;

3-((Piperidin-4-yl)methylamino)-2-(3,4,5-trimethoxyphenyl)-1H-imidazo[1,2-b]pyrazole-7-carbonitrile;

3-(3-Fluoro-4-(4-(pyrrolidin-1-yl)piperidin-1-yl)phenylamino)-2-(3,4,5-trimethoxyphenyl)-1H-imidazo[1,2-b]pyrazole-7-carbonitrile;

(S)-Methyl 2-(7-cyano-2-(3,4,5-trimethoxyphenyl)-1H-imidazo[1,2-b]pyrazol-3-ylamino)-3-phenylpropanoate;

Methyl 3-(7-cyano-2-(3,4-dimethoxyphenyl)-1H-imidazo[1,2-b]pyrazol-3-ylamino)benzoate;

Methyl 3-(2-(3-chloro-4,5-dimethoxyphenyl)-7-cyano-1H-imidazo[1,2-b]pyrazol-3-ylamino)benzoate;

3-(3,4,5-Trimethoxyphenylamino)-2-(4-morpholinophenyl)-1H-imidazo[1,2-b]pyrazole-7-carbonitrile;

3-(4-Bromophenylamino)-2-(4-morpholinophenyl)-1H-imidazo[1,2-b]pyrazole-7-carbonitrile;

4-(3-(3,4,5-Trimethoxyphenylamino)-7-cyano-1H-imidazo[1,2-b]pyrazol-2-yl)benzamide;

3-Amino-2-(3,4,5-trimethoxyphenyl)-5-(4-methoxyphenyl)-5H-imidazo[1,2-b]pyrazole-7-carbonitrile;

N-(4-(7-Cyano-2-(3,4,5-trimethoxyphenyl)-5H-imidazo[1,2-b]pyrazol-3-ylamino)benzyl)nicotinamide;

Methyl 3-(2-(4-((methoxycarbonyl)methoxy)-3-methoxyphenyl)-7-cyano-1H-imidazo[1,2-b]pyrazol-3-ylamino)benzoate;

3-(2,3-Dihydrobenzo[b][1,4]dioxin-6-ylamino)-2-(4-((methoxycarbonyl)methoxy)-3-methoxyphenyl)-1H-imidazo[1,2-b]pyrazole-7-carbonitrile;

2-(5-(7-Cyano-3-(3-(methoxycarbonyl)phenylamino)-1H-imidazo[1,2-b]pyrazol-2-yl)-2-methoxyphenoxy)acetic acid;

3-(4-Fluoro-3-methoxyphenylamino)-2-(3,4,5-trimethoxyphenyl)-1H-imidazo[1,2-b]pyrazole-7-carbonitrile;

6-(4-Chlorophenyl)-2-(3,4-dimethoxyphenyl)-5H-imidazo[1,2-b]pyrazole-7-carbonitrile;

N-(4-(7-Cyano-2-(3,4,5-trimethoxyphenyl)-5H-imidazo[1,2-b]pyrazol-3-ylamino)benzyl)-3,4-dimethoxybenzamide;

N-(4-(7-Cyano-2-(3,4,5-trimethoxyphenyl)-5H-imidazo[1,2-b]pyrazol-3-ylamino)benzyl)-3-(4-hydroxyphenyl)propanamide;

N-(4-(7-Cyano-2-(3,4,5-trimethoxyphenyl)-5H-imidazo[1,2-b]pyrazol-3-ylamino)benzyl)-3-(piperidin-1-yl)propanamide;

N-(4-(7-Cyano-2-(3,4,5-trimethoxyphenyl)-5H-imidazo[1,2-b]pyrazol-3-ylamino)benzyl)-4-cyanobenzamide;

N-(4-(7-Cyano-2-(3,4,5-trimethoxyphenyl)-5H-imidazo[1,2-b]pyrazol-3-ylamino)benzyl)-1-methylpiperidine-4-carboxamide;

N-(4-(7-Cyano-2-(3,4,5-trimethoxyphenyl)-5H-imidazo[1,2-b]pyrazol-3-ylamino)benzyl)-1H-indazole-3-carboxamide;

N-(4-(7-Cyano-2-(3,4,5-trimethoxyphenyl)-5H-imidazo[1,2-b]pyrazol-3-ylamino)benzyl)-1,6-dihydro-6-oxopyridine-3-carboxamide;

3-((1-Nicotinoylpiperidin-4-yl)methylamino)-2-(3,4,5-trimethoxyphenyl)-5H-imidazo[1,2-b]pyrazole-7-carbonitrile;

4-(3-(2,3-Dihydrobenzo[b][1,4]dioxin-6-ylamino)-7-cyano-1H-imidazo[1,2-b]pyrazol-2-yl)benzamide;

4-(3-(4-Bromophenylamino)-7-cyano-1H-imidazo[1,2-b]pyrazol-2-yl)benzamide;

Methyl 2-(4-(7-cyano-3-(3,4-dimethoxyphenylamino)-1H-imidazo[1,2-b]pyrazol-2-yl)-2-methoxyphenoxy)acetate;

3-(3,4-Dimethoxyphenylamino)-2-(3-hydroxy-4,5-dimethoxyphenyl)-1H-imidazo[1,2-b]pyrazole-7-carbonitrile;

2-(4-(2-Hydroxyethoxy)-3-methoxyphenyl)-3-(3,4-dimethoxyphenylamino)-1H-imidazo[1,2-b]pyrazole-7-carbonitrile;

3-(4-Fluoro-3-methoxyphenylamino)-2-(3,4-dimethoxyphenyl)-5H-imidazo[1,2-b]pyrazole-7-carbonitrile;

4-(3-(3,4-Dimethoxyphenylamino)-7-cyano-1H-imidazo[1,2-b]pyrazol-2-yl)benzamide;

3-(3,4-Dimethoxyphenylamino)-2-(4-morpholinophenyl)-1H-imidazo[1,2-b]pyrazole-7-carbonitrile;

3-(3,4-Dimethoxyphenylamino)-2-(3-morpholinophenyl)-1H-imidazo[1,2-b]pyrazole-7-carbonitrile;
3-(3,4-Dimethoxyphenylamino)-2-(3-(cyclopentyloxy)-4-methoxyphenyl)-1H-imidazo[1,2-b]pyrazole-7-carbonitrile;
3-(3,4-Dimethoxyphenylamino)-2-(4-(2-pyrrolidin-1-yl)ethoxy)-1H-imidazo[1,2-b]pyrazole-7-carbonitrile;
2-(4-(2-Methoxyethoxy)-3-methoxyphenyl)-3-(3,4-dimethoxyphenylamino)-1H-imidazo[1,2-b]pyrazole-7-carbonitrile;
3-(4-Fluoro-3-methoxyphenylamino)-2-(3,4-dihydro-3-oxo-2H-benzo[b][1,4]oxazin-6-yl)-1H-imidazo[1,2-b]pyrazole-7-carbonitrile;
3-(3-(Trifluoromethoxy)phenyl)-2-(3,4,5-trimethoxyphenyl)-1H-imidazo[1,2-b]pyrazole-7-carbonitrile;
3-(3-Chloro-4-methoxyphenylamino)-2-(3,4,5-trimethoxyphenyl)-1H-imidazo[1,2-b]pyrazole-7-carbonitrile;
3-(3,4-Dimethoxyphenylamino)-2-(3-hydroxyphenyl)-1H-imidazo[1,2-b]pyrazole-7-carbonitrile;
Methyl 2-(4-(7-cyano-3-(3,4-dimethoxyphenylamino)-1H-imidazo[1,2-b]pyrazol-2-yl)phenoxy)acetate;
N-(3-(7-Cyano-3-(3,4-dimethoxyphenylamino)-1H-imidazo[1,2-b]pyrazol-2-yl)phenyl)methanesulfonamide;
3-(3-(Cyclopentyloxy)-4-methoxyphenylamino)-2-(3,4,5-trimethoxyphenyl)-1H-imidazo[1,2-b]pyrazole-7-carbonitrile;
2-(4-(2-Hydroxyethoxy)-3-methoxyphenyl)-3-(4-fluoro-3-methoxyphenylamino)-1H-imidazo[1,2-b]pyrazole-7-carbonitrile;
4-(3-(4-Fluoro-3-methoxyphenylamino)-7-cyano-1H-imidazo[1,2-b]pyrazol-2-yl)benzamide;
3-(4-Fluoro-3-methoxyphenylamino)-2-(3-hydroxy-4,5-dimethoxyphenyl)-1H-imidazo[1,2-b]pyrazole-7-carbonitrile;
3-(4-Fluoro-3-methoxyphenylamino)-2-(3-(cyclopentyloxy)-4-methoxyphenyl)-1H-imidazo[1,2-b]pyrazole-7-carbonitrile;
3-(4-Fluoro-3-methylphenylamino)-2-(3,4,5-trimethoxyphenyl)-1H-imidazo[1,2-b]pyrazole-7-carbonitrile;
3-(3-Fluoro-4-methylphenylamino)-2-(3,4,5-trimethoxyphenyl)-1H-imidazo[1,2-b]pyrazole-7-carbonitrile;
2-(4-(2-Methoxyethoxy)-3-methoxyphenyl)-3-(4-fluoro-3-methoxyphenylamino)-1H-imidazo[1,2-b]pyrazole-7-carbonitrile;
Methyl 2-(4-(7-cyano-3-(4-fluoro-3-methoxyphenylamino)-1H-imidazo[1,2-b]pyrazol-2-yl)-2-methoxyphenoxy)acetate;
2-(4-(2-Morpholinoethoxy)phenyl)-3-(3,4-dimethoxyphenylamino)-1H-imidazo[1,2-b]pyrazole-7-carbonitrile;
2-(5-(7-Cyano-3-(3,4-dimethoxyphenylamino)-1H-imidazo[1,2-b]pyrazol-2-yl)-2-methoxyphenoxy)acetamide;
3-(3-Isopropoxy-4-methoxyphenylamino)-2-(3,4,5-trimethoxyphenyl)-1H-imidazo[1,2-b]pyrazole-7-carbonitrile;
3-(3-Fluoro-4-methoxyphenylamino)-2-(3,4,5-trimethoxyphenyl)-1H-imidazo[1,2-b]pyrazole-7-carbonitrile;
3-(4-(Cyclopentyloxy)-3-methoxyphenylamino)-2-(3,4,5-trimethoxyphenyl)-1H-imidazo[1,2-b]pyrazole-7-carbonitrile;
3-(4-(2-(Pyrrolidin-1-yl)ethoxy)-3-methoxyphenylamino)-2-(3,4,5-trimethoxyphenyl)-1H-imidazo[1,2-b]pyrazole-7-carbonitrile;
3-(4-Fluoro-3-(trifluoromethyl)phenylamino)-2-(3,4,5-trimethoxyphenyl)-1H-imidazo[1,2-b]pyrazole-7-carbonitrile;
3-(4-(Trifluoromethoxy)phenylamino)-2-(3,4,5-trimethoxyphenyl)-1H-imidazo[1,2-b]pyrazole-7-carbonitrile;
3-(4-Chloro-3-methoxyphenylamino)-2-(3,4,5-trimethoxyphenyl)-1H-imidazo[1,2-b]pyrazole-7-carbonitrile;
3-(4-Fluoro-3-isopropoxyphenylamino)-2-(3,4,5-trimethoxyphenyl)-1H-imidazo[1,2-b]pyrazole-7-carbonitrile;
3-(3-Fluoro-4-(pyrrolidin-1-yl)phenylamino)-2-(3,4,5-trimethoxyphenyl)-1H-imidazo[1,2-b]pyrazole-7-carbonitrile;
2-(4-(7-Cyano-3-(3,4-dimethoxyphenylamino)-1H-imidazo[1,2-b]pyrazol-2-yl)-2-methoxyphenoxy)acetamide;
3-(3,4-Dimethoxyphenylamino)-2-(4-methoxy-3,5-dimethylphenyl)-1H-imidazo[1,2-b]pyrazole-7-carbonitrile;
3-(3,4-Dihydro-3-oxo-2H-benzo[b][1,4]oxazin-6-ylamino)-2-(3,4,5-trimethoxyphenyl)-1H-imidazo[1,2-b]pyrazole-7-carbonitrile;
2-(5-(7-Cyano-3-(4-fluoro-3-methoxyphenylamino)-1H-imidazo[1,2-b]pyrazol-2-yl)-2-methoxyphenoxy)acetamide;
2-(4-(7-Cyano-3-(4-fluoro-3-methoxyphenylamino)-1H-imidazo[1,2-b]pyrazol-2-yl)-2-methoxyphenoxy)acetamide;
2-(4-(7-Cyano-3-(3,4-dimethoxyphenylamino)-1H-imidazo[1,2-b]pyrazol-2-yl)-2-methoxyphenoxy)-N-cyclopropylacetamide;
3-(3-Chloro-4-isopropoxyphenylamino)-2-(3,4,5-trimethoxyphenyl)-1H-imidazo[1,2-b]pyrazole-7-carbonitrile;
3-(3,5-Dimethoxyphenylamino)-2-(3,4,5-trimethoxyphenyl)-1H-imidazo[1,2-b]pyrazole-7-carbonitrile;
3-(3,5-Difluoro-4-methoxyphenylamino)-2-(3,4,5-trimethoxyphenyl)-1H-imidazo[1,2-b]pyrazole-7-carbonitrile;
3-(3-Ethoxy-4-fluorophenylamino)-2-(3,4,5-trimethoxyphenyl)-1H-imidazo[1,2-b]pyrazole-7-carbonitrile;
3-(3-(Cyclopentyloxy)-4-fluorophenylamino)-2-(3,4,5-trimethoxyphenyl)-1H-imidazo[1,2-b]pyrazole-7-carbonitrile;
N-(3-(7-Cyano-2-(3,4,5-trimethoxyphenyl)-1H-imidazo[1,2-b]pyrazol-3-ylamino)benzyl)nicotinamide;
N-(3-(7-Cyano-2-(3,4,5-trimethoxyphenyl)-1H-imidazo[1,2-b]pyrazol-3-ylamino)benzyl)picolinamide;
N-(3-(7-Cyano-2-(3,4,5-trimethoxyphenyl)-1H-imidazo[1,2-b]pyrazol-3-ylamino)benzyl)isonicotinamide;
N-(4-(7-Cyano-2-(3,4,5-trimethoxyphenyl)-1H-imidazo[1,2-b]pyrazol-3-ylamino)benzyl)picolinamide;
N-(4-(7-Cyano-2-(3,4,5-trimethoxyphenyl)-1H-imidazo[1,2-b]pyrazol-3-ylamino)benzyl)isonicotinamide;
N-(4-(7-Cyano-2-(3,4,5-trimethoxyphenyl)-1H-imidazo[1,2-b]pyrazol-3-ylamino)benzyl)-6-cyanopyridine-3-carboxamide;
N-(4-(7-Cyano-2-(3,4,5-trimethoxyphenyl)-1H-imidazo[1,2-b]pyrazol-3-ylamino)benzyl)-2-methylpyridine-3-carboxamide;
N-(4-(7-Cyano-2-(3,4,5-trimethoxyphenyl)-1H-imidazo[1,2-b]pyrazol-3-ylamino)benzyl)-2-methoxypyridine-3-carboxamide;

N-(4-(7-Cyano-2-(3,4,5-trimethoxyphenyl)-1H-imidazo[1,2-b]pyrazol-3-ylamino)benzyl)-6-methylpyridine-3-carboxamide;

N-(4-(7-Cyano-2-(3,4,5-trimethoxyphenyl)-1H-imidazo[1,2-b]pyrazol-3-ylamino)benzyl)-4-(trifluoromethyl)pyridine-3-carboxamide;

N-(4-(7-Cyano-2-(3,4,5-trimethoxyphenyl)-1H-imidazo[1,2-b]pyrazol-3-ylamino)benzyl)-6-(trifluoromethyl)pyridine-3-carboxamide; and 3-(3-Fluoro-4-(methylthio)phenylamino)-2-(3,4,5-trimethoxyphenyl)-1H-imidazo[1,2-b]pyrazole-7-carbonitrile.

13. A pharmaceutical composition comprising an effective amount of a compound of claim 1 and a pharmaceutically acceptable carrier.

14. A pharmaceutical composition comprising:

an effective amount of a compound having the formula Ib:

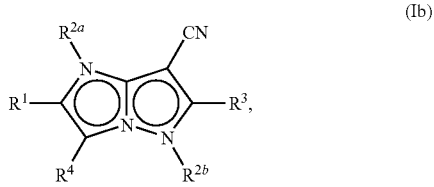

(Ib)

wherein

R$^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

R$^{2a}$ and R$^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either R$^{2a}$ or R$^{2b}$ is present;

R$^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

R$^4$ is selected from amino and —NR$^5$R$^6$;

R$^5$ is selected from hydrogen, alkyl, and substituted alkyl; and

R$^6$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

or a salt or stereoisomer thereof; and a pharmaceutically acceptable carrier.

15. The pharmaceutical composition of claim 14 comprising a compound having the formula IIb:

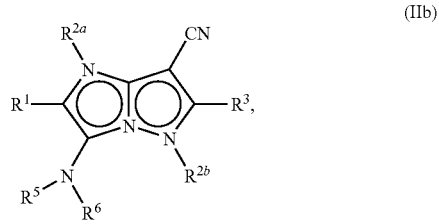

(IIb)

wherein

R$^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

R$^{2a}$ and R$^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either R$^{2a}$ or R$^{2b}$ is present;

R$^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

R$^5$ is selected from hydrogen, alkyl, and substituted alkyl; and

R$^6$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

or a salt or stereoisomer thereof.

16. The pharmaceutical composition of claim 14 comprising a compound having the formula IIIb:

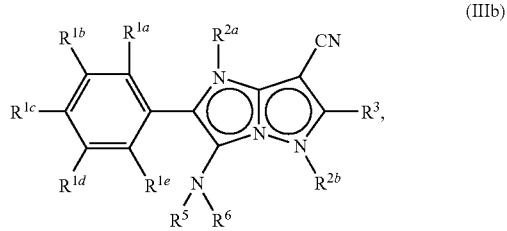

(IIIb)

wherein

R$^{1a}$, R$^{1b}$, R$^{1c}$, R$^{1d}$, and R$^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl; or wherein any two of $R^{1a}$, $R^{1b}$, $R^{1c}$, $R^{1d}$, and $R^{1e}$ vicinal to one another are taken together with the carbon atoms to which they are attached to form carbocyclic, substituted carbocyclic, heterocyclic, or substituted heterocyclic ring, wherein the ring is a 4-10 membered ring;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

or a salt or stereoisomer thereof.

17. The pharmaceutical composition of claim 14 comprising a compound having the formula IVb:

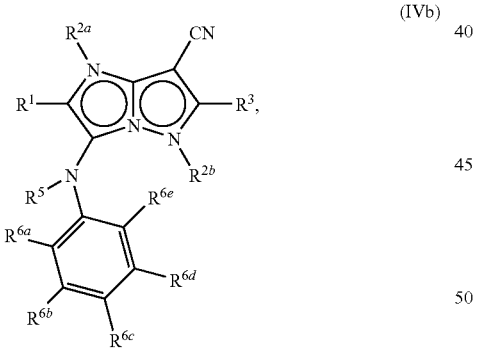

(IVb)

wherein $R^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —SO$_2$-alkyl, —SO$_2$-aryl, —SO$_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^{6a}$, $R^{6b}$, $R^{6c}$, $R^{6d}$, and $R^{6e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl; or wherein any two of $R^{6a}$, $R^{6b}$, $R^{6c}$, $R^{6d}$, and $R^{6e}$ vicinal to one another are taken together with the carbon atoms to which they are attached to form carbocyclic, substituted carbocyclic, heterocyclic, or substituted heterocyclic ring, wherein the ring is a 6-10 membered ring;

or a salt or stereoisomer thereof.

18. The pharmaceutical composition of claim 14 comprising a compound having the formula Vb:

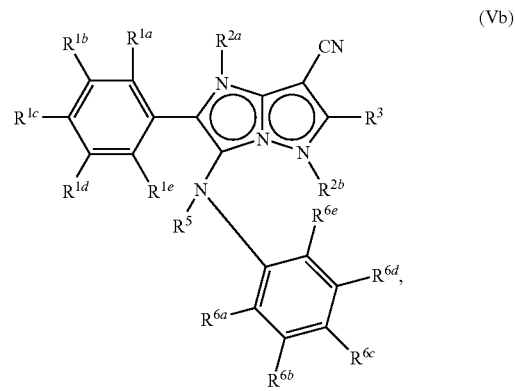

(Vb)

wherein $R^{1a}$, $R^{1b}$, $R^{1c}$, $R^{1d}$, and $R^{1e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —SO$_2$-alkyl, —SO$_2$-aryl, —SO$_2$-heteroaryl, —NH—SO-alkyl, —NH—SO-aryl, —NH—SO-heteroaryl, —NH—SO$_2$-alkyl, —NH—SO$_2$-aryl, and —NH—SO$_2$-heteroaryl; or wherein any two of $R^{1a}$, $R^{1b}$, $R^{1c}$, $R^{1d}$, and $R^{1e}$ vicinal to one another are taken together with the carbon atoms to which they are attached to form carbocyclic, substituted carbocyclic, heterocyclic, or substituted heterocyclic ring, wherein the ring is a 4-10 membered ring;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —$SO_2$-alkyl, —$SO_2$-aryl, —$SO_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^{6a}$, $R^{6b}$, $R^{6c}$, $R^{6d}$, and $R^{6e}$ are independently selected from hydrogen, alkyl, substituted alkyl, alkoxy, substituted alkoxy, acyl, acylamino, acyloxy, aminoacyl, oxyacyl, amino, substituted amino, aminocarbonyloxy, alkoxycarbonylamino, azido, cyano, halogen, hydroxyl, hydroxyamino, alkoxyamino, nitro, carboxyl, thiol, thioalkoxy, substituted thioalkoxy, arylthio, heteroarylthio, heterocyclylthio, cycloalkyl, substituted cycloalkyl, cycloalkenyl, substituted cycloalkenyl, aryl, substituted aryl, heteroaryl, substituted heteroaryl, heterocyclic, substituted heterocyclic, aryloxy, heteroaryloxy, heterocyclooxy, —SO-alkyl, —SO-aryl, —SO-heteroaryl, —$SO_2$-alkyl, —$SO_2$-aryl, —$SO_2$-heteroaryl, —NH—SO-alkyl, —NH—SO-aryl, —NH—SO-heteroaryl, —NH—$SO_2$-alkyl, —NH—$SO_2$-aryl, and —NH—$SO_2$-heteroaryl; or wherein any two of $R^{6a}$, $R^{6b}$, $R^{6c}$, $R^{6d}$, and $R^{6e}$ together with the carbon atoms to which they are attached form carbocyclic, substituted carbocyclic, heterocyclic, or substituted heterocyclic ring, wherein the ring is a 4-10 membered ring;

or a salt or stereoisomer thereof.

19. The pharmaceutical composition of claim 14 comprising a compound having the formula VIb:

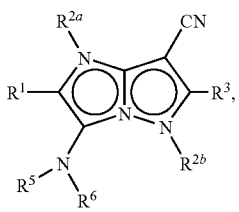

(VIb)

wherein $R^1$ is selected from heteroaryl and substituted heteroaryl;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —$SO_2$-alkyl, —$SO_2$-aryl, —$SO_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl; and $R^6$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

or a salt or stereoisomer thereof.

20. A pharmaceutical composition comprising:
a compound having the formula VIIb:

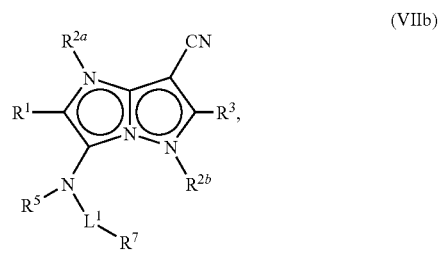

(VIIb)

wherein $R^1$ is selected from aryl, substituted aryl, heteroaryl, substituted heteroaryl, cycloalkyl, substituted cycloalkyl, cycloalkenyl, substituted cycloalkenyl, heterocyclyl, substituted heterocyclyl, aralkyl, heteroaralkyl, hydrogen, alkyl, substituted alkyl, alkenyl, substituted alkenyl, alkynyl, substituted alkynyl, acyl, acylamino, and acyloxy;

$R^{2a}$ and $R^{2b}$ are independently selected from hydrogen, alkyl, substituted alkyl, acyl, acylamino, acyloxy, —SO-alkyl, —SO-aryl, —SO-heteroaryl, —$SO_2$-alkyl, —$SO_2$-aryl, —$SO_2$-heteroaryl, aryl, substituted aryl, heteroaryl, heterocyclyl, aralkyl, and heteroaralkyl, and wherein either $R^{2a}$ or $R^{2b}$ is present;

$R^3$ is selected from hydrogen, alkyl, substituted alkyl, alkenyl, substituted alkenyl, halo, nitro, cyano, hydroxy, alkoxy, carboxyl, acyl, acylamino, aminoacyl, acyloxy, oxyacyl, amino, substituted amino, aryl, substituted aryl, heteroaryl, and substituted heteroaryl;

$R^5$ is selected from hydrogen, alkyl, and substituted alkyl;

$L^1$ is —$CH_2$— or —C(O)—; and $R^7$ is selected from aryl, substituted aryl, heteroaryl, substituted heteroaryl, heterocyclyl, substituted heterocyclyl;

or a salt or stereoisomer thereof; and
a pharmaceutically acceptable carrier.

21. The pharmaceutical composition of claim 13, further comprising an additional agent selected from anti-inflammatory agent, a chemotherapeutic agent, and bone modulating agent.

22. The pharmaceutical composition of claim 21, wherein the additional anti-inflammatory agent is selected from steroidal anti-inflammatory agent, non-steroidal anti-inflammatory agent, lipoxygenase antagonist, 5-lipoxygenase activating protein (FLAP) antagonist, antihistamine, beta-agonist, anti-metabolite, statin, and anti-TNF-alpha agent.

23. The pharmaceutical composition of claim 14, further comprising an additional agent selected from anti-inflammatory agent, a chemotherapeutic agent, and bone modulating agent.

24. The pharmaceutical composition of claim 23, wherein the additional anti-inflammatory agent is selected from steroidal anti-inflammatory agent, non-steroidal anti-inflammatory agent, lipoxygenase antagonist, 5-lipoxygenase activating protein (FLAP) antagonist, antihistamine, beta-agonist, anti-metabolite, statin, and anti-TNF-alpha agent.

25. A method of inhibiting a Syk activity in a biological sample or a patient, which method comprises contacting the biological sample or administering to the patient a compound of claim 1.

26. A method of inhibiting a Syk activity in a biological sample or a patient, which method comprises contacting the biological sample or administering to the patient a pharmaceutical composition of claim 14.

* * * * *